United States Patent
Overman et al.

(10) Patent No.: US 10,246,471 B2
(45) Date of Patent: *Apr. 2, 2019

(54) ETP DERIVATIVES

(71) Applicants: City of Hope, Duarte, CA (US); The Regents of the University of California, Oakland, CA (US)

(72) Inventors: Larry Eugene Overman, Corona Del Mar, CA (US); Marcus Baumann, Durham (GB); Sangkil Nam, Tujunga, CA (US); David Horne, Altadena, CA (US); Richard Jove, Pasadena, CA (US); Jun Xie, Duarte, CA (US); Claudia Kowolik, Redondo Beach, CA (US)

(73) Assignees: City of Hope, Duarte, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/796,363

(22) Filed: Oct. 27, 2017

(65) Prior Publication Data

US 2018/0155367 A1   Jun. 7, 2018

Related U.S. Application Data

(63) Continuation of application No. 15/242,318, filed on Aug. 19, 2016, now Pat. No. 9,856,273, which is a continuation of application No. 14/689,682, filed on Apr. 17, 2015, now Pat. No. 9,527,868, which is a continuation of application No. PCT/US2013/066252, filed on Oct. 22, 2013.

(60) Provisional application No. 61/799,160, filed on Mar. 15, 2013, provisional application No. 61/716,803, filed on Oct. 22, 2012.

(51) Int. Cl.

| | |
|---|---|
| *C07D 513/18* | (2006.01) |
| *A61K 45/06* | (2006.01) |
| *A61K 31/44* | (2006.01) |
| *A61K 31/548* | (2006.01) |
| *A61K 31/706* | (2006.01) |
| *A61K 31/7068* | (2006.01) |
| *C07D 487/04* | (2006.01) |

(52) U.S. Cl.
CPC ........... *C07D 513/18* (2013.01); *A61K 31/44* (2013.01); *A61K 31/548* (2013.01); *A61K 31/706* (2013.01); *A61K 31/7068* (2013.01); *A61K 45/06* (2013.01); *C07D 487/04* (2013.01)

(58) Field of Classification Search
CPC .................................................. C07D 513/18
USPC .......................................................... 549/1
See application file for complete search history.

(56) References Cited

U.S. PATENT DOCUMENTS

| 7,186,721 B2 | 3/2007 | Peschke et al. |
| 8,044,103 B2 | 10/2011 | Kozikowski et al. |
| 9,527,868 B2 | 12/2016 | Overman et al. |
| 9,856,273 B2 | 1/2018 | Overman et al. |
| 2007/0037816 A1 | 2/2007 | Edwards et al. |
| 2010/0305182 A1 | 12/2010 | Blackwell et al. |
| 2015/0291622 A1 | 10/2015 | Overman et al. |

FOREIGN PATENT DOCUMENTS

| CN | 1215433 A | 4/1999 |
| CN | 101248071 A | 8/2008 |
| EP | 0 926 242 A1 | 6/1999 |
| GB | 1 409 185 A | 10/1975 |
| WO | WO-97/48706 A1 | 12/1997 |
| WO | WO-98/24926 A1 | 6/1998 |
| WO | WO-99/40931 A1 | 8/1999 |
| WO | WO-2005/110982 A2 | 11/2005 |
| WO | WO-2005/110982 A3 | 11/2005 |
| WO | WO-2006/066775 A1 | 6/2006 |
| WO | WO-2007/021574 A1 | 2/2007 |
| WO | WO-2007/117180 A1 | 10/2007 |
| WO | WO-2008/112014 A1 | 9/2008 |
| WO | WO-2014/189343 A1 | 11/2014 |

OTHER PUBLICATIONS

Chen et al., "Convergent diversity-oriented synthesis of small-molecule hybrids," Angew Chem Int Ed Engl., 44(15):2249-2252 (2005).
Chen et al., "Supporting Information—Convergent diversity-oriented synthesis of small-molecule hybrids," pp. 1-38 (2005).
Extended European Supplementary Search Report in EP 13 84 9813 dated Mar. 21, 2016, 13 pages.
International Search Report in International Publication No. PCT/US2013/066252 dated Feb. 11, 2014, 5 pages.
Jainta et al., "Microwave-assisted stereoselective one-pot synthesis of symmetrical and unsymmetrical 2,5-Diketopiperazines from unprotected amino acids," European Journal of Organic Chemistry, 32:5418-5424 (2008).
Lopez-Rodriguez et al., "Synthesis and structure-activity relationships of a new model of arylpiperazines. 8. Computational simulation of ligand-receptor interaction of 5-HT(1A)R agonists with selectivity over alpha1-adrenoceptors," Journal of Medicinal Chemistry, 48(7):2548-2558 (2005).
Moldvai et al., "Enantioefficient synthesis of alpha-ergocryptine: first direct synthesis of (+)-lysergic acid," Journal of Organic Chemistry, 69(18):5993-6000 (2004).
Monbaliu et al., "A new benzotriazole-mediated stereoflexible gateway to hetero-2,5-diketopiperazines," Chemistry—A European Journal, 18(9):2632-2638 (2012).
Oehler, E. and U. Schmidt, Über Aminosäuren und Peptide, XV-1,2. "Hydroxylsubstituierte cyclodipeptide durch ringschluβ von pyruvoylaminosäureamiden, II-3, Zweifacher Ringschlud," Chemische Berichte, 108(9):2907-2916 (1975). In German with an English Language abstract.

(Continued)

*Primary Examiner* — Taofiq A Solola
(74) *Attorney, Agent, or Firm* — Mintz Levin

(57) ABSTRACT

Provided herein, inter alia, is the synthesis of ETP derivatives. The uses of the ETP derivatives described herein include treatment of cancer.

21 Claims, 33 Drawing Sheets

Specification includes a Sequence Listing.

(56) References Cited

OTHER PUBLICATIONS

Overman, L. and T. Sato, "Construction of epidithiodioxopiperazines by directed oxidation of hydroxyproline-derived dioxopiperazines," *Organic Letters*, 9(25):5267-5270 (2007).
Poisel, H. and U. Schmidt, Ueber Aminosaeuren und Peptide, XVI-1, "Ueber dehydro-aminosaeuren, III. Additionen an alpha-iminocaronsaeuren," *Chemische Berichte*, 108(9):2917-2922 (1975). In German with an English Language abstract.
PubChemCompound, datasheet [online compound summary] for CID 98951, retrieved from the Internet:<URL:pubchem.ncbi.nlm.nih.gov/search/search.cgi>, 14 pages, create date Mar. 26, 2005.
Stark et al., "Structures, sensory activity, and dose/response functions of 2,5 diketopiperazines in roasted cocoa nibs (*Theobroma cacao*)," Journal of Agricultural and Food Chemistry, American Chemical Society, 53(18):7222-7231 (2005).
Wang, L. and D. Clive, "Synthetic studies related to MPC1001: formation of a model epidithiodiketopiperazine," Tetrahedron Letters, 53(12):1504-1506 (2012).
Chinese Patent Application No. 201380065997.2, First Office Action dated Apr. 19, 2016, 16 pages. (English Translation Provided).
Fujishiro et al., Epidithiodiketopiperazine as a pharmacophore for protein lysine methyltransferase G9a inhibitors: reducing cytotoxicity by structural simplification. Bioorganic & Medicinal Chemistry Letters, 23:733-736, 2013.
Blaha et al, Collection Czechoslovok Chem. Cornrnun. [vol. 52] [1987] pp. 2295-2308.
DeLorbe et al. J Am Chem Soc. Mar. 13, 2013; 135(10) pp. 1-30.
Imamura et al, Peptides 24 (2003) 445-448.
Kobayashi et al, Chem. Pharm. Bull. 42(12) 2449-2451 (1994).
Banfi, L. et al. (Oct. 22, 2007). "A Convergent Synthesis of Enantiopure Bicyclic Scaffolds through Multicomponent Ugi Reaction," *Tetrahedreon* 64:1114-1134.
Guenoun, F. et al. (1997). "Pyrrolidinopiperazinedione as Chiral Auxiliary and its Use in Asymmetric Mannich Synthesis," *Tetrahedron Letters* 38(9):1563-1566.
Occelli, E. et al. (Jan. 1, 1984). "Sostanze Attive Sul Sistema Nervose Centrale," *Farmaco* 39(8):718-738 (English translation of Summary only).
Gardiner, D.M. et al. (Apr. 2005). "The epipolythiodioxopiperazine (ETP) class of fungal toxins: distribution, mode of action, functions and biosynthesis," *Microbiology* 151(Pt 4):1021-1032.

FIG. 5

IC50 Summary:

| | Methyltransferase | Substrate | Compound stock | Compound IC50* (M): Rac | Compound IC50* (M): S | Compound IC50* (M): R | Chaetocin IC50* (M): |
|---|---|---|---|---|---|---|---|
| 1 | G9a | Histone H3 | 10 mM | | | | 1.97E-06 |
| 2 | G9a | Histone H3 | 1 mM | >1.00E-05 | | | 2.39E-06 |
| 3 | SUV39H1 | Histone H3 | 10 mM | 1.16E-06 | 1.51E-06 | 2.09E-06 | 2.01E-07 |
| 4 | SUV39H1 | Histone H3 | 1 mM | 1.16E-06 | 1.44E-06 | 1.76E-06 | 2.57E-07 |

* Empty cells indicate no inhibition or compound activity that could not be fit to an IC50 curve
ND   Indicates compound not tested against enzyme

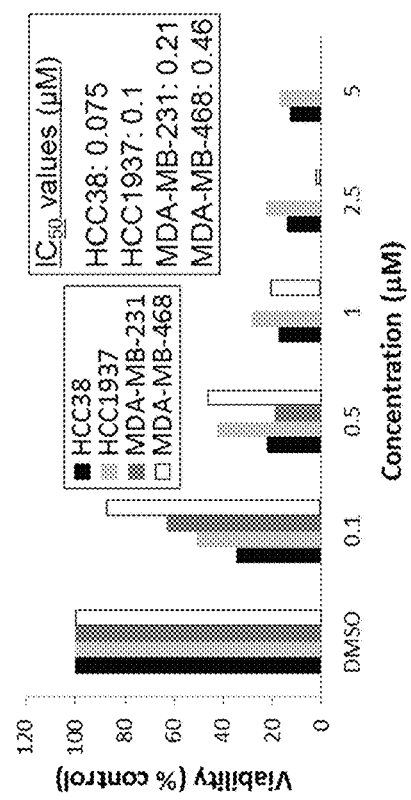
FIG. 6A
IC$_{50}$ values (µM) against cancer cells
|  | DU145 (prostate) | A2058 (melanoma) | SKOV3 (ovarian) |
|---|---|---|---|
| ETP6 | >5 | >5 | |
| ETP8 | >5 | >5 | |
| ETP12 | 4.2 | >5 | |
| ETP14 | 4.1 | 3.5 | |
| ETP27 | >5 | >5 | |
| ETP49 | >5 | 5 | |
| ETP56 | >5 | >5 | |
| ETP69 | 0.13 | 0.1 | 0.09 |
FIG. 6B
IC$_{50}$ values (µM) against triple negative breast cancer cells
IC$_{50}$ values (µM)
HCC38: 0.075
HCC1937: 0.1
MDA-MB-231: 0.21
MDA-MB-468: 0.46
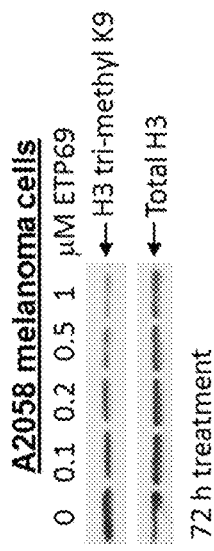
FIG. 6C
A2058 melanoma cells
0  0.1  0.2  0.5  1   µM ETP69
← H3 tri-methyl K9
← Total H3
72 h treatment

FIG. 7

Inhibition of Histone-modifying enzymes *in vitro*

IC$_{50}$ value (μM)

| His. Methyltrasferase | ETP69 | **Chaetocin |
|---|---|---|
| DOT1 | > 10 | N/A |
| EZH1 | > 10 | N/A |
| EZH2 | > 10 | N/A |
| GLP | 6.31 | 0.69 |
| MLL1 | 4.24 | 0.22 |
| MLL2 | 8.4 | 0.4 |
| MLL3 | > 10 | 0.28 |
| MLL4 | > 10 | 0.31 |
| NSD2 | 2.79 | 0.24 |
| SET1b | 1.64 | 0.21 |
| SET7/9 | > 10 | N/A |
| SET8 | > 10 | N/A |
| SETMAR | > 10 | N/A |
| SMYD2 | > 10 | N/A |
| SUV39H1 | 0.084 | 0.33 |
| SUV39H2 | 3.31 | 0.48 |
| G9a | 0.251 | 0.16 |
| His. Acetyltransferase | | |
| p300 | > 10 | N/A |
| DNA Methyltrasferase | | |
| DNMT1 | > 10 | N/A |

Activity (%)

| Conc.(M) | S enantiomer |
|---|---|
| 1.00E-04 | 108.14 |
| 3.33E-05 | 105.67 |
| 1.11E-05 | 106.39 |
| 3.70E-06 | 108.95 |
| 1.23E-06 | 105.37 |
| 4.12E-07 | 104.94 |
| 1.37E-07 | 107.59 |
| 4.57E-08 | 99.18 |
| 1.52E-08 | 98.50 |
| 5.08E-09 | 94.98 |
| DMSO | 94.69 |

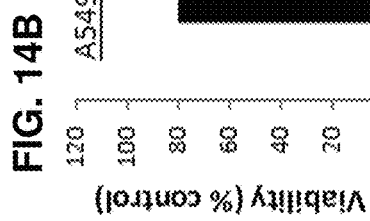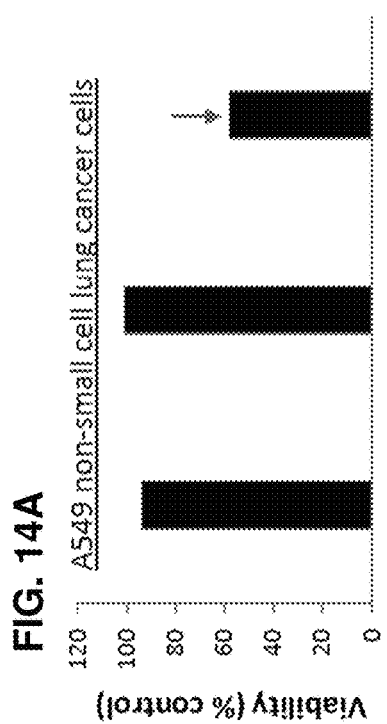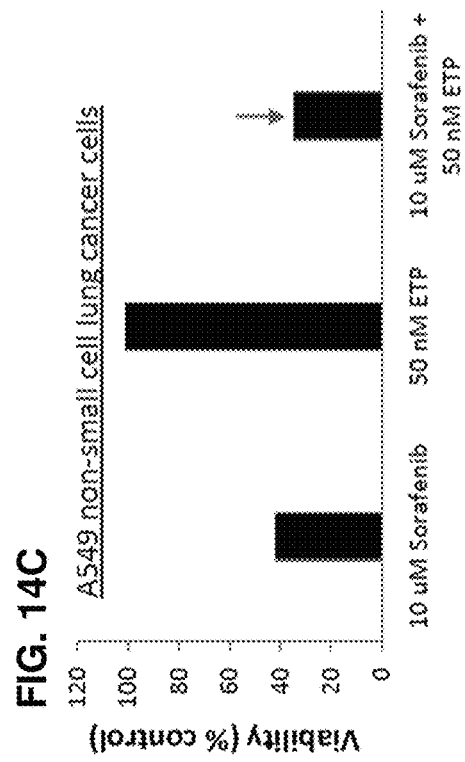
FIG. 14A
FIG. 14B
FIG. 14C

FIG. 19

| Intraperitoneal (20 mg/kg) | | | | |
|---|---|---|---|---|
| Time point (hr) | Mouse # | Conc. (ng/mL) | Average (ng/mL) | SD |
| 0 (predose) | 141 | BLOQ | ND | ND |
| | 142 | BLOQ | | |
| | 143 | BLOQ | | |
| 0.25 | 105 | 13700 | 9053 | 4025 |
| | 106 | 6630 | | |
| | 107 | 6830 | | |
| 0.50 | 108 | 4200 | 4740 | 480 |
| | 109 | 5120 | | |
| | 110 | 4900 | | |
| 1.0 | 111 | 17200 | 8057 | 7919 |
| | 112 | 3550 | | |
| | 113 | 3420 | | |
| 2.0 | 114 | 3500 | 2870 | 764 |
| | 115 | 2020 | | |
| | 116 | 3090 | | |
| 4.0 | 117 | 2120 | 4000 | 3256 |
| | 118 | 2120 | | |
| | 119 | 7760 | | |
| 8.0 | 120 | 824 | 696 | 193 |
| | 121 | 791 | | |
| | 122 | 474 | | |
| Pharmacokinetic Parameters | | | | |
| $C_{max}$(±SE, ng/mL) | | | 9053 ± 2324 | |
| $t_{max}$(hr) | | | 0.25 | |
| $t_{1/2}$(hr) | | | 2.41 | |
| $AUC_{last}$ (±SE, hr·ng/mL) | | | 27781 ± 6664 | |
| $AUC_{\infty}$ (hr·ng/mL) | | | 30206 | |

FIG. 20

| Oral (20 mg/kg) | | | | |
|---|---|---|---|---|
| Time point (hr) | Mouse # | Conc. (ng/mL) | Average (ng/mL) | SD |
| 0 (predose) | 141 | BLOQ | ND | ND |
| | 142 | BLOQ | | |
| | 143 | BLOQ | | |
| 0.25 | 123 | 5000 | 4677 | 293 |
| | 124 | 4430 | | |
| | 125 | 4600 | | |
| 0.50 | 126 | 4970 | 4820 | 167 |
| | 127 | 4640 | | |
| | 128 | 4850 | | |
| 1.0 | 129 | 3780 | 3327 | 605 |
| | 130 | 3560 | | |
| | 131 | 2640 | | |
| 2.0 | 132 | 5010 | 3440 | 1366 |
| | 133 | 2790 | | |
| | 134 | 2520 | | |
| 4.0 | 135 | 1410 | 1820 | 376 |
| | 136 | 1900 | | |
| | 137 | 2150 | | |
| 8.0 | 138 | 645 | 612 | 322 |
| | 139 | 275 | | |
| | 140 | 917 | | |
| Pharmacokinetic Parameters | | | | |
| $C_{max}$(±SE, ng/mL) | | | 4820 ± 96.4 | |
| $t_{max}$ (hr) | | | 0.50 | |
| $t_{1/2}$ (hr) | | | 2.43 | |
| $AUC_{last}$ (±SE, hr·ng/mL) | | | 17316 ± 1427 | |
| $AUC_{\infty}$ (hr·ng/mL) | | | 19461 | |

IC$_{50}$ value (nM)
S enantiomer: 7.8
R enantiomer: 33.1
Racemic: 15.0

IC$_{50}$ value (nM)
S enantiomer: 2.7
R enantiomer: 85.5
Racemic: 2.4

NT shRNA  SUV39H1 shRNA

Senescence-associated β-galactosidase activity

DMSO  100 nM ETP69

SEQUENCE LISTING

<160> NUMBER OF SEQ ID NOS: 6

<210> SEQ ID NO 1
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 1
gtcatggagt acgtgggaga g    21

<210> SEQ ID NO 2
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 2
cctgacggtc gtagatctgg    20

<210> SEQ ID NO 3
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 3
tagtgtggtg gtgccctatg    20

<210> SEQ ID NO 4
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 4
cacatgtagt tgtagtggat ggtg    24

<210> SEQ ID NO 5
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 5
agccacatcg ctcagacac    19

```
<210> SEQ ID NO 6
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 6
gcccaatacg accaaatcc                                                19
```

ETP DERIVATIVES

CROSS-REFERENCES TO RELATED APPLICATIONS

This application is a continuation of U.S. application Ser. No. 15/242,318, filed Aug. 19, 2016, which is a continuation of U.S. application Ser. No. 14/689,682, filed Apr. 17, 2015, now U.S. Pat. No. 9,527,868, which is a continuation of International Application No. PCT/US2013/066252, filed Oct. 22, 2013, which claims priority to U.S. Provisional Application No. 61/716,803, filed Oct. 22, 2012, and to U.S. Provisional Application No. 61/799,160, filed Mar. 15, 2013. The disclosure of each of the prior applications is considered part of and is incorporated by reference in the disclosure of this application.

STATEMENT AS TO RIGHTS TO INVENTIONS MADE UNDER FEDERALLY SPONSORED RESEARCH AND DEVELOPMENT

This invention was made with government support under grant 2R01-GM030859 and 5F32GM090473 awarded by the NIH National Institute of General Medical Sciences. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48440-514C01US_ST25.TXT, created on Aug. 18, 2016, 1,673 bytes, machine format IBM-PC, MS-Windows operating system, is hereby incorporated by reference.

BACKGROUND OF THE INVENTION

ETP natural products represent an intriguing class of (typically) fungal secondary metabolites with a large variety of biological activities ranging from antibiotic to antiviral to antimalarial properties. High levels of toxicity, however, has so far prevented any clinical studies of known ETP structures. No detailed SAR studies of ETPs and their analogues have been reported to date. Furthermore, introduction and elaboration of functional groups for ETP structures has not been previously reported thereby preventing modification of crucial properties such as water solubility, membrane permeability or metabolic stability in biological systems. Accordingly a synthetic route to synthesize ETP analogues for medicinal purposes is crucial and has significant value. Provided herein are solutions to these and other problems in the art.

BRIEF SUMMARY OF THE INVENTION

Provided herein, inter alia, are synthetic analogues of ETP compounds. The analogues may be used in the treatment of cancer and may be effective as synergistically combined with other cancer treating compounds. Methods of synthesizing and use are also provided.

In a first aspect is a compound having the formula:

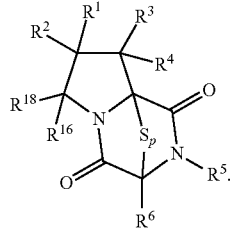

(I)

The symbol p is 2, 3 or 4. $R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34b}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, $-N_3$, $-CF_3$, $-CCl_3$, $-CBr_3$, $-CI_3$, $-CN$, $-CHO$, $-OR^{33C}$, $-NR^{34C}R^{35C}$, $-COOR^{33C}$, $-CONR^{34C}R^{35C}$, $-NO_2$, $-SR^{36C}$, $-SO_{n3}R^{34C}$, $-SO_{n3}OR^{34C}$, $-SO_{n3}NR^{34C}R^{35C}$, $-NHNR^{34C}R^{35C}$, $-ONR^{34C}R^{35C}$, $-NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen, halogen, $-N_3$, $-CF_3$, $-CCl_3$, $-CBr_3$, $-CI_3$, $-CN$, $-CHO$, $-OR^{33D}$, $-NR^{34D}R^{35D}$, $-COOR^{33D}$, $-CONR^{34D}R^{35D}$, $-NO_2$, $-SR^{36D}$, $-SO_{n4}R^{34D}$, $-SO_{n4}OR^{34D}$, $-SO_{n4}NR^{34D}R^{35D}$, $-NHNR^{34D}R^{35D}$, $-ONR^{34D}R^{35D}$, $-NHC(O)NHNR^{34D}R^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is hydrogen, halogen, $-N_3$, $-CF_3$, $-CCl_3$, $-CBr_3$, $-CI_3$, $-CN$, $-CHO$, $-OR^{33E}$, $-NR^{34E}R^{35E}$, $-COOR^{33E}$, $-CONR^{34E}R^{35E}$, $-NO_2$, $-SR^{36E}$, $-SO_{n5}R^{34E}$, $-SO_{n5}OR^{34E}$, $-SO_{n5}NR^{34E}R^{35E}$, $-NHNR^{34E}R^{35E}$, $-ONR^{34E}R^{35E}$, $-NHC(O)NHNR^{34E}R^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, halogen, $-N_3$, $-CF_3$, $-CCl_3$, $-CBr_3$, $-CI_3$, $-CN$, $-CHO$, $-OR^{33F}$, $-NR^{34F}R^{35F}$, $-COOR^{33F}$, $-CONR^{34F}R^{35F}$, $-NO_2$, $-SR^{36F}$, $-SO_{n6}R^{34F}$, $-SO_{n6}OR^{34F}$, $-SO_{n6}NR^{34F}R^{35F}$, $-NHNR^{34F}R^{35F}$, $-ONR^{34F}R^{35F}$, $-NHC(O)NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is hydrogen, halogen, $-N_3$, $-CF_3$, $-CCl_3$, $-CBr_3$, $-CI_3$, $-CN$, $-CHO$, $-OR^{33G}$, $-NR^{34G}R^{35G}$, $-COOR^{33G}$, $-CONR^{34G}R^{35G}$, $-NO_2$, $-SR^{36G}$, $-SO_{n7}R^{34G}$, $-SO_{n7O}R^{34G}$, $-SO_{n7}NR^{34G}R^{35G}$, $-NHNR^{34G}R^{35G}$, $-ONR^{34G}R^{35G}$, $-NHC(O)NHNR^{34G}R^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{18}$ is hydrogen, halogen, $-N_3$, $-CF_3$, $-CCl_3$, $-CBr_3$, $-CI_3$, $-CN$, $-CHO$, $-OR^{33H}$, $-NR^{34H}R^{35H}$, $-COOR^{33H}$, $-CONR^{34H}R^{35H}$, $-NO_2$, $-SR^{36H}$, $-SO_{n8}R^{34H}$, $-SO_{n8}OR^{34H}$, $-SO_{n5}NR^{34H}R^{35H}$, $-NHNR^{34H}R^{35H}$, $-ONR^{34H}R^{35H}$, $-NHC(O)NHNR^{34H}R^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{33A}$, $R^{34A}$, $R^{35A}$, $R^{36A}$, $R^{33B}$, $R^{34B}$, $R^{35B}$, $R^{36B}$, $R^{33C}$, $R^{34C}$, $R^{35C}$, $R^{36C}$, $R^{33D}$, $R^{34D}$, $R^{35D}$, $R^{36D}$, $R^{33E}$, $R^{34E}$, $R^{35E}$, $R^{36E}$, $R^{33F}$, $R^{34F}$, $R^{35F}$, $R^{36F}$, $R^{33G}$, $R^{34G}$, $R^{35G}$, $R^{36G}$, $R^{33H}$, $R^{34H}$, $R^{35H}$, and $R^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n1, n2, n3, n4, n5, n6, n7, and n8 are independently 1 or 2.

In another aspect is a compound having the formula:

$$\text{(VII)}$$

[Structure with substituents $R^1$, $R^2$, $R^3$, $R^4$, $R^5$, $R^6$, $R^{16}$, $R^{18}$, $R^{25}$, $R^{26}$]

$R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34b}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, $-N_3$, $-CF_3$, $-CCl_3$, $-CBr_3$, $-CI_3$, $-CN$, $-CHO$, $-OR^{33C}$, $-NR^{34C}R^{35C}$, $-COOR^{33C}$, $-CONR^{34C}R^{35C}$, $-NO_2$, $-SR^{36C}$, $-SO_{n3}R^{34C}$, $-SO_{n3O}R^{34C}$, $-SO_{n3}NR^{34C}R^{35C}$, $-NHNR^{34C}R^{35C}$, $-ONR^{34C}R^{35C}$, $-NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen, halogen, $-N_3$, $-CF_3$, $-CCl_3$, $-CBr_3$, $-CI_3$, $-CN$, $-CHO$, $-OR^{33D}$, $-NR^{34}R^{35D}$, $-COOR^{33D}$, $-CONR^{34D}R^{35D}$, $-NO_2$, $-SR^{36D}$, $-SO_{n4}R^{34D}$, $-SO_{n4}OR^{34D}$, $-SO_{n4}NR^{34D}R^{35D}$, $-NHNR^{34D}R^{35D}$, $-ONR^{34D}R^{35D}$, $-NHC(O)NHNR^{34D}R^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is hydrogen, halogen, $-N_3$, $-CF_3$, $-CCl_3$, $-CBr_3$, $-CI_3$, $-CN$, $-CHO$, $-OR^{33E}$, $-NR^{34E}R^{35E}$, $-COOR^{33E}$, $-CONR^{34E}R^{35E}$, $-NO_2$, $-SR^{36E}$, $-SO_{n5}R^{34E}$, $-SO_{n5}OR^{34E}$, $-SO_{n5}NR^{34E}R^{35E}$, $-NHNR^{34E}R^{35E}$, $-ONR^{34E}R^{35E}$, $-NHC(O)NHNR^{34E}R^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, halogen, $-N_3$, $-CF_3$, $-CCl_3$, $-CBr_3$, $-CI_3$, $-CN$, $-CHO$, $-OR^{33F}$, $-NR^{34F}R^{35F}$, $-COOR^{33F}$, $-CONR^{34F}R^{35F}$, $-NO_2$, $-SR^{36F}$, $-SO_{n6}R^{34F}$, $-SO_{n6}OR^{34F}$, $-SO_{n6}NR^{34F}R^{35F}$, $-NHNR^{34F}R^{35F}$, $-ONR^{34F}R^{35F}$, $-NHC(O)NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is hydrogen, halogen, $-N_3$, $-CF_3$, $-CCl_3$, $-CBr_3$, $-CI_3$, $-CN$, $-CHO$, $-OR^{33G}$, $-NR^{34G}R^{35G}$, $-COOR^{33G}$, $-CONR^{34G}R^{35G}$, $-NO_2$, $-SR^{36G}$, $-SO_{n7}R^{34G}$, $-SO_{n7}OR^{34G}$, $-SO_{n7}NR^{34G}R^{35G}$, $-NHNR^{34G}R^{35G}$, $-ONR^{34G}R^{35G}$, $-NHC(O)NHNR^{34G}R^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{18}$ is hydrogen, halogen, $-N_3$, $-CF_3$, $-CCl_3$, $-CBr_3$, $-CI_3$, $-CN$, $-CHO$, $-OR^{33H}$, $-NR^{34H}R^{35H}$, $-COOR^{33H}$, $-CONR^{34H}R^{35H}$, $-NO_2$, $-SR^{36H}$, $-SO_{n8}R^{34H}$, $-SO_{n8}OR^{34H}$, $-SO_{n5}NR^{34H}R^{35H}$, $-NHNR^{34H}R^{35H}$, $-ONR^{34H}R^{35H}$, $-NHC(O)NHNR^{34H}R^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{33A}$, $R^{34A}$, $R^{35A}$, $R^{36A}$, $R^{33B}$, $R^{34B}$, $R^{35B}$, $R^{36B}$, $R^{33C}$, $R^{34C}$, $R^{35C}$, $R^{36C}$, $R^{33D}$, $R^{34D}$, $R^{35D}$, $R^{36D}$, $R^{33E}$, $R^{34E}$, $R^{35E}$, $R^{36E}$, $R^{33F}$, $R^{34F}$, $R^{35F}$, $R^{36F}$, $R^{33G}$, $R^{34G}$, $R^{35G}$, $R^{36G}$, $R^{33H}$, $R^{34H}$, $R^{35H}$, and $R^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n1, n2, n3, n4, n5, n6, n7, and n8 are independently 1 or 2. $R^{25}$ and $R^{26}$ are independently hydrogen, substituted or unsubstituted alkyl, substituted or unsubstituted heteroalkyl, substituted or unsubstituted aryl, or substituted or unsubstituted heteroaryl.

In another aspect is a compound having formula:

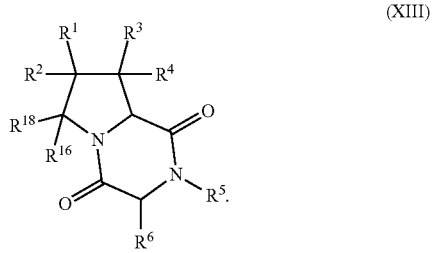

(XIII)

R$^1$ is hydrogen, halogen, —N$_3$, —CF$_3$, —CCl$_3$, —CBr$_3$, —CI$_3$, —CN, —CHO, —OR$^{33A}$, —NR$^{34A}$R$^{35A}$, —COOR$^{33A}$, —CONR$^{34A}$R$^{35A}$, —NO$_2$, —SR$^{36A}$, —SO$_{n1}$R$^{34A}$, —SO$_{n1}$OR$^{34A}$, —SO$_{n1}$NR$^{34A}$R$^{35A}$, —NHNR$^{34A}$R$^{35A}$, —ONR$^{34A}$R$^{35A}$, —NHC(O)NHNR$^{34A}$R$^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is hydrogen, halogen, —N$_3$, —CF$_3$, —CCl$_3$, —CBr$_3$, —CI$_3$, —CN, —CHO, —OR$^{33B}$, —NR$^{34B}$R$^{35B}$, —COOR$^{33B}$, —CONR$^{34B}$R$^{35B}$, —NO$_2$, —SR$^{36B}$, —SO$_{n2}$R$^{34b}$, —SO$_{n2}$OR$^{34B}$, —SO$_{n2}$NR$^{34B}$R$^{35B}$, —NHNR$^{34B}$R$^{35B}$, —ONR$^{34B}$R$^{35B}$, —NHC(O)NHNR$^{34B}$R$^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is hydrogen, halogen, —N$_3$, —CF$_3$, —CCl$_3$, —CBr$_3$, —CI$_3$, —CN, —CHO, —OR$^{33C}$, —NR$^{34C}$R$^{35C}$, —COOR$^{33C}$, —CONR$^{34C}$R$^{35C}$, —NO$_2$, —SR$^{36C}$, —SO$_{n3}$R$^{34C}$, —SO$_{n30}$R$^{34C}$, —SO$_{n3}$NR$^{34C}$R$^{35C}$, —NHNR$^{34C}$R$^{35C}$, —ONR$^{34C}$R$^{35C}$, —NHC(O)NHNR$^{34C}$R$^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —N$_3$, —CF$_3$, —CCl$_3$, —CBr$_3$, —CI$_3$, —CN, —CHO, —OR$^{33D}$, —NR$^{34D}$R$^{35D}$, —COOR$^{33D}$, —CONR$^{34D}$R$^{35D}$, —NO$_2$, —SR$^{36D}$, —SO$_{n4}$R$^{34D}$, —SO$_{n4}$OR$^{34D}$, —SO$_{n4}$NR$^{34D}$R$^{35D}$, —NHNR$^{34D}$R$^{35D}$, —ONR$^{34D}$R$^{35D}$, —NHC(O)NHNR$^{34D}$R$^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$ is hydrogen, halogen, —N$_3$, —CF$_3$, —CCl$_3$, —CBr$_3$, —CI$_3$, —CN, —CHO, —OR$^{33E}$, —NR$^{34E}$R$^{35E}$, —COOR$^{33E}$, —CONR$^{34E}$R$^{35E}$, —NO$_2$, —SR$^{36E}$, —SO$_{n5}$R$^{34E}$, —SO$_{n5}$OR$^{34E}$, —SO$_{n5}$NR$^{34E}$R$^{35E}$, —NHNR$^{34E}$R$^{35E}$, —ONR$^{34E}$R$^{35E}$, —NHC(O)NHNR$^{34E}$R$^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, halogen, —N$_3$, —CF$_3$, —CCl$_3$, —CBr$_3$, —CI$_3$, —CN, —CHO, —OR$^{33F}$, —NR$^{34F}$R$^{35F}$, —COOR$^{33F}$, —CONR$^{34F}$R$^{35F}$, —NO$_2$, —SR$^{36F}$, —SO$_{n6}$R$^{34F}$, —SO$_{n6}$OR$^{34F}$, —SO$_{n6}$NR$^{34F}$R$^{35F}$, —NHNR$^{34F}$R$^{35F}$, —ONR$^{34F}$R$^{35F}$, —NHC(O)NHNR$^{34F}$R$^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{16}$ is hydrogen, halogen, —N$_3$, —CF$_3$, —CCl$_3$, —CBr$_3$, —CI$_3$, —CN, —CHO, —OR$^{33G}$, —NR$^{34G}$R$^{35G}$, —COOR$^{33G}$, —CONR$^{34G}$R$^{35G}$, —NO$_2$, —SR$^{36G}$, —SO$_{n7}$R$^{34G}$, —SO$_{n70}$R$^{34G}$, —SO$_{n7}$NR$^{34G}$R$^{35G}$, —NHNR$^{34G}$R$^{35G}$, —ONR$^{34G}$R$^{35G}$, —NHC(O)NHNR$^{34G}$R$^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{18}$ is hydrogen, halogen, —N$_3$, —CF$_3$, —CCl$_3$, —CBr$_3$, —CI$_3$, —CN, —CHO, —OR$^{33H}$, —NR$^{34H}$R$^{35H}$, —COOR$^{33H}$, —CONR$^{34H}$R$^{35H}$, —NO$_2$, —SR$^{36H}$, —SO$_{n8}$R$^{34H}$, —SO$_{n8}$OR$^{34H}$, —SO$_{n5}$NR$^{34H}$R$^{35H}$, —NHNR$^{34H}$R$^{35H}$, —ONR$^{34H}$R$^{35H}$, —NHC(O)NHNR$^{34H}$R$^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n1, n2, n3, n4, n5, n6, n7, and n8 are independently 1 or 2.

In another aspect a pharmaceutical composition is provided. The pharmaceutical composition includes a compound as provided herein (e.g. of formula (I), (II), (III), (IV), (V), (VI), (VII), (VIII), (IX), (X), (XI), (XII), (XIII), (XIV), (XV), (XVI), (XVII), or (XVIII)) and a pharmaceutically acceptable excipient.

In another aspect, a pharmaceutical composition is provided including a compound as provided herein (e.g. of formula (I), (II), (III), (IV), (V), (VI), (VII), (VIII), (IX), (X), (XI), (XII), (XIII), (XIV), (XV), (XVI), (XVII), or (XVIII)), a pharmaceutically acceptable excipient, and at least one additional anticancer agent.

In another aspect a method of treating cancer is provided. The method includes administering to a subject in need thereof a therapeutically effective amount of a compound of formula (I), (II), (III), (IV), (V), (VI), (VII), (VIII), (IX), (X), (XI), (XII), (XIII), (XIV), (XV), (XVI), (XVII), or (XVIII)), including embodiments thereof.

BRIEF DESCRIPTION OF THE DRAWINGS

FIG. 5: Testing of enantiomerically pure ETP69 shows the (S) enantiomer to be slightly more active than the racemic mixture or the (R) enantiomer; compounds where tested in 10-dose $IC_{50}$ mode with 3-fold serial dilution starting at 10 μM; curve fits were performed with the activities at the highest concentration of compounds were less than 65%.

FIGS. 6A-6C: Testing of ETP analogues described herein against various cancer cell lines: FIG. 6A) shows viability inhibition on DU145 prostate cancer cells, A2058 melanoma cells, and SKOV3 ovarian cancer cells by ETP analogues described herein; FIG. 6B) shows viability inhibition on HCC38, HCC1937, MDA-MB-231, and MDA-MB-468 triple neagive breast cancer cells after administration of ETP69; FIG. 6C) shows inhibition of H3K9 trimethylation by ETP69 in A2058 melanoma cells.

FIG. 7: ETP69 selectively inhibits SUV39H1 and G9a in vitro. Comparison of inhibition of ETP69 and known HMT inhibitor Chaetocin shows SUV39H1 and G9a selectivity inhibited by ETP69.

FIG. 12A: 1 μM azacitidine; FIG. 12B: 2.5 μM azacitidine; FIG. 12C: 5 μM azacitidine; FIG. 12D: 10 μM azacitidine.

FIG. 13A: 0.1 μM decitabine; FIG. 13B: 0.25 μM decitabine; FIG. 13C: 1 μM decitabine.

FIGS. 14A-14C: Synergystic effect of ETP derivatives and multi-kinase inhibitors. ETP 69 and sorafenib exhibit a greater effect on reducing viabilities of A549 non-small cell lung cancer cells than when administer alone. FIG. 14A: 2.5 μM Sorafenib; FIG. 14B: 5 μM Sorafenib; FIG. 14C: 10 μM Sorafenib.

FIG. 15A: Treatment with ETP69 results in decreased tumor volume and tumor weight of mice with no observable toxicity symptoms. FIG. 15B: Histogram of tumor weight for vehicle (left column) and ETP59 (right column).

FIG. 16A: Treatment with ETP69 results in decreased tumor volume and tumor weight of mice with no observable toxicity symptoms. FIG. 16B: Histogram of tumor weight for vehicle (left column) and ETP59 (right column).

FIG. 19: Pharmacokinetic parameters for intraperitoneal administration of ETP69 in male CD-1 mice: $C_0$: Maximum plasma concentration extrapolated to t=0; $t_{max}$: Time of maximum plasma concentration; $t_{1/2}$: half-life, data points used for half-life determination are in bold; $AUC_{last}$: Area Under the Curve, calculated to the last observable time point; $AUC_\infty$: Area Under the Curve, extrapolated to infinity; ND: Not Determined; BLOQ: Below the limit of quantitation (2.5 ng/mL); $^a$Values are estimates because the correlation coefficient for the half-life determination was <0.85 (actual value was 0.838).

FIG. 20: Pharmacokinetic parameters for oral administration of ETP69 in male CD-1 mice: $C_0$: Maximum plasma concentration extrapolated to t=0; $t_{max}$: Time of maximum plasma concentration; $t_{1/2}$: half-life, data points used for half-life determination are in bold; $AUC_{last}$: Area Under the Curve, calculated to the last observable time point; $AUC_\infty$: Area Under the Curve, extrapolated to infinity; ND: Not Determined; BLOQ: Below the limit of quantitation (2.5 ng/mL)

FIG. 25A: MOLM13 AML cells; FIG. 25B: MV4-12 AML cells.

DETAILED DESCRIPTION

I. Definitions

Figure 1:
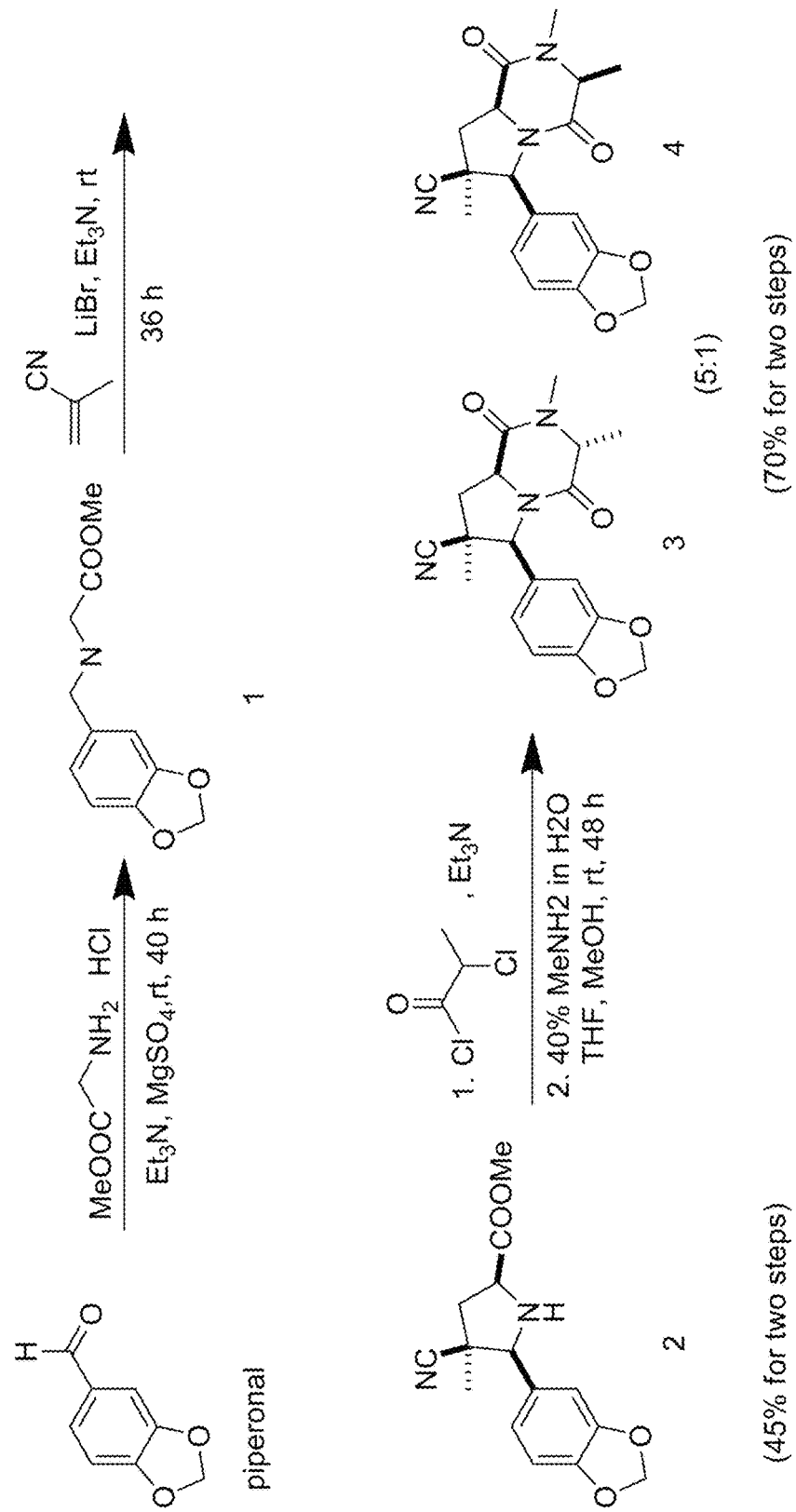
FIG. 1: Synthesis of racemic ETP derivatives herein: the three step synthesis results in a 5:1 ratio of epimeric derivatives 3 and 4.
Figure 2:
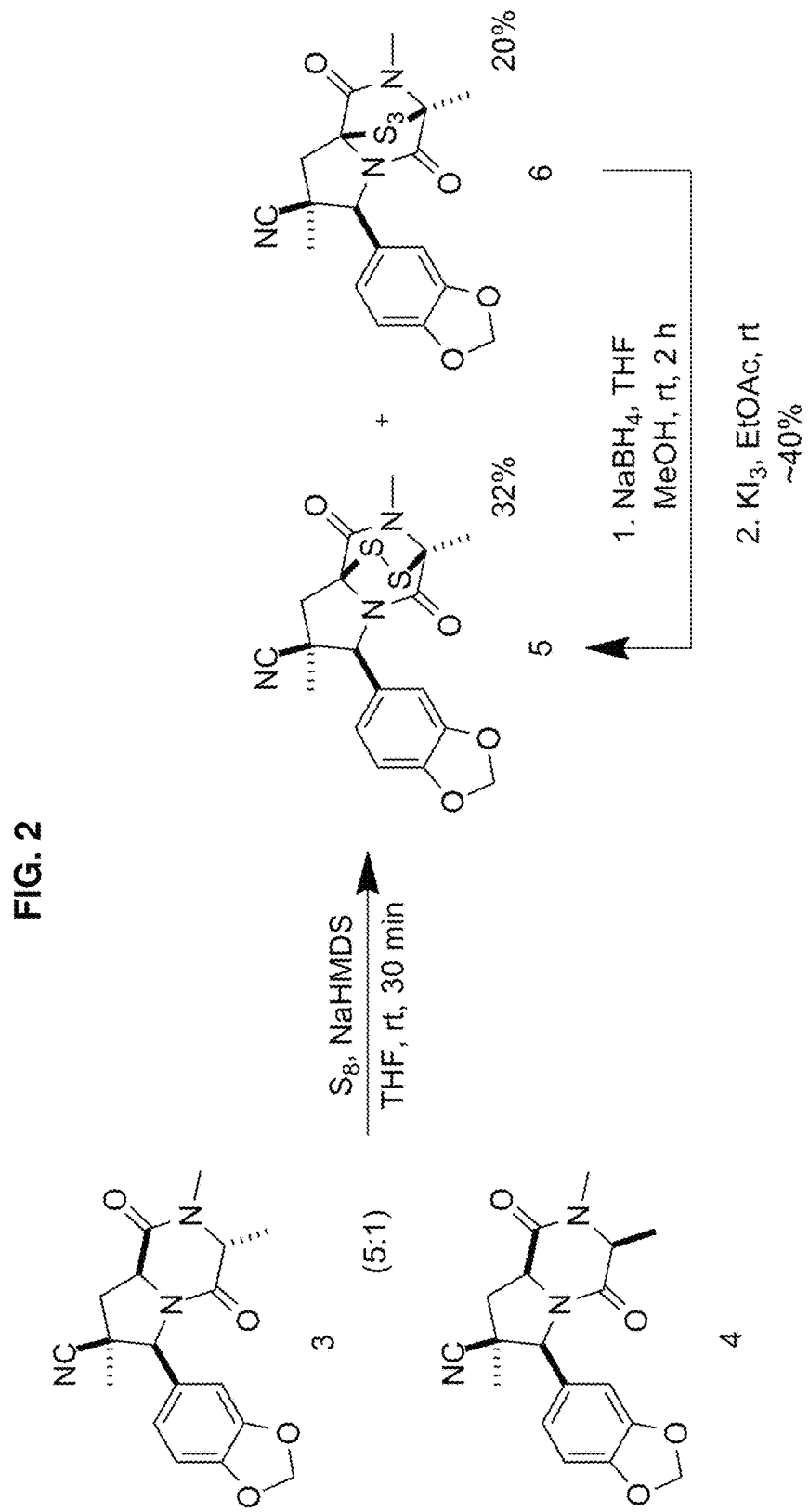
FIG. 2: Synthesis of ETP69: installation of the disulfide bridge results in compounds 5 (e.g. ETP69) and compound 6 with an overall 10% yield.
Figure 3:
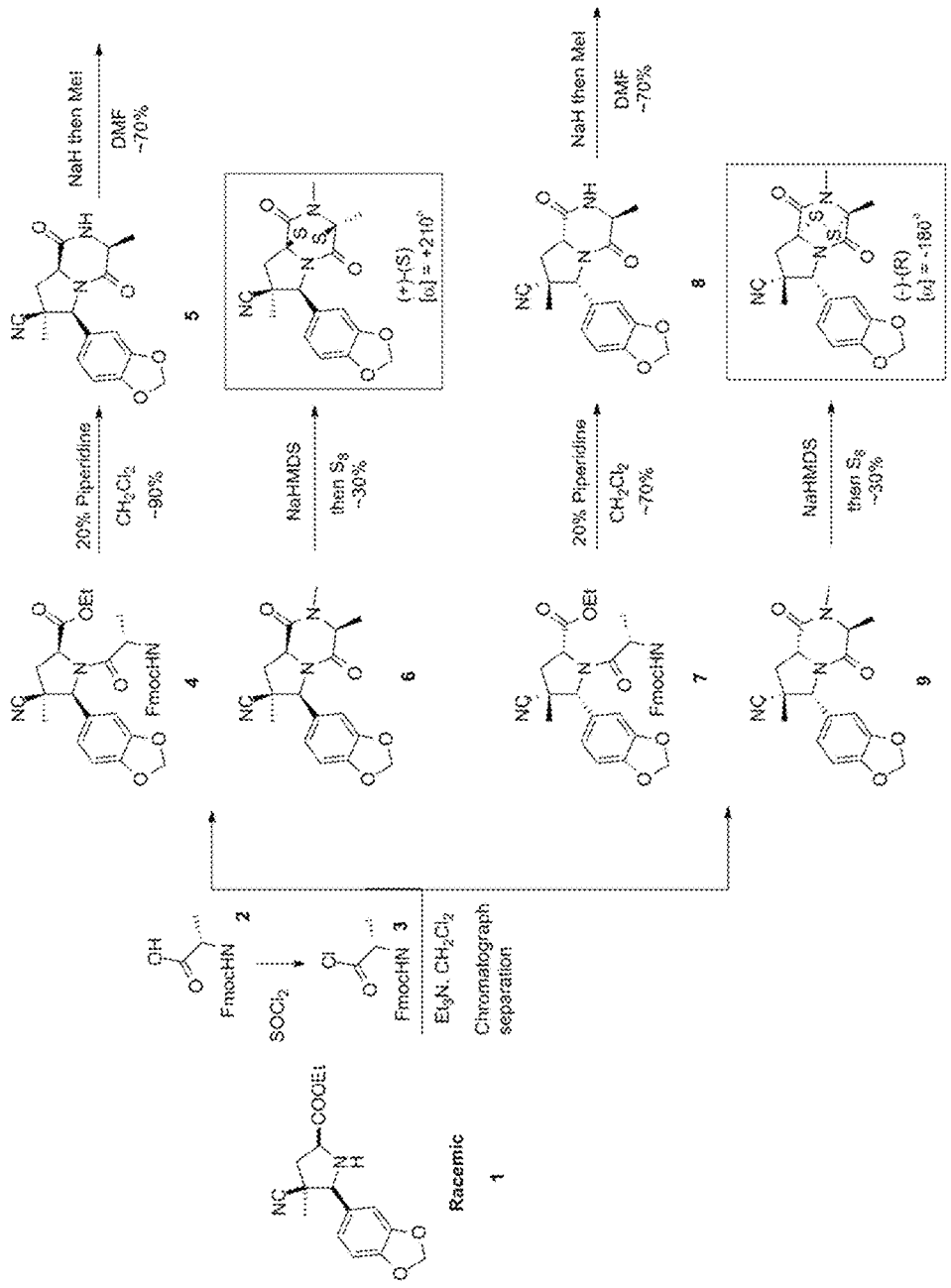
FIG. 3: Enantioselective synthetic route for ETP derivatives: enantiomerically pure (S) and (R) derivatives of ETP derivatives may be synthesized from racemic starting material 1.
Figure 4:
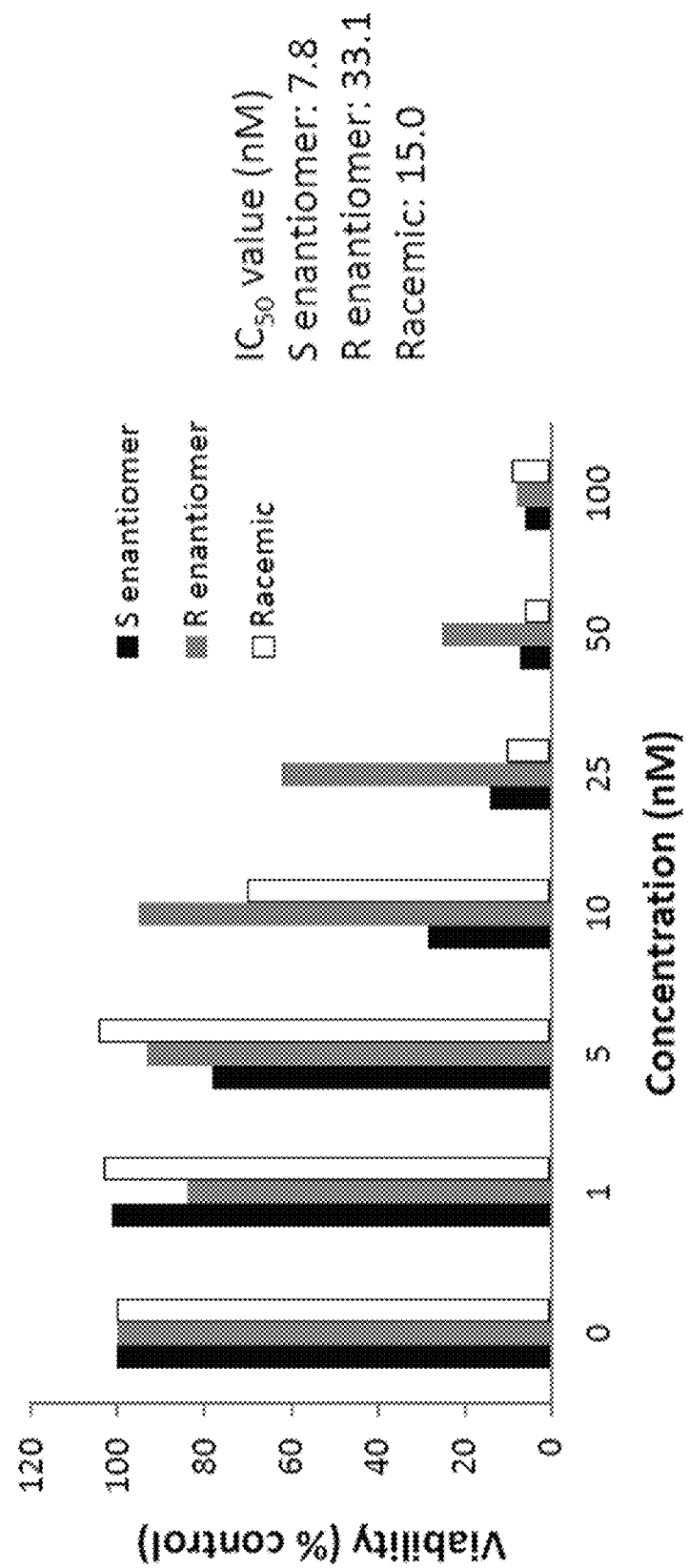
FIG. 4: Comparison of ETP69 enantiomeric activity on MOLM-13 AML cells. The (S) enantiomer of ETP69 shows about a 4× fold increase in inhibitory capacity when compared to the (R) enantiomer.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetra-hydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substitutents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substitutents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single bonded to carbon or to another sulfur.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OOCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O) NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol " $\sim\hspace{-4pt}\sim$ " denotes the point of attachment of a chemical moiety to the remainder of a molecule or chemical formula.

"$S_p$", "$S_t$", or "$S_n$" refers to a sulfide bridge having p, t, or n sulfurs (e.g. $S_2$ is —S—S—, $S_3$ is —S—S—S—, $S_4$ is —S—S—S—S—).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

A "therapeutically effective amount" or "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Patient," "subject," "patient in need thereof," and "subject in need thereof" are herein used interchangeabley and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies, for example epigenetic inhibitors or multi-kinase inhibitors. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The term "associated" or "associated with" in the context of a substance or substance activity or function associated with a disease means that the disease is caused by (in whole or in part), a symptom of the disease is caused by (in whole or inpart) the substance or substance activity or function, or a side-effect of the compound (e.g. toxicity) is caused by (in whole or inpart) the substance or substance activity or function.

As used herein, the term "cancer" refers to all types of cancer, neoplasm, or malignant tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, and carcinoma *villosum*.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anticancer agent" as used herein refers to a molecule (e.g. compound, peptide, protein, nucleic acid, antibody) used to treat cancer through destruction or inhibition of cancer cells or tissues. Anticancer agents may be selective for certain cancers or certain tissues. In embodiments, anticancer agents herein may include epigenetic inhibitors and multi-kinase inhibitors.

An "epigenetic inhibitor" as used herein, refers to an inhibitor of an epigenetic process, such as DNA methylation (a DNA methylation Inhibitor) or modification of histones (a Histone Modification Inhibitor). An epigenetic inhibitor may be a histone-deacetylase (HDAC) inhibitor, a DNA methyltransferase (DNMT) inhibitor, a histone methyltransferase (HMT) inhibitor, a histone demethylase (HDM) inhibitor, or a histone acetyltransferase (HAT). Examples of HDAC inhibitors include Vorinostat, romidepsin, CI-994, Belinostat, Panobinostat, Givinostat, Entinostat, Mocetinostat, SRT501, CUDC-101, JNJ-26481585, or PCI24781. Examples of DNMT inhibitors include azacitidine and decitabine. Examples of HMT inhibitors include EPZ-5676. Examples of HDM inhibitors include pargyline and tranylcypromine. Examples of HAT inhibitors include CCT077791 and garcinol.

A "multi-kinase inhibitor" is a small molecule inhibitor of at least one protein kinase, including tyrosine protein kinases and serine/threonine kinases. A multi-kinase inhibitor may include a single kinase inhibitor. Multi-kinase inhibitors may block phosphorylation. Multi-kinases inhibitors may act as covalent modifiers of protein kinases. Multi-kinase inhibitors may bind to the kinase active site or to a secondary or tertiary site inhibiting protein kinase activity. A multi-kinase inhibitor may be an anti-cancer multi-kinase inhibitor. Exemplary anti-cancer multi-kinase inhibitors include dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib.

"Selective" or "selectivity" or the like of a compound refers to the compound's ability to discriminate between molecular targets (e.g. a compound having selectivity toward HMT SUV39H1 and/or HMT G9a).

"Specific", "specifically", "specificity", or the like of a compound refers to the compound's ability to cause a particular action, such as inhibition, to a particular molecular target with minimal or no action to other proteins in the cell (e.g. a compound having specificity towards HMT SUV39H1 and/or HMT G9a displays inhibition of the activity of those HMTs whereas the same compound displays little-to-no inhibition of other HMTs such as DOT1, EZH1, EZH2, GLP, MLL1, MLL2, MLL3, MLL4, NSD2, SET1b, SET7/9, SET8, SETMAR, SMYD2, SUV39H2).

"HMT SUV39H1," "SUV39H1," or "suppressor of varigation 3-9 homolgue 1" is a histone methyltransferase protein that trimethylates H3K9 (NCBI GI No. 49456451). HMT SUV39H1 may methylate H3K9.

"HMT G9a" or "G9a" is a histone methyltransferse that dimethylates H3K9 (NCBI GI No. 287865). HMT G9a may dimethylate H3K9.

"H3K9 trimetylation" refers to tri-methylation of lysine 9 of Histone H3. H3K9 trimethylation may be performed by histone methyl transferases such as SUV39H1.

Azacitidine is an epigenetic inhibitor having the formula:

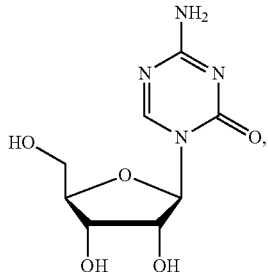

including pharmaceutically acceptable salts thereof.

Azacitidine is an anti-cancer epigenetic inhibitor.

Decitadine is an epigenetic inhibitor having the formula:

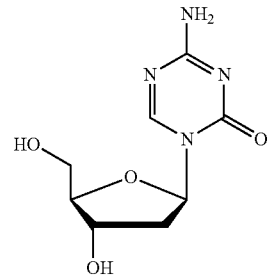 [SMILES: Nc1ncn([C@H]2C[C@@H](O)[C@@H](CO)O2)c(=O)n1]

including pharmaceutically acceptable salts thereof.

Decitadine is an anti-cancer epigenetic inhibitor.

Sorafenib is a multi-kinase inhibitor having the formula:

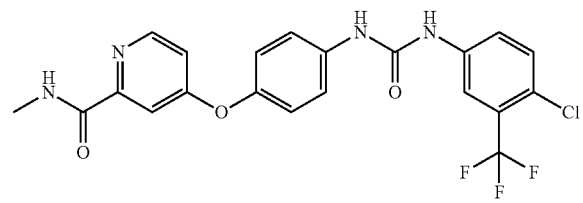 [SMILES: CNC(=O)c1cc(Oc2ccc(NC(=O)Nc3ccc(Cl)c(C(F)(F)F)c3)cc2)ccn1]

including pharmaceutically acceptable salts thereof.

Sorafenib is an anti-cancer multi-kinase inhibitor.

The terms "synergy", "synergism" "synergistic" and "synergistic therapeutic effect" are used herein interchangeably and refer to a measured effect of compounds administered in combination where the measured effect is greater than the sum of the individual effects of each of the compounds administered alone as a single agent.

II. Compositions

In a first aspect is a compound having the formula

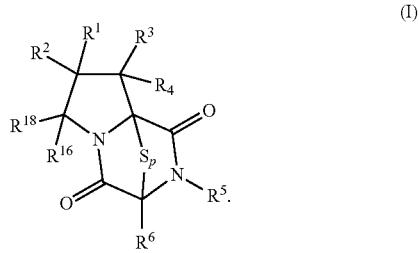

The symbol p is 2, 3 or 4. $R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, —NO$_2$, —SR$^{36B}$, —SO$_{n2}$R$^{34b}$, —SO$_{n2}$OR$^{34B}$, —SO$_{n2}$NR$^{34B}$R$^{35B}$, —NHNR$^{34B}$R$^{35B}$, —ONR$^{34B}$R$^{35B}$, —NHC(O)NHNR$^{34B}$R$^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is hydrogen, halogen, —N$_3$, —CF$_3$, —CCl$_3$, —CBr$_3$, —CI$_3$, —CN, —CHO, —OR$^{33C}$, —NR$^{34C}$R$^{35C}$, —COOR$^{33C}$, —CONR$^{34C}$R$^{35C}$, —NO$_2$, —SR$^{35C}$, —SO$_{n3}$R$^{34C}$, —SO$_{n3}$OR$^{34C}$, —SO$_{n3}$NR$^{34C}$R$^{35C}$, —NHNR$^{34C}$R$^{35C}$, —ONR$^{34C}$R$^{35C}$, —NHC(O)NHNR$^{34C}$R$^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —N$_3$, —CF$_3$, —CCl$_3$, —CBr$_3$, —CI$_3$, —CN, —CHO, —OR$^{33D}$, —NR$^{34}$R$^{35D}$, —COOR$^{33D}$, —CONR$^{34D}$R$^{35D}$, —NO$_2$, —SR$^{36D}$, —SO$_{n4}$R$^{34D}$, —SO$_{n4}$OR$^{34D}$, —SO$_{n4}$NR$^{34D}$R$^{35D}$, —NHNR$^{34D}$R$^{35D}$, —ONR$^{34D}$R$^{35D}$, —NHC(O)NHNR$^{34D}$R$^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$ is hydrogen, halogen, —N$_3$, —CF$_3$, —CCl$_3$, —CBr$_3$, —CI$_3$, —CN, —CHO, —OR$^{33E}$, —NR$^{34E}$R$^{35E}$, —COOR$^{33E}$, —CONR$^{34E}$R$^{35E}$, —NO$_2$, —SR$^{36E}$, —SO$_{n5}$R$^{34E}$, —SO$_{n5}$OR$^{34E}$, —SO$_{n5}$NR$^{34E}$R$^{35E}$, —NHNR$^{34E}$R$^{35E}$, —ONR$^{34E}$R$^{35E}$, —NHC(O)NHNR$^{34E}$R$^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, halogen, —N$_3$, —CF$_3$, —CCl$_3$, —CBr$_3$, —CI$_3$, —CN, —CHO, —OR$^{33F}$, —NR$^{34F}$R$^{35F}$, —COOR$^{33F}$, —CONR$^{34F}$R$^{35F}$, —NO$_2$, —SR$^{36F}$, —SO$_{n6}$R$^{34F}$, —SO$_{n6}$OR$^{34F}$, —SO$_{n6}$NR$^{34F}$R$^{35F}$, —NHNR$^{34F}$R$^{35F}$, —ONR$^{34F}$R$^{35F}$, —NHC(O)NHNR$^{34F}$R$^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{16}$ is hydrogen, halogen, —N$_3$, —CF$_3$, —CCl$_3$, —CBr$_3$, —CI$_3$, —CN, —CHO, —OR$^{33G}$, —NR$^{34G}$R$^{35G}$, —COOR$^{33G}$, —CONR$^{34G}$R$^{35G}$, —NO$_2$, —SR$^{36G}$, —SO$_{n7}$R$^{34G}$, —SO$_{n7}$OR$^{34G}$, —SO$_{n7}$NR$^{34G}$R$^{35G}$, —NHNR$^{34G}$R$^{35G}$, —ONR$^{34G}$R$^{35G}$, —NHC(O)NHNR$^{34G}$R$^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{18}$ is hydrogen, halogen, —N$_3$, —CF$_3$, —CCl$_3$, —CBr$_3$, —CI$_3$, —CN, —CHO, —OR$^{33H}$, —NR$^{34H}$R$^{35H}$, —COOR$^{33H}$, —CONR$^{34H}$R$^{35H}$, —NO$_2$, —SR$^{36H}$, —SO$_{n8}$R$^{34H}$, —SO$_{n8}$OR$^{34H}$, —SO$_{n5}$NR$^{34H}$R$^{35H}$, —NHNR$^{34H}$R$^{35H}$, —ONR$^{34H}$R$^{35H}$, —NHC(O)NHNR$^{34H}$R$^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n5, n6, n7, and n8 are independently 1 or 2.

R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33G}$, R$^{34G}$, R$^{35G}$, R$^{36G}$, R$^{33H}$, R$^{34H}$, R$^{35H}$, and R$^{36H}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl.

In embodiments, the compound may have the formula:

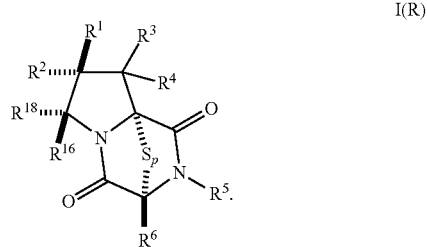

I(R)

In embodiments, the compound may have the formula:

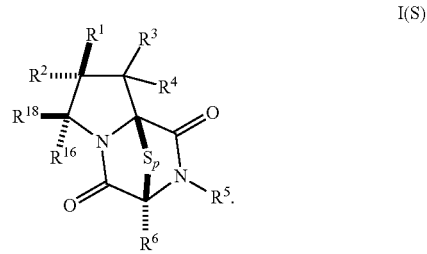

I(S)

The symbol p may be 2. The symbol p may be 3. The symbol p may be 4.

R$^1$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g. C$_1$-C$_8$ alkyl), substituted or unsubstituted heteroalkyl (e.g. 2 to 8 membered heteroalkyl). R$^1$ may be halogen, —CF$_3$, —CCl$_3$, —CBr$_3$, —CI$_3$, —CN, substituted or unsubstituted alkyl, or substituted or unsubstituted heteroalkyl. R$^1$ may be —CN, substituted or unsubstituted alkyl, or substituted or unsubstituted heteroalkyl. R$^1$ may be —CN or substituted or unsubstituted alkyl. R$^1$ may be —CN or unsubstituted alkyl. R$^1$ may be —CN, or unsubstituted heteroalkyl.

R$^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^1$ may be unsubstituted alkyl, unsubstituted heteroalkyl, unsubstituted cycloalkyl, unsubstituted heterocycloalkyl, unsubstituted aryl, unsubstituted heteroaryl, or unsubstituted membered heteroaryl.

R$^1$ may be substituted or unsubstituted C$_1$-C$_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 or 8 membered heteroaryl.

$R^1$ may be unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 or 8 membered heteroaryl.

$R^1$ may be substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3-6 membered heterocycloalkyl, substituted or unsubstituted 5 to 6 membered aryl, or substituted or unsubstituted 5 to 6 membered heteroaryl. $R^1$ may be unsubstituted $C_1$-$C_5$ alkyl, unsubstituted 2 to 5 membered heteroalkyl, unsubstituted 3 to 5 membered cycloalkyl, unsubstituted 3-6 membered heterocycloalkyl, unsubstituted 5 to 6 membered aryl, or unsubstituted 5 to 6 membered heteroaryl.

$R^1$ may be substituted or unsubstituted $C_1$-$C_3$ alkyl, substituted or unsubstituted 2 to 3 membered heteroalkyl. $R^1$ may be substituted or unsubstituted 3 membered cycloalkyl, substituted or unsubstituted 4 membered cycloalkyl, or substituted or unsubstituted 5 membered cycloalkyl. $R^1$ may be substituted or unsubstituted 4 membered heterocycloalkyl, substituted or unsubstituted 5 membered heterocycloalkyl, or substituted or unsubstituted 6 membered heterocycloalkyl. $R^1$ may be substituted or unsubstituted 5 membered aryl, substituted or unsubstituted 5 membered aryl, substituted or unsubstituted 6 membered aryl, or substituted or unsubstituted 6 membered heteroaryl. $R^1$ may be unsubstituted $C_1$-$C_3$ alkyl or unsubstituted 2 to 3 membered heteroalkyl. $R^1$ may be unsubstituted 3 membered cycloalkyl, unsubstituted 4 membered cycloalkyl or unsubstituted 5 membered cycloalkyl. $R^1$ may be unsubstituted 4 membered heterocycloalkyl, unsubstituted 5 membered heterocycloalkyl, or unsubstituted 6 membered heterocycloalkyl. $R^1$ may be unsubstituted 5 membered aryl, unsubstituted 5 membered aryl, unsubstituted 6 membered aryl, or unsubstituted 6 membered heteroaryl.

$R^1$ may be $R^{1a}$-substituted or unsubstituted alkyl, $R^{1a}$-substituted or unsubstituted heteroalkyl, $R^{1a}$-substituted or unsubstituted cycloalkyl, $R^{1a}$-substituted or unsubstituted heterocycloalkyl, $R^{1a}$-substituted or unsubstituted aryl, or $R^{1a}$-substituted or unsubstituted heteroaryl. $R^1$ may be unsubstituted alkyl, unsubstituted heteroalkyl, unsubstituted cycloalkyl, unsubstituted heterocycloalkyl, unsubstituted aryl, or unsubstituted heteroaryl.

$R^1$ may be $R^{1a}$-substituted or unsubstituted $C_1$-$C_8$ alkyl, $R^{1a}$-substituted or unsubstituted 2 to 8 membered heteroalkyl, $R^{1a}$-substituted or unsubstituted 3 to 8 membered cycloalkyl, $R^{1a}$-substituted or unsubstituted 3 to 8 membered heterocycloalkyl, $R^{1a}$-substituted or unsubstituted 5 to 8 membered aryl, or $R^{1a}$-substituted or unsubstituted 5 to 8 membered heteroaryl. $R^1$ may be unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

$R^1$ may be $R^{1a}$-substituted or unsubstituted $C_1$-$C_5$ alkyl, $R^{1a}$-substituted or unsubstituted 2 to 5 membered heteroalkyl, $R^{1a}$-substituted or unsubstituted 3 to 5 membered cycloalkyl, $R^{1a}$-substituted or unsubstituted 3-6 membered heterocycloalkyl, $R^{1a}$-substituted or unsubstituted 5 to 6 membered aryl, or $R^{1a}$-substituted or unsubstituted 5 to 6 membered heteroaryl. $R^1$ may be unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, or unsubstituted 5 to 6 membered aryl, or unsubstituted 5 to 6 membered heteroaryl.

$R^1$ may be $R^{1a}$-substituted or unsubstituted $C_1$-$C_3$ alkyl or $R^{1a}$-substituted or unsubstituted 2 to 3 membered heteroalkyl. $R^1$ may be $R^{1a}$-substituted or unsubstituted 3 membered cycloalkyl, $R^{1a}$-substituted or unsubstituted 4 membered cycloalkyl, or $R^{1a}$-substituted or unsubstituted 5 membered cycloalkyl. $R^1$ may be $R^{1a}$-substituted or unsubstituted 5 membered heterocycloalkyl, $R^{1a}$-substituted or unsubstituted 6 membered heterocycloalkyl, $R^{1a}$-substituted or unsubstituted 5 membered aryl, $R^{1a}$-substituted or unsubstituted 6 membered aryl, $R^{1a}$-substituted or unsubstituted 5 membered heteroaryl, or $R^{1a}$-substituted or unsubstituted 6 membered heteroaryl. $R^1$ may be unsubstituted $C_1$-$C_3$ alkyl or unsubstituted 2 to 3 membered heteroalkyl. $R^1$ may be unsubstituted 3 membered cycloalkyl, unsubstituted 4 membered cycloalkyl, unsubstituted 5 membered cycloalkyl, unsubstituted 5 membered heterocycloalkyl, unsubstituted 6 membered heterocycloalkyl, unsubstituted 5 membered aryl, unsubstituted 6 membered aryl, unsubstituted 5 membered heteroaryl, or unsubstituted 6 membered heteroaryl.

$R^1$ may be $R^{1a}$-substituted or unsubstituted methyl, $R^{1a}$-substituted or unsubstituted ethyl, or $R^{1a}$-substituted or unsubstituted propyl. $R^1$ may be methyl, ethyl, or propyl.

$R^1$ may be halogen, —$CF_3$, —$CCl_3$, —$CBr_3$, —$CI_3$, —CN, —CHO, —OH, —$NH_2$, $NO_2$, or —$COOR^{33A}$. $R^{33A}$ may be hydrogen, $C_1$-$C_3$ unsubstituted alkyl, 2 to 5 membered unsubstituted heteroalkyl, or 5 or 6 membered unsubstituted aryl. In embodiments, $R^1$ is —$COOR^{33A}$, wherein $R^{33A}$ is $C_1$-$C_3$ unsubstituted alkyl. $R^{33}$ may be unsubstituted methyl, unsubstituted ethyl, or unsubstituted propyl. $R^1$ may be —$COOCH_3$. $R^1$ may be halogen, —$CF_3$, —$CCl_3$, —$CBr_3$, —$CI_3$, —CN, —$NH_2$, or $NO_2$. $R^1$ may be —CN. $R^1$ may be unsubstituted 2 to 5 membered heteroalkyl.

$R^{1a}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{1b}$-substituted or unsubstituted alkyl (e.g. $C_1$-$C_8$ alkyl), $R^{1b}$-substituted or unsubstituted heteroalkyl (e.g. 2 to 8 membered heteroalkyl), $R^{1b}$-substituted or unsubstituted cycloalkyl (e.g. $C_3$-$C_8$ cycloalkyl), $R^{1b}$-substituted or unsubstituted heterocycloalkyl (e.g. 3 to 6 membered heterocycloalkyl), $R^{1b}$-substituted or unsubstituted aryl (e.g. 5 or 6 membered aryl), or $R^{1b}$-substituted or unsubstituted heteroaryl (e.g. 5 or 6 membered heteroaryl).

$R^{1b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$-$C_8$ alkyl), heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

$R^1$ may be an electron withdrawing group (EWG) (e.g. halogen, —$N_3$, —$NO_2$, —$CF_3$, —$CCl_3$, —$CBr_3$, —$CI_3$, —CN, —CHO, —$CONH_2$, or substituted or unsubstituted 2 to 8 membered heteroalkyl). An "electron withdrawing group" is used herein according to its common meaning in the art and refers to a chemical moiety that tends to remove electrons (electron density) from a portion of the compound to which it is attached (e.g. a deactivating group). $R^1$ may be —CN. $R^1$ may be —$NO_2$. $R^1$ may be —$CF_3$, —$CCl_3$, —$CBr_3$, or —$CI_3$. $R^1$ may be substituted or unsubstituted 2 to 8 membered heteroalkyl. $R^1$ may be —$COOCH_3$.

$R^2$ may be hydrogen, halogen, —$N_3$, —$CF_3$, —$CCl_3$, —$CBr_3$, —$CI_3$, —CN, —CHO, —OH, —$NH_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g. C$_1$-C$_8$ alkyl), or substituted or unsubstituted heteroalkyl (e.g. 2 to 8 membered heteroalkyl), or substituted or unsubstituted heterocycloalkyl (e.g. 3 to 6 membered heterocycloalkyl). R$^2$ may be halogen, —CF$_3$, —CCl$_3$, —CBr$_3$, —CI$_3$, —CN, substituted or unsubstituted alkyl, or substituted or unsubstituted heteroalkyl. R$^2$ may be —CN, substituted or unsubstituted alkyl, or substituted or unsubstituted heteroalkyl. R$^2$ may be —CN or substituted or unsubstituted alkyl. R$^2$ may be —CN or unsubstituted methyl. R$^2$ may be —CN, or unsubstituted heteroalkyl. R$^2$ may be substituted alkyl or substituted heteroalkyl.

R$^2$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ may be unsubstituted alkyl, unsubstituted heteroalkyl, unsubstituted cycloalkyl, unsubstituted heterocycloalkyl, unsubstituted aryl, or unsubstituted heteroaryl.

R$^2$ may be substituted or unsubstituted C$_1$-C$_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 or 8 membered aryl, or substituted or unsubstituted 5 or 8 membered heteroaryl. R$^2$ may be unsubstituted C$_1$-C$_8$ alkyl, unsubstituted 2 to 8 membered heteroalkyl, unsubstituted 3 to 8 membered cycloalkyl, unsubstituted 3 to 8 membered heterocycloalkyl, unsubstituted 5 or 8 membered aryl, or unsubstituted 5 or 8 membered heteroaryl.

R$^2$ may be substituted or unsubstituted C$_1$-C$_5$ alkyl, substituted or unsubstituted 2 to 5 membered heteroalkyl, substituted or unsubstituted 3 to 5 membered cycloalkyl, or substituted or unsubstituted 3 to 6 membered heterocycloalkyl, substituted or unsubstituted 5 or 6 membered aryl, or substituted or unsubstituted 5 or 6 membered heteroaryl. R$^2$ may be unsubstituted C$_1$-C$_5$ alkyl, unsubstituted 2 to 5 membered heteroalkyl, unsubstituted 3 to 5 membered cycloalkyl, or unsubstituted 3 to 6 membered heterocycloalkyl, unsubstituted 5 or 6 membered aryl, or unsubstituted 5 or 6 membered heteroaryl. R$^2$ may be unsubstituted C$_1$-C$_5$ alkyl or unsubstituted 2 to 5 membered heteroalkyl.

R$^2$ may be substituted or unsubstituted C$_1$-C$_3$ alkyl or substituted or unsubstituted 2 to 3 membered heteroalkyl. R$^2$ may be substituted or unsubstituted 3 membered cycloalkyl, substituted or unsubstituted 4 membered cycloalkyl, or substituted or unsubstituted 5 membered cycloalkyl. R$^2$ may be substituted or unsubstituted 4 membered heterocycloalkyl, substituted or unsubstituted 5 membered heterocycloalkyl, substituted or unsubstituted 6 membered heterocycloalkyl, substituted or unsubstituted 5 membered aryl, substituted or unsubstituted 6 membered aryl, substituted or unsubstituted 5 membered heteroaryl, or substituted or unsubstituted 6 membered heteroaryl. R$^2$ may be unsubstituted C$_1$-C$_3$ alkyl or unsubstituted 2 to 3 membered heteroalkyl. R$^2$ may be unsubstituted 3 membered cycloalkyl, unsubstituted 4 membered cycloalkyl or unsubstituted 5 membered cycloalkyl. R$^2$ may be unsubstituted 4 membered heterocycloalkyl, unsubstituted 5 membered heterocycloalkyl, unsubstituted 6 membered heterocycloalkyl, unsubstituted 5 membered aryl, unsubstituted 6 membered aryl, unsubstituted 5 membered heteroaryl, or unsubstituted 6 membered heteroaryl.

R$^2$ may be R$^{2a}$-substituted or unsubstituted alkyl, R$^{2a}$-substituted or unsubstituted heteroalkyl, R$^{2a}$-substituted or unsubstituted cycloalkyl, R$^{2a}$-substituted or unsubstituted heterocycloalkyl, R$^{2a}$-substituted or unsubstituted aryl, or R$^{2a}$-substituted or unsubstituted heteroaryl. R$^2$ may be R$^{2a}$-substituted or unsubstituted alkyl or R$^{2a}$-substituted or unsubstituted heteroalkyl.

R$^2$ may be R$^{2a}$-substituted or unsubstituted C$_1$-C$_8$ alkyl, R$^{2a}$-substituted or unsubstituted 2 to 8 membered heteroalkyl, R$^{2a}$-substituted or unsubstituted 3 to 8 membered cycloalkyl, R$^{2a}$-substituted or unsubstituted 3 to 8 membered heterocycloalkyl, R$^{2a}$-substituted or unsubstituted 5 or 8 membered aryl, or R$^{2a}$-substituted or unsubstituted 5 or 8 membered heteroaryl. R$^2$ may be R$^{2a}$-substituted or unsubstituted C$_1$-C$_8$ alkyl or R$^{2a}$-substituted or unsubstituted 2 to 8 membered heteroalkyl, R$^{2a}$-substituted or unsubstituted 3 to 8 membered cycloalkyl, R$^{2a}$-substituted or unsubstituted 3 to 8 membered heterocycloalkyl, R$^{2a}$-substituted or unsubstituted 5 to 8 membered aryl, or R$^{2a}$-substituted or unsubstituted 5 to 8 membered heteroaryl.

R$^2$ may be R$^{2a}$-substituted or unsubstituted C$_1$-C$_5$ alkyl, R$^{2a}$-substituted or unsubstituted 2 to 5 membered heteroalkyl, R$^{2a}$-substituted or unsubstituted 3 to 5 membered cycloalkyl, R$^{2a}$-substituted or unsubstituted 3 to 6 membered heterocycloalkyl, R$^{2a}$-substituted or unsubstituted 5 or 6 membered aryl, or R$^{2a}$-substituted or unsubstituted 5 to 6 membered heteroaryl. R$^2$ may be R$^{2a}$-substituted or unsubstituted C$_1$-C$_5$ alkyl or R$^{2a}$-substituted or unsubstituted 2 to 5 membered heteroalkyl.

R$^2$ may be R$^{2a}$-substituted or unsubstituted C$_1$-C$_3$ alkyl or R$^{2a}$-substituted or unsubstituted 2 to 3 membered heteroalkyl. R$^2$ may be R$^{2a}$-substituted or unsubstituted 3 membered cycloalkyl, R$^{2a}$-substituted or unsubstituted 4 membered cycloalkyl, or R$^{2a}$-substituted or unsubstituted 5 membered cycloalkyl. R$^2$ may be R$^{2a}$-substituted or unsubstituted 4 membered heterocycloalkyl, R$^{2a}$-substituted or unsubstituted 5 membered heterocycloalkyl, R$^{2a}$-substituted or unsubstituted 6 membered heterocycloalkyl, R$^{2a}$-substituted or unsubstituted 5 membered aryl, R$^{2a}$-substituted or unsubstituted 6 membered aryl, R$^{2a}$-substituted or unsubstituted 5 membered heteroaryl, or R$^{2a}$-substituted or unsubstituted 6 membered heteroaryl.

R$^{2a}$ is halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, R$^{2b}$-substituted or unsubstituted alkyl (e.g. C$_1$-C$_8$ alkyl), R$^{2b}$-substituted or unsubstituted heteroalkyl (e.g. 2 to 8 membered heteroalkyl), R$^{2b}$-substituted or unsubstituted cycloalkyl (e.g. 3 to 8 membered cycloalkyl), R$^{2b}$-substituted or unsubstituted heterocycloalkyl (e.g. 3 to 6 membered heterocycloalkyl), R$^{2b}$-substituted or unsubstituted aryl (e.g. 5 or 6 membered aryl), or R$^{2b}$-substituted or unsubstituted heteroaryl (e.g. 5 or 6 membered heteroaryl). R$^{2a}$ may be 3 to 6 membered heterocycloalkyl, R$^{2b}$-substituted or unsubstituted 5 or 6 membered aryl, or R$^{2b}$-substituted or unsubstituted 5 or 6 membered heteroaryl. R$^{2a}$ may be unsubstituted pyridine. R$^{2a}$ may be unsubstituted morpholino. R$^{2a}$ may be unsubstituted methyl.

R$^{2b}$ is halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, unsubstituted alkyl (e.g. C$_1$-C$_8$ alkyl), unsubstituted heteroalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

$R^2$ may be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{2a}$-substituted or unsubstituted $C_1$-$C_8$ alkyl, $R^{2a}$-substituted or unsubstituted 2 to 8 membered heteroalkyl, $R^{2a}$-substituted or unsubstituted 3 to 8 membered cycloalkyl, $R^{2a}$-substituted or unsubstituted 3 to 6 membered heterocycloalkyl, $R^{2a}$-substituted or unsubstituted 5 or 6 membered aryl, or $R^{2a}$-substituted or unsubstituted 5 or 6 membered heteroaryl. $R^2$ may be $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2Ph$, $-SO_2NH_2$, $-NHNH_2$, $-ONH_2$, $R^{2a}$-substituted or unsubstituted $C_1$-$C_3$ alkyl, or 1 to 3 membered $R^{2a}$-substituted or unsubstituted heteroalkyl. In embodiments $R^2$ is unsubstituted $C_1$-$C_5$ alkyl or unsubstituted 2 to 5 membered heteroalkyl. In embodiments $R^2$ is unsubstituted methyl. In embodiments $R^2$ is unsubstituted methoxy (e.g. $-OCH_3$).

$R^2$ may be $R^{2a}$-substituted or unsubstituted $C_1$-$C_5$ alkyl (e.g. $R^{2a}$-substituted or unsubstituted methylene). $R^2$ may be $R^{2a}$-substituted $C_1$-$C_5$ alkyl. When $R^2$ is substituted or unsubstituted $C_1$-$C_5$ alkyl, $R^{2a}$ may be unsubstituted heterocycloalkyl, unsubstituted aryl, or unsubstituted heteroaryl. $R^{2a}$ may be unsubstituted or unsubstituted morpholino (e.g. $R^{2b}$-substituted or unsubstituted morpholino). $R^2$ may be $R^{2a}$-substituted or unsubstituted 2 to 5 membered heteroalkyl. When $R^2$ is substituted or unsubstituted 2 to 5 membered heteroalkyl, $R^{2a}$ may be may be unsubstituted $C_1$-$C_5$ alkyl, unsubstituted heterocycloalkyl, unsubstituted aryl, or unsubstituted heteroaryl. $R^2$ may be $-OCH_3$. $R^2$ may be unsubstituted methyl. $R^2$ may be $-CN$.

In embodiments, $R^1$ is halogen, $-N_3$, $-NO_2$, $-CF_3$, $CCl_3$, $CBr_3$, $CI_3$, $-CN$, $-CHO$, $-CONH_2$, or substituted or unsubstituted 2 to 8 membered heteroalkyl and $R^2$ is hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{2a}$-substituted or unsubstituted $C_1$-$C_8$ alkyl, $R^{2a}$-substituted or unsubstituted 2 to 8 membered heteroalkyl, $R^{2a}$-substituted or unsubstituted 3 to 8 membered cycloalkyl, $R^{2a}$-substituted or unsubstituted 3 to 6 membered heterocycloalkyl, $R^{2a}$-substituted or unsubstituted 5 or 6 membered aryl, or $R^{2a}$-substituted or unsubstituted 5 or 6 membered heteroaryl heteroaryl. In embodiments, at least one of $R^1$ and $R^2$ is an electron withdrawing group (EWG) (e.g. halogen, $-N_3$, $-NO_2$, $-CF_3$, $CCl_3$, $CBr_3$, $CI_3$, $-CN$, $-CHO$, $-CONH_2$, or substituted or unsubstituted 3 to 8 membered heteroalkyl. When $R^1$ is CN, $R^2$ may be $-CN$. When $R^1$ is halogen, $R^2$ may be halogen. When $R^1$ is $-CN$, $R^2$ may be unsubstituted $C_1$-$C_5$ alkyl. When $R^1$ is $-CN$, $R^2$ may be unsubstituted methyl. When $R^1$ is unsubstituted 2 to 8 membered heteroalkyl (e.g. $-COOCH_3$), $R^2$ may be may be unsubstituted $C_1$-$C_5$ alkyl. When $R^1$ is $-CN$, $R^2$ may be $R^{2a}$-substituted or unsubstituted $C_1$-$C_5$ alkyl. When $R^1$ is $-CN$, $R^2$ may be $R^{2a}$-substituted or unsubstituted $C_1$-$C_5$ heteroalkyl. $R^{2a}$ may be unsubstituted alkyl, unsubstituted cycloalkyl, unsubstituted heterocycloalkyl, unsubstituted aryl, or unsubstituted heteroaryl.

In embodiments, $R^2$ is a polar substituent and provides polarity to the compounds provided herein (e.g. where $R^2$ is a substituted or unsubstituted 2 to 8 membered heteroalkyl). A "polar substituent" is understood by one skilled in the art to be a moiety that creates a dipole moment, thereby forming a positive or negative charge on a molecule. $R^2$ may be an aqueous solubility enhancing substituent (e.g. a moiety that increases the water solubility of the compound), where germinal substitution at $R^2$ with a substituent other than methyl improves the solubility of the compound in an aqueous medium. Solubility enhancing substituents may include basic substituents or groups that add polarity.

$R^3$ and $R^4$ may independently be substituted or unsubstituted heteroalkyl, substituted or unsubstituted 2 to 8 membered heteroalkyl, substituted or unsubstituted 2 to 5 membered heteroalkyl, substituted or unsubstituted 2 to 3 membered heteroalkyl, $R^{30a}$-substituted or unsubstituted heteroalkyl, $R^{30a}$-substituted or unsubstituted 2 to 8 membered heteroalkyl, $R^{30a}$-substituted or unsubstituted 2 to 5 membered heteroalkyl, or $R^{30a}$-substituted or unsubstituted 2 to 3 membered heteroalkyl. $R^3$ and $R^4$ may independently be unsubstituted heteroalkyl, unsubstituted 2 to 8 membered heteroalkyl, or unsubstituted 2 to 5 membered heteroalkyl, unsubstituted 2 to 3 membered heteroalkyl.

$R^3$ and $R^4$ may independently be substituted or unsubstituted cycloalkyl, substituted or unsubstituted 3 to 8 membered cycloalkyl, substituted or unsubstituted 3 to 5 membered cycloalkyl, substituted or unsubstituted 3 membered cycloalkyl, substituted or unsubstituted 4 membered cycloalkyl, substituted or unsubstituted 5 membered cycloalkyl. $R^3$ and $R^4$ may independently be $R^{30a}$-substituted or unsubstituted cycloalkyl, $R^{30a}$-substituted or unsubstituted 3 to 8 membered cycloalkyl, $R^{30a}$-substituted or unsubstituted 3 to 5 membered cycloalkyl, $R^{30a}$-substituted or unsubstituted 3 membered cycloalkyl, $R^{30a}$-substituted or unsubstituted 4 membered cycloalkyl, or $R^{30a}$-substituted or unsubstituted 5 membered cycloalkyl.

$R^3$ and $R^4$ may independently be substituted or unsubstituted heterocycloalkyl, substituted or unsubstituted 3 to 6 membered heterocycloalkyl, substituted or unsubstituted 4 membered heterocycloalkyl, substituted or unsubstituted 5 membered heterocycloalkyl, substituted or unsubstituted 6 membered heterocycloalkyl. $R^3$ and $R^4$ may independently be $R^{30a}$-substituted or unsubstituted heterocycloalkyl, $R^{30a}$-substituted or unsubstituted 3 to 6 membered heterocycloalkyl, $R^{30a}$-substituted or unsubstituted 4 membered heterocycloalkyl, $R^{30a}$-substituted or unsubstituted 5 membered heterocycloalkyl, or $R^{30a}$-substituted or unsubstituted 6 membered heterocycloalkyl.

$R^3$ and $R^4$ may independently be substituted or unsubstituted aryl, substituted or unsubstituted 5 to 6 membered aryl, substituted or unsubstituted 5 membered aryl, or substituted or unsubstituted 6 membered aryl. $R^3$ and $R^4$ may independently be $R^{30a}$-substituted or unsubstituted aryl, $R^{30a}$-substituted or unsubstituted 5 to 6 membered aryl, $R^{30a}$-substituted or unsubstituted 5 membered aryl, or $R^{30a}$-substituted or unsubstituted 6 membered aryl. $R^3$ and $R^4$ may independently be substituted or unsubstituted heteroaryl, substituted or unsubstituted 5 to 6 membered heteroaryl, substituted or unsubstituted 5 membered heteroaryl, or substituted or unsubstituted 6 membered heteroaryl. $R^3$ and $R^4$ may independently be $R^{30a}$-substituted or unsubstituted heteroaryl, $R^{30a}$-substituted or unsubstituted 5 to 6 membered heteroaryl, $R^{30a}$-substituted or unsubstituted 5 membered heteroaryl, or $R^{30a}$-substituted or unsubstituted 6 membered heteroaryl.

$R^3$ may be hydrogen, halogen, or $R^{30a}$-substituted or unsubstituted $C_1$-$C_8$ alkyl. $R^3$ may be hydrogen. $R^3$ may be unsubstituted methyl, unsubstituted ethyl, or unsubstituted propyl.

$R^4$ may be hydrogen, halogen, or $R^{30a}$-substituted or unsubstituted $C_1$-$C_8$ alkyl. $R^4$ may be hydrogen. $R^4$ may be unsubstituted methyl, unsubstituted ethyl, or unsubstituted propyl. In embodiments, $R^3$ and $R^4$ are hydrogen.

$R^{30a}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{30b}$-substituted or unsubstituted alkyl (e.g. $C_1$-$C_8$ alkyl), $R^{30b}$-substituted or unsubstituted heteroalkyl (e.g. 2 to 8 membered heteroalkyl), $R^{3b}$-substituted or unsubstituted cycloalkyl (e.g. 3 to 8 membered cycloalkyl), $R^{3b}$-substituted or unsubstituted heterocycloalkyl (e.g. 3 to 6 membered heterocycloalkyl), $R^{3b}$-substituted or unsubstituted aryl (e.g. 5 to 6 membered aryl), or $R^{30b}$-substituted or unsubstituted heteroaryl (e.g. 5 to 6 membered heteroaryl).

$R^{30b}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl), unsubstituted heteroalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 to 6 membered aryl), or unsubstituted heteroaryl (e.g. 5 to 6 membered heteroaryl).

$R^5$ may be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$. $R^5$ may be halogen, $-CHO$, $-COOH$, $-CONH_2$, $-SH$, $-NHNH_2$, $-ONH_2$, $-NHC(O)NHNH_2$, substituted or unsubstituted alkyl (e.g. $C_1$-$C_5$ alkyl), or substituted or unsubstituted heteroalkyl (e.g. 2 to 6 membered heteroalkyl). $R^5$ may be halogen, $-CHO$, $-COOH$, $-CONH_2$, $-SH$, $-NHNH_2$, $-ONH_2$, $-NHC(O)NHNH_2$, $R^{5a}$-substituted or unsubstituted alkyl (e.g. $C_1$-$C_5$ alkyl), or $R^{5a}$-substituted or unsubstituted heteroalkyl (e.g. 2 to 6 membered heteroalkyl).

$R^5$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ may be unsubstituted alkyl, unsubstituted heteroalkyl, unsubstituted cycloalkyl, unsubstituted heterocycloalkyl, unsubstituted aryl, or unsubstituted heteroaryl.

$R^5$ may be substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, or substituted or unsubstituted 5 to 8 membered aryl, or substituted or unsubstituted 5 to 8 membered heteroaryl. $R^5$ may be unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, or unsubstituted 5 to 8 membered aryl, or unsubstituted 5 to 8 membered heteroaryl.

$R^5$ may be substituted or unsubstituted $C_1$-$C_5$ alkyl, substituted or unsubstituted 2 to 5 membered heteroalkyl, substituted or unsubstituted 3 to 5 membered cycloalkyl, or be substituted or unsubstituted 3 to 6 membered heterocycloalkyl, substituted or unsubstituted 5 to 6 membered aryl, or substituted or unsubstituted 5 to 6 membered heteroaryl. $R^5$ may be unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

$R^5$ may be substituted or unsubstituted $C_1$-$C_3$ alkyl or substituted or unsubstituted 2 to 3 membered heteroalkyl. $R^5$ may be substituted or unsubstituted 3 membered cycloalkyl. $R^5$ may be substituted or unsubstituted 4 membered cycloalkyl or substituted or unsubstituted 5 membered cycloalkyl. $R^5$ may be substituted or unsubstituted 4 membered heterocycloalkyl, substituted or unsubstituted 5 membered heterocycloalkyl, substituted or unsubstituted 6 membered heterocycloalkyl. $R^5$ may be substituted or unsubstituted 5 membered aryl, substituted or unsubstituted 6 membered aryl, substituted or unsubstituted 5 membered heteroaryl, or substituted or unsubstituted 6 membered heteroaryl. $R^5$ may be unsubstituted $C_1$-$C_3$ alkyl or unsubstituted 2 to 3 membered heteroalkyl. $R^5$ may be unsubstituted 3 membered cycloalkyl. $R^5$ may be unsubstituted 4 membered cycloalkyl or unsubstituted 5 membered cycloalkyl. $R^5$ may be unsubstituted 4 membered heterocycloalkyl, unsubstituted 5 membered heterocycloalkyl, unsubstituted 6 membered heterocycloalkyl. $R^5$ may be unsubstituted 5 membered aryl, unsubstituted 6 membered aryl, unsubstituted 5 membered heteroaryl, or unsubstituted 6 membered heteroaryl.

$R^5$ may be $R^{5a}$-substituted or unsubstituted alkyl, $R^{5a}$-substituted or unsubstituted heteroalkyl, $R^{5a}$-substituted or unsubstituted cycloalkyl, $R^{5a}$-substituted or unsubstituted heterocycloalkyl, $R^{5a}$-substituted or unsubstituted aryl, or substituted or unsubstituted heteroaryl. $R^5$ may be unsubstituted alkyl, unsubstituted heteroalkyl, unsubstituted cycloalkyl, unsubstituted heterocycloalkyl, unsubstituted aryl, or substituted or unsubstituted heteroaryl.

$R^5$ may be $R^{5a}$-substituted or unsubstituted $C_1$-$C_8$ alkyl, $R^{5a}$-substituted or unsubstituted 3 to 8 membered heteroalkyl, $R^{5a}$-substituted or unsubstituted 3 to 8 membered cycloalkyl, $R^{5a}$-substituted or unsubstituted 3 to 8 membered heterocycloalkyl, $R^{5a}$-substituted or unsubstituted 5 to 8 membered aryl, or $R^{5a}$-substituted or unsubstituted 5 to 8 membered heteroaryl. $R^5$ may be unsubstituted $C_1$-$C_8$ alkyl, unsubstituted 3 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

$R^5$ may be $R^{5a}$-substituted or unsubstituted $C_1$-$C_5$ alkyl, $R^{5a}$-substituted or unsubstituted 2 to 5 membered heteroalkyl, $R^{5a}$-substituted or unsubstituted 3 to 5 membered cycloalkyl, $R^{5a}$-substituted or unsubstituted 3 to 6 membered heterocycloalkyl, $R^{5a}$-substituted or unsubstituted 5 to 6 membered aryl, or $R^{5a}$-substituted or unsubstituted 5 to 6 membered heteroaryl. $R^5$ may be unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

$R^5$ may be $R^{5a}$-substituted or unsubstituted $C_1$-$C_3$ alkyl or $R^{5a}$-substituted or unsubstituted 2 to 3 membered heteroalkyl. $R^5$ may be $R^{5a}$-substituted or unsubstituted 3 membered cycloalkyl, $R^{5a}$-substituted or unsubstituted 4 membered cycloalkyl, or $R^{5a}$-substituted or unsubstituted 5 membered cycloalkyl. $R^5$ may be $R^{5a}$-substituted or unsubstituted 4 membered heterocycloalkyl, $R^{5a}$-substituted or unsubstituted 5 membered heterocycloalkyl, or $R^{5a}$-substituted or unsubstituted 6 membered heterocycloalkyl. $R^5$ may be $R^{5a}$-substituted or unsubstituted 5 membered aryl, $R^{5a}$-substituted or unsubstituted 6 membered aryl, $R^{5a}$-substituted or unsubstituted 5 membered heteroaryl, or $R^{5a}$-substituted or unsubstituted 6 membered heteroaryl. $R^5$ may be unsubstituted $C_1$-$C_3$ alkyl or unsubstituted 2 to 3 membered heteroalkyl. $R^5$ may be or unsubstituted 3 membered cycloalkyl, or unsubstituted 4 membered cycloalkyl, or unsubstituted 5 membered cycloalkyl. $R^5$ may be or unsubstituted 4 membered heterocycloalkyl, or unsubstituted 5 membered heterocycloalkyl, or unsubstituted 6 membered heterocycloalkyl. $R^5$ may be or unsubstituted 5 membered aryl, or unsubstituted 6 membered aryl, or unsubstituted 5 membered heteroaryl, or unsubstituted 6 membered heteroaryl.

$R^{5a}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{5b}$-substituted or unsubstituted alkyl (e.g. $C_1$-$C_8$ alkyl), $R^{5b}$-substituted or unsubstituted heteroalkyl (e.g. 2 to 8 membered heteroalkyl), $R^{5b}$-substituted or unsubstituted cycloalkyl (e.g. 3 to 8 membered cycloalkyl), $R^{5b}$-substituted or unsubstituted heterocycloalkyl (e.g. 3 to 6 membered heterocycloalkyl), $R^{5b}$-substituted or unsubstituted aryl (e.g. 5 to 6 membered aryl), or $R^{5b}$-substituted or unsubstituted heteroaryl (e.g. 5 to 6 membered heteroaryl).

$R^{5b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$-$C_8$ alkyl), unsubstituted heteroalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 to 6 membered aryl), or unsubstituted heteroaryl (e.g. 5 to 6 membered heteroaryl).

$R^5$ may be $R^{5a}$-substituted or unsubstituted $C_1$-$C_8$ alkyl, $R^{5a}$-substituted or unsubstituted 2 to 8 membered heteroalkyl, unsubstituted 3 to 5 membered cycloalkyl, or unsubstituted 3 to 5 membered heterocycloalkyl. $R^5$ may be unsubstituted $C_1$-$C_8$ alkyl. $R^5$ may be unsubstituted methyl, unsubstituted ethyl, or unsubstituted propyl. $R^5$ may be methyl, ethyl, or propyl. $R^5$ may be unsubstituted methyl. $R^5$ may be unsubstituted ethyl. $R^5$ may be unsubstituted propyl. $R^5$ may be unsubstituted allyl. $R^5$ may be $R^{5a}$-substituted alkyl. $R^{5a}$ may be unsubstituted 5 or 6 membered heterocycloalkyl. $R^{5a}$ may be unsubstituted morpholino. In embodiments, $R^5$ is substituted or unsubstituted 2 to 8 membered heteroalkyl. $R^5$ may be —$(CH_2)_3N(CH_3)_3$. $R^5$ may be unsubstituted 3 to 5 membered cycloalkyl. In embodiments, $R^5$ is unsubstituted cyclopropane.

$R^6$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$. $R^6$ may be hydrogen, halogen, —$CF_3$, —$CCl_3$, —$CBr_3$, —$CI_3$, —CN, —CHO, —OH, —$NH_2$, —COOH, —$CONH_2$, —$NO_2$, —SH, or substituted or unsubstituted alkyl (e.g. $C_1$-$C_5$ alkyl), or substituted or unsubstituted heteroalkyl (e.g. 2 to 6 membered heteroalkyl). $R^6$ may be halogen, —CHO, —COOH, —$CONH_2$, —SH, —$NHNH_2$, —$ONH_2$, —NHC(O)$NHNH_2$, $R^{6a}$-substituted or unsubstituted alkyl (e.g. $C_1$-$C_5$ alkyl), or $R^{6a}$-substituted or unsubstituted heteroalkyl (e.g. 2 to 6 membered heteroalkyl).

$R^6$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ may be unsubstituted alkyl, unsubstituted heteroalkyl, unsubstituted cycloalkyl, unsubstituted heterocycloalkyl, unsubstituted aryl, or unsubstituted heteroaryl.

$R^6$ may be substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, or substituted or unsubstituted 5 to 8 membered aryl, or substituted or unsubstituted 5 to 8 membered heteroaryl. $R^6$ may be unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, or unsubstituted 5 to 8 membered aryl, or unsubstituted 5 to 8 membered heteroaryl.

$R^6$ may be substituted or unsubstituted $C_1$-$C_5$ alkyl, substituted or unsubstituted 2 to 5 membered heteroalkyl, substituted or unsubstituted 3 to 5 membered cycloalkyl, or be substituted or unsubstituted 3 to 6 membered heterocycloalkyl, substituted or unsubstituted 5 to 6 membered aryl, or substituted or unsubstituted 5 to 6 membered heteroaryl. $R^6$ may be unsubstituted $C_1$-$C_5$ alkyl, unsubstituted 2 to 5 membered heteroalkyl, unsubstituted 3 to 5 membered cycloalkyl, or be unsubstituted 3 to 6 membered heterocycloalkyl, unsubstituted 5 to 6 membered aryl, or unsubstituted 5 to 6 membered heteroaryl.

$R^6$ may be substituted or unsubstituted $C_1$-$C_3$ alkyl or substituted or unsubstituted 2 to 3 membered heteroalkyl. $R^6$ may be substituted or unsubstituted 3 membered cycloalkyl, substituted or unsubstituted 4 membered cycloalkyl, or substituted or unsubstituted 5 membered cycloalkyl. $R^6$ may be substituted or unsubstituted 4 membered heterocycloalkyl, substituted or unsubstituted 5 membered heterocycloalkyl, substituted or unsubstituted 6 membered heterocycloalkyl. $R^6$ may be substituted or unsubstituted 5 membered aryl, substituted or unsubstituted 6 membered aryl, substituted or unsubstituted 5 membered heteroaryl, or substituted or unsubstituted 6 membered heteroaryl. $R^6$ may be unsubstituted $C_1$-$C_3$ alkyl or unsubstituted 2 to 3 membered heteroalkyl. $R^6$ may be unsubstituted 3 membered cycloalkyl, unsubstituted 4 membered cycloalkyl, or unsubstituted 5 membered cycloalkyl. $R^6$ may be unsubstituted 4 membered heterocycloalkyl, unsubstituted 5 membered heterocycloalkyl, unsubstituted 6 membered heterocycloalkyl. $R^6$ may be unsubstituted 5 membered aryl, unsubstituted 6 membered aryl, unsubstituted 5 membered heteroaryl, or unsubstituted 6 membered heteroaryl.

$R^6$ may be $R^{6a}$-substituted or unsubstituted alkyl, $R^{6a}$-substituted or unsubstituted heteroalkyl, $R^{6a}$-substituted or unsubstituted cycloalkyl, $R^{6a}$-substituted or unsubstituted heterocycloalkyl, $R^{6a}$-substituted or unsubstituted aryl, or substituted or unsubstituted heteroaryl. $R^6$ may be unsubstituted alkyl, unsubstituted heteroalkyl, unsubstituted cycloalkyl, unsubstituted heterocycloalkyl, unsubstituted aryl, or substituted or unsubstituted heteroaryl.

$R^6$ may be $R^{6a}$-substituted or unsubstituted $C_1$-$C_8$ alkyl, $R^{6a}$-substituted or unsubstituted 3 to 8 membered heteroalkyl, $R^{6a}$-substituted or unsubstituted 3 to 8 membered cycloalkyl, $R^{6a}$-substituted or unsubstituted 3 to 8 membered heterocycloalkyl, $R^{6a}$-substituted or unsubstituted 5 to 8 membered aryl, or $R^{6a}$-substituted or unsubstituted 5 to 8 membered heteroaryl. $R^6$ may be unsubstituted $C_1$-$C_8$ alkyl, unsubstituted 3 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 to 8 membered heteroaryl.

$R^6$ may be $R^{6a}$-substituted or unsubstituted $C_1$-$C_5$ alkyl, $R^{6a}$-substituted or unsubstituted 2 to 5 membered heteroalkyl, $R^{6a}$-substituted or unsubstituted 3 to 5 membered cycloalkyl, $R^{6a}$-substituted or unsubstituted 3 to 6 membered heterocycloalkyl, $R^{6a}$-substituted or unsubstituted 5 to 6 membered aryl, or $R^{6a}$-substituted or unsubstituted 5 to 6 membered heteroaryl. $R^6$ may be unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

$R^6$ may be $R^{6a}$-substituted or unsubstituted $C_1$-$C_3$ alkyl or $R^{6a}$-substituted or unsubstituted 2 to 3 membered heteroalkyl. $R^6$ may be $R^{6a}$-substituted 3 membered cycloalkyl, $R^{6a}$-substituted or unsubstituted 4 membered cycloalkyl, or $R^{6a}$-substituted or unsubstituted 5 membered cycloalkyl. $R^6$ may be $R^{6a}$-substituted or unsubstituted 4 membered heterocycloalkyl, $R^{6a}$-substituted or unsubstituted 5 membered heterocycloalkyl, or $R^{6a}$-substituted or unsubstituted 6 membered heterocycloalkyl. $R^6$ may be $R^{6a}$-substituted or unsubstituted 5 membered aryl, $R^{6a}$-substituted or unsubstituted 6 membered aryl, $R^{6a}$-substituted or unsubstituted 5 membered heteroaryl, or $R^{6a}$-substituted or unsubstituted 6 membered heteroaryl. $R^6$ may be unsubstituted $C_1$-$C_3$ alkyl or unsubstituted 2 to 3 membered heteroalkyl. $R^6$ may be or unsubstituted 3 membered cycloalkyl, or unsubstituted 4 membered cycloalkyl, or unsubstituted 5 membered cycloalkyl. $R^6$ may be or unsubstituted 4 membered heterocycloalkyl, or unsubstituted 5 membered heterocycloalkyl, or unsubstituted 6 membered heterocycloalkyl. $R^6$ may be or unsubstituted 5 membered aryl, or unsubstituted 6 membered aryl, or unsubstituted 5 membered heteroaryl, or unsubstituted 6 membered heteroaryl.

$R^{6a}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{6b}$-substituted or unsubstituted alkyl (e.g. $C_1$-$C_8$ alkyl), $R^{6b}$-substituted or unsubstituted heteroalkyl (e.g. 2 to 8 membered heteroalkyl), $R^{6b}$-substituted or unsubstituted cycloalkyl (e.g. 3 to 8 membered cycloalkyl), $R^{6b}$-substituted or unsubstituted heterocycloalkyl (e.g. 3 to 6 membered heterocycloalkyl), $R^{6b}$-substituted or unsubstituted aryl (e.g. 5 to 6 membered aryl), or $R^{6b}$-substituted or unsubstituted heteroaryl (e.g. 5 to 6 membered heteroaryl).

$R^{6b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$-$C_8$ alkyl), unsubstituted heteroalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 to 6 membered aryl), or unsubstituted heteroaryl (e.g. 5 to 6 membered heteroaryl).

$R^6$ may be hydrogen, halogen, $R^{6a}$-substituted or unsubstituted $C_1$-$C_8$ alkyl, or unsubstituted 5 or 6 membered aryl. $R^6$ may be hydrogen. $R^6$ may be halogen. $R^6$ may be $R^{6a}$-substituted or unsubstituted $C_1$-$C_8$ alkyl. $R^6$ may be $R^{6a}$-substituted or unsubstituted $C_1$-$C_5$ alkyl. $R^6$ may be unsubstituted $C_1$-$C_8$ alkyl. $R^6$ may be unsubstituted methyl. $R^6$ may be unsubstituted ethyl. $R^6$ may be unsubstituted propyl. $R^6$ may be unsubstituted allyl. $R^6$ may be unsubstituted aryl. $R^6$ may be unsubstituted phenyl.

$R^5$ and $R^6$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, unsubstituted alkyl, or unsubstituted cycloalkyl. $R^5$ and $R^6$ are independently hydrogen, $C_1$-$C_3$ unsubstituted alkyl or 3 to 5 membered cycloalkyl. $R^5$ and $R^6$ are independently hydrogen, unsubstituted methyl, unsubstituted ethyl, unsubstituted allyl, or unsubstituted cyclopropyl. $R^5$ and $R^6$ may independently be hydrogen or halogen. $R^5$ and $R^6$ may independently be $C_1$-$C_3$ substituted or unsubstituted alkyl. $R^5$ and $R^6$ may be unsubstituted methyl. $R^5$ and $R^6$ may independently be unsubstituted methyl or unsubstituted ethyl.

$R^{16}$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$. $R^{16}$ may be substituted or unsubstituted alkyl. $R^{16}$ may be substituted or unsubstituted $C_1$-$C_8$ alkyl. $R^{16}$ may be substituted or unsubstituted $C_1$-$C_5$ alkyl. $R^{16}$ may be substituted or unsubstituted $C_1$-$C_3$ alkyl. $R^{16}$ may be $R^{16a}$-substituted or unsubstituted alkyl. $R^{16}$ may be $R^{16a}$-substituted or unsubstituted $C_1$-$C_8$ alkyl. $R^{16}$ may be $R^{16a}$-substituted or unsubstituted $C_1$-$C_5$ alkyl. $R^{16}$ may be $R^{16a}$-substituted or unsubstituted $C_1$-$C_3$ alkyl.

$R^{16}$ may be substituted or unsubstituted heteroalkyl. $R^{16}$ may be substituted or unsubstituted 2 to 8 membered heteroalkyl. $R^{16}$ may be substituted or unsubstituted 2 to 5 membered heteroalkyl. $R^{16}$ may be substituted or unsubstituted 2 to 3 membered heteroalkyl. $R^{16}$ may be $R^{16a}$-substituted or unsubstituted heteroalkyl. $R^{16}$ may be $R^{16a}$-substituted or unsubstituted 2 to 8 membered heteroalkyl. $R^{16}$ may be $R^{16a}$-substituted or unsubstituted 2 to 5 membered heteroalkyl. $R^{16}$ may be $R^{16a}$-substituted or unsubstituted 2 to 3 membered heteroalkyl.

$R^{16}$ may be substituted or unsubstituted cycloalkyl. $R^{16}$ may be substituted or unsubstituted 3 to 8 membered cycloalkyl. $R^{16}$ may be substituted or unsubstituted 3 to 5 membered cycloalkyl. $R^{16}$ may be substituted or unsubstituted 3 membered cycloalkyl. $R^{16}$ may be substituted or unsubstituted 4 membered cycloalkyl. $R^{16}$ may be substituted or unsubstituted 5 membered cycloalkyl. $R^{16}$ may be $R^{16a}$-substituted or unsubstituted cycloalkyl. $R^{16}$ may be $R^{16a}$-substituted or unsubstituted 3 to 8 membered cycloalkyl. $R^{16}$ may be $R^{16a}$-substituted or unsubstituted 3 to 5 membered cycloalkyl. $R^{16}$ may be $R^{16a}$-substituted or unsubstituted 3 membered cycloalkyl. $R^{16}$ may be $R^{16a}$-substituted or unsubstituted 4 membered cycloalkyl. $R^{16}$ may be $R^{16a}$-substituted or unsubstituted 5 membered cycloalkyl.

$R^{16}$ may be substituted or unsubstituted heterocycloalkyl. $R^{16}$ may be substituted or unsubstituted 3 to 6 membered heterocycloalkyl. $R^{16}$ may be substituted or unsubstituted 4 membered heterocycloalkyl. $R^{16}$ may be substituted or unsubstituted 5 membered heterocycloalkyl. $R^{16}$ may be substituted or unsubstituted 6 membered heterocycloalkyl. $R^{16}$ may be $R^{16a}$-substituted or unsubstituted heterocycloalkyl. $R^{16}$ may be $R^{16a}$-substituted or unsubstituted 3 to 6 membered heterocycloalkyl. $R^{16}$ may be $R^{16a}$-substituted or unsubstituted 4 membered heterocycloalkyl. $R^{16}$ may be $R^{16a}$-substituted or unsubstituted 5 membered heterocycloalkyl. $R^{16}$ may be $R^{16a}$-substituted or unsubstituted 6 membered heterocycloalkyl.

$R^{16}$ may be substituted or unsubstituted aryl. $R^{16}$ may be substituted or unsubstituted 5 to 6 membered aryl. $R^{16}$ may be substituted or unsubstituted 5 membered aryl. $R^{16}$ may be substituted or unsubstituted 6 membered aryl. $R^{16}$ may be $R^{16a}$-substituted or unsubstituted aryl. $R^{16}$ may be $R^{16a}$-substituted or unsubstituted 5 to 6 membered aryl. $R^{16}$ may be $R^{16a}$-substituted or unsubstituted 5 membered aryl. $R^{16}$ may be $R^{16a}$-substituted or unsubstituted 6 membered aryl. $R^{16}$ may be substituted or unsubstituted heteroaryl. $R^{16}$ may be substituted or unsubstituted 5 to 6 membered heteroaryl.

$R^{16}$ may be substituted or unsubstituted 5 membered heteroaryl. $R^{16}$ may be substituted or unsubstituted 6 membered heteroaryl. $R^{16}$ may be $R^{16a}$-substituted or unsubstituted heteroaryl. $R^{16}$ may be $R^{16a}$-substituted or unsubstituted 5 to 6 membered heteroaryl. $R^{16}$ may be $R^{16a}$-substituted or unsubstituted 5 membered heteroaryl. $R^{16}$ may be $R^{16a}$-substituted or unsubstituted 6 membered heteroaryl.

$R^{16a}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $R^{16b}$-substituted or unsubstituted alkyl (e.g. $C_1$-$C_8$ alkyl), $R^{16b}$-substituted or unsubstituted heteroalkyl (e.g. 2 to 8 membered heteroalkyl), $R^{16b}$-substituted or unsubstituted cycloalkyl (e.g. 3 to 8 membered cycloalkyl), $R^{16b}$-substituted or unsubstituted heterocycloalkyl (e.g. 3 to 6 membered heterocycloalkyl), $R^{16b}$-substituted or unsubstituted aryl (e.g. 5 to 6 membered aryl), or $R^{16b}$-substituted or unsubstituted heteroaryl (e.g. 5 to 6 membered heteroaryl).

$R^{16b}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl), unsubstituted heteroalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 to 6 membered aryl), or unsubstituted heteroaryl (e.g. 5 to 6 membered heteroaryl).

$R^{16}$ may be hydrogen, halogen or substituted or unsubstituted alkyl. $R^{16}$ may be hydrogen. $R^{16}$ may be halogen. $R^{16}$ may be substituted or unsubstituted alkyl. $R^{16}$ may be substituted or unsubstituted $C_1$-$C_5$ alkyl. $R^{16}$ may be $R^{16a}$-substituted or unsubstituted alkyl. $R^{16}$ may be $R^{16a}$-substituted or unsubstituted $C_1$-$C_5$ alkyl. In embodiments, $R^3$, $R^4$, and $R^{16}$ are hydrogen.

$R^{18}$ may be halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{18}$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{18}$ may be unsubstituted alkyl, unsubstituted heteroalkyl, unsubstituted cycloalkyl, unsubstituted heterocycloalkyl, unsubstituted aryl, unsubstituted heteroaryl, or unsubstituted membered heteroaryl.

$R^{18}$ may be substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 or 8 membered heteroaryl. $R^{18}$ may be unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 or 8 membered heteroaryl.

$R^{18}$ may be substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 or 6 membered heteroaryl. $R^{18}$ may be unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 or 6 membered heteroaryl.

$R^{18}$ may be substituted or unsubstituted $C_1$-$C_3$ alkyl, substituted or unsubstituted 2 to 3 membered heteroalkyl. $R^{18}$ may be substituted or unsubstituted 3 membered cycloalkyl, substituted or unsubstituted 4 membered cycloalkyl, or substituted or unsubstituted 5 membered cycloalkyl. $R^{18}$ may be substituted or unsubstituted 4 membered heterocycloalkyl, substituted or unsubstituted 5 membered heterocycloalkyl, or substituted or unsubstituted 6 membered heterocycloalkyl. $R^{18}$ may be substituted or unsubstituted 5 membered aryl, substituted or unsubstituted 6 membered aryl, substituted or unsubstituted 5 membered heteroaryl, or substituted or unsubstituted 6 membered heteroaryl. $R^{18}$ may be unsubstituted $C_1$-$C_3$ alkyl or unsubstituted 2 to 3 membered heteroalkyl. $R^{18}$ may be unsubstituted 3 membered cycloalkyl, unsubstituted 4 membered cycloalkyl or unsubstituted 5 membered cycloalkyl. $R^{18}$ may be unsubstituted 4 membered heterocycloalkyl, unsubstituted 5 membered heterocycloalkyl, or unsubstituted 6 membered heterocycloalkyl. $R^{18}$ may be unsubstituted 5 membered aryl, unsubstituted 6 membered aryl, unsubstituted 5 membered heteroaryl, or unsubstituted 6 membered heteroaryl.

$R^{18}$ may be $R^{18a}$-substituted or unsubstituted alkyl, $R^{18a}$-substituted or unsubstituted heteroalkyl, $R^{18a}$-substituted or unsubstituted cycloalkyl, $R^{18a}$-substituted or unsubstituted heterocycloalkyl, $R^{18a}$-substituted or unsubstituted aryl, or $R^{18a}$-substituted or unsubstituted heteroaryl.

$R^{18}$ may be $R^{18a}$-substituted or unsubstituted $C_1$-$C_8$ alkyl, $R^{18a}$-substituted or unsubstituted 2 to 8 membered heteroalkyl, $R^{18a}$-substituted or unsubstituted 3 to 8 membered cycloalkyl, $R^{18a}$-substituted or unsubstituted 3 to 8 membered heterocycloalkyl, $R^{18a}$-substituted or unsubstituted 5 to 8 membered aryl, or $R^{18a}$-substituted or unsubstituted 5 to 8 membered heteroaryl.

$R^{18}$ may be $R^{18a}$-substituted or unsubstituted $C_1$-$C_5$ alkyl, $R^{18a}$-substituted or unsubstituted 2 to 5 membered heteroalkyl, $R^{18a}$-substituted or unsubstituted 3 to 5 membered cycloalkyl, $R^{18a}$-substituted or unsubstituted 3-6 membered heterocycloalkyl, $R^{18a}$-substituted or unsubstituted 5 to 6 membered aryl, or $R^{18a}$-substituted or unsubstituted 5 to 6 membered heteroaryl.

$R^{18}$ may be $R^{18a}$-substituted or unsubstituted $C_1$-$C_3$ alkyl or $R^{18a}$-substituted or unsubstituted 2 to 3 membered heteroalkyl. $R^{18}$ may be $R^{18a}$-substituted or unsubstituted 3 membered cycloalkyl, $R^{18a}$-substituted or unsubstituted 4 membered cycloalkyl, or $R^{18a}$-substituted or unsubstituted 5 membered cycloalkyl. $R^{18}$ may be $R^{18a}$-substituted or unsubstituted 5 membered heterocycloalkyl, $R^{18a}$-substituted or unsubstituted 6 membered heterocycloalkyl, $R^{18a}$-substituted or unsubstituted 5 membered aryl, $R^{18a}$-substituted or unsubstituted 6 membered aryl, $R^{18a}$-substituted or unsubstituted 5 membered heteroaryl, or $R^{18a}$-substituted or unsubstituted 6 membered heteroaryl.

$R^{18a}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2Ph$, $-SO_2NH_2$, $-NHNH_2$, $-ONH_2$, $-NHC(O)NHNH_2$, $R^{18b}$-substituted or unsubstituted alkyl (e.g. $C_1$-$C_8$ alkyl), $R^{18b}$-substituted or unsubstituted alkyl (e.g. 2 to 8 membered heteroalkyl), $R^{18b}$-substituted or unsubstituted cycloalkyl (e.g. 3 to 8 membered cycloalkyl), $R^{18b}$-substituted or unsubstituted heterocycloalkyl (e.g. 3 to 6 membered heterocycloalkyl), $R^{18b}$-substituted or unsubstituted aryl (e.g. 5 to 6 membered aryl), or $R^{18b}$-substituted or unsubstituted heteroaryl (e.g. 5 to 6 membered heteroaryl).

$R^{18b}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl), unsubstituted heterocycloalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 to 6 membered aryl), or unsubstituted heteroaryl (e.g. 5 to 6 membered heteroaryl).

$R^{18}$ may be substituted or unsubstituted heterocycloalkyl, substituted or unsubstituted aryl, or substituted or unsubstituted heteroaryl. $R^{18}$ may be $R^{18a}$-substituted or unsubstituted 5 membered heterocycloalkyl, $R^{18a}$-substituted or unsubstituted 6 membered aryl, $R^{18a}$-substituted or unsubstituted 6 membered heteroaryl, $R^{18a}$-substituted or unsubstituted 6,6 fused ring aryl-heterocycloalkyl, $R^{18a}$-substituted or unsubstituted 6,5 fused ring aryl-heterocycloalkyl, $R^{18a}$-substituted or unsubstituted 5,6 fused ring aryl-heterocycloalkyl, where $R^{18a}$ and $R^{18b}$ are as described herein, including embodiments thereof.

$R^{18}$ may be $R^{18a}$-substituted or unsubstituted 5 membered heterocycloalkyl, $R^{18a}$-substituted 6 membered aryl, $R^{18a}$-substituted or unsubstituted 6 membered heteroaryl, $R^{18a}$-substituted or unsubstituted 6,6 fused ring aryl, $R^{18a}$-substituted or unsubstituted 6,6 fused ring heteroaryl, $R^{18a}$-substituted or unsubstituted 6,5 fused ring aryl, $R^{18a}$-substituted or unsubstituted 6,5 fused ring heteroaryl, $R^{18a}$-substituted or unsubstituted 5,6 fused ring aryl, $R^{18a}$-substituted 5,6 fused ring heteroaryl, $R^{18a}$-substituted or unsubstituted 6,6 fused ring aryl-heterocycloalkyl, $R^{18a}$-substituted or unsubstituted 6,5 fused ring aryl-heterocycloalkyl, or $R^{18a}$-substituted or unsubstituted 5,6 fused ring aryl-heterocycloalkyl.

$R^{18}$ may be $R^{18a}$-substituted or unsubstituted 3 to 6 membered heterocycloalkyl. The $R^{18a}$-substituted or unsubstituted 3 to 6 membered heterocycloalkyl may be $R^{18a}$-substituted or unsubstituted thiophenyl, $R^{18a}$-substituted or unsubstituted thiazolyl, $R^{18a}$-substituted or unsubstituted oxazolyl, $R^{18a}$-substituted or unsubstituted imidazolyl, or derivatives thereof. $R^{18}$ may be $R^{18a}$-substituted or unsubstituted 6 membered aryl. $R^{18}$ may be $R^{18a}$-substituted or unsubstituted 6 membered heteroaryl. $R^{18}$ may be $R^{18a}$-substituted or unsubstituted 6,6 fused ring aryl-heterocycloalkyl. The $R^{18a}$-substituted or unsubstituted 6,6 fused ring aryl-heteroaryl may be $R^{15a}$-substituted or unsubstituted dihydrobenzo[1,4]dioxinyl. $R^{18}$ may be $R^{18a}$-substituted or unsubstituted 6,5 fused ring aryl-heterocycloalkyl or $R^{18a}$-substituted or unsubstituted 5,6 fused ring aryl-heterocycloalkyl. The $R^{18a}$-substituted or unsubstituted 6,5 or 5,6 fused ring aryl-heterocycloalkyl may be dihydro-indenyl, benzo[1,3]dioxolyl, or indolyl. $R^{18a}$ may be halogen, $SO_2Ph$, $C_1$-$C_5$ $R^{18b}$-substituted or unsubstituted alkyl, or 2 to 5 membered $R^{18b}$-substituted or unsubstituted heteroalkyl.

In one embodiment, $R^1$ and $R^{18}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings). In one embodiment, $R^1$ and $R^{16}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings).

In one embodiment, $R^2$ and $R^{18}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings). In one embodiment, $R^2$ and $R^{16}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings).

In one embodiment, $R^1$ and $R^{18}$ are not hydrogen. In one embodiment the compound of formula (I) does not have the formula (3R,8S,8aR)-8-hydroxy-2-methyltetrahydro-1H-3,8a-epidithiopyrrolo[1,2-a]pyrazine-1,4(6H)-dione. In one embodiment, the compound of formula (I) does not have the formula (3R,8S,8aR)-2-methyl-1,4-dioxohexahydro-1H-3,8a-epidithiopyrrolo[1,2-a]pyrazin-8-yl acetate. In one embodiment the compound of formula (I) does not have the formula (3R,6R,8S,8aR)-6-(((tert-butyldiphenylsilyl)oxy)methyl)-8-hydroxy-2-methyltetrahydro-1H-3,8a-epidithiopyrrolo[1,2-a]pyrazine-1,4(6H)-dione. In one embodiment, the compound does not have the formula 2,3-dimethyltetrahydro-1H-3,8a-epidithiopyrrolo[1,2-a]pyrazine-1,4(6H)-dione. In one embodiment, the compound does not have the formula 3-(hydroxymethyl)-2-methyltetrahydro-1H-3,8a-epidithiopyrrolo[1,2-a]pyrazine-1,4(6H)-dione.

The compound of formula (I) may have the formula:

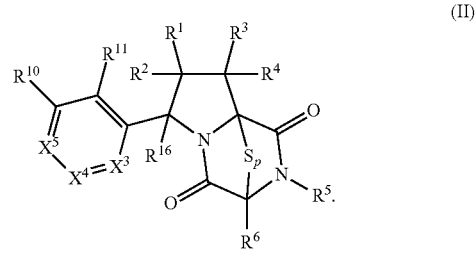

(II)

p, $R^1$, $R^2$, $R^3$, $R^4$, $R^5$, $R^6$ and $R^{16}$ are as described herein. $X^3$ is N or $CR^7$. $X^4$ is N or $CR^8$. $X^5$ is N or $CR^9$. $R^7$ is hydrogen, halogen, $-N_3$, $-CF_3$, $-CCl_3$, $-CBr_3$, $-CI_3$, $-CN$, $-CHO$, $-OR^{33I}$, $-NR^{34I}R^{35I}$, $-COOR^{33I}$, $-CONR^{34I}R^{35I}$, $-NO_2$, $-SR^{36I}$, $-SO_{n9}R^{34I}$, $-SO_{n9}OR^{34I}$, $-SO_{n9}NR^{34I}R^{35I}$, $-NHNR^{34I}R^{35I}$, $-ONR^{34I}R^{35I}$, $-NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ is hydrogen, halogen, $-N_3$, $-CF_3$, $-CCl_3$, $-CBr_3$, $-CI_3$, $-CN$, $-CHO$, $-OR^{33J}$, $-NR^{34J}R^{35J}$, $-COOR^{33J}$, $-CONR^{34J}R^{35J}$, $-NO_2$, $-SR^{36J}$, $-SO_{n10}R^{34J}$, $-SO_{n10}OR^{34J}$, $-SO_{n10}NR^{34J}R^{35J}$, $-NHNR^{34J}R^{35J}$, $-ONR^{34J}R^{35J}$, $-NHC(O)NHNR^{34J}R^{35J}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-N_3$, $-CF_3$, $-CCl_3$, $-CBr_3$, $-CI_3$, $-CN$, $-CHO$, $-OR^{33K}$, $-NR^{34K}R^{35K}$, $-COOR^{33K}$, —CONR$^{34K}$R$^{35K}$, —NO$_2$, —SR$^{36K}$, —SO$_{n11}$R$^{34K}$, —SO$_{n11}$R$^{34K}$, —SO$_{n11}$NR$^{34K}$R$^{35K}$, —NHNR$^{34K}$R$^{35K}$, —ONR$^{34K}$R$^{35K}$, —NHC(O)NHNR$^{34K}$R$^{35K}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{10}$ and R$^{11}$ are independently hydrogen, halogen, —N$_3$, —CF$_3$, —CCl$_3$, —CBr$_3$, —CI$_3$, —CN, —CHO, —OR$^{33L}$, —NR$^{34L}$R$^{35L}$, —COOR$^{33L}$, —CONR$^{34L}$R$^{35L}$, —NO$_2$, —SR$^{36L}$, —SO$_{n12}$R$^{34L}$, —SO$_{n12}$OR$^{34L}$, —SO$_{n12}$NR$^{34L}$R$^{35L}$, —NHNR$^{34L}$R$^{35L}$, —ONR$^{34L}$R$^{35L}$, —NHC(O)NHNR$^{34L}$R$^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl. R$^{33I}$, R$^{34I}$, R$^{35I}$, R$^{36I}$, R$^{33J}$, R$^{34J}$, R$^{35J}$, R$^{36J}$, R$^{33K}$, R$^{34K}$, R$^{35K}$, R$^{36K}$, R$^{33L}$, R$^{34L}$, R$^{35L}$, and R$^{36L}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n9, n10, n11, and n12 are independently 1 or 2.

R$^{10}$ and R$^{11}$ are optionally joined together to form a substituted or unsubstituted cycloalkyl, a substituted or unsubstituted heterocycloalkyl, a substituted or unsubstituted aryl, or a substituted or unsubstituted heteroaryl. R$^7$ and R$^8$ are optionally joined together to form a substituted or unsubstituted cycloalkyl, a substituted or unsubstituted heterocycloalkyl, a substituted or unsubstituted aryl, or a substituted or unsubstituted heteroaryl. R$^8$ and R$^9$ are optionally joined together to form a substituted or unsubstituted cycloalkyl, a substituted or unsubstituted heterocycloalkyl, a substituted or unsubstituted aryl, or a substituted or unsubstituted heteroaryl. R$^9$ and R$^{10}$ are optionally joined together to form a substituted or unsubstituted cycloalkyl, a substituted or unsubstituted heterocycloalkyl, a substituted or unsubstituted aryl, or a substituted or unsubstituted heteroaryl. p may be 2, 3, or 4.

When X$^3$ is N, X$^4$ may be CR$^8$ and X$^5$ may be CR$^9$. When X$^4$ is N, X$^3$ may be CR$^7$ and X$^5$ may be CR$^9$. When X$^5$ is N, X$^3$ may be CR$^7$ and X$^4$ may be CR$^8$. X$^3$, X$^4$, and X$^5$ may be CR$^7$, CR$^8$, and CR$^9$ respectively.

R$^7$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g. C$_1$-C$_8$ alkyl), or substituted or unsubstituted heteroalkyl (e.g. 2 to 8 membered heteroalkyl). R$^7$ may be halogen, —CF$_3$, —CCl$_3$, —CBr$_3$, —CI$_3$, —CN, substituted or unsubstituted alkyl, or substituted or unsubstituted heteroalkyl. R$^7$ may be halogen, substituted or unsubstituted alkyl, or substituted or unsubstituted heteroalkyl. R$^7$ may be halogen or substituted or unsubstituted alkyl. R$^7$ may be halogen or substituted or unsubstituted heteroalkyl. R$^7$ may be halogen, or unsubstituted heteroalkyl. R$^7$ may be halogen, halogen, —CF$_3$, —CCl$_3$, —CBr$_3$, or —CI$_3$.

R$^7$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^7$ may be unsubstituted alkyl, unsubstituted heteroalkyl, unsubstituted cycloalkyl, unsubstituted heterocycloalkyl, unsubstituted aryl, or unsubstituted membered heteroaryl.

R$^7$ may be substituted or unsubstituted C$_1$-C$_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 or 8 membered heteroaryl. R$^7$ may be unsubstituted C$_1$-C$_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 or 8 membered heteroaryl.

R$^7$ may be substituted or unsubstituted C$_1$-C$_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 to 6 membered heteroaryl. R$^7$ may be unsubstituted C$_1$-C$_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 to 6 membered heteroaryl.

R$^7$ may be substituted or unsubstituted C$_1$-C$_3$ alkyl, substituted or unsubstituted 2 to 3 membered heteroalkyl. R$^7$ may be substituted or unsubstituted 3 membered cycloalkyl, substituted or unsubstituted 4 membered cycloalkyl, or substituted or unsubstituted 5 membered cycloalkyl. R$^7$ may be substituted or unsubstituted 4 membered heterocycloalkyl, substituted or unsubstituted 5 membered heterocycloalkyl, or substituted or unsubstituted 6 membered heterocycloalkyl. R$^7$ may be substituted or unsubstituted 5 membered aryl, substituted or unsubstituted 6 membered aryl, substituted or unsubstituted 5 membered heteroaryl, or substituted or unsubstituted 6 membered heteroaryl. R$^7$ may be unsubstituted C$_1$-C$_3$ alkyl or unsubstituted 2 to 3 membered heteroalkyl. R$^7$ may be unsubstituted 3 membered cycloalkyl, unsubstituted 4 membered cycloalkyl or unsubstituted 5 membered cycloalkyl. R$^7$ may be unsubstituted 4 membered heterocycloalkyl, unsubstituted 5 membered heterocycloalkyl, or unsubstituted 6 membered heterocycloalkyl. R$^7$ may be unsubstituted 5 membered aryl, unsubstituted 6 membered aryl, unsubstituted 5 membered heteroaryl, or unsubstituted 6 membered heteroaryl.

R$^7$ may be R$^{7a}$-substituted or unsubstituted alkyl, R$^{7a}$-substituted or unsubstituted heteroalkyl, R$^{7a}$-substituted or unsubstituted cycloalkyl, R$^{7a}$-substituted or unsubstituted heterocycloalkyl, R$^{7a}$-substituted or unsubstituted aryl, or R$^{7a}$-substituted or unsubstituted heteroaryl.

R$^7$ may be R$^{7a}$-substituted or unsubstituted C$_1$-C$_8$ alkyl, R$^{7a}$-substituted or unsubstituted 2 to 8 membered heteroalkyl, R$^{7a}$-substituted or unsubstituted 3 to 8 membered cycloalkyl, R$^{7a}$-substituted or unsubstituted 3 to 8 membered heterocycloalkyl, R$^{7a}$-substituted or unsubstituted 5 to 8 membered aryl, or R$^{7a}$-substituted or unsubstituted 5 to 8 membered heteroaryl.

R$^7$ may be R$^{7a}$-substituted or unsubstituted C$_1$-C$_5$ alkyl, R$^{7a}$-substituted or unsubstituted 2 to 5 membered heteroalkyl, R$^{7a}$-substituted or unsubstituted 3 to 5 membered cycloalkyl, R$^{7a}$-substituted or unsubstituted 3 to 6 membered heterocycloalkyl, R$^{7a}$-substituted or unsubstituted 5 to 6 membered aryl, or R$^{7a}$-substituted or unsubstituted 5 to 6 membered heteroaryl.

R$^7$ may be R$^{7a}$-substituted or unsubstituted C$_1$-C$_3$ alkyl or R$^{7a}$-substituted or unsubstituted 2 to 3 membered heteroalkyl. $R^7$ may be $R^{7a}$-substituted or unsubstituted 3 membered cycloalkyl, $R^{7a}$-substituted or unsubstituted 4 membered cycloalkyl, or $R^{7a}$-substituted or unsubstituted 5 membered cycloalkyl. $R^7$ may be $R^{7a}$-substituted or unsubstituted 5 membered heterocycloalkyl, $R^{7a}$-substituted or unsubstituted 6 membered heterocycloalkyl, $R^{7a}$-substituted or unsubstituted 5 membered aryl, $R^{7a}$-substituted or unsubstituted 6 membered aryl, $R^{7a}$-substituted or unsubstituted 5 membered heteroaryl, or $R^{7a}$-substituted or unsubstituted 6 membered heteroaryl.

$R^{7a}$ is halogen, $—N_3$, $—CF_3$, $—CCl_3$, $—CBr_3$, $—CI_3$, $—CN$, $—CHO$, $—OH$, $—NH_2$, $—COOH$, $—CONH_2$, $—NO_2$, $—SH$, $—SO_2Cl$, $—SO_3H$, $—SO_4H$, $—SO_2NH_2$, $—NHNH_2$, $—ONH_2$, $—NHC(O)NHNH_2$, $R^{7b}$-substituted or unsubstituted alky (e.g. $C_1$-$C_8$ alkyl, $R^{7b}$-substituted or unsubstituted heteroalkyl (e.g. 2 to 8 membered heteroalkyl), $R^{7b}$-substituted or unsubstituted cycloalkyl (e.g. 3 to 8 membered cycloalkyl), $R^{7b}$-substituted or unsubstituted heterocycloalkyl (e.g. 3 to 6 membered heterocycloalkyl), $R^{7b}$-substituted or unsubstituted aryl (e.g. 5 to 6 membered aryl), or $R^{7b}$-substituted or unsubstituted heteroaryl (e.g. 5 to 6 membered heteroaryl).

$R^{7b}$ is halogen, $—N_3$, $—CF_3$, $—CCl_3$, $—CBr_3$, $—CI_3$, $—CN$, $—CHO$, $—OH$, $—NH_2$, $—COOH$, $—CONH_2$, $—NO_2$, $—SH$, $—SO_2Cl$, $—SO_3H$, $—SO_4H$, $—SO_2NH_2$, $—NHNH_2$, $—ONH_2$, $—NHC(O)NHNH_2$, unsubstituted alky (e.g. $C_1$-$C_8$ alkyl), unsubstituted heteroalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 to 6 membered aryl), or unsubstituted heteroaryl (e.g. 5 to 6 membered heteroaryl).

$R^8$ and $R^9$ may independently be hydrogen, halogen, $—N_3$, $—CF_3$, $—CCl_3$, $—CBr_3$, $—CI_3$, $—CN$, $—CHO$, $—OH$, $—NH_2$, $—COOH$, $—CONH_2$, $—NO_2$, $—SH$, $—SO_2Cl$, $—SO_3H$, $—SO_4H$, $—SO_2NH_2$, $—NHNH_2$, $—ONH_2$, $—NHC(O)NHNH_2$. $R^8$ and $R^9$ may independently be hydrogen, halogen, $—N_3$, $—CF_3$, $—CCl_3$, $—CBr_3$, $—CI_3$, $—OH$, $—NH_2$, $—COOH$, $—CONH_2$, $—NO_2$, $—SH$, or $—SO_2$. $R^8$ and $R^9$ may independently be hydrogen, halogen, $—CF_3$, $—CCl_3$, $—CBr_3$, $—CI_3$, $—OH$, or $—NH_2$.

$R^8$ and $R^9$ may independently be hydrogen, halogen, $—N_3$, $—CF_3$, $—CCl_3$, $—CBr_3$, $—CI_3$, $—CN$, $—CHO$, $—OH$, $—NH_2$, $—COOH$, $—CONH_2$, $—NO_2$, $—SH$, $—SO_2Cl$, $—SO_3H$, $—SO_4H$, $—SO_2NH_2$, $—NHNH_2$, $—ONH_2$, $—NHC(O)NHNH_2$, substituted or unsubstituted alkyl (e.g. $C_1$-$C_8$ alkyl), or substituted or unsubstituted heteroalkyl (e.g. 2 to 8 membered heteroalkyl).

$R^8$ and $R^9$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ and $R^9$ may independently be unsubstituted alkyl, unsubstituted heteroalkyl, unsubstituted cycloalkyl, unsubstituted heterocycloalkyl, unsubstituted aryl, unsubstituted heteroaryl, or unsubstituted membered heteroaryl.

$R^8$ and $R^9$ may independently be substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 or 8 membered heteroaryl. $R^8$ and $R^9$ may independently be unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 or 8 membered heteroaryl.

$R^8$ and $R^9$ may independently be substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3 to 6 membered heterocycloalkyl, substituted or unsubstituted 5 to 6 membered aryl, or substituted or unsubstituted 5 or 6 membered heteroaryl. $R^8$ and $R^9$ may independently be unsubstituted $C_1$-$C_5$ alkyl, unsubstituted 2 to 5 membered heteroalkyl, unsubstituted 3 to 5 membered cycloalkyl, unsubstituted 3 to 6 membered heterocycloalkyl, unsubstituted 5 to 6 membered aryl, or unsubstituted 5 or 6 membered heteroaryl.

$R^8$ and $R^9$ may independently be substituted or unsubstituted $C_1$-$C_3$ alkyl, substituted or unsubstituted 2 to 3 membered heteroalkyl. $R^8$ and $R^9$ may independently be substituted or unsubstituted 3 membered cycloalkyl, substituted or unsubstituted 4 membered cycloalkyl, or substituted or unsubstituted 5 membered cycloalkyl. $R^8$ and $R^9$ may independently be substituted or unsubstituted 4 membered heterocycloalkyl, substituted or unsubstituted 5 membered heterocycloalkyl, or substituted or unsubstituted 6 membered heterocycloalkyl. $R^8$ and $R^9$ may independently be substituted or unsubstituted 5 membered aryl, substituted or unsubstituted 5 membered aryl, substituted or unsubstituted 6 membered aryl, or substituted or unsubstituted 6 membered heteroaryl. $R^8$ and $R^9$ may independently be unsubstituted $C_1$-$C_3$ alkyl or unsubstituted 2 to 3 membered heteroalkyl. $R^8$ and $R^9$ may independently be unsubstituted 3 membered cycloalkyl, unsubstituted 4 membered cycloalkyl or unsubstituted 5 membered cycloalkyl. $R^8$ and $R^9$ may independently be unsubstituted 4 membered heterocycloalkyl, unsubstituted 5 membered heterocycloalkyl, or unsubstituted 6 membered heterocycloalkyl. $R^8$ and $R^9$ may independently be be unsubstituted 5 membered aryl, unsubstituted 6 membered aryl, unsubstituted 5 membered aryl, or unsubstituted 6 membered heteroaryl.

$R^8$ and $R^9$ may independently be $R^{31a}$-substituted or unsubstituted alkyl, $R^{31a}$-substituted or unsubstituted heteroalkyl, $R^{31a}$-substituted or unsubstituted cycloalkyl, $R^{31a}$-substituted or unsubstituted heterocycloalkyl, $R^{31a}$-substituted or unsubstituted aryl, or $R^{31a}$-substituted or unsubstituted heteroaryl.

$R^8$ and $R^9$ may independently be $R^{31a}$-substituted or unsubstituted $C_1$-$C_8$ alkyl, $R^{31a}$-substituted or unsubstituted 2 to 8 membered heteroalkyl, $R^{31a}$-substituted or unsubstituted 3 to 8 membered cycloalkyl, $R^{31a}$-substituted or unsubstituted 3 to 8 membered heterocycloalkyl, $R^{31a}$-substituted or unsubstituted 5 to 8 membered aryl, or $R^{31a}$-substituted or unsubstituted 5 to 8 membered heteroaryl.

$R^8$ and $R^9$ may independently be $R^{31a}$-substituted or unsubstituted $C_1$-$C_5$ alkyl, $R^{31a}$-substituted or unsubstituted 2 to 5 membered heteroalkyl, $R^{31a}$-substituted or unsubstituted 3 to 5 membered cycloalkyl, $R^{31a}$-substituted or unsubstituted 3-6 membered heterocycloalkyl, $R^{31a}$-substituted or unsubstituted 5 to 6 membered aryl, or $R^{31a}$-substituted or unsubstituted 5 to 6 membered heteroaryl.

$R^8$ and $R^9$ may independently be $R^{31a}$-substituted or unsubstituted $C_1$-$C_3$ alkyl or $R^{31a}$ substituted or unsubstituted 2 to 3 membered heteroalkyl. $R^8$ and $R^9$ may independently be $R^{31a}$-substituted or unsubstituted 3 membered cycloalkyl, $R^{31a}$-substituted or unsubstituted 4 membered cycloalkyl, or $R^{31a}$-substituted or unsubstituted 5 membered cycloalkyl. $R^8$ and $R^9$ may independently be $R^{31a}$-substituted or unsubstituted 5 membered heterocycloalkyl, $R^{31a}$- substituted or unsubstituted 6 membered heterocycloalkyl, $R^{31a}$-substituted or unsubstituted 5 membered aryl, $R^{31a}$-substituted or unsubstituted 6 membered aryl, $R^{31a}$-substituted or unsubstituted 5 membered heteroaryl, or $R^{31a}$-substituted or unsubstituted 6 membered heteroaryl.

$R^8$ may be hydrogen, halogen or substituted or unsubstituted alkyl. $R^8$ may be hydrogen. $R^8$ may be halogen. $R^8$ may be substituted or unsubstituted alkyl. $R^8$ may be substituted or unsubstituted $C_1$-$C_5$ alkyl. $R^8$ may be $R^{31a}$-substituted alkyl. $R^8$ may be hydrogen or —$OR^{33J}$ and $R^9$, $R^{10}$, and $R^{11}$ may independently be hydrogen or halogen. $R^{33}$ may be hydrogen, or unsubstituted alkyl. $R^8$ may be $R^{31a}$-substituted $C_1$-$C_5$ alkyl. $R^9$ may be hydrogen, halogen substituted or unsubstituted alkyl, or unsubstituted or unsubstituted heteroalkyl. $R^9$ may be substituted or unsubstituted $C_1$-$C_5$ alkyl. $R^9$ may be $R^{8a}$-substituted or unsubstituted alkyl. $R^9$ may be $R^{31a}$-substituted $C_1$-$C_5$ or unsubstituted alkyl. $R^9$ may be $R^{31a}$-substituted or unsubstituted heteroalkyl. $R^9$ may be $R^{31a}$-substituted or unsubstituted 2 to 6 membered heteroalkyl.

$R^{31a}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{31b}$-substituted or unsubstituted alkyl (e.g. $C_1$-$C_8$ alkyl), $R^{31b}$-substituted or unsubstituted heteroalkyl (e.g. 2 to 8 membered heteroalkyl), $R^{31b}$-substituted or unsubstituted cycloalkyl (e.g. 3 to 8 membered cycloalkyl), $R^{31b}$-substituted or unsubstituted heterocycloalkyl (e.g. 3 to 6 membered heterocycloalkyl), $R^{31b}$-substituted or unsubstituted aryl (e.g. 5 to 6 membered aryl), or $R^{31b}$-substituted or unsubstituted heteroaryl (e.g. 5 to 6 membered heteroaryl).

$R^{31b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alky (e.g. $C_1$-$C_8$ alkyl), unsubstituted heteroalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 to 6 membered aryl), or unsubstituted heteroaryl (e.g. 5 to 6 membered heteroaryl).

$R^8$ and $R^9$ may be joined together to form a substituted or unsubstituted cycloalkyl (e.g. 3 to 8 membered cycloalkyl). $R^8$ and $R^9$ may be joined together to form a substituted or unsubstituted heterocycloalkyl (e.g. 3 to 8 membered heterocycloalkyl). $R^8$ and $R^9$ may be joined together to form a substituted or unsubstituted aryl (e.g. 3 to 8 membered aryl). $R^8$ and $R^9$ may be joined together to form a substituted or unsubstituted heteroaryl (e.g. 3 to 8 membered heteroaryl).

$R^7$ and $R^8$ may be joined together to form a substituted or unsubstituted cycloalkyl (e.g. 3 to 8 membered cycloalkyl). $R^7$ and $R^8$ may be joined together to form a substituted or unsubstituted heterocycloalkyl (e.g. 3 to 8 membered heterocycloalkyl). $R^7$ and $R^8$ may be joined together to form a substituted or unsubstituted aryl (e.g. 3 to 8 membered aryl). $R^7$ and $R^8$ may be joined together to form a substituted or unsubstituted heteroaryl (e.g. 3 to 8 membered heteroaryl).

$R^{10}$ and $R^{11}$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$. $R^{10}$ and $R^{11}$ may independently be hydrogen, halogen, —$N_3$, —$CF_3$, —$CCl_3$, —$CBr_3$, —$CI_3$, —OH, —$NH_2$, —COOH, —$CONH_2$, —$NO_2$, —SH, or —$SO_2$. $R^{10}$ and $R^{11}$ may independently be hydrogen, halogen, —$CF_3$, —$CCl_3$, —$CBr_3$, —$CI_3$, —OH, or —$NH_2$.

$R^{10}$ and $R^{11}$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl (e.g. $C_1$-$C_8$ alkyl), or substituted or unsubstituted heteroalkyl (e.g. 2 to 8 membered heteroalkyl).

$R^{10}$ and $R^{11}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ and $R^{11}$ may independently be unsubstituted alkyl, unsubstituted heteroalkyl, unsubstituted cycloalkyl, unsubstituted heterocycloalkyl, unsubstituted aryl, unsubstituted heteroaryl, or unsubstituted membered heteroaryl.

$R^{10}$ and $R^{11}$ may independently be substituted or unsubstituted $C_1$-$C_8$ alkyl, substituted or unsubstituted 2 to 8 membered heteroalkyl, substituted or unsubstituted 3 to 8 membered cycloalkyl, substituted or unsubstituted 3 to 8 membered heterocycloalkyl, substituted or unsubstituted 5 to 8 membered aryl, or substituted or unsubstituted 5 or 8 membered heteroaryl. $R^{10}$ and $R^{11}$ may independently be unsubstituted $C_1$-$C_8$ alkyl, unsubstituted 2 to 8 membered heteroalkyl, unsubstituted 3 to 8 membered cycloalkyl, unsubstituted 3 to 8 membered heterocycloalkyl, unsubstituted 5 to 8 membered aryl, or unsubstituted 5 or 8 membered heteroaryl.

$R^{10}$ and $R^{11}$ may independently be substituted or unsubstituted $C_1$-$C_5$ alkyl, substituted or unsubstituted 2 to 5 membered heteroalkyl, substituted or unsubstituted 3 to 5 membered cycloalkyl, substituted or unsubstituted 3-6 membered heterocycloalkyl, substituted or unsubstituted 5 to 6 membered aryl, or substituted or unsubstituted 5 or 6 membered heteroaryl. $R^{10}$ and $R^{11}$ may independently be unsubstituted $C_1$-$C_5$ alkyl, unsubstituted 2 to 5 membered heteroalkyl, unsubstituted 3 to 5 membered cycloalkyl, unsubstituted 3-6 membered heterocycloalkyl, unsubstituted 5 to 6 membered aryl, or unsubstituted 5 or 6 membered heteroaryl.

$R^{10}$ and $R^{11}$ may independently be substituted or unsubstituted $C_1$-$C_3$ alkyl, substituted or unsubstituted 2 to 3 membered heteroalkyl. $R^{10}$ and $R^{11}$ may independently be substituted or unsubstituted 3 membered cycloalkyl, substituted or unsubstituted 4 membered cycloalkyl, or substituted or unsubstituted 5 membered cycloalkyl. $R^{10}$ and $R^{11}$ may independently be substituted or unsubstituted 4 membered heterocycloalkyl, substituted or unsubstituted 5 membered heterocycloalkyl, or substituted or unsubstituted 6 membered heterocycloalkyl. $R^{10}$ and $R^{11}$ may independently be substituted or unsubstituted 5 membered aryl, substituted or unsubstituted 5 membered aryl, substituted or unsubstituted 6 membered aryl, or substituted or unsubstituted 6 membered heteroaryl. $R^{10}$ and $R^{11}$ may independently be unsubstituted $C_1$-$C_3$ alkyl or unsubstituted 2 to 3 membered heteroalkyl. $R^{10}$ and $R^{11}$ may independently be unsubstituted 3 membered cycloalkyl, unsubstituted 4 membered cycloalkyl or unsubstituted 5 membered cycloalkyl. $R^{10}$ and $R^1$ may independently be unsubstituted 4 membered heterocycloalkyl, unsubstituted 5 membered heterocycloalkyl, or unsubstituted 6 membered heterocycloalkyl. $R^{10}$ and $R^{11}$ may independently be be unsubstituted 5 membered aryl, unsubstituted 5 membered aryl, unsubstituted 6 membered aryl, or unsubstituted 6 membered heteroaryl.

$R^{10}$ and $R^{11}$ may independently be $R^{32a}$-substituted or unsubstituted alkyl, $R^{32a}$-substituted or unsubstituted heteroalkyl, $R^{32a}$-substituted or unsubstituted cycloalkyl, $R^{32a}$-substituted or unsubstituted heterocycloalkyl, $R^{32a}$-substituted or unsubstituted aryl, or $R^{32a}$-substituted or unsubstituted heteroaryl.

$R^{10}$ and $R^{11}$ may independently be $R^{32a}$-substituted or unsubstituted $C_1$-$C_8$ alkyl, $R^{32a}$-substituted or unsubstituted 2 to 8 membered heteroalkyl, $R^{32a}$-substituted or unsubstituted 3 to 8 membered cycloalkyl, $R^{32a}$-substituted or unsubstituted 3 to 8 membered heterocycloalkyl, $R^{32a}$-substituted or unsubstituted 5 to 8 membered aryl, or $R^{32a}$-substituted or unsubstituted 5 to 8 membered heteroaryl.

$R^{10}$ and $R^{11}$ may independently be $R^{32a}$-substituted or unsubstituted $C_1$-$C_5$ alkyl, $R^{32a}$-substituted or unsubstituted 2 to 5 membered heteroalkyl, $R^{32a}$-substituted or unsubstituted 3 to 5 membered cycloalkyl, $R^{32a}$-substituted or unsubstituted 3-6 membered heterocycloalkyl, $R^{32a}$-substituted or unsubstituted 5 to 6 membered aryl, or $R^{32a}$-substituted or unsubstituted 5 to 6 membered heteroaryl.

$R^{10}$ and $R^{11}$ may independently be $R^{32a}$-substituted or unsubstituted $C_1$-$C_3$ alkyl or $R^{32a}$-substituted or unsubstituted 2 to 3 membered heteroalkyl. $R^{10}$ and $R^{11}$ may independently be $R^{32a}$-substituted or unsubstituted 3 membered cycloalkyl, $R^{32a}$-substituted or unsubstituted 4 membered cycloalkyl, or $R^{32a}$-substituted or unsubstituted 5 membered cycloalkyl. $R^{10}$ and $R^{11}$ may independently be $R^{32a}$-substituted or unsubstituted 5 membered heterocycloalkyl, $R^{32a}$-substituted or unsubstituted 6 membered heterocycloalkyl, $R^{32a}$-substituted or unsubstituted 5 membered aryl, $R^{32a}$-substituted or unsubstituted 6 membered aryl, $R^{32a}$-substituted or unsubstituted 5 membered heteroaryl, or $R^{32a}$-substituted or unsubstituted 6 membered heteroaryl.

$R^{32a}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{32b}$-substituted or unsubstituted alkyl (e.g. $C_1$-$C_8$ alkyl), $R^{32b}$-substituted or unsubstituted heteroalkyl (e.g. 2 to 8 membered heteroalkyl), $R^{32b}$-substituted or unsubstituted cycloalkyl (e.g. 3 to 8 membered cycloalkyl), $R^{32b}$-substituted or unsubstituted heterocycloalkyl (e.g. 3 to 6 membered heterocycloalkyl), $R^{32b}$-substituted or unsubstituted aryl (e.g. 5 to 6 membered aryl), or $R^{32b}$-substituted or unsubstituted heteroaryl (e.g. 5 to 6 membered heteroaryl).

$R^{32b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alky (e.g. $C_1$-$C_8$ alkyl), unsubstituted heteroalkyl (e.g. 2 to 8 membered heteroalkyl), unsubstituted cycloalkyl (e.g. 3 to 8 membered cycloalkyl), unsubstituted heterocycloalkyl (e.g. 3 to 6 membered heterocycloalkyl), unsubstituted aryl (e.g. 5 to 6 membered aryl), or unsubstituted heteroaryl (e.g. 5 to 6 membered heteroaryl).

$R^9$ and $R^{10}$ may be joined together to form a substituted or unsubstituted 3 to 8 membered cycloalkyl. $R^9$ and $R^{10}$ may be joined together to form a substituted or unsubstituted 3 to 8 membered heterocycloalkyl. $R^9$ and $R^{10}$ may be joined together to form a substituted or unsubstituted 3 to 8 membered aryl. $R^9$ and $R^{10}$ may be joined together to form a substituted or unsubstituted 3 to 8 membered heteroaryl.

$R^{10}$ and $R^{11}$ may be joined together to form a substituted or unsubstituted 3 to 8 membered cycloalkyl. $R^{10}$ and $R^{11}$ may be joined together to form a substituted or unsubstituted 3 to 8 membered heterocycloalkyl. $R^{10}$ and $R^{11}$ may be joined together to form a substituted or unsubstituted 3 to 8 membered aryl. $R^{10}$ and $R^{11}$ may be joined together to form a substituted or unsubstituted 3 to 8 membered heteroaryl.

In embodiments, $R^7$, $R^8$, $R^9$, $R^{10}$ and $R^{11}$ are independently hydrogen, halogen, $C_1$-$C_5$ unsubstituted alkyl, 2 to 5 membered unsubstituted heteroalkyl. $R^7$, $R^8$, $R^9$, $R^{10}$ and $R^{11}$ may independently be hydrogen, halogen, unsubstituted methyl, —$OCH_3$ or —$O(CH_2)_2$=$CH_2$. $R^{10}$ and $R^{11}$ may be hydrogen.

The compound of formula (II) may have the formula:

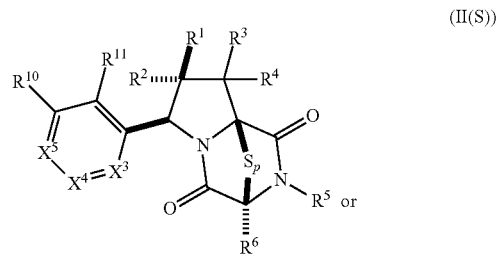

(II(S))

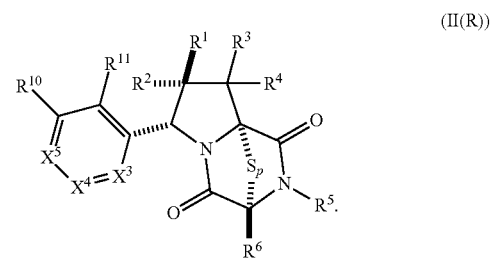

(II(R))

The symbol p, $X^3$, $X^4$, $X^5$, p, $R^1$, $R^2$, $R^3$, $R^4$, $R^5$, $R^6$, $R^7$, $R^8$, $R^9$, $R^{10}$, and $R^1$ are as described herein, including embodiments thereof. $R^5$ and $R^6$ may independently be unsubstituted $C_1$-$C_3$ alkyl or unsubstituted 3 to 5 membered cycloalkyl. $R^7$, $R^8$, $R^9$, and $R^{10}$ may independently be hydrogen, halogen, unsubstituted methyl, —$OCH_3$ or —$O(CH_2)_2$=$CH_2$. $R^1$ may be —CN or unsubstituted 2 to 5 membered heteroalkyl. $R^1$ may be —CN. $R^1$ may be —$COOCH_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ may be hydrogen. $R^{10}$ and $R^{11}$ may be hydrogen.

The compound of formula (II) may have the formula:

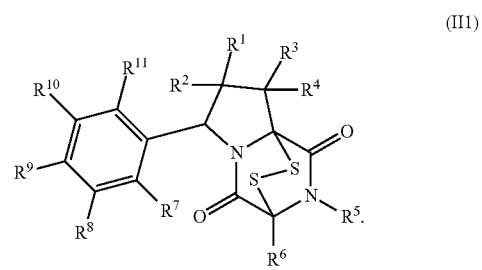

(III)

In embodiments, $R^8$ is hydrogen or —$OR^{33J}$. $R^9$, $R^{10}$, and $R^{11}$ may independently be hydrogen or halogen. $R^{33J}$ may be hydrogen, or unsubstituted alkyl (e.g. unsubstituted methyl, unsubstituted ethyl, or unsubstituted propyl).

The compound of formula (II) may have the formula:

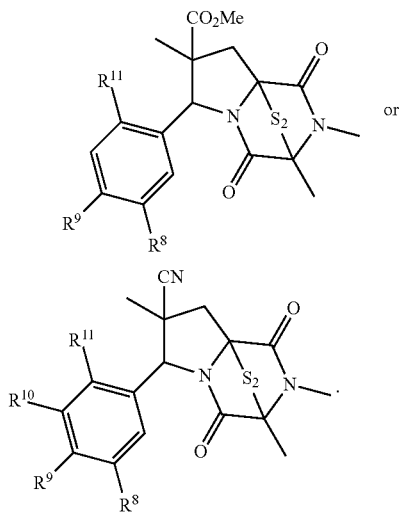

R⁸ may be hydrogen or —OR³³ᴶ. R⁹, R¹⁰, and R¹¹ may independently be hydrogen or halogen. R³³ᴶ may be hydrogen, or unsubstituted alkyl.

The compound of formula (II1) may have the formula:

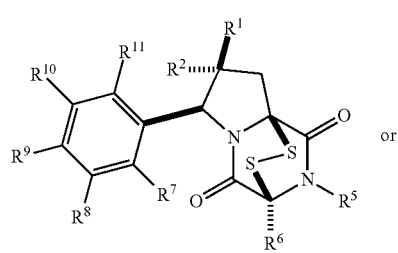

(II1(S))

or (II1(R))

The compound of formula (II) may have the formula:

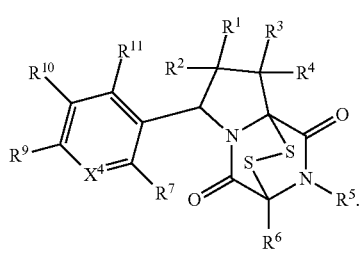

(II2)

The compound of formula (II2) may have the formula:

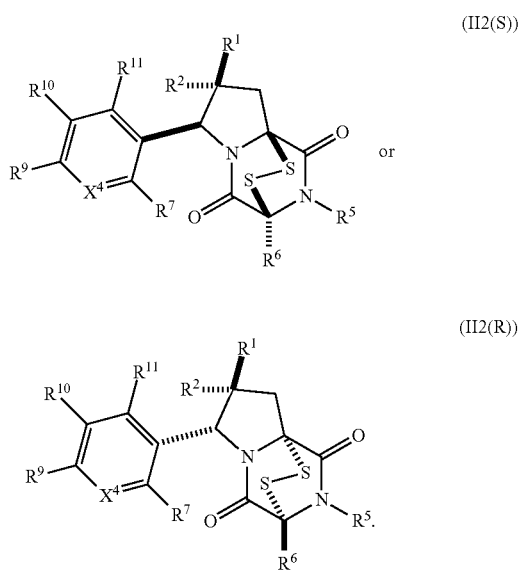

(II2(S))

or (II2(R))

The compound of formula (II) may have the formula:

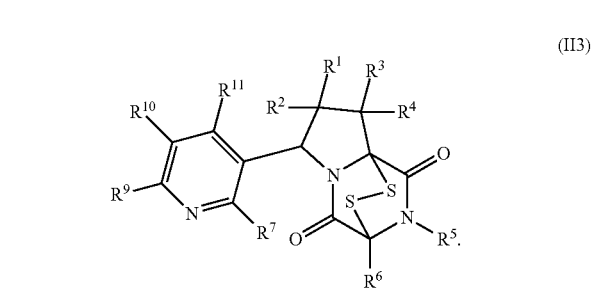

(II3)

The compound of formula (II3) may have the formula:

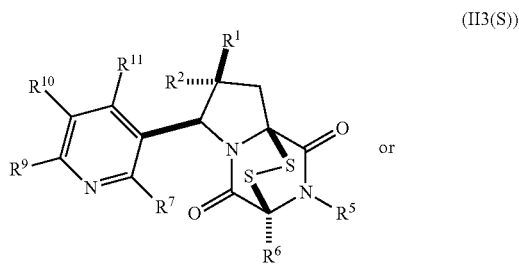

(II3(S))

or

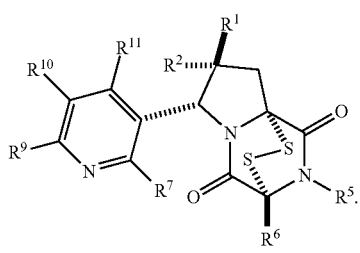

(II3(R))

The compound of formula (II) may have the formula:

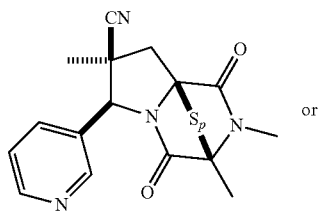

(II4)

or

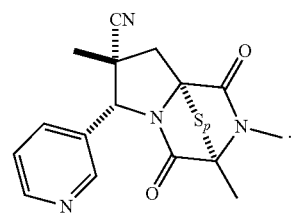

(II5)

The compound of formula (I) may have the formula:

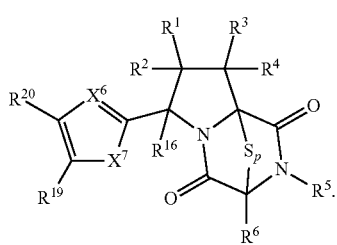

(III)

The symbol p, $R^1$, $R^2$, $R^3$, $R^4$, $R^5$, $R^6$, and $R^{16}$ are as described herein, including embodiments thereof. $R^5$ and $R^6$ may independently be unsubstituted $C_1$-$C_3$ alkyl or unsubstituted 3 to 5 membered cycloalkyl. $R^7$, $R^8$, $R^9$, and $R^{10}$ may independently be hydrogen, halogen, unsubstituted methyl, —$OCH_3$ or —$O(CH_2)_2$=$CH_2$. $R^1$ may be —CN or unsubstituted 2 to 5 membered heteroalkyl. $R^1$ may be —CN. $R^1$ may be —$COOCH_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ may be hydrogen. $R^{10}$ and $R^{11}$ may be hydrogen.

$X^6$ is $CR^{21}$ or N. $X^7$ is $CR^{22}R^{23}$, S, O, or $NR^{23}$. $R^{19}$, $R^{20}$, $R^{21}$, $R^{22}$ and $R^{23}$ are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —$NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n13 is 1 or 2.

$R^{19}$, $R^{20}$, $R^{21}$, $R^{22}$ and $R^{23}$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$. $R^{19}$, $R^{20}$, $R^{21}$, $R^{22}$ and $R^{23}$ may independently be substituted or unsubstituted $C_1$-$C_8$ alkyl, substituted or unsubstituted 2 to 8 membered heteroalkyl, substituted or unsubstituted 3 to 6 membered cycloalkyl, substituted or unsubstituted 3 to 6 membered heterocycloalkyl, substituted or unsubstited 5 to 6 membered aryl, substituted or unsubstituted 5 to 6 membered heteroaryl. $R^{19}$, $R^{20}$, $R^{21}$, $R^{22}$ and $R^{23}$ may be fused to form a substituted or unsubstituted 5 or 6 membered heterocycloalkyl, a substituted or unsubstituted 5 or 6 membered aryl, or a substituted or unsubstituted 5 or 6 membered heteroaryl.

$R^{19}$, $R^{20}$, $R^{21}$, $R^{22}$ and $R^{23}$ may independently be substituted or unsubstituted alkyl. $R^{19}$, $R^{20}$, $R^{21}$, $R^{22}$ and $R^{23}$ may independently be substituted or unsubstituted $C_1$-$C_8$ alkyl. $R^{19}$, $R^{20}$, $R^{21}$, $R^{22}$ and $R^{23}$ may independently be substituted or unsubstituted $C_1$-$C_5$ alkyl. $R^{19}$, $R^{20}$, $R^{21}$, $R^{22}$ and $R^{23}$ may independently be substituted or unsubstituted $C_1$-$C_3$ alkyl. $R^{19}$, $R^{20}$, $R^{21}$, $R^{22}$ and $R^{23}$ may independently be $R^{37a}$-substituted or unsubstituted alkyl. $R^{19}$, $R^{20}$, $R^{21}$, $R^{22}$ and $R^{23}$ may independently be $R^{37a}$-substituted or unsubstituted $C_1$-$C_8$ alkyl. $R^{19}$, $R^{20}$, $R^{21}$, $R^{22}$ and $R^{23}$ may independently be $R^{37a}$-substituted or unsubstituted $C_1$-$C_5$ alkyl. $R^{19}$, $R^{20}$, $R^{21}$, $R^{22}$ and $R^{23}$ may independently be $R^{37a}$-substituted or unsubstituted $C_1$-$C_3$ alkyl.

$R^{19}$, $R^{20}$, $R^{21}$, $R^{22}$ and $R^{23}$ may independently be substituted or unsubstituted heteroalkyl. $R^{19}$, $R^{20}$, $R^{21}$, $R^{22}$ and $R^{23}$ may independently be substituted or unsubstituted 2 to 8 membered heteroalkyl. $R^{19}$, $R^{20}$, $R^{21}$, $R^{22}$ and $R^{23}$ may independently be substituted or unsubstituted 2 to 5 membered heteroalkyl. $R^{19}$, $R^{20}$, $R^{21}$, $R^{22}$ and $R^{23}$ may independently be substituted or unsubstituted 2 to 3 membered heteroalkyl. $R^{19}$, $R^{20}$, $R^{21}$, $R^{22}$ and $R^{23}$ may independently be $R^{37a}$-substituted or unsubstituted heteroalkyl. $R^{19}$, $R^{20}$, $R^{21}$, $R^{22}$ and $R^{23}$ may independently be $R^{37a}$-substituted or unsubstituted 2 to 8 membered heteroalkyl. $R^{19}$, $R^{20}$, $R^{21}$, $R^{22}$ and $R^{23}$ may independently be $R^{37a}$-substituted or unsubstituted 2 to 5 membered heteroalkyl. $R^{19}$, $R^{20}$, $R^{21}$, $R^{22}$ and $R^{23}$ may independently be $R^{37a}$-substituted or unsubstituted 2 to 3 membered heteroalkyl.

$R^{19}$, $R^{20}$, $R^{21}$, $R^{22}$ and $R^{23}$ may independently be substituted or unsubstituted cycloalkyl. $R^{19}$, $R^{20}$, $R^{21}$, $R^{22}$ and $R^{23}$ may independently be substituted or unsubstituted 3 to 8 membered cycloalkyl. $R^{19}$, $R^{20}$, $R^{21}$, $R^{22}$ and $R^{23}$ may independently be substituted or unsubstituted 3 to 5 membered cycloalkyl. $R^{19}$, $R^{20}$, $R^{21}$, $R^{22}$ and $R^{23}$ may independently be substituted or unsubstituted 3 membered cycloalkyl. $R^{19}$, $R^{20}$, $R^{21}$, $R^{22}$ and $R^{23}$ may independently be substituted or unsubstituted 4 membered cycloalkyl. $R^{19}$, $R^{20}$, $R^{21}$, $R^{22}$ and $R^{23}$ may independently be substituted or unsubstituted 5 membered cycloalkyl. $R^{19}$, $R^{20}$, $R^{21}$, $R^{22}$ and $R^{23}$ may independently be $R^{37a}$-substituted or unsubstituted cycloalkyl. $R^{19}$, $R^{20}$, $R^{21}$, $R^{22}$ and $R^{23}$ may independently be $R^{37a}$-substituted or unsubstituted 3 to 8 membered cycloalkyl. $R^{19}$, $R^{20}$, $R^{21}$, $R^{22}$ and $R^{23}$ may independently be $R^{37a}$-substituted or unsubstituted 3 to 5 membered cycloalkyl. $R^{19}$, $R^{20}$, $R^{21}$, $R^{22}$ and $R^{23}$ may independently be $R^{37a}$-substituted or unsubstituted 3 membered cycloalkyl. $R^{19}$, $R^{20}$, $R^{21}$, $R^{22}$ and $R^{23}$ may independently be $R^{37a}$-substituted or unsubstituted 4 membered cycloalkyl. $R^{19}$, $R^{20}$, $R^{21}$, $R^{22}$ and $R^{23}$ may independently be $R^{37a}$-substituted or unsubstituted 5 membered cycloalkyl.

$R^{19}$, $R^{20}$, $R^{21}$, $R^{22}$ and $R^{23}$ may independently be substituted or unsubstituted heterocycloalkyl. $R^{19}$, $R^{20}$, $R^{21}$, $R^{22}$ and $R^{23}$ may independently be substituted or unsubstituted 3 to 6 membered heterocycloalkyl. $R^{19}$, $R^{20}$, $R^{21}$, $R^{22}$ and $R^{23}$ may independently be substituted or unsubstituted 4 membered heterocycloalkyl. $R^{19}$, $R^{20}$, $R^{21}$, $R^{22}$ and $R^{23}$ may independently be substituted or unsubstituted 5 membered heterocycloalkyl. $R^{19}$, $R^{20}$, $R^{21}$, $R^{22}$ and $R^{23}$ may independently be substituted or unsubstituted 6 membered heterocycloalkyl. $R^{19}$, $R^{20}$, $R^{21}$, $R^{22}$ and $R^{23}$ may independently be $R^{37a}$-substituted or unsubstituted heterocycloalkyl. $R^{19}$, $R^{20}$, $R^{21}$, $R^{22}$ and $R^{23}$ may independently be $R^{37a}$-substituted or unsubstituted 3 to 6 membered heterocycloalkyl. $R^{19}$, $R^{20}$, $R^{21}$, $R^{22}$ and $R^{23}$ may independently be $R^{37a}$-substituted or unsubstituted 4 membered heterocycloalkyl. $R^{19}$, $R^{20}$, $R^{21}$, $R^{22}$ and $R^{23}$ may independently be $R^{37a}$-substituted or unsubstituted 5 membered heterocycloalkyl. $R^{19}$, $R^{20}$, $R^{21}$, $R^{22}$ and $R^{23}$ may independently be $R^{37a}$-substituted or unsubstituted 6 membered heterocycloalkyl.

$R^{19}$, $R^{20}$, $R^{21}$, $R^{22}$ and $R^{23}$ may independently be substituted or unsubstituted aryl. $R^{19}$, $R^{20}$, $R^{21}$, $R^{22}$ and $R^{23}$ may independently be substituted or unsubstituted 5 to 6 membered aryl. $R^{19}$, $R^{20}$, $R^{21}$, $R^{22}$ and $R^{23}$ may independently be substituted or unsubstituted 5 membered aryl. $R^{19}$, $R^{20}$, $R^{21}$, $R^{22}$ and $R^{23}$ may independently be substituted or unsubstituted 6 membered aryl. $R^{19}$, $R^{20}$, $R^{21}$, $R^{22}$ and $R^{23}$ may independently be $R^{37a}$-substituted or unsubstituted aryl. $R^{19}$, $R^{20}$, $R^{21}$, $R^{22}$ and $R^{23}$ may independently be $R^{37a}$-substituted or unsubstituted 5 to 6 membered aryl. $R^{19}$, $R^{20}$, $R^{21}$, $R^{22}$ and $R^{23}$ may independently be $R^{37a}$-substituted or unsubstituted 5 membered aryl. $R^{19}$, $R^{20}$, $R^{21}$, $R^{22}$ and $R^{23}$ may independently be $R^{37a}$-substituted or unsubstituted 6 membered aryl. $R^{19}$, $R^{20}$, $R^{21}$, $R^{22}$ and $R^{23}$ may independently be substituted or unsubstituted heteroaryl. $R^{19}$, $R^{20}$, $R^{21}$, $R^{22}$ and $R^{23}$ may independently be substituted or unsubstituted 5 to 6 membered heteroaryl. $R^{19}$, $R^{20}$, $R^{21}$, $R^{22}$ and $R^{23}$ may independently be substituted or unsubstituted 5 membered heteroaryl. $R^{19}$, $R^{20}$, $R^{21}$, $R^{22}$ and $R^{23}$ may independently be substituted or unsubstituted 6 membered heteroaryl. $R^{19}$, $R^{20}$, $R^{21}$, $R^{22}$ and $R^{23}$ may independently be $R^{37a}$-substituted or unsubstituted heteroaryl. $R^{19}$, $R^{20}$, $R^{21}$, $R^{22}$ and $R^{23}$ may independently be $R^{37a}$-substituted or unsubstituted 5 to 6 membered heteroaryl. $R^{19}$, $R^{20}$, $R^{21}$, $R^{22}$ and $R^{23}$ may independently be $R^{37a}$-substituted or unsubstituted 5 membered heteroaryl. $R^{19}$, $R^{20}$, $R^{21}$, $R^{22}$ and $R^{23}$ may independently be $R^{37a}$-substituted or unsubstituted 6 membered heteroaryl. $R^{37a}$ is as described herein, including embodiments thereof.

$R^{19}$ and $R^{20}$ may optionally be bonded together to form a substituted or unsubstituted 3 to 6 membered cycloalkyl, substituted or unsubstituted 3 to 6 membered heterocycloalkyl, substituted or unsubstituted 5 to 6 membered aryl, or substituted or unsubstituted 5 to 6 membered heteroaryl.

$R^{19}$ and $R^{22}$ may optionally be bonded together to form a substituted or unsubstituted 3 to 6 membered cycloalkyl, substituted or unsubstituted 3 to 6 membered heterocycloalkyl, substituted or unsubstituted 5 to 6 membered aryl, or substituted or unsubstituted 5 to 6 membered heteroaryl.

$R^{20}$ and $R^{21}$ may optionally be bonded together to form a substituted or unsubstituted 3 to 6 membered cycloalkyl, substituted or unsubstituted 3 to 6 membered heterocycloalkyl, substituted or unsubstituted 5 to 6 membered aryl, or substituted or unsubstituted 5 to 6 membered heteroaryl.

When $X^7$ is S, $X^6$ may be N or $CR^{21}$. When $X^7$ is NH, $X^6$ may be N or $CR^{21}$. When $X^7$ is $NR^{23}$, $X^6$ may $CR^{21}$ or N. When $X^7$ is O, $X^6$ may be N, CH, or $CR^{21}$. In certain embodiments, $X^7$ is S and $X^6$ is CH. p may be 2, 3, or 4. In certain embodiments p is 2.

The compound of formula (III) may have the formula:

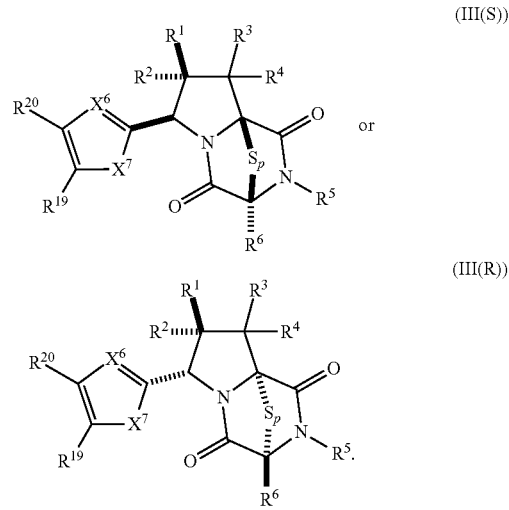

The compound of formula (III) may have the formula:

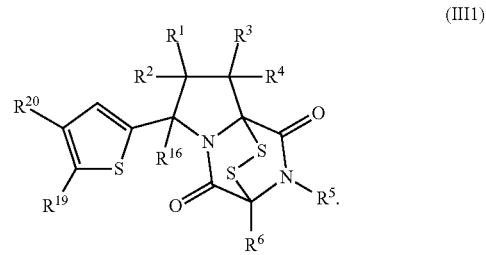

The compound of formula (III1) may have the formula:

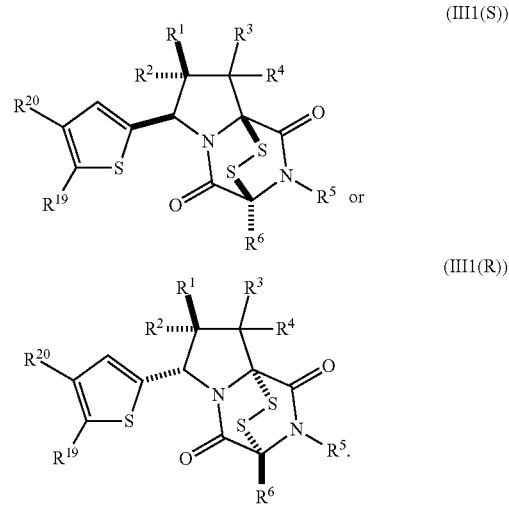

The compound of formula (III) may have the formula:

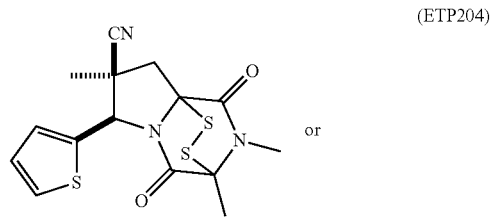

-continued

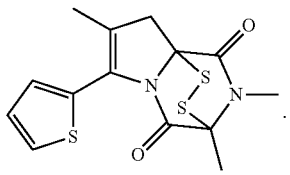

(ETP206)

The compound of formula (I) may have the formula:

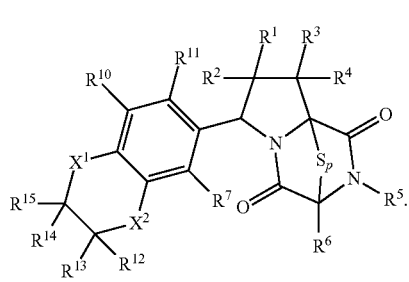

(IV)

The symbol p, $R^1$, $R^2$, $R^3$, $R^4$, $R^5$, $R^6$, $R^7$, $R^{10}$, $R^{11}$, and $R^{16}$ are as described herein, including embodiments thereof. $R^{12}$, $R^{13}$, $R^{14}$, $R^{15}$ $R^{21}$ $R^{21A}$, $R^{22}$, and $R^{22A}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{33M}R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n13 is 1 or 2.

$X^1$ is $CR^{21}R^{21A}$, O, $NR^{21A}$, or S. $X^2$ is $CR^{22}R^{22A}$, O, $NR^{22A}$, or S. $R^5$ and $R^6$ may independently be unsubstituted $C_1$-$C_3$ alkyl or unsubstituted 3 to 5 membered cycloalkyl. $R^7$, $R^8$, $R^9$, and $R^{10}$ may independently be hydrogen, halogen, unsubstituted methyl, $-OCH_3$ or $-O(CH_2)_2=CH_2$. $R^1$ may be $-CN$ or unsubstituted 2 to 5 membered heteroalkyl. $R^1$ may be $-CN$. $R^1$ may be $-COOCH_3$. $R^1$ may be unsubstituted methyl. $R^2$ may be $C_1$-$C_3$ unsubstituted alkyl. When $R^1$ is $-CN$, $R^2$ may be unsubstituted methyl. $R^3$ and $R^4$ may be hydrogen. $R^{10}$ and $R^{11}$ may be hydrogen. $R^{12}$, $R^{13}$, $R^{14}$, and $R^{15}$ may be hydrogen.

$R^{12}$, $R^{13}$, $R^{14}$, $R^{15}$ $R^{21}$, $R^{21A}$, $R^{22}$, and $R^{22A}$ may independently be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$. $R^{12}$, $R^{13}$, $R^{14}$, $R^{15}$ $R^{21}$, $R^{21A}$, $R^{22}$, and $R^{22A}$ may independently be substituted or unsubstituted $C_1$-$C_8$ alkyl, substituted or unsubstituted 2 to 8 membered heteroalkyl, substituted or unsubstituted 3 to 6 membered cycloalkyl, substituted or unsubstituted 3 to 6 membered heterocycloalkyl, substituted or unsubstited 5 to 6 membered aryl, substituted or unsubstituted 5 to 6 membered heteroaryl. $R^{12}$, $R^{13}$, $R^{14}$, $R^{15}$ $R^{21}$, $R^{21A}$, $R^{22}$, and $R^{22A}$ may be fused to form a substituted or unsubstituted 5 or 6 membered heterocycloalkyl, a substituted or unsubstituted 5 or 6 membered aryl, or a substituted or unsubstituted 5 or 6 membered heteroaryl.

$R^{12}$, $R^{13}$, $R^{14}$, and $R^{15}$ may independently be substituted or unsubstituted alkyl. $R^{12}$, $R^{13}$, $R^{14}$, $R^{15}$ $R^{21}$, $R^{21A}$, $R^{22}$, and $R^{22A}$ may independently be substituted or unsubstituted $C_1$-$C_8$ alkyl. $R^{12}$, $R^{13}$, $R^{14}$, $R^{15}$ $R^{21}$, $R^{21A}$, $R^{22}$, and $R^{22A}$ may independently be substituted or unsubstituted $C_1$-$C_5$ alkyl. $R^{12}$, $R^{13}$, $R^{14}$, $R^{15}$ $R^{21}$, $R^{21A}$, $R^{22}$, and $R^{22A}$ may independently be substituted or unsubstituted $C_1$-$C_3$ alkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted alkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted $C_1$-$C_8$ alkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted $C_1$-$C_5$ alkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted $C_1$-$C_3$ alkyl.

$R^{12}$, $R^{13}$, $R^{14}$, $R^{15}$ $R^{21}$, $R^{21A}$, $R^{22}$, and $R^{22A}$ may independently be substituted or unsubstituted heteroalkyl. $R^{12}$, $R^{13}$, $R^{14}$, $R^{15}$ $R^{21}$, $R^{21A}$, $R^{22}$, and $R^{22A}$ may independently be substituted or unsubstituted 2 to 8 membered heteroalkyl. $R^{12}$, $R^{13}$, $R^{14}$, $R^{15}$ $R^{21}$, $R^{21A}$, $R^{22}$, and $R^{22A}$ may independently be substituted or unsubstituted 2 to 5 membered heteroalkyl. $R^{12}$, $R^{13}$, $R^{14}$, $R^{15}$ $R^{21}$, $R^{21A}$, $R^{22}$, and $R^{22A}$ may independently be substituted or unsubstituted 2 to 3 membered heteroalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted heteroalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 2 to 8 membered heteroalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 2 to 5 membered heteroalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 2 to 3 membered heteroalkyl.

$R^{12}$, $R^{13}$, $R^{14}$, $R^{15}$ $R^{21}$, $R^{21A}$, $R^{22}$, and $R^{22A}$ may independently be substituted or unsubstituted cycloalkyl. $R^{12}$, $R^{13}$, $R^{14}$, $R^{15}$ $R^{21}$, $R^{21A}$, $R^{22}$, and $R^{22A}$ may independently be substituted or unsubstituted 3 to 8 membered cycloalkyl. $R^{12}$, $R^{13}$, $R^{14}$, $R^{15}$ $R^{21}$, $R^{21A}$, $R^{22}$, and $R^{22A}$ may independently be substituted or unsubstituted 3 to 5 membered cycloalkyl. $R^{12}$, $R^{13}$, $R^{14}$, $R^{15}$ $R^{21}$, $R^{21A}$, $R^{22}$, and $R^{22A}$ may independently be substituted or unsubstituted 3 membered cycloalkyl. $R^{12}$, $R^{13}$, $R^{14}$, $R^{15}$ $R^{21}$, $R^{21A}$, $R^{22}$, and $R^{22A}$ may independently be substituted or unsubstituted 4 membered cycloalkyl. $R^{12}$, $R^{13}$, $R^{14}$, $R^{15}$ $R^{21}$, $R^{21A}$, $R^{22}$, and $R^{22A}$ may independently be substituted or unsubstituted 5 membered cycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted cycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 3 to 8 membered cycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 3 to 5 membered cycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 3 membered cycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 4 membered cycloalkyl. $R^{12}$, $R^{13}$, $R^{14}$, $R^{15}$ $R^{21}$ $R^{21A}$, $R^{22}$, and $R^{22A}$ may independently be $R^{37a}$-substituted or unsubstituted 5 membered cycloalkyl.

$R^{12}$, $R^{13}$, $R^{14}$, $R^{15}$ $R^{21}$, $R^{21A}$, $R^{22}$, and $R^{22A}$ may independently be substituted or unsubstituted heterocycloalkyl. $R^{12}$, $R^{13}$, $R^{14}$, $R^{15}$ $R^{21}$, $R^{21A}$, $R^{22}$, and $R^{22A}$ may independently be substituted or unsubstituted 3 to 6 membered heterocycloalkyl. $R^{12}$, $R^{13}$, $R^{14}$, $R^{15}$ $R^{21}$, $R^{21A}$, $R^{22}$, and $R^{22A}$ may independently be substituted or unsubstituted 4 membered heterocycloalkyl. $R^{12}$, $R^{13}$, $R^{14}$, $R^{15}$ $R^{21}$, $R^{21A}$, $R^{22}$, and $R^{22A}$ may independently be substituted or unsubstituted 5 membered heterocycloalkyl. $R^{12}$, $R^{13}$, $R^{14}$, $R^{15}$ $R^{21}$, $R^{21A}$, $R^{22}$, and $R^{22A}$ may independently be substituted or unsubstituted 6 membered heterocycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted heterocycloalkyl. $R^{12}$, $R^{13}$, $R^{14}$, $R^{15}$ $R^{21}$, $R^{21A}$ $R^{22}$, and $R^{22A}$ may independently be $R^{37a}$-substituted or unsubstituted 3 to 6 membered heterocycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 4 membered heterocycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 5 membered heterocycloalkyl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 6 membered heterocycloalkyl.

$R^{12}$, $R^{13}$, $R^{14}$, $R^{15}$ $R^{21}$, $R^{21A}$, $R^{22}$, and $R^{22A}$ may independently be substituted or unsubstituted aryl. $R^{12}$, $R^{13}$, $R^{14}$, $R^{15}$ $R^{21}$, $R^{21A}$, $R^{22}$, and $R^{22A}$ may independently be substituted or unsubstituted 5 to 6 membered aryl. $R^{12}$, $R^{13}$, $R^{14}$, $R^{15}$ $R^{21}$, $R^{21A}$, $R^{22}$, and $R^{22A}$ may independently be substituted or unsubstituted 5 membered aryl. $R^{12}$, $R^{13}$, $R^{14}$, $R^{15}$ $R^{21}$, $R^{21A}$, $R^{22}$, and $R^{22A}$ may independently be substituted or unsubstituted 6 membered aryl. $R^{12}$, $R^{13}$, $R^{14}$, $R^{15}$ $R^{21}$, $R^{21A}$, $R^{22}$ and $R^{22A}$ may independently be $R^{37a}$-substituted or unsubstituted aryl. $R^{12}$, $R^{13}$, $R^{14}$, $R^{15}$ $R^{21}$, $R^{21A}$ $R^{22}$, and $R^{22A}$ may independently be $R^{37a}$-substituted or unsubstituted 5 to 6 membered aryl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 5 membered aryl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 6 membered aryl. $R^{12}$, $R^{13}$, $R^{14}$, $R^{15}$ $R^{21}$, $R^{21A}$, $R^{22}$, and $R^{22A}$ may independently be substituted or unsubstituted heteroaryl. $R^{12}$, $R^{13}$, $R^{14}$, $R^{15}$ $R^{21}$, $R^{21A}$, $R^{22}$, and $R^{22A}$ may independently be substituted or unsubstituted 5 to 6 membered heteroaryl. $R^{12}$, $R^{13}$, $R^{14}$, $R^{15}$ $R^{21}$, $R^{21A}$, $R^{22}$, and $R^{22A}$ may independently be substituted or unsubstituted 5 membered heteroaryl. $R^{12}$, $R^{13}$, $R^{14}$, $R^{15}$ $R^{21}$, $R^{21A}$, $R^{22}$, and $R^{22A}$ may independently be substituted or unsubstituted 6 membered heteroaryl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted heteroaryl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 5 to 6 membered heteroaryl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 5 membered heteroaryl. $R^{12}$, $R^{13}$, $R^{14}$, $R^{15}$ $R^{21}$, $R^{21A}$, $R^{22}$, and $R^{22A}$ may independently be $R^{37a}$-substituted or unsubstituted 6 membered heteroaryl.

The compound of formula (IV) may have the formula:

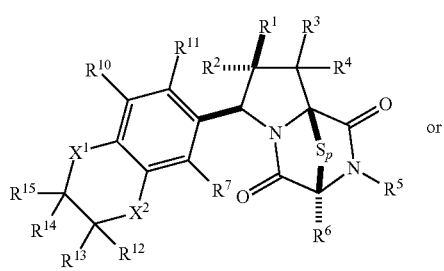

(IV(S))

or

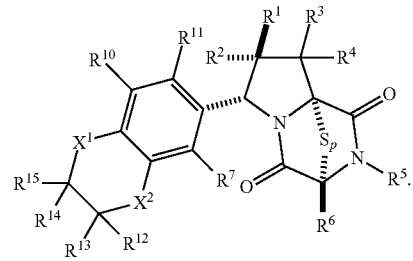

(IV(R))

The compound of formula (IV) may have the formula:

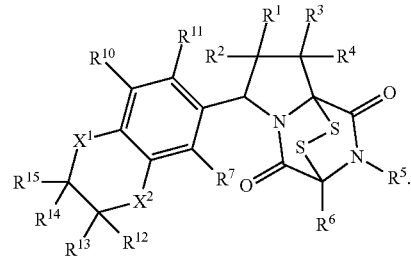

(IV1)

The compound of formula (IV1) may have the formula:

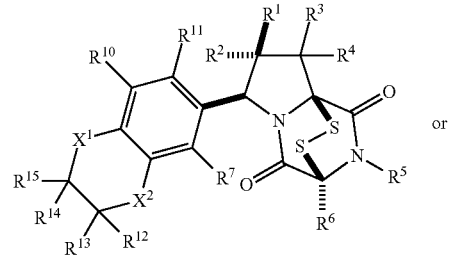

(IV1(S))

or

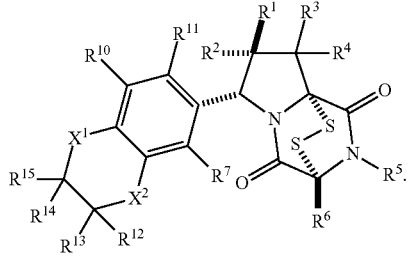

(IV1(R))

The compound of formula (IV1) may have the formula:

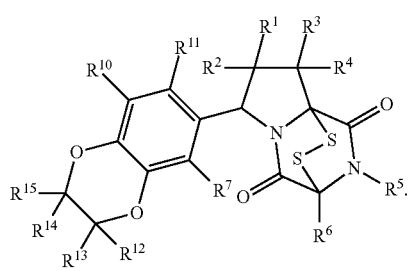

(IV2)

The compound of formula (IV2) may have the formula:

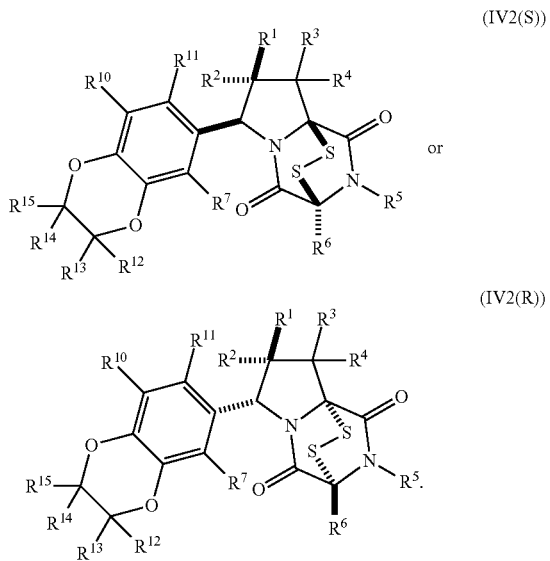

The compound of formula (I) may have the formula:

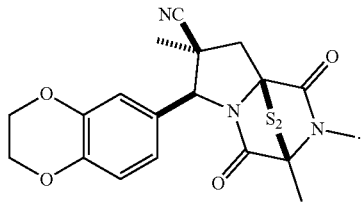

$X^1$, $X^2$, p, $R^1$, $R^2$, $R^3$, $R^4$, $R^5$, $R^6$, $R^7$, $R^{10}$, $R^{11}$ $R^{12}$, $R^{13}$, and $R^{16}$ are as described herein, including embodiments thereof.

In embodiments $R^7$ is hydrogen, halogen, —$N_3$, —$CF_3$, —$CCl_3$, —$CBr_3$, —$CI_3$, —CN, —CHO, —$OR^{33I}$, —$NR^{34I}R^{35I}$, —$COOR^{33I}$, —$CONR^{34I}R^{35I}$, —$NO_2$, —$SR^{36I}$, —$SO_{n9}R^{34I}$, —$SO_{n9}OR^{34I}$, —$SO_{n9}NR^{34I}R^{35I}$, —$NHNR^{34I}R^{35I}$, —$ONR^{34I}R^{35I}$, —NHC(O)NHNR$^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments $R^{10}$ and $R^{11}$ are independently hydrogen, halogen, —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —NHC(O)NHNR$^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl. In embodiments, $R^{12}$, $R^{13}$, $R^{21}$, $R^{21A}$, $R^{22}$ and $R^{22A}$ are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —NHC(O)NHNR$^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{33M}R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n9, n11, and n13 may independently be 1 or 2.

$R^5$ and $R^6$ may independently be unsubstituted $C_1$-$C_3$ alkyl or unsubstituted 3 to 5 membered cycloalkyl. $R^7$, $R^{10}$, and $R^{11}$ may independently be hydrogen, halogen, unsubstituted methyl, —$OCH_3$ or —$O(CH_2)_2$=$CH_2$. $R^1$ may be —CN or unsubstituted 2 to 5 membered heteroalkyl. $R^1$ may be —CN. $R^1$ may be —$COOCH_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ may be hydrogen. $R^{10}$ and $R^{11}$ may be hydrogen. $R^{12}$ and $R^{13}$ may be hydrogen.

The compound of formula (V) may have the formula:

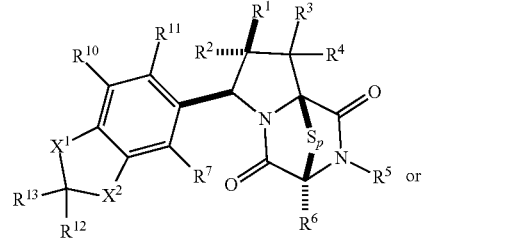

The compound of formula (V) may have the formula:

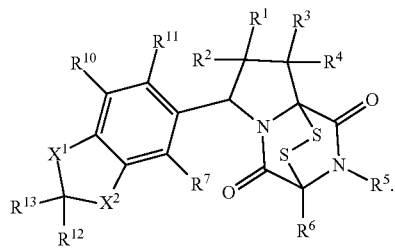

The compound of formula (V1) may have the formula:
(V1(S))
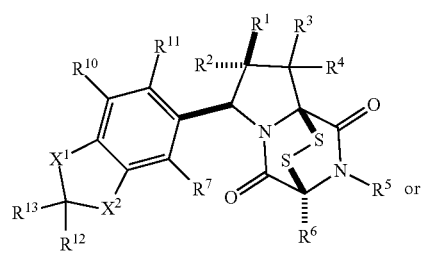
(V1(R))
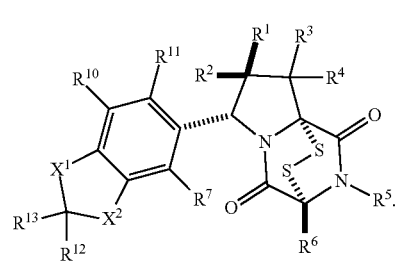
The compound of formula (V1) may have the formula:
(V2)
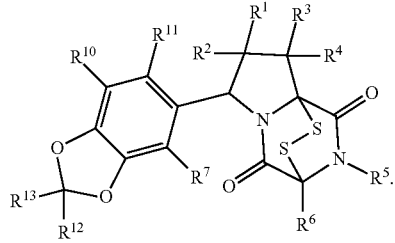
The compound of formula (V2) may have the formula:
(V2(S))
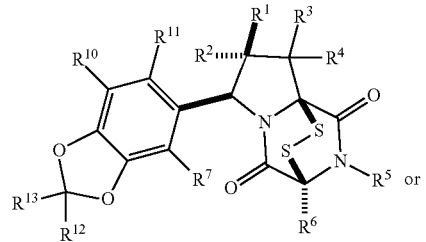
(V2(R))
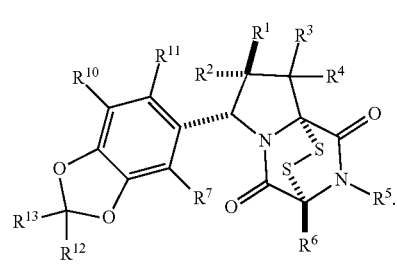
The compound of formula (V) may have the formula:
(V3)
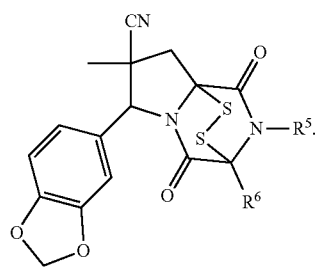
The compound of formula (V2) may have the formula:
(ETP69)
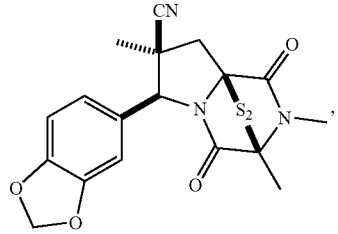
(ETP128)
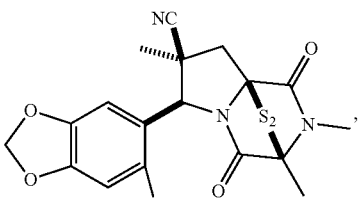
(ETP344)
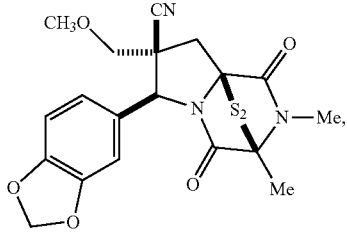
(ETP382)
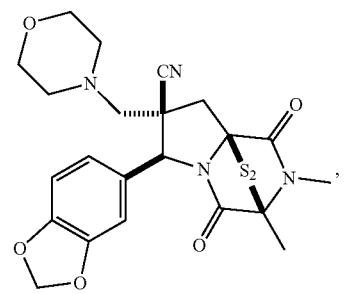
(ETP406)
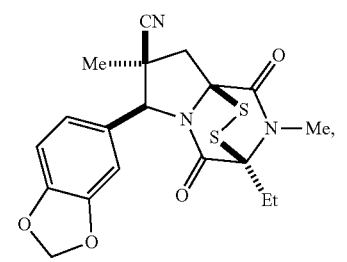

-continued (ETP417)
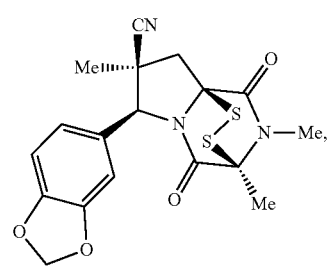

(ETP422)
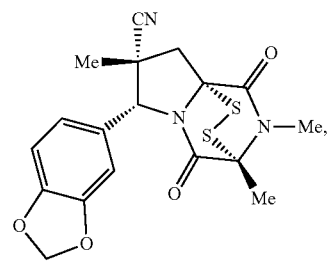

(ETP425)
(ETP452)
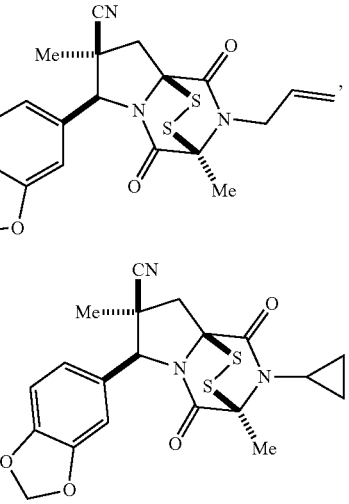

The compound of formula (V) may have the formula:

(ETP341)
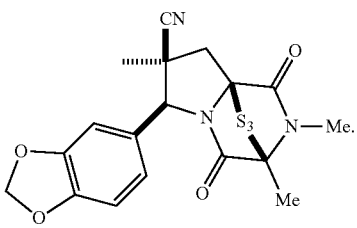

The compound of formula (V1) may have the formula:

(V4)
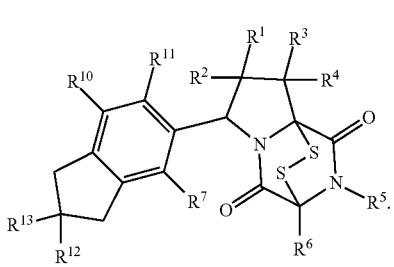

The compound of formula (V3) may have the formula:

(V4(S))

(V4(R))
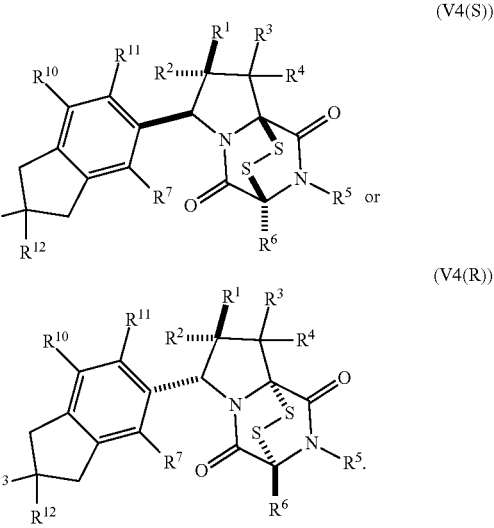

The compound of formula (V4) may have the formula:

(ETP493)
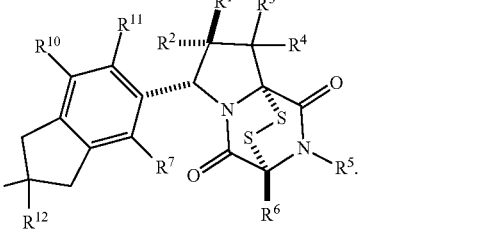

The compound of formula (I) may have the formula:

(VI)
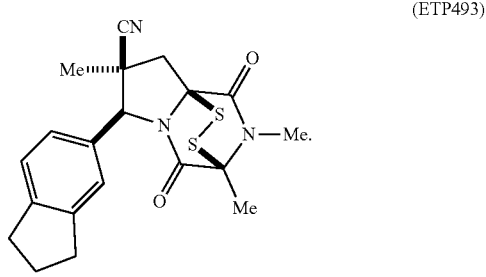

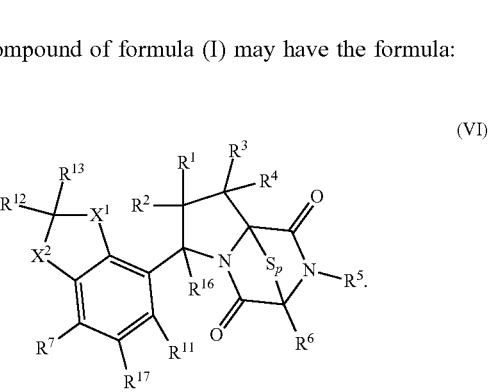

$X^1$, $X^2$, p, $R^1$, $R^2$, $R^3$, $R^4$, $R^5$, $R^6$, $R^7$, $R^{11}$, $R^{12}$, $R^{13}$, and $R^{16}$ are as described herein, including embodiments thereof. $R^{17}$ is hydrogen, halogen, —$N_3$, —$CF_3$, —$CCl_3$, —$CBr_3$, —$CI_3$, —CN, —CHO, —OR$^{33P}$, —NR$^{34P}$R$^{35P}$, —COOR$^{33P}$, —CONR$^{34P}$R$^{35P}$, —NO$_2$, —SR$^{36P}$, —SO$_{n15}$R$^{34P}$, —SO$_{n15}$OR$^{34P}$, —SO$_{n15}$NR$^{34P}$R$^{35P}$, —NHNR$^{34P}$R$^{35P}$, —ONR$^{34P}$R$^{35P}$, —NHC(O)NHNR$^{34P}$R$^{35P}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl. $R^{33I}$, $R^{34I}$, $R^{35I}$, $R^{36I}$, $R^{33L}$, $R^{34L}$, $R^{35L}$, $R^{36L}$, $R^{33M}$, $R^{34M}$, $R^{35M}$, $R^{36M}$, $R^{33P}$, $R^{34P}$, $R^{35P}$, and $R^{36P}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n9, n12, n13 and n15 are independently 1 or 2.

In embodiments $X^1$ is $CR^{21}R^{21A}$, O, $NR^{21A}$, or S. In embodiments $X^2$ is $CR^{22}R^{22A}$, O, $NR^{22A}$, or S. In embodiments $R^7$ is hydrogen, halogen, —$N_3$, —$CF_3$, —$CCl_3$, —$CBr_3$, —$CI_3$, —CN, —CHO, —$OR^{33I}$, —$NR^{34I}R^{35I}$, —$COOR^{33I}$, —$CONR^{34I}R^{35I}$, —$NO_2$, —$SR^{36I}$, —$SO_{n9}R^{34I}$, —$SO_{n9}OR^{34I}$, —$SO_{n9}NR^{34I}R^{35I}$, —$NHNR^{34I}R^{35I}$, —$ONR^{34I}R^{35I}$, —$NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments $R^{11}$ is hydrogen, halogen, —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —$NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl. In embodiments, $R^{12}$, $R^{13}$, $R^{21}$, $R^{21A}$, $R^{22}$, and $R^{22A}$ are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —$NHNR^{34M}R^{35M}$, —$ONR^{34M}R^{35M}$, —$NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ and $R^6$ may independently be unsubstituted $C_1$-$C_3$ alkyl or unsubstituted 3 to 5 membered cycloalkyl. $R^7$, $R^{10}$, and $R^{11}$ may independently be hydrogen, halogen, unsubstituted methyl, —$OCH_3$ or —$O(CH_2)_2$=$CH_2$. $R^1$ may be —CN or unsubstituted 2 to 5 membered heteroalkyl. $R^1$ may be —CN. $R^1$ may be —$COOCH_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ may be hydrogen. $R^{10}$ and $R^{11}$ may be hydrogen. $R^{12}$ and $R^{13}$ may be hydrogen. $R^7$, $R^{10}$, and $R^{17}$ may be hydrogen.

$R^{17}$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$. $R^{17}$ may be substituted or unsubstituted alkyl. $R^{17}$ may be substituted or unsubstituted $C_1$-$C_8$ alkyl. $R^{17}$ may be substituted or unsubstituted $C_1$-$C_5$ alkyl. $R^{17}$ may be substituted or unsubstituted $C_1$-$C_3$ alkyl. $R^1$ may be $R^{17a}$-substituted or unsubstituted alkyl. $R^{17}$ may be $R^{17a}$-substituted or unsubstituted $C_1$-$C_8$ alkyl. $R^1$ may be $R^{17a}$-substituted or unsubstituted $C_1$-$C_5$ alkyl. $R^{17}$ may be $R^{17a}$-substituted or unsubstituted $C_1$-$C_3$ alkyl.

$R^{17}$ may be substituted or unsubstituted heteroalkyl. $R^{17}$ may be substituted or unsubstituted 2 to 8 membered heteroalkyl. $R^{17}$ may be substituted or unsubstituted 2 to 5 membered heteroalkyl. $R^{17}$ may be substituted or unsubstituted 2 to 3 membered heteroalkyl. $R^{17}$ may be $R^{17a}$-substituted or unsubstituted heteroalkyl. $R^{17}$ may be $R^{17a}$-substituted or unsubstituted 2 to 8 membered heteroalkyl. $R^{17}$ may be $R^{17a}$-substituted or unsubstituted 2 to 5 membered heteroalkyl. $R^{17}$ may be $R^{17a}$-substituted or unsubstituted 2 to 3 membered heteroalkyl.

$R^{17}$ may be substituted or unsubstituted cycloalkyl. $R^{17}$ may be substituted or unsubstituted 3 to 8 membered cycloalkyl. $R^{17}$ may be substituted or unsubstituted 3 to 5 membered cycloalkyl. $R^{17}$ may be substituted or unsubstituted 3 membered cycloalkyl. $R^{17}$ may be substituted or unsubstituted 4 membered cycloalkyl. $R^{17}$ may be substituted or unsubstituted 5 membered cycloalkyl. $R^{17}$ may be $R^{17a}$-substituted or unsubstituted cycloalkyl. $R^{17}$ may be $R^{17a}$-substituted or unsubstituted 3 to 8 membered cycloalkyl. $R^{17}$ may be $R^{17a}$-substituted or unsubstituted 3 to 5 membered cycloalkyl. $R^{17}$ may be $R^{17a}$-substituted or unsubstituted 3 membered cycloalkyl. $R^{17}$ may be $R^{17a}$-substituted or unsubstituted 4 membered cycloalkyl. $R^{17}$ may be $R^{17a}$-substituted or unsubstituted 5 membered cycloalkyl.

$R^{17}$ may be substituted or unsubstituted heterocycloalkyl. $R^{17}$ may be substituted or unsubstituted 3 to 6 membered heterocycloalkyl. $R^{17}$ may be substituted or unsubstituted 4 membered heterocycloalkyl. $R^{17}$ may be substituted or unsubstituted 5 membered heterocycloalkyl. $R^{17}$ may be substituted or unsubstituted 6 membered heterocycloalkyl. $R^{17}$ may be $R^{17a}$-substituted or unsubstituted heterocycloalkyl. $R^{17}$ may be $R^{17a}$-substituted or unsubstituted 3 to 6 membered heterocycloalkyl. $R^{17}$ may be $R^{17a}$-substituted or unsubstituted 4 membered heterocycloalkyl. $R^{17}$ may be $R^{17a}$-substituted or unsubstituted 5 membered heterocycloalkyl. $R^{17}$ may be $R^{17a}$-substituted or unsubstituted 6 membered heterocycloalkyl.

$R^{17}$ may be substituted or unsubstituted aryl. $R^{17}$ may be substituted or unsubstituted 5 to 6 membered aryl. $R^{17}$ may be substituted or unsubstituted 5 membered aryl. $R^{17}$ may be substituted or unsubstituted 6 membered aryl. $R^{17}$ may be $R^{17a}$-substituted or unsubstituted aryl. $R^{17}$ may be $R^{17a}$-substituted or unsubstituted 5 to 6 membered aryl. $R^{17}$ may be $R^{17a}$-substituted or unsubstituted 5 membered aryl. $R^{17}$ may be $R^{17a}$-substituted or unsubstituted 6 membered aryl. $R^{17}$ may be substituted or unsubstituted heteroaryl. $R^{17}$ may be substituted or unsubstituted 5 to 6 membered heteroaryl. $R^{17}$ may be substituted or unsubstituted 5 membered heteroaryl. $R^{17}$ may be substituted or unsubstituted 6 membered heteroaryl. $R^{17}$ may be $R^{17a}$-substituted or unsubstituted heteroaryl. $R^{17}$ may be $R^{17a}$-substituted or unsubstituted 5 to 6 membered heteroaryl. $R^{17}$ may be $R^{17a}$-substituted or unsubstituted 5 membered heteroaryl. $R^{17}$ may be $R^{17a}$-substituted or unsubstituted 6 membered heteroaryl.

$R^{17a}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{17b}$-substituted or unsubstituted alkyl (e.g. $C_1$-$C_8$ alkyl), $R^{17b}$-substituted or unsubstituted heteroalkyl (e.g. 2 to 8 membered heteroalkyl), $R^{17b}$-substituted or unsubstituted cycloalkyl (e.g. $C_3$-$C_8$ cycloalkyl), $R^{17b}$-substituted or unsubstituted heterocycloalkyl (e.g. 3 to 6 membered heterocycloalkyl), $R^{17b}$-substituted or unsubstituted aryl (e.g. 5 or 6 membered aryl), or $R^{17b}$-substituted or unsubstituted heteroaryl (e.g. 5 or 6 membered heteroaryl).

$R^{17b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$-$C_8$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. 5 or 6 membered aryl), or unsubstituted heteroaryl (e.g. 5 or 6 membered heteroaryl).

The compound of formula (VI) may have the formula:

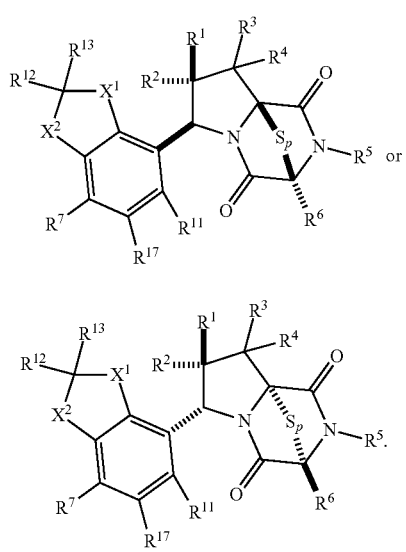

(VI(S))

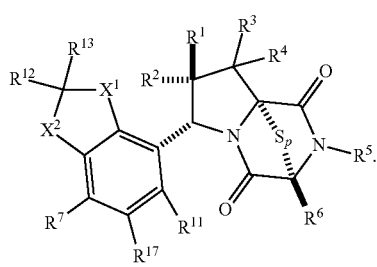

(VI(R))

The compound of formula (VI) may have the formula:

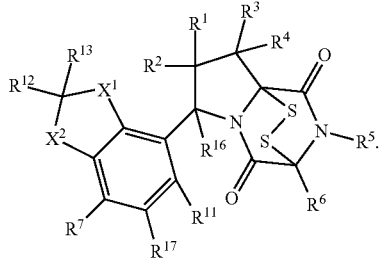

(VI1)

The compound of formula (VI1) may have the formula:

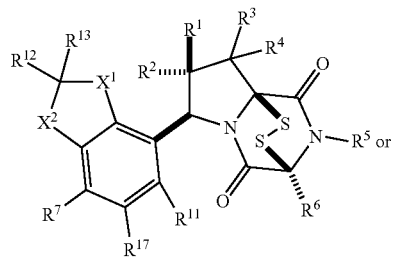

(VI1(S))

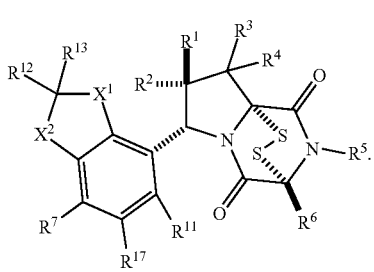

(VI1(R))

The compound of formula (VI) may have the formula:

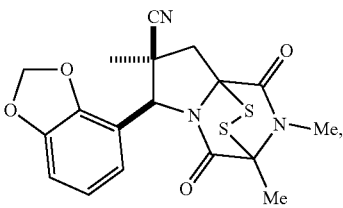

(ETP365)

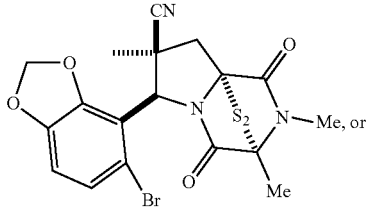

(ETP328)

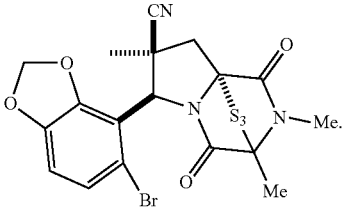

(ETP331)

In another aspect is a compound having the formula:

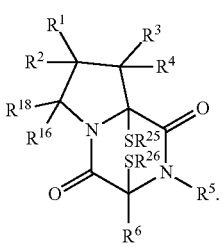

(VII)

$R^1$, $R^2$, $R^3$, $R^4$, $R^5$, $R^6$, $R^{16}$ and $R^{18}$ are as described herein, including embodiments thereof. $R^{25}$ and $R^{26}$ are independently hydrogen substituted or unsubstituted alkyl, substituted or unsubstituted heteroalkyl, substituted or unsubstituted aryl, or substituted or unsubstituted heteroaryl.

In embodiments, $R^{25}$ and $R^{26}$ are independently, hydrogen, trityl, para-methoxybenzyl, para-methylbenzyl, acetamidomethyl, tert-butyl, tert-butyl thiol, unsubstituted benzyl, unsubstituted methyl, phenylacyl, or unsubstituted benzyloxycarbonyl.

The compound of formula (VII) may have the formula:

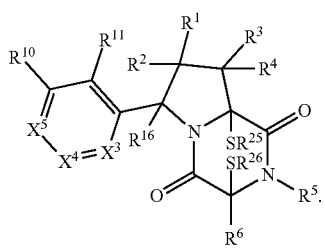

(VIII)

$X^3$, $X^4$, $X^5$ and $R^1$, $R^2$, $R^3$, $R^4$, $R^5$, $R^6$, $R^{10}$, $R^{11}$, $R^{16}$, $R^{25}$, and $R^{26}$ are as described herein, including embodiments thereof. $R^8$ and $R^9$ may be bound together to form an unsubstituted or $R^{31a}$-substituted 5 or 6 membered heterocycloalkyl. $R^8$ and $R^9$ may be oxo. $R^5$ and $R^6$ may independently be hydrogen, unsubstituted 3 to 5 membered cycloalkyl, or $R^{5a}$-substituted or unsubstituted $C_1$-$C_5$ alkyl. $R^{5a}$ may be unsubstituted 2 to 5 membered heteroalkyl or 5 to 6 membered heterocycloalkyl. $R^{5a}$ may be —N(CH$_3$)$_2$ or unsubstituted morpholino. $R^1$ may be —CN. $R^1$ may be —COOCH$_3$. $R^1$ may be unsubstituted methyl. $R^2$ may be $C_1$-$C_3$ unsubstituted alkyl. When $R^1$ is —CN, $R^2$ may be unsubstituted methyl. $R^{11}$ may be hydrogen or halogen.

The compound of formula (VIII) may have the formula:

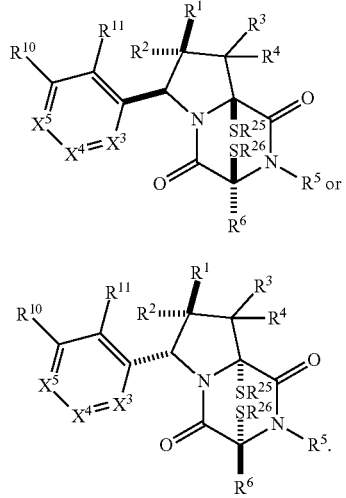

(VIII(S))

(VIII(R))

The compound of formula (III) may have the formula:

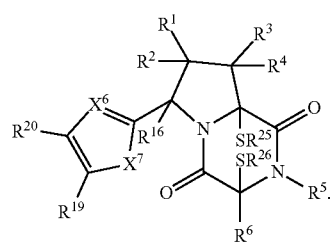

(IX)

$X^6$, $X^7$, $R^1$, $R^2$, $R^3$, $R^4$, $R^5$, $R^6$, $R^7$, $R^{19}$, $R^{20}$, $R^{25}$, and $R^{26}$ are as described herein, including embodiments thereof. $R^5$ and $R^6$ may independently be unsubstituted 3 to 5 membered cycloalkyl or $R^{5a}$-substituted or unsubstituted $C_1$-$C_5$ alkyl. $R^{5a}$ may be unsubstituted 2 to 5 membered heteroalkyl or 5 to 6 membered heterocycloalkyl. $R^{5a}$ may be —N(CH$_3$)$_2$ or unsubstituted morpholino. $R^1$ may be —CN. $R^1$ may be —COOCH$_3$. $R^1$ may be unsubstituted methyl. $R^2$ may be $C_1$-$C_3$ unsubstituted alkyl. When $R^1$ is —CN, $R^2$ may be unsubstituted methyl. $R^1$ may be hydrogen or halogen.

The compound of formula (IX) may have the formula:

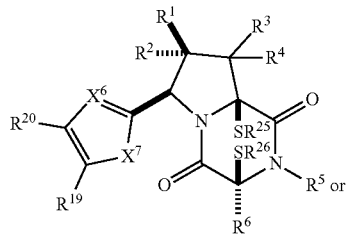

(IX(S))

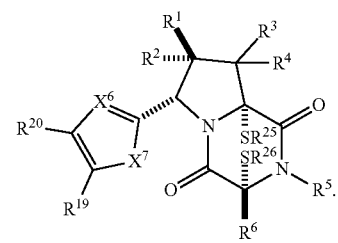

(IX(R))

The compound of formula (VII) may have the formula:

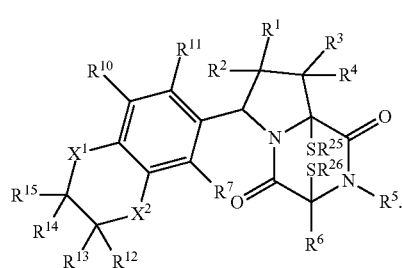

(X)

$X^1$, $X^2$, $R^1$, $R^2$, $R^3$, $R^4$, $R^5$, $R^6$, $R^7$, $R^{10}$, $R^{11}$, $R^{12}$, $R^{13}$, $R^{14}$, $R^{15}$, $R^{25}$, and $R^{26}$ are as described herein, including embodiments thereof. $R^5$ and $R^6$ may independently be unsubstituted 3 to 5 membered cycloalkyl or $R^{5a}$-substituted or unsubstituted $C_1$-$C_5$ alkyl. $R^{5a}$ may be unsubstituted 2 to 5 membered heteroalkyl or 5 to 6 membered heterocycloalkyl. $R^{5a}$ may be —N(CH$_3$)$_2$ or unsubstituted morpholino. $R^1$ may be —CN. $R^1$ may be —COOCH$_3$. $R^1$ may be unsubstituted methyl. $R^2$ may be $C_1$-$C_3$ unsubstituted alkyl. When $R^1$ is —CN, $R^2$ may be unsubstituted methyl. $R^{11}$ may be hydrogen or halogen.

The compound of formula (X) may have the formula:

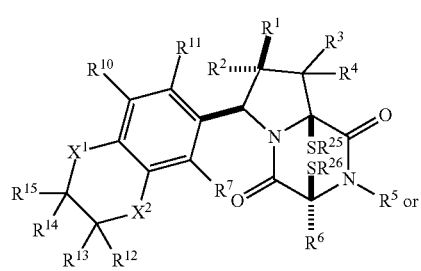

(X(S))

-continued

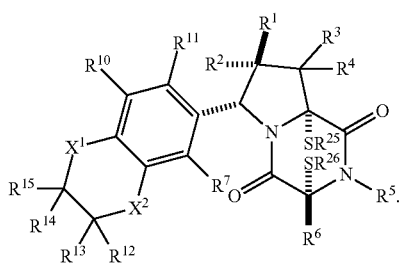
(X(R))

The compound of formula (VII) may have the formula:

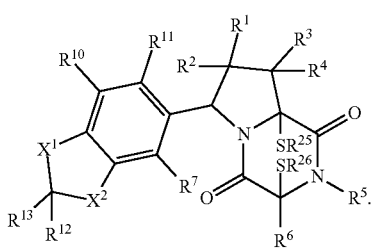
(XI)

$X^1, X^2, R^1, R^2, R^3, R^4, R^5, R^6, R^7, R^{10}, R^{11}, R^{12}, R^{13}, R^{25}$, and $R^{26}$ are as described herein, including embodiments thereof. $R^5$ and $R^6$ may independently be unsubstituted 3 to 5 membered cycloalkyl or $R^{5a}$-substituted or unsubstituted $C_1$-$C_5$ alkyl. $R^{5a}$ may be unsubstituted 2 to 5 membered heteroalkyl or 5 to 6 membered heterocycloalkyl. $R^{5a}$ may be —N(CH$_3$)$_2$ or unsubstituted morpholino. $R^1$ may be —CN. $R^1$ may be —COOCH$_3$. $R^1$ may be unsubstituted methyl. $R^2$ may be $C_1$-$C_3$ unsubstituted alkyl. When $R^1$ is —CN, $R^2$ may be unsubstituted methyl. $R^{11}$ may be hydrogen or halogen.

The compound of formula (XI) may have the formula:

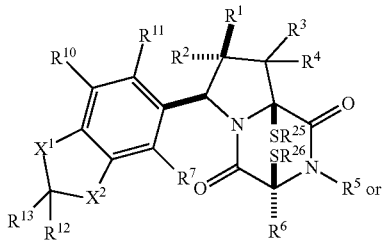
(XI(S)) or

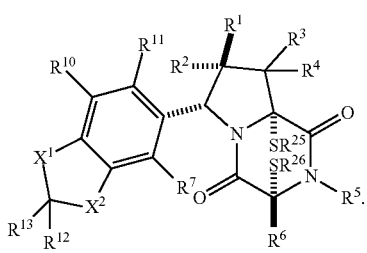
(XI(R))

The compound of formula (VII) may have the formula:

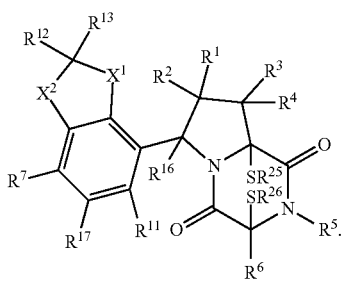
(XII)

$X^1, X^2, R^1, R^2, R^3, R^4, R^5, R^6, R^7, R^{10}, R^{11}, R^{12}, R^{13}, R^{25}$, and $R^{26}$ are as described herein, including embodiments thereof. $R^5$ and $R^6$ may independently be unsubstituted 3 to 5 membered cycloalkyl or $R^{5a}$-substituted or unsubstituted $C_1$-$C_5$ alkyl. $R^{5a}$ may be unsubstituted 2 to 5 membered heteroalkyl or 5 to 6 membered heterocycloalkyl. $R^{5a}$ may be —N(CH$_3$)$_2$ or unsubstituted morpholino. $R^1$ may be —CN. $R^1$ may be —COOCH$_3$. $R^1$ may be unsubstituted methyl. $R^2$ may be $C_1$-$C_3$ unsubstituted alkyl. When $R^1$ is —CN, $R^2$ may be unsubstituted methyl. $R^{11}$ may be hydrogen or halogen.

The compound of formula (XII) may have the formula:

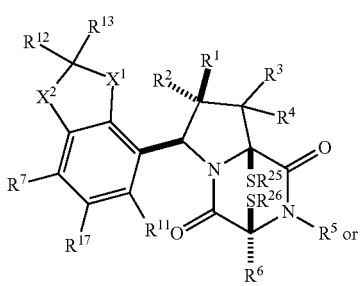
(XII(S))

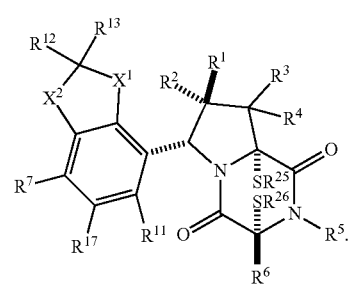
(XII(R))

In another aspect is a compound having formula:

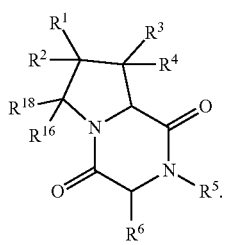
(XIII)

$R^1$, $R^2$, $R^3$, $R^4$, $R^5$, $R^6$, $R^{16}$, and $R^{18}$ are as described herein, including embodiments thereof.

The compound of formula (XIII) may have the formula:

(XIV)

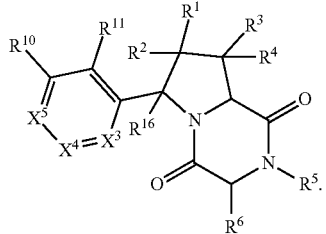

The compound of formula (XIV) may have the formula:

(XIV(S))

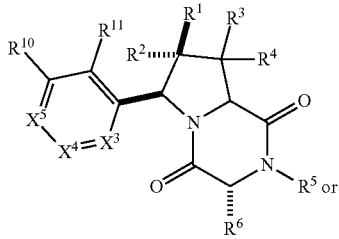

or (XIV(R))

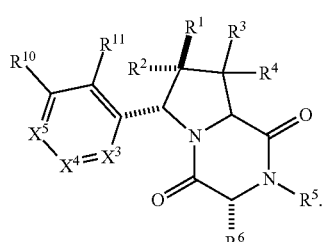

The compound of formula (XIII) may have the formula:

(XV)

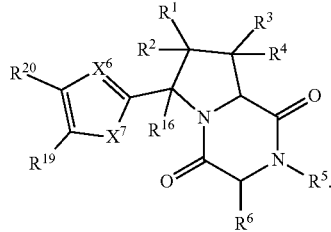

The compound of formula (XV) may have the formula:

(XV(S))

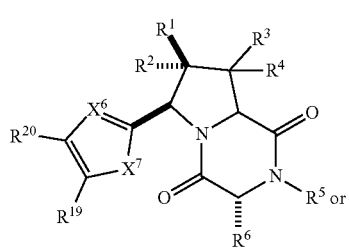

or

-continued (XV(R))

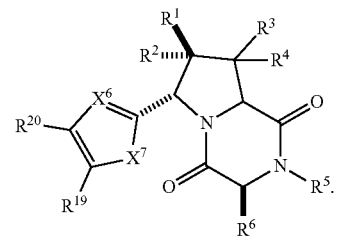

The compound of formula (XIII) may have the formula:

(XVI)

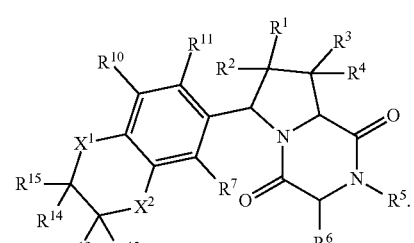

The compound of formula (XVI) may have the formula:

(XVI(S))

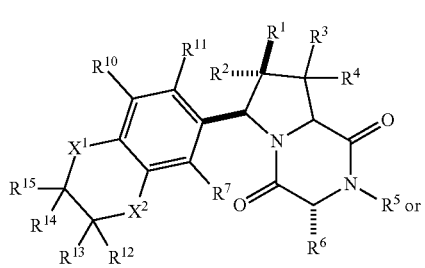

or (XVI(R))

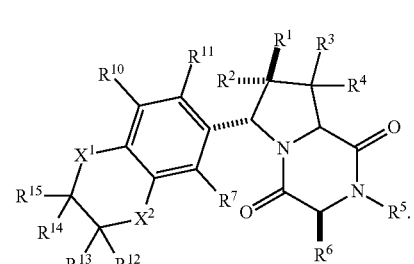

The compound of formula (XIII) may have the formula:

(XVII)

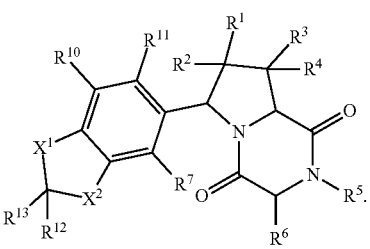

The compound of formula (XVII) may have the formula:

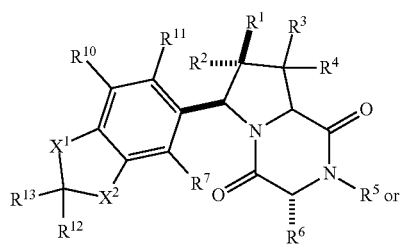

(XVII(S))

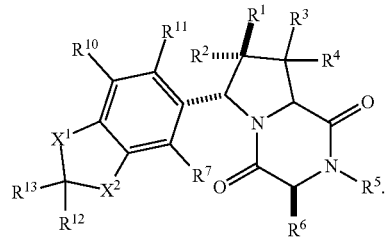

(XVII(R))

The compound of formula (XIII) may have the formula:

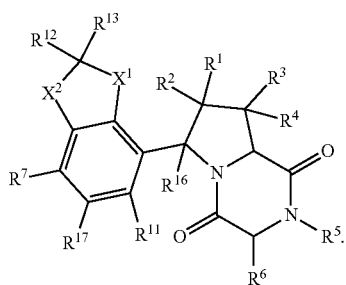

(XVIII)

The compound of formula (XVIII) may have the formula:

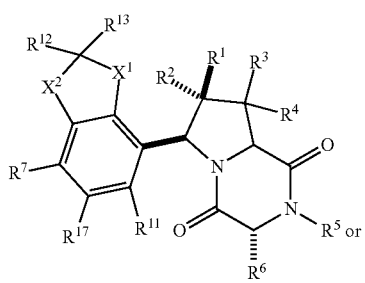

(XVIII(S))

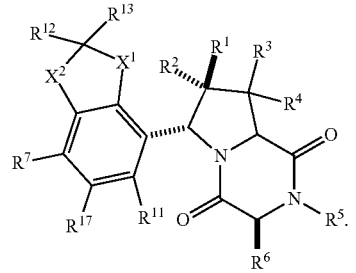

(XVIII(R))

In embodiments, $R^2$ of the compounds provided herein (e.g. formula (VII), (VIII), (IX), (X), (XI), (XII), (XIII), (XIV), (XV), (XVI), (XVII), or (XVII), including embodiments thereof) is a polar substituent. In embodiments, $R^2$ of the compounds provided herein (e.g. formula (VII), (VIII), (IX), (X), (XI), (XII), (XIII), (XIV), (XV), (XVI), (XVII), or (XVII), including embodiments thereof) is $N_3$, —$CF_3$, —$CCl_3$, —$CBr_3$, —$Cl_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2a}$-substituted or unsubstituted $C_1$-$C_3$ alkyl, or 1 to 3 membered $R^{2a}$-substituted or unsubstituted heteroalkyl. $R^{2a}$ may be —$N_3$, —$CF_3$, —$CCl_3$, —$CBr_3$, —$Cl_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2b}$-substituted or unsubstituted $C_1$-$C_5$ alkyl, $R^{2b}$-substituted or unsubstituted 2 to 5 membered heteroalkyl, $R^{2b}$-substituted or unsubstituted 3 to 6 membered heterocycloalkyl, $R^{2b}$-substituted or unsubstituted 5 or 6 membered aryl, or $R^{2b}$-substituted or unsubstituted 5 or 6 membered heteroaryl. $R^{2b}$ may be halogen, —$N_3$, —$CF_3$, —$CCl_3$, —$CBr_3$, —$Cl_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted $C_1$-$C_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

In embodiments, $R^2$ of the compounds provided herein (e.g. formula (VII), (VIII), (IX), (X), (XI), (XII), (XIII), (XIV), (XV), (XVI), (XVII), or (XVII), including embodiments thereof) is $R^{2a}$-substituted or unsubstituted $C_1$-$C_3$ alkyl, or 1 to 3 membered $R^{2a}$-substituted or unsubstituted heteroalkyl, where $R^{2a}$ is unsubstituted 3 to 6 membered heterocycloalkyl, unsubstituted 5 or 6 membered aryl, or unsubstituted 5 or 6 membered heteroaryl. In embodiments, $R^2$ of the compounds provided herein (e.g. formula (VII), (VIII), (IX), (X), (XI), (XII), (XIII), (XIV), (XV), (XVI), (XVII), or (XVII), including embodiments thereof) is unsubstituted methyl or unsubstituted methoxy. In embodiments, $R^{2a}$ of the compounds provided herein (e.g. formula (VII), (VIII), (IX), (X), (XI), (XII), (XIII), (XIV), (XV), (XVI), (XVII), or (XVII), including embodiments thereof) is unsubstituted pyridine.

In embodiments, $R^5$ and $R^6$ of the compounds provided herein (e.g. formula (VII), (VIII), (IX), (X), (XI), (XII), (XIII), (XIV), (XV), (XVI), (XVII), or (XVII), including embodiments thereof) are independently hydrogen, halogen, —$N_3$, —$CF_3$, —$CCl_3$, —$CBr_3$, —$Cl_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, unsubstituted alkyl, or unsubstituted cycloalkyl. In embodiments, $R^5$ and $R^6$ of the compounds provided herein (e.g. formula (VII), (VIII), (IX), (X), (XI), (XII), (XIII), (XIV), (XV), (XVI), (XVII), or (XVII), including embodiments thereof) are independently hydrogen, $C_1$-$C_3$ unsubstituted alkyl or 3 to 5 membered cycloalkyl. In embodiments, $R^5$ and $R^6$ of the compounds provided herein (e.g. formula (VII), (VIII), (IX), (X), (XI), (XII), (XIII), (XIV), (XV), (XVI), (XVII), or (XVII), including embodiments thereof) are independently hydrogen, unsubstituted methyl, unsubstituted ethyl, unsubstituted allyl, or unsubstituted cyclopropyl.

In embodiments, $R^1$ of the compounds provided herein (e.g. formula (VII), (VIII), (IX), (X), (XI), (XII), (XIII), (XIV), (XV), (XVI), (XVII), or (XVII), including embodiments thereof) is —CN or unsubstituted heteroalkyl. In embodiments, $R^1$ of the compounds provided herein (e.g.

formula (VII), (VIII), (IX), (X), (XI), (XII), (XIII), (XIV), (XV), (XVI), (XVII), or (XVII), including embodiments thereof) is —CN.

In embodiments, the compounds provided herein are prodrugs as described herein, including embodiments thereof. Such prodrugs may take the form of formula (VII), (VIII), (IX), (X), (XI), (XII), (XIII), (XIV), (XV), (XVI), (XVII), or (XVII), including embodiments thereof. In embodiments, the prodrugs described herein exist in an inactive form whereupon the compound may be converted to an active form in vivo. Prodrugs may also be converted to an active form ex-vivo prior to administration (e.g. by chemical modification of the prodrug prior to delivery).

In embodiments, the compounds provided herein inhibit HMT SUV39H1 activity. In embodiments, the compounds provided herein specifically inhibit HMT SUV39H1 activity (e.g. relative to other HMT's such as one or more of G9a, DOT1, EZH1, EZH2, GLP, MLL1, MLL2, MLL3, MLL4, NSD2, SET1b, SET7/9, SET8, SETMAR, SMYD2, SUV39H2). The inhibition may be at least about 2, 3, 4, 5, 10, 100, or 1000 fold greater inhibition relative to inhibition of other HMT's such as one or more of G9a, DOT1, EZH1, EZH2, GLP, MLL1, MLL2, MLL3, MLL4, NSD2, SET1b, SET7/9, SET8, SETMAR, SMYD2, SUV39H2. In embodiments, the inhibition of SUV39H1 may be at least 2 fold greater than the inhibition of other HMTs described herein. In embodiments, the inhibition of SUV39H1 may be at least 3 fold greater than the inhibition of other HMTs described herein. In embodiments, the inhibition of SUV39H1 may be at least 4 fold greater than the inhibition of other HMTs described herein. In embodiments, the inhibition of SUV39H1 may be at least 5 fold greater than the inhibition of other HMTs described herein. In embodiments, the inhibition of SUV39H1 may be at least 6 fold greater than the inhibition of other HMTs described herein. In embodiments, the inhibition of SUV39H1 may be at least 7 fold greater than the inhibition of other HMTs described herein. In embodiments, the inhibition of SUV39H1 may be at least 8 fold greater than the inhibition of other HMTs described herein. In embodiments, the inhibition of SUV39H1 may be at least 9 fold greater than the inhibition of other HMTs described herein. In embodiments, the inhibition of SUV39H1 may be at least 10 fold greater than the inhibition of other HMTs described herein.

In embodiments, the inhibition of SUV39H1 may be at least 10 fold greater than the inhibition of other HMTs described herein. In embodiments, the inhibition of SUV39H1 may be at least 20 fold greater than the inhibition of other HMTs described herein. In embodiments, the inhibition of SUV39H1 may be at least 30 fold greater than the inhibition of other HMTs described herein. In embodiments, the inhibition of SUV39H1 may be at least 40 fold greater than the inhibition of other HMTs described herein. In embodiments, the inhibition of SUV39H1 may be at least 50 fold greater than the inhibition of other HMTs described herein. In embodiments, the inhibition of SUV39H1 may be at least 60 fold greater than the inhibition of other HMTs described herein. In embodiments, the inhibition of SUV39H1 may be at least 70 fold greater than the inhibition of other HMTs described herein. In embodiments, the inhibition of SUV39H1 may be at least 80 fold greater than the inhibition of other HMTs described herein. In embodiments, the inhibition of SUV39H1 may be at least 90 fold greater than the inhibition of other HMTs described herein. In embodiments, the inhibition of SUV39H1 may be at least 100 fold greater than the inhibition of other HMTs described herein.

The compounds provided herein may inhibit HMT G9a activity. The compounds provided herein may specifically inhibiting HMT G9a activity (e.g. relative to other HMT's such as one or more of SUV39H1, DOT1, EZH1, EZH2, GLP, MLL1, MLL2, MLL3, MLL4, NSD2, SET1b, SET7/9, SET8, SETMAR, SMYD2, SUV39H2). The inhibition may be at least about 2, 3, 4, 5, 10, 100, or 1000 fold greater inhibition relative to inhibition of other HMT's such as one or more of SUV39H1, DOT1, EZH1, EZH2, GLP, MLL1, MLL2, MLL3, MLL4, NSD2, SET1b, SET7/9, SET8, SETMAR, SMYD2, SUV39H2. In embodiments, the inhibition of G9A may be at least 2 fold greater than the inhibition of other HMTs described herein. In embodiments, the inhibition of G9A may be at least 3 fold greater than the inhibition of other HMTs described herein. In embodiments, the inhibition of G9A may be at least 4 fold greater than the inhibition of other HMTs described herein. In embodiments, the inhibition of G9A may be at least 5 fold greater than the inhibition of other HMTs described herein. In embodiments, the inhibition of G9A may be at least 6 fold greater than the inhibition of other HMTs described herein. In embodiments, the inhibition of G9A may be at least 7 fold greater than the inhibition of other HMTs described herein. In embodiments, the inhibition of G9A may be at least 8 fold greater than the inhibition of other HMTs described herein. In embodiments, the inhibition of G9A may be at least 9 fold greater than the inhibition of other HMTs described herein. In embodiments, the inhibition of G9A may be at least 10 fold greater than the inhibition of other HMTs described herein.

In embodiments, the inhibition of G9A may be at least 10 fold greater than the inhibition of other HMTs described herein. In embodiments, the inhibition of G9A may be at least 20 fold greater than the inhibition of other HMTs described herein. In embodiments, the inhibition of G9A may be at least 30 fold greater than the inhibition of other HMTs described herein. In embodiments, the inhibition of G9A may be at least 40 fold greater than the inhibition of other HMTs described herein. In embodiments, the inhibition of G9A may be at least 50 fold greater than the inhibition of other HMTs described herein. In embodiments, the inhibition of G9A may be at least 60 fold greater than the inhibition of other HMTs described herein. In embodiments, the inhibition of G9A may be at least 70 fold greater than the inhibition of other HMTs described herein. In embodiments, the inhibition of G9A may be at least 80 fold greater than the inhibition of other HMTs described herein. In embodiments, the inhibition of G9A may be at least 90 fold greater than the inhibition of other HMTs described herein. In embodiments, the inhibition of G9A may be at least 100 fold greater than the inhibition of other HMTs described herein.

The compounds provided herein may also inhibiting both HMT SUV39H1 and the activity of HMT G9a. The compounds provided herein may specifically inhibiting both HMT SUV39H1 and the activity of HMT G9a (e.g. relative to other HMT's such as one or more of DOT1, EZH1, EZH2, GLP, MLL1, MLL2, MLL3, MLL4, NSD2, SET1b, SET7/9, SET8, SETMAR, SMYD2, SUV39H2). The inhibition may be at least about 2, 3, 4, 5, 10, 100, or 1000 fold greater inhibition relative to inhibition of other HMT's such as one or more of DOT1, EZH1, EZH2, GLP, MLL1, MLL2, MLL3, MLL4, NSD2, SET1b, SET7/9, SET8, SETMAR, SMYD2, SUV39H2. Thus, in embodiments, the compounds provided herein are capable of specifically inhibiting H3K9 dimethylation or trimethylation (e.g. relative to other epigenetic events). The compounds provided herein may be capable of specifically inhibiting H3K9 dimethylation. The compounds provided herein may be capable of specifically inhibiting trimethylation. The compounds provided herein may be capable of specifically inhibiting both H3K9 dimethylation and H3K9 trimethylation.

In embodiments, the inhibition of SUV39H1 and G9a may be at least 2 fold greater than the inhibition of other HMTs described herein. In embodiments, the inhibition of SUV39H1 and G9a may be at least 3 fold greater than the inhibition of other HMTs described herein. In embodiments, the inhibition of SUV39H1 and G9a may be at least 4 fold greater than the inhibition of other HMTs described herein. In embodiments, the inhibition of SUV39H1 and G9a may be at least 5 fold greater than the inhibition of other HMTs described herein. In embodiments, the inhibition of SUV39H1 and G9a may be at least 6 fold greater than the inhibition of other HMTs described herein. In embodiments, the inhibition of SUV39H1 and G9a may be at least 7 fold greater than the inhibition of other HMTs described herein. In embodiments, the inhibition of SUV39H1 and G9a may be at least 8 fold greater than the inhibition of other HMTs described herein. In embodiments, the inhibition of SUV39H1 and G9a may be at least 9 fold greater than the inhibition of other HMTs described herein. In embodiments, the inhibition of SUV39H1 and G9a may be at least 10 fold greater than the inhibition of other HMTs described herein.

In embodiments, the inhibition of SUV39H1 and G9a may be at least 10 fold greater than the inhibition of other HMTs described herein. In embodiments, the inhibition of SUV39H1 and G9a may be at least 20 fold greater than the inhibition of other HMTs described herein. In embodiments, the inhibition of SUV39H1 and G9a may be at least 30 fold greater than the inhibition of other HMTs described herein. In embodiments, the inhibition of SUV39H1 and G9a may be at least 40 fold greater than the inhibition of other HMTs described herein. In embodiments, the inhibition of SUV39H1 and G9a may be at least 50 fold greater than the inhibition of other HMTs described herein. In embodiments, the inhibition of SUV39H1 and G9a may be at least 60 fold greater than the inhibition of other HMTs described herein. In embodiments, the inhibition of SUV39H1 and G9a may be at least 70 fold greater than the inhibition of other HMTs described herein. In embodiments, the inhibition of SUV39H1 and G9a may be at least 80 fold greater than the inhibition of other HMTs described herein. In embodiments, the inhibition of SUV39H1 and G9a may be at least 90 fold greater than the inhibition of other HMTs described herein. In embodiments, the inhibition of SUV39H1 and G9a may be at least 100 fold greater than the inhibition of other HMTs described herein.

In embodiments, a compound herein (e.g. formula (VII), (VIII), (IX), (X), (XI), (XII), (XIII), (XIV), (XV), (XVI), (XVII), or (XVII), including embodiments thereof) is an epigenetic inhibitor. In embodiments, the compound inhibits H3K9 trimethylation or dimethylation.

In certain embodiments the compound is a compound as set forth in Table 1.

TABLE 1

Exemplary embodiments of compounds provided herein.

| Structure | Reference |
|---|---|
| 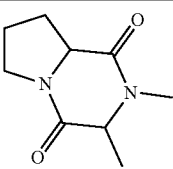 | ETP6 |
| 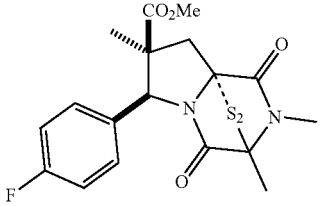 | ETP8 |
| 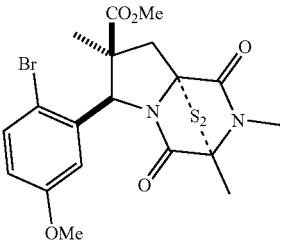 | ETP12 |
| 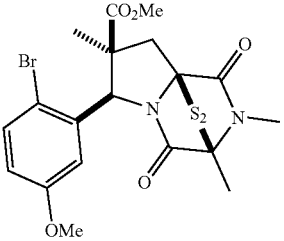 | ETP14 |
| 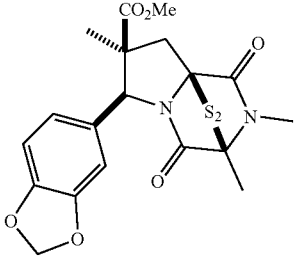 | ETP27 |
| 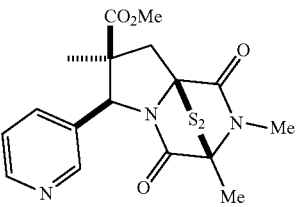 | ETP49 |
| 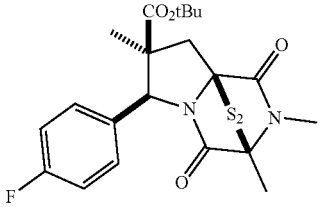 | ETP56 |

TABLE 1-continued

Exemplary embodiments of compounds provided herein.

| Structure | Reference |
|---|---|
| 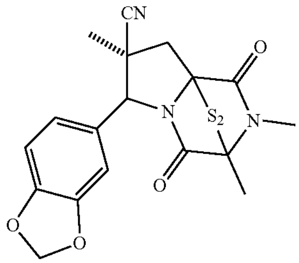 | ETP69 |
| 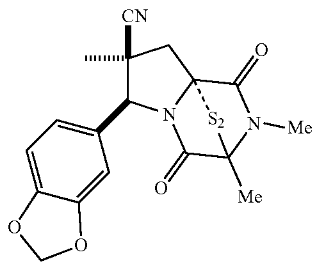 | ETP95 |
| 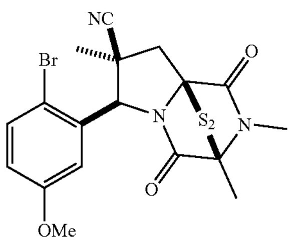 | ETP100 |
| 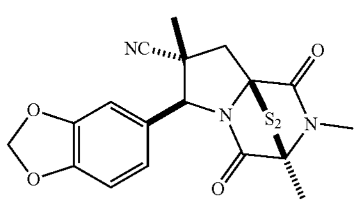 | ETP120 |
| 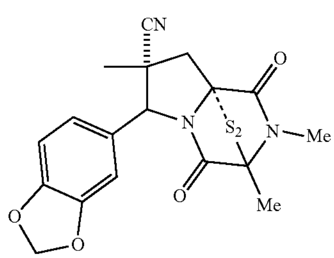 | ETP125 |
| 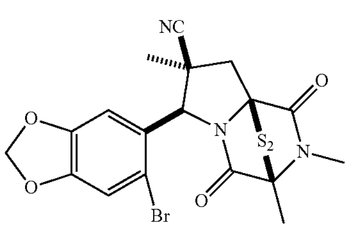 | ETP128 |
| 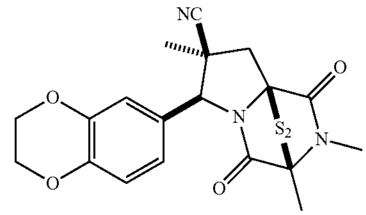 | ETP130 |
| 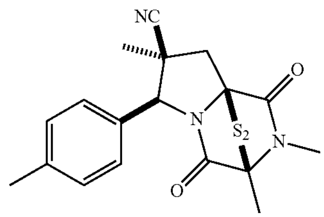 | ETP154 |
| 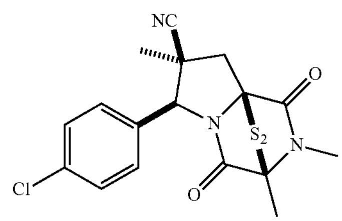 | ETP167 |
| 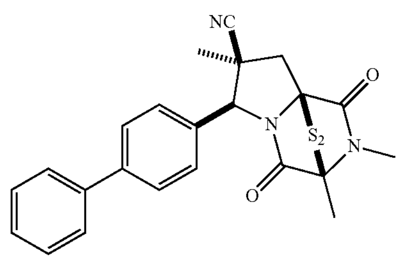 | ETP178 |
| 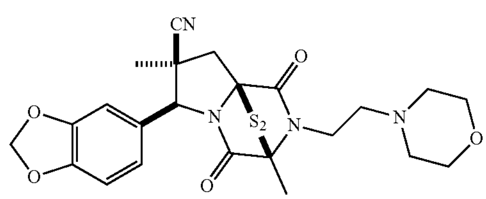 | ETP195 |
| 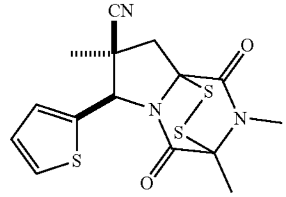 [SMILES: CN1C(=O)C23C[C@](C)(C#N)[C@H](c4cccs4)N2C(=O)C1(C)SS3] | ETP204 |
| 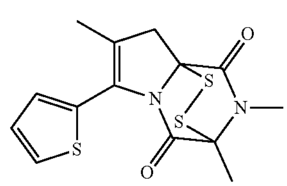 [SMILES: CC1=C(c2cccs2)N2C(=O)C3(C)SSC2(C1)C(=O)N3C] | ETP206 |

TABLE 1-continued

Exemplary embodiments of compounds provided herein.

| Structure | Reference |
|---|---|
| | ETP214 |
| | ETP218 |
| | ETP223 |
| | ETP229 |
| | ETP303 |
| | ETP309 (3:1 mix epimers) |
| | ETP313 (3:1 mix epimers) |
| | ETP328 |
| | ETP331 |
| | ETP341 |
| | ETP344 |
| | ETP356 |
| | ETP359 |

TABLE 1-continued

Exemplary embodiments of compounds provided herein.

| Structure | Reference |
|---|---|
| 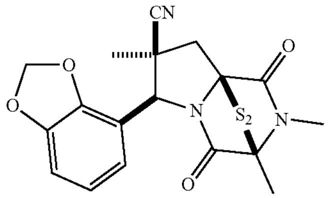 | ETP365 |
| 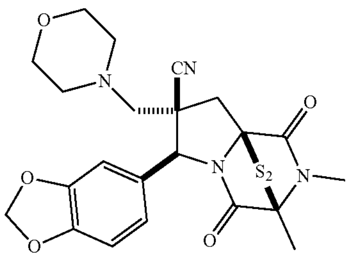 | ETP382 |
| 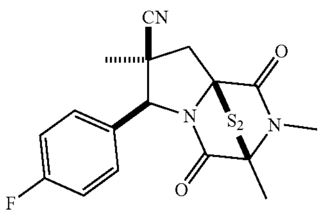 | ETP384 |
| 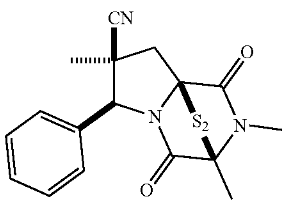 | ETP390 |
| 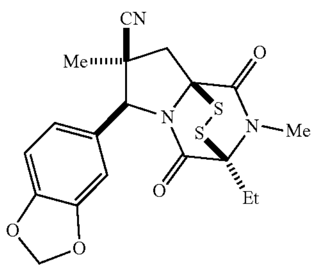 [SMILES: CC[C@]12SS[C@@]3(C[C@](C)(C#N)[C@H](c4ccc5c(c4)OCO5)N3C1=O)C(=O)N2C] | ETP406 |
| 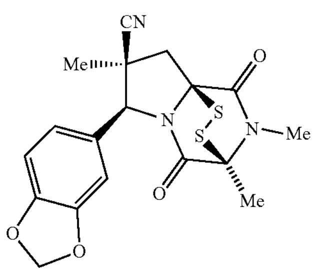 [SMILES: CN1C(=O)[C@@]23C[C@](C)(C#N)[C@H](c4ccc5c(c4)OCO5)N2C(=O)[C@]1(C)SS3] | ETP417 |
| 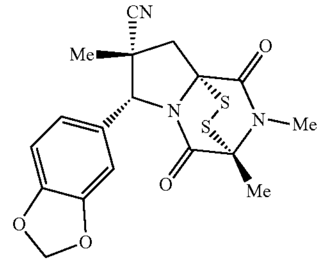 [SMILES: CN1C(=O)[C@]23C[C@@](C)(C#N)[C@@H](c4ccc5c(c4)OCO5)N2C(=O)[C@@]1(C)SS3] | ETP422 |
| 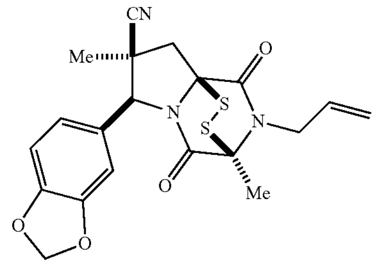 [SMILES: C=CCN1C(=O)[C@@]23C[C@](C)(C#N)[C@H](c4ccc5c(c4)OCO5)N2C(=O)[C@]1(C)SS3] | ETP425 |
| 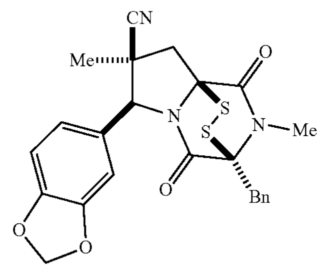 | ETP442 |
| 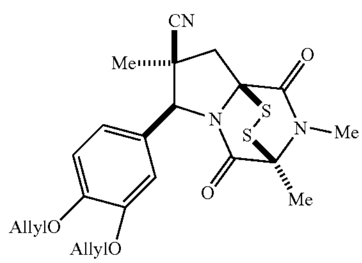 | ETP450 |
| 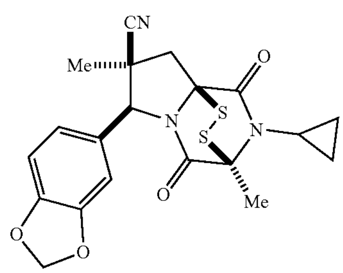 [SMILES: C[C@]1(C#N)C[C@@]23SS[C@@](C)(C(=O)N2[C@H]1c1ccc2c(c1)OCO2)N(C1CC1)C3=O] | ETP452 |

TABLE 1-continued

Exemplary embodiments of compounds provided herein.

| Structure | Reference |
|---|---|
| 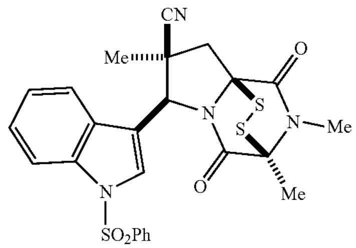 | ETP469 |
| 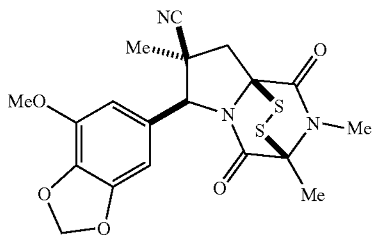 [SMILES: COc1cc([C@@H]2N3C(=O)[C@]4(C)SS[C@@]3(C[C@]2(C)C#N)C(=O)N4C)cc2c1OCO2] | ETP484 |
| 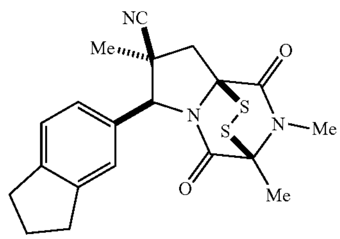 [SMILES: CN1C(=O)[C@@]23C[C@](C)(C#N)[C@H](c4ccc5c(c4)CCC5)N2C(=O)[C@]1(C)SS3] | ETP493 |

III. Pharmaceutical Compositions

In another aspect a pharmaceutical composition is provided. The pharmaceutical composition includes a compound as provided herein (e.g. of formula (I), (II), (III), (IV), (V), (VI), (VII), (VIII), (IX), (X), (XI), (XII), (XIII), (XIV), (XV), (XVI), (XVII), or (XVIII)) and a pharmaceutically acceptable excipient. The compound may be provided in a therapeutically effective amount (e.g. for treating cancer as described herein). The compound may be provided as a prodrug, as described herein, including embodiments thereof. When provided as a prodrug, the prodrug be converted to an active form in-vivo or ex-vivo according to the methods described herein.

In another aspect, a pharmaceutical composition is provided including a compound as provided herein (e.g. of formula (I), (II), (III), (IV), (V), (VI), (VII), (VIII), (IX), (X), (XI), (XII), (XIII), (XIV), (XV), (XVI), (XVII), or (XVIII)), a pharmaceutically acceptable excipient, and an additional anticancer agent. The anticancer agent may be an epigenetic inhibitor or a multi-kinase inhibitor. The epigenetic inhibitor may be a DNA methyltransferase (DNMT) inhibitor. The epigenetic inhibitor may be azacitidine or decitabine. The multi-kinase inhibitor may include a single kinase inhibitor. The multi-kinase inhibitor may be sorafenib. In embodiments the pharmaceutical composition includes more than one multi-kinase inhibitor or more than one epigenetic inhibitor and a compound as provided herein (e.g. of formula (I), (II), (III), (IV), (V), (VI), (VII), (VIII), (IX), (X), (XI), (XII), (XIII), (XIV), (XV), (XVI), (XVII), or (XVIII)). In embodiments the pharmaceutical composition includes a compound as provided herein (e.g. of formula (I), (II), (III), (IV), (V), (VI), (VII), (VIII), (IX), (X), (XI), (XII), (XIII), (XIV), (XV), (XVI), (XVII), or (XVIII)), a pharmaceutically acceptable excipient, at least one multi-kinase inhibitor (e.g. a single kinase inhibitor), and at least one epigenetic inhibitor. In embodiments, the epigenetic inhibitor, DNMT inhibitor, multi-kinase inhibitor and single kinase inhibitor are anti-cancer agents. The anti-cancer agents include those described herein and embodiments thereof.

The pharmaceutical composition may include a first amount of a compound as described herein, including embodiments thereof, and a second amount of the multi-kinase inhibitor. The first amount and second amount may be together an effective amount to provide a synergistic therapeutic effect (e.g. the measured effect of compounds administered in combination is greater than the sum of the individual effects of each of the compounds administered alone as a single agent). The multi-kinase inhibitor may be sorafenib. The pharmaceutical composition of may include a first amount of a compound as described herein, including embodiments thereof, and a second amount of the epigenetic inhibitor, wherein the first amount and second amount are together an effective amount to provide a synergistic therapeutic effect. The epigenetic inhibitor may be azacitidine or decitabine.

The multi-kinase inhibitor of pharmaceutical composition may be dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib. The multi-kinase inhibitor of the pharmaceutical composition may be sorafenib. The epigenetic inhibitor may be azacitidine or decitadine. The epigenetic inhibitor may be azacitidine. The epigenetic inhibitor may be decitadine. In some dosage forms, the compound and the multi-kinase inhibitor or the epigenetic inhibitor may be co-administered as a single dosage form.

The pharmaceutical compositions described herein, including embodiments thereof may be used in the treatment of cancers. The pharmaceutical compositions described herein, including embodiments thereof may be used in the treatment of solid and blood tumors, including ovarian cancer, breast cancer, lung cancer, leukemia (e.g. AML or CML), lymphoma, pancreatic cancer, kidney cancer, melanoma, liver cancer, colon cancer, sarcoma, multiple myeloma, brain cancer or prostate cancer. The pharmaceutical compositions described herein, including embodiments thereof may be used in the treatment of non-small cell lung cancer. The pharmaceutical composition of may be used in the treatment of colon cancer. The pharmaceutical composition of may be used in the treatment of AML. The pharmaceutical composition of may be used in the treatment of CML. The pharmaceutical composition of may be used in the treatment of ovarian cancer. The pharmaceutical composition of may be used in the treatment of melanoma. The pharmaceutical composition of may be used in the treatment of breast cancer. The pharmaceutical composition of may be used in the treatment of prostate cancer. The pharmaceutical composition of may be used in the treatment of pancreatic cancer. The pharmaceutical composition of may be used in the treatment of liver cancer.

IV. Methods

In another aspect a method of treating cancer is provided. The method includes administering to a subject in need thereof a therapeutically effective amount of a compound of formula (I), (II), (III), (IV), (V), (VI), (VII), (VIII), (IX), (X), (XI), (XII), (XIII), (XIV), (XV), (XVI), (XVII), or (XVIII)), including embodiments thereof. In embodiments, the therapeutically effective amount is of a compound having formula (I), (II), (III), (IV), (V), (VI), or (VII), including embodiments thereof. The compound may have formula (I). The compound may have formula (II). The compound may have formula (III). The compound may have formula (IV). The compound may have formula (V). The compound may have formula (VI). The compound may have formula (VII). The compound may be a compound as set forth in Table 1. In embodiments, the compound is formulated as a pharmaceutical composition as described herein, including embodiments thereof.

The cancer may be a solid and blood tumor, including ovarian cancer, breast cancer, lung cancer, leukemia (e.g. AML or CML), lymphoma, pancreatic cancer, kidney cancer, melanoma, liver cancer, colon cancer, sarcoma, multiple myeloma, brain cancer or prostate cancer. The cancer may be ovarian cancer. The cancer may be lung cancer. The lung cancer may be non-small cell lung cancer. The cancer may be pancreatic cancer. The cancer may be kidney cancer. The cancer may be melanoma. The cancer may be liver cancer. The cancer may be colon cancer. The cancer may be brain cancer. The cancer may be prostate cancer. The cancer may be a sarcoma. The cancer may be a leukemia. The leukemia may be CML. The cancer may be AML. In embodiments the cancer being treated is AML, wherein the AML expresses Flt3 kinase protein.

In embodiments, the cancer is caused by misregulation of a histone methyltransferase (HMT). The misregulation may be overexpression, downregulation, intragenic mutation, translocation or promotor DNA methylation. The HMT may be SUV39H1/2 (KMT A/B), G9a (KMT1C), MLL1 (KMT2A), MLL4 (KMT2D), SMYD3, DOT1L (KMT4), SET8/PR-SET7 (KMT5A) or EZH2 (KMT6). In embodiments, the HMT is SUV39H1/2 (KMT1A/B). In embodiments, the HMT is SUV39H1.

The method may also include administering an additional anticancer agent. The anticancer agent may be an epigenetic inhibitor or a multi-kinase inhibitor. The administration may include a first amount of the compound and a second amount of the epigenetic inhibitor, wherein the first amount and second amount are together an effective amount to provide a synergistic therapeutic effect. The epigenetic inhibitor may be azacitidine or decitadine. The compound and the epigenetic inhibitor may be co-administered as a pharmaceutical composition. In certain embodiments the epigenetic inhibitor is a DNMT inhibitor. The administration of the pharmaceutical compound may be useful in treating ovarian cancer. The administration of the pharmaceutical compound may be useful in treating lung cancer. The lung cancer may be non-small cell lung cancer.

The method may include administering a first amount of the compound and a second amount of the multi-kinase inhibitor, wherein the first amount and second amount are together an effective amount to provide a synergistic therapeutic effect. The multi-kinase inhibitor may be sorafenib. The compound and the multi-kinase inhibitor may be co-administered as a pharmaceutical composition. The administration of the pharmaceutical compound may be useful in treating ovarian cancer. The administration of the pharmaceutical compound may be useful in treating lung cancer. The lung cancer may be non-small cell lung cancer.

In embodiments, the methods of treatment described herein yield a suppression of tumor growth. The suppressed tumor growth may indicate the absence of toxicity symptoms (e.g. body weight loss). Those skilled in the art understand that body weight loss observed during may cancer treatments is a result of toxicity associated with the treatment (e.g. killing of healthy tissue). Accordingly, the compounds described herein may provide effective therapeutic value without toxicity issues normally associated with cancer treatments.

Compounds described herein, including embodiments thereof, may be administered in as a therapeutically effective amount. The compound may be administered in any effective size dose or effect dosage regimen (e.g. one dose daily). A therapeutically effective dose may be determined by one of skill in the art using methods described herein and those known in the art.

In another aspect, a method of inhibiting a histone methyltransferase (HMT) is provided. The method includes contacting a methyltransferase with a compound provided herein (a compound of formula (I), (II), (III), (IV), (V), (VI), (VII), (VIII), (IX), (X), (XI), (XII), (XIII), (XIV), (XV), (XVI), (XVII), or (XVIII)), including embodiments thereof). In embodiments, the histone methyltransferase is a lysine-specific HMT. In embodiments, the histone methyltransferase is an arginine-specific HMT. The HMT may be SUV39H1/2 (KMT1A/B), G9a (KMT1C), MLL1 (KMT2A), MLL4 (KMT2D), SMYD3, DOT1L (KMT4), SET8/PR-SET7 (KMT5A) or EZH2 (KMT6). In embodiments, the HMT is SUV39H1/2 (KMT1A/B). In embodiments, the HMT is SUV39H1. In embodiments, the method of inhibiting is performed in vitro.

In embodiments, the HMT is within a cell. Thus, in embodiments, the cell is within an organism.

In another aspect, a method of inhibiting growth of a cancer cell in vivo is provided. The method includes contactin a cancer cell with a compound provided herein (a compound of formula (I), (II), (III), (IV), (V), (VI), (VII), (VIII), (IX), (X), (XI), (XII), (XIII), (XIV), (XV), (XVI), (XVII), or (XVIII)), including embodiments thereof). The cancer cell may be derived from a solid and blood tumor, including ovarian cancer, breast cancer, lung cancer, leukemia (e.g. AML or CML), lymphoma, pancreatic cancer, kidney cancer, melanoma, liver cancer, colon cancer, sarcoma, multiple myeloma, brain cancer or prostate cancer. The cancer cell may be an ovarian cancer cell. The cancer cell may be a lung cancer cell. The lung cancer cell may be a non-small cell lung cancer cell. The cancer cell may be pancreatic cancer cell. The cancer cell may be a kidney cancer cell. The cancer cell may be a melanoma cell. The cancer cell may be a liver cancer cell. The cancer cell may be a colon cancer cell. The cancer cell may be a brain cancer cell. The cancer cell may be a prostate cancer cell. The cancer cell may be a sarcoma cell. The cancer cell may be a leukemia cell. The leukemia cell may be a CML cell. The cancer cell may be an AML cell. In embodiments the cancer cell is an AML cell, wherein the AML cell expresses Flt3 kinase protein.

V. Examples

Example 1

The compounds of Formulae I-XVIII can be prepared in a number of ways well known to those skilled in the art, including both solid phase and solution phase techniques. The compounds can be synthesized, for example, by the methods described below, or variations thereof as appreciated by the skilled artisan. Although these syntheses are illustrated for preparation of ETPs having substituted aryl substituents at C6, identical sequences can be employed to prepare ETPs with substituted heteroaryl substituents at C6. See e.g. Martins, M. M.; Carvalho *Tetrahedron* 2007, 63, 9923-9932; Borthwick, A. D. *Chem Rev* 2012, 112, 3641-3716; Iwasa, E.; Hamashima, Y.; Sodeoka, M. Isr. *J. Chem.* 2011, 51, 420-433; Nicolaou, K. C.; Lu, M.; Totokotsopoulos, S.; Heretsch, P.; Gigubre, D.; Sun, Y.-P.; Sarlah, D.; Nguyen, T. H.; Wolf, I. C.; Smee, D. F.; Day, C. W.; Bopp, S.; Winzeler, E. A. *J. Am. Chem. Soc.* 2012, 134, 17320-17332. All processes disclosed in association with the pres- Scheme 1: Synthesis of racemic ETP derivatives described herein.

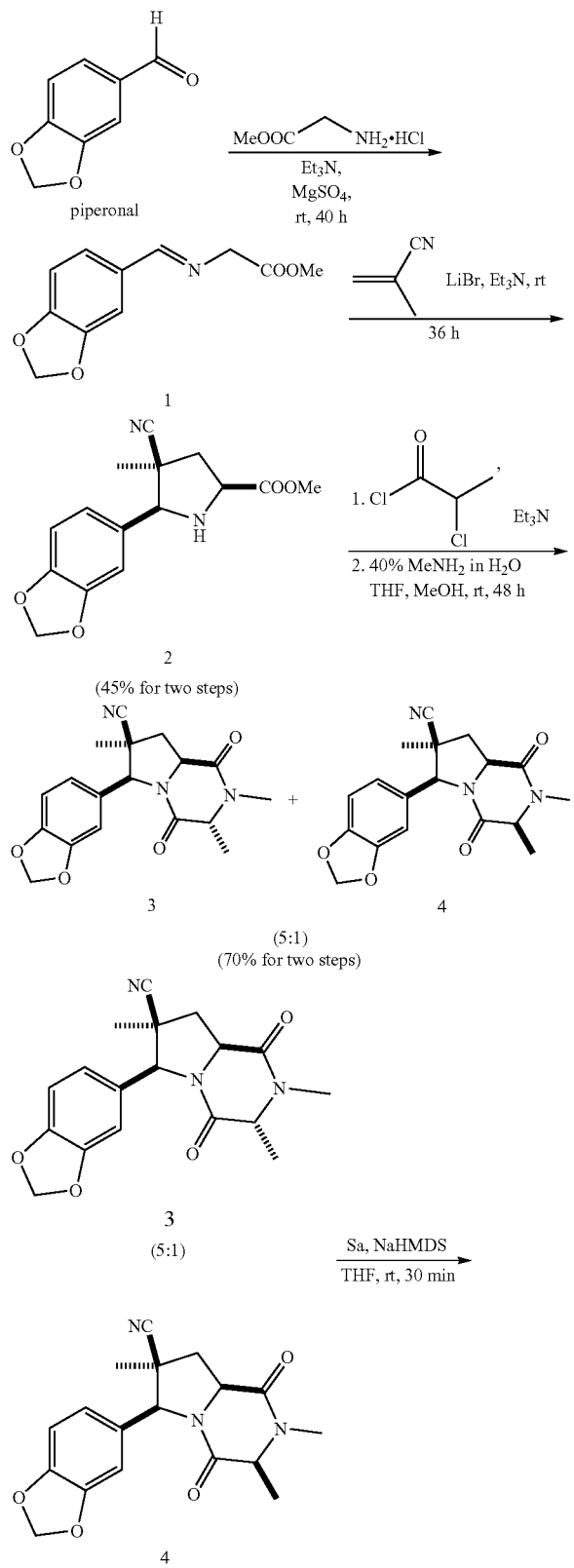

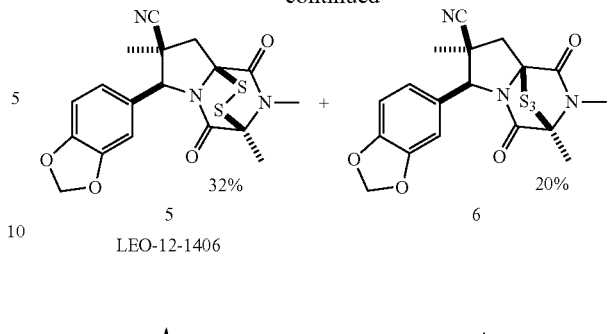

LEO-12-1406

1. NaBH₄, THF
   MeOH, rt, 2 h
2. KI₃, EtOAc, rt
   ~40%

Embodiments of Formula I may be prepared as shown in Scheme 1 above. Dehydrative condensation of an aldehyde with a glycine derivative renders an intermediate imine such as 1, which when treated with base in the presence of lithium bromide generates an azomethine ylide that subsequently undergoes a dipolar cycloaddition reaction to generate the desired pyrrolidine product such as 2. The azomethine ylide can be generated and the cycloaddition accomplished in many ways known in the art (Grigg, R. and V. Sridharan (1993). Azomethine Ylide Cycloadditions via 1,2-Prototropy and Metallo-Dipole Formation from Imines. Advances in Cycloaddition. D. P. Curran. Greenwich, Conn., Jai Press Inc. 3: 161-204). For example, the cycloaddition may be carried out by simply heating the components in a solvent or by the use of other metal complexes or salts and other bases. Compounds 2 are typically generated as mixtures of diastereoisomers, the isomer exemplified by 2 can be separated from the mixture based on its reduced solubility in solvent mixtures like MeOH/DCM (1:1). If required, the diastereoisomer products can be obtained in high purity by column chromatography; the subsequent steps can be performed with the separated stereoisomers or carried out with the mixture of stereoisomers with separation being accomplished by column chromatography, crystallization or other common techniques after the polysulfur bridge is incorporated.

The product of this cycloaddition reaction is a pyrrolidine ester, which can be converted to a dioxopiperazine in many well-known ways (Martins, M. B., Ivone, C. (2007) Diketopiperazines: biological activity and synthesis. *Tetrahedron* 63, 9923-9932). For example, the pyrrolidine ester can be acylated on the free nitrogen with an α-halo acid chloride to yield the corresponding amide. These compounds can be treated with an excess of a primary amine to undergo a cyclocondensation reaction furnishing the desired diketopiperazine ring, compounds, exmplified by 3 and 4. In general the diketopiperazine was isolated as mixture of diastereoisomers which need not be separated at this stage. Alternatively, the pyrrolidine ester can be coupled with an α-aminoester (typically protected on nitrogen) to give a dipeptide, which directly or upon removal of the nitrogen-protecting group can be cyclized to the dioxopiperazine intermediate.

The diketopiperazine then undergoes a sulfidation process, one example of which is illustrated in Scheme 1, to yield the desired ETP. Alternatively, the intermediate in this sequence, can be reduced and the dithiol product protected on the two sulfur atoms. The conversion of the diooxopiperazine intermediate to an ETP poduct can be accomplished in many ways well known in the art (Iwasa, E.; Hamashima, Y.; Sodeoka, M. (2011) Epipolythiodiketopiperazine Alkaloids: Total Syntheses and Biological Activities Isr. *J. Chem.* 51, 420-433. Nicolaou, K. C., et al. (2011) Synthesis and Biological Evaluation of Epidithio-, Epitetrathio-, and bis-(Methylthio)diketopiperazines: Synthetic Methodology, Enantioselective Total Synthesis of Epicoccin G, 8,8'-epi-ent-Rostratin B, Gliotoxin, Gliotoxin G, Emethallicin E, and Haematocin and Discovery of New Antiviral and Antimalarial Agents *J. Am. Chem. Soc.*, 133, 8150-8153.)

Synthetic scheme for enantioselective synthesis of ETP analogues described herein.

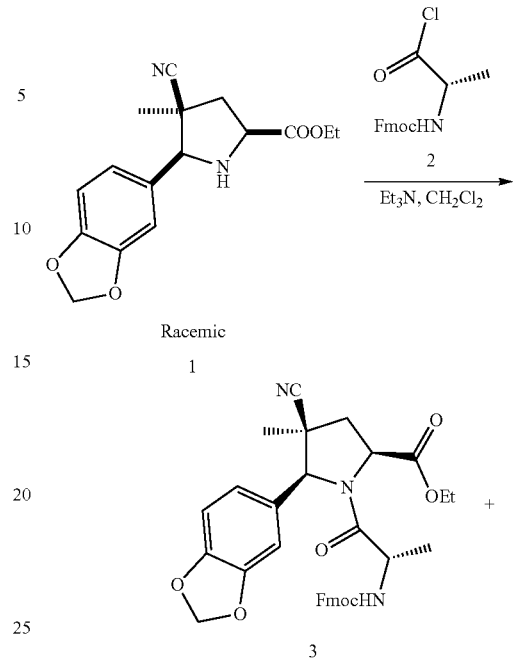

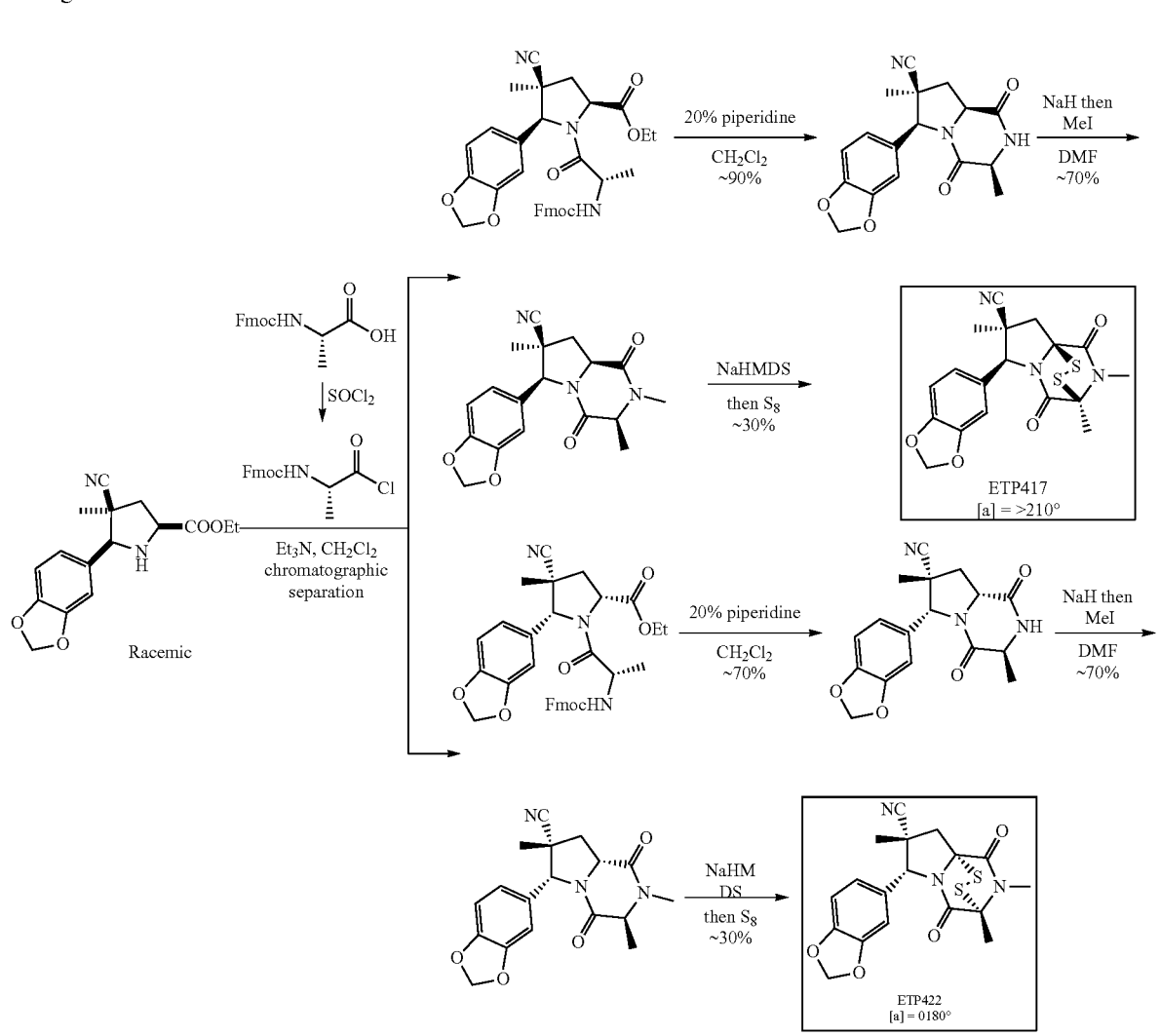

-continued

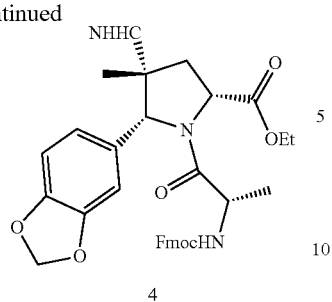

4

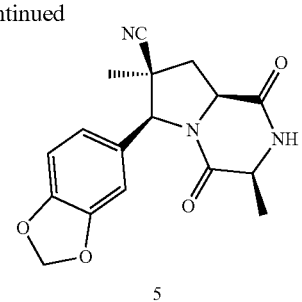

5

To a stirred solution of racemic 1 (2.1 g, 7 mmol) in CH$_2$Cl$_2$ (14 mL) were added Et$_3$N (1.4 g, 14 mmol) and acyl chloride 2 (3.25 g, 10 mmol) in CH$_2$Cl$_2$ (14 mL) at 0° C. The reaction was stirred overnight. The reaction was quenched with sat. NaHCO$_3$ and extracted with CH$_2$Cl$_2$. The combined organic layer was dried over MgSO$_4$ and evaporated to dryness. The crude product was purified by silica gel column chromatography by elution with 33% EtOAc/Hexane to afford 1.9 g (46%) of compound 3 and 1.7 g (40%) of compound 4. For compound 3: $^1$H NMR (400 MHz, CDCl$_3$) δ/ppm 7.75 (d, 2H, J=7.4 Hz), 7.55 (d, 2H, J=7.4 Hz), 7.40 (t, 2H, J=7.4 Hz), 7.30 (t, 2H, J=7.4 Hz), 7.30 (s, 1H), 7.19 (dd, 1H, J=1.4, 8.0 Hz), 6.86 (d, 2H, J=7.8 Hz), 6.00 (d, 2H, J=6.6 Hz), 5.22 (s, 1H), 5.19 (d, 2H, J=7.8 Hz), 4.60 (dd, 1H, J=7.4, 9.8 Hz), 4.39-4.22 (m, 4H), 4.20-4.14 (m, 2H), 2.59 (dd, 1H, J=9.8, 13.8 Hz), 2.35 (dd, 1H, J=7.0, 13.8 Hz), 1.61 (s, 3H), 1.35 (t, 3H, J=7.0 Hz), 0.98 (d, 3H, J=7.0 Hz); $^{13}$C NMR (100 MHz, CDCl$_3$) δ/ppm 174.0, 170.2, 156.1, 148.31, 148.27, 143.70, 143.65, 141.3, 131.8, 127.75, 127.72, 127.0, 125.1, 125.0, 121.3, 120.0, 108.6, 107.8, 101.4, 70.3, 67.2, 61.9, 58.2, 47.8, 47.0, 44.5, 37.3, 24.3, 17.4, 14.1;

For compound 4 (main rotamer): $^1$H NMR (400 MHz, CDCl$_3$) δ/ppm 7.75 (d, 2H, J=7.4 Hz), 7.55 (d, 2H, J=7.4 Hz), 7.40 (t, 2H, J=7.4 Hz), 7.30 (t, 2H, J=7.4 Hz), 7.30 (s, 1H), 7.19 (dd, 1H, J=1.4, 8.0 Hz), 7.03 (s, 1H), 6.93 (d, 1H, J=7.8 Hz), 6.80 (d, 1H, J=8.2 Hz), 5.95 (d, 2H, J=2.2 Hz), 5.37 (dd, 1H, J=3.4, 8.2 Hz), 5.27 (d, 1H, J=7.6 Hz), 4.76 (s, 1H), 4.40-4.10 (m, 6H), 2.90 (dd, 1H, J=3.4, 13.2 Hz), 2.41 (dd, 1H, J=2.3, 13.2 Hz), 1.62 (s, 3H), 1.40 (d, 3H, J=7.0 Hz), 1.39 (t, 3H, J=7.0 Hz); $^{13}$C NMR (100 MHz, CDCl$_3$) δ/ppm 174.0, 170.9, 156.3, 147.9, 147.7, 143.64, 143.62, 141.3, 130.6, 127.8, 127.7, 127.0, 125.1, 125.0, 120.2, 120.0, 108.3, 107.0, 101.1, 70.8, 67.2, 62.6, 59.3, 48.4, 47.0, 43.4, 40.8, 23.1, 17.8, 14.1;

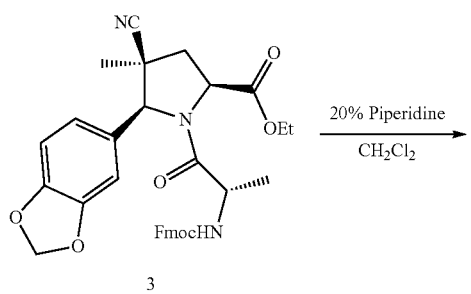

3

To a stirred solution of compound 3 (2.8 g, 4.7 mmol) in CH$_2$Cl$_2$ (18 mL) was added piperidine (4.0 g, 47 mmol). After 30 min, the solvent was removed. The crude product was purified by silica gel column chromatography by elution with 3% MeOH/CH$_2$Cl$_2$ to afford 1.4 g (91%) of compound 5 as white solid. $^1$H NMR (400 MHz, CDCl$_3$) δ/ppm 6.79 (d, 2H, J=7.8 Hz), 6.63 (dd, 1H, J=2.0, 8.2 Hz), 6.57 (d, 2H, J=2.0 Hz), 5.96 (s, 2H), 5.91 (s, 1H), 4.87 (s, 1H), 4.43 (dd, 1H, J=6.6, 11.0 Hz), 4.17 (q, 1H, J=6.6 Hz), 2.82 (dd, 1H, J=11.4, 13.4 Hz), 2.35 (dd, 1H, J=6.6, 13.4 Hz), 1.68 (s, 3H), 1.44 (d, 3H, J=6.6 Hz); $^{13}$C NMR (100 MHz, CDCl$_3$) δ/ppm 168.9, 166.9, 148.3, 148.2, 130.8, 119.7, 108.7, 106.2, 101.4, 69.3, 57.5, 51.6, 42.8, 35.8, 25.3, 15.4;

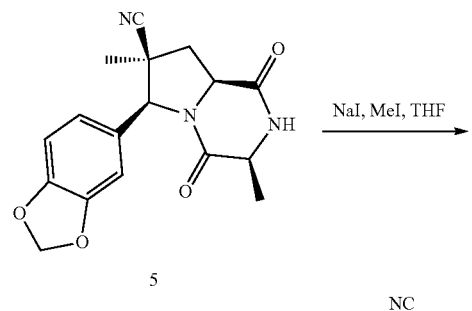

5

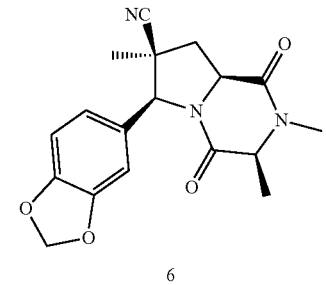

6

To a stirred solution of compound 5 (1.4 g, 4.3 mmol) in THF (43 mL) was added NaH (60%, 260 mg, 6.5 mmol) at 0° C. After 20 min at 23° C., MeI (1.85 g, 13 mmol) was added at 0° C. After 2 h at 23° C., the reaction was quenched with sat. NH4Cl. The solvent was removed and the residue was extracted with CH$_2$Cl$_2$. The combined organic layer was dried over MgSO$_4$ and evaporated to dryness. The crude product was purified by silica gel column chromatography by elution with 25% EtOAc/Hexane to afford 1.25 g (86%) of compound 6. $^1$H NMR (400 MHz, CDCl$_3$) δ/ppm 6.82 (d, 2H, J=8.2 Hz), 6.73 (d, 1H, J=2.0 Hz), 6.71 (s, 1H), 5.98 (s, 2H), 4.73 (dd, 1H, J=6.2, 10.6 Hz), 3.88 (q, 1H, J=7.0 Hz), 3.01 (s, 3H), 2.93 (dd, 1H, J=6.2, 13.0 Hz), 2.26 (dd, 1H, J=10.6, 13.0 Hz), 1.60 (s, 3H), 1.54 (d, 3H, J=7.4 Hz); $^{13}$C NMR (100 MHz, CDCl$_3$) δ/ppm 165.9, 165.2, 148.2, 148.1, 129.3, 120.3, 119.4, 108.6, 106.1, 101.4, 70.2, 60.6, 58.4, 44.1, 41.6, 32.1, 22.7, 16.7;

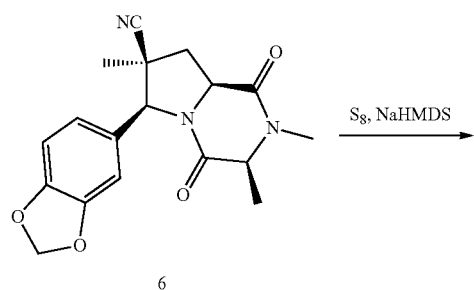

6

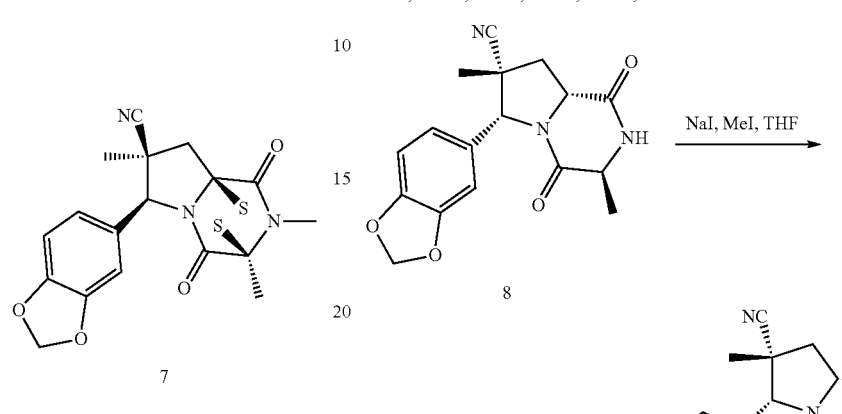

To a suspension of elemental sulfur (300 mg, 9.4 mmol) in dry THF (10 mL) NaHMDS (0.6 M in toluene, 7.40 mL) is being added dropwise. The resulting yellow reaction mixture is stirred at ambient temperature for one minute and then combined with a slurry of the substrate 6 (340 mg, 1.0 mmol in 5 mL dry THF). A second portion of NaHMDS (0.6 M in toluene, 4.8 mL) is subsequently added resulting in an orange mixture which is stirred at ambient temperature for 30 minutes. After quenching with saturated aqueous ammonium chloride, the solvent was removed and the residue was extracted with $CH_2Cl_2$. The combined organic layer was dried over $MgSO_4$ and evaporated to dryness. The crude product was purified by silica gel column chromatography by elution with 2% $EtOAc/CH_2Cl_2$ to afford 129 mg (32%) of compound 7. $^1$H-NMR (400 MHz, $CDCl_3$): δ/ppm 6.96 (s, 1H), 6.91 (s, 2H), 6.06 (s, 2H), 4.89 (s, 1H), 3.36 (d, 1H, J=14.5 Hz), 3.14 (s, 3H), 3.06 (d, 1H, J=14.5 Hz), 2.00 (s, 3H), 1.73 (s, 3H); $^{13}$C-NMR (100 MHz, $CDCl_3$): δ/ppm 165.6, 162.1, 148.6, 148.3, 127.5, 120.7, 120.3, 108.6, 107.2, 101.6, 73.4, 73.3, 72.4, 44.4, 42.8, 27.8, 24.8, 18.1. $α[D]_{20}$=+240°, ee %>99%.

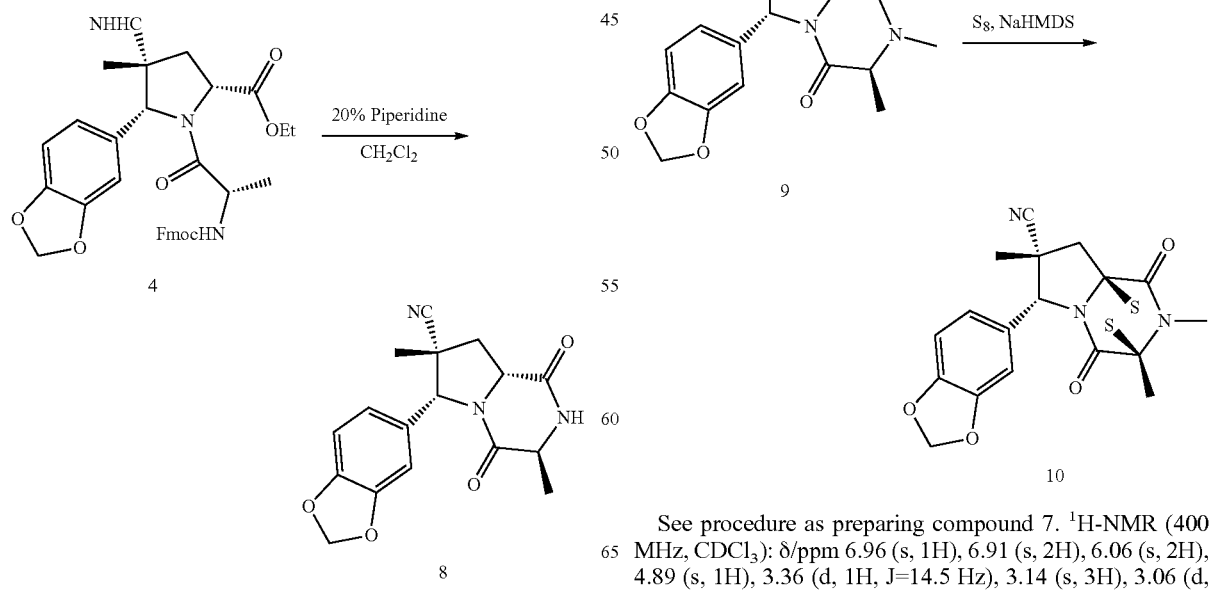

See procedure as preparing compound 5. $^1$H NMR (400 MHz, DMSO-$d_6$) δ/ppm 8.45 (d, 1H, J=4.2 Hz), 6.88 (d, 1H, J=8.2 Hz), 6.70 (s, 1H), 6.60 (d, 1H, J=7.4 Hz), 6.00 (s, 2H), 4.87 (s, 1H), 4.73 (dd, 1H, J=6.6, 11.0 Hz), 3.78-3.70 (m, 1H), 2.42-2.26 (m, 2H), 1.62 (s, 3H), 1.35 (d, 3H, J=7.4 Hz); $^{13}$C NMR (100 MHz, DMSO-$d_6$) δ/ppm 168.6, 167.6, 147.7, 147.4, 133.2, 121.4, 119.8, 108.6, 107.1, 101.7, 68.3, 55.8, 53.5, 42.6, 36.1, 24.4, 18.8;

See procedure as preparing compound 6. $^1$H-NMR (400 MHz, $CDCl_3$): δ/ppm 6.79 (d, 1H, J=9.0 Hz), 6.63 (d, 1H, J=9.0 Hz), 6.57 (s, 1H), 5.96 (s, 2H), 4.82 (s, 1H), 4.36 (dd, 1H, J=6.5, 11.0 Hz), 3.90 (q, 1H, J=7.0 Hz), 3.04 (s, 3H), 2.76 (t, 1H, J=7.0 Hz), 2.45 (dd, 1H, J=6.5, 13.5 Hz), 1.66 (s, 3H), 1.47 (d, 3H, J=7.0 Hz); $^{13}$C-NMR (100 MHz, $CDCl_3$): δ/ppm 166.6, 166.0, 148.2, 148.1, 130.8, 119.9, 119.8, 108.6, 106.2, 101.4, 69.6, 60.8, 56.1, 42.6, 36.7, 32.0, 25.1, 15.3;

See procedure as preparing compound 7. $^1$H-NMR (400 MHz, $CDCl_3$): δ/ppm 6.96 (s, 1H), 6.91 (s, 2H), 6.06 (s, 2H), 4.89 (s, 1H), 3.36 (d, 1H, J=14.5 Hz), 3.14 (s, 3H), 3.06 (d, 1H, J=14.5 Hz), 2.00 (s, 3H), 1.73 (s, 3H); $^{13}$C-NMR (100

MHz, CDCl$_3$): δ/ppm 165.6, 162.1, 148.6, 148.3, 127.5, 120.7, 120.3, 108.6, 107.2, 101.6, 73.4, 73.3, 72.4, 44.4, 42.8, 27.8, 24.8, 18.1. $\alpha[D]_{20}$=−216°, ee %>95%.

Example 2

General Procedure for the Synthesis of Polyfunctionalized Pyrrolidine Esters

Dimethyl rac-(2S,4S,5S)-5-(4-Fluorophenyl)-4-methylpyrrolidine-2,4-dicarboxylate

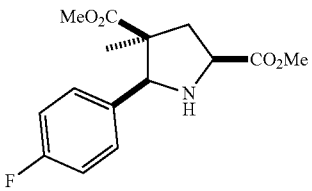

Chemical Formula: C$_{15}$H$_{18}$FNO$_4$
Exact Mass: 295.12

4-Fluorobenzaldehyde (1.24 g, 10 mmol) was dissolved in 15 mL of MeCN containing triethylamine (1.5 mL, 11 mmol) and glycine methyl ester hydrochloride (1.35 g, 11 mmol). The reaction mixture was stirred for 5 h at room temperature. After removing the solvent in vacuo, the solid residue was re-dissolved in CH$_2$Cl$_2$ and washed twice from water to give the imine intermediate as colourless oil. To a solution of this material in 20 mL of THF, solid LiBr (1.1 g, 12 mmol) and triethylamine (1.7 mL, 12 mmol) were added portionwise. After 2 min, methyl methacrylate (1.5 g, 15 mmol) was added and the resulting solution was stirred at room temperature for 8 h. After evaporation of the solvent in vacuo and extractive work-up (3 times, CH$_2$Cl$_2$/water), the desired product was isolated as yellow oil (2.6 g, 90% yield, as a single diastereomer). In some cases the cycloadduct was isolated as a mixture of C$_4$ epimers, which were separated by crystallization or chromatography.

$^1$H-NMR (500 MHz, CDCl$_3$): δ/ppm 7.30 (2H, m), 7.03 (2H, t, J=8.5 Hz), 4.09 (1H, s), 4.06 (1H, t, J=7.0 Hz), 3.86 (3H, s), 3.30 (3H, s), 2.95 (1H, br. s, NH), 2.76 (1H, dd, J=7.0, 13.5 Hz), 2.14 (1H, dd, J=13.0, 13.5 Hz), 1.43 (s, 3H); $^{13}$C-NMR (125 MHz, CDCl$_3$): δ/ppm 174.6 (C), 174.3 (C), 162.3 (C, J$_{C-F}$=245 Hz), 134.7 (C, J$_{C-F}$=3 Hz), 128.4 (2CH, d, J$_{C-F}$=8 Hz), 115.0 (2CH, d, J$_{C-F}$=21 Hz), 73.1 (CH), 58.8 (CH), 54.6 (C), 52.3 (CH$_3$), 51.5 (CH$_3$), 41.1 (CH$_2$), 22.5 (CH$_3$). LR-MS: 295.96; HR-MS (ESI) calculated for C$_{15}$H$_{18}$NO$_4$FCl: 296.1298 (M+H$^+$), found: 296.1302.

2-Ethyl rac-4-Methyl (2S,4S,5S)-4-methyl-5-(pyridin-3-yl)pyrrolidine-2,4-dicarboxylate

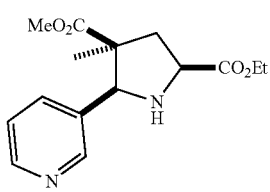

Chemical Formula: C$_{15}$H$_{20}$N$_2$O$_4$
Exact Mass: 292.14

Isolated as pale yellow oil, dr (diastereomer ratio)>9:1. $^1$H-NMR (500 MHz, CDCl$_3$): δ/ppm 8.26 (1H, s), 8.23 (1H, dd, J=1.5, 4.5 Hz), 7.45 (1H, dd, J=1.5, 8.0 Hz), 6.98 (1H, dd, J=4.5, 9.0 Hz), 4.00-4.12 (2H, m), 3.85 (2H, s), 3.78 (1H, app. t, J=7.5 Hz), 2.99 (3H, s), 2.48 (1H, dd, J=8.0, 13.0 Hz), 1.86 (1H, dd, J=8.0, 13.0 Hz), 1.17 (3H, s), 1.07 (3H, t, J=7.0 Hz); $^{13}$C-NMR (125 MHz, CDCl$_3$): δ/ppm 173.9 (C), 173.3 (C), 148.9 (CH), 148.6 (CH), 134.9 (C), 133.9 (CH), 122.8 (CH), 70.7 (CH), 60.8 (CH$_2$), 58.5 (CH), 54.4 (C), 51.1 (CH$_3$), 40.3 (CH$_2$), 22.4 (CH$_3$), 14.0 (CH$_3$). IR (film): v/cm$^{-1}$ 3380, 2981, 2950, 1732, 1430, 1210, 1110, 1029, 716. LR-MS: 293.1 (M+H$^+$); HR-MS (ESI) calculated for C$_{15}$H$_{20}$N$_2$O$_4$Na: 315.1321 (M+Na$^+$), found: 315.1315.

2-Ethyl 4-Methyl rac-(2S,4S,5S)-5-(5-Bromo-2-methoxyphenyl)-4-methylpyrrolidine-2,4-dicarboxylate

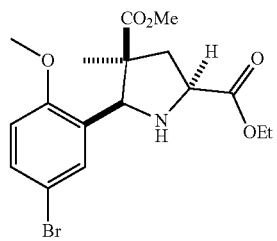

Chemical Formula: C$_{17}$H$_{22}$BrNO$_5$
Exact Mass: 399.07

Isolated as brown oil (single diastereomer). $^1$H-NMR (500 MHz, CDCl$_3$): δ/ppm 7.45 (1H, d, J=2.5 Hz), 7.28 (1H, dd, J=2.5, 9.0 Hz), 6.70 (1H, d, J=9.0 Hz), 4.45 (1H, s), 4.25 (2H, q, J=7.0 Hz), 3.96 (1H, app. t, J=8.0 Hz), 3.74 (3H, s), 3.30 (3H, s), 2.72 (1H, dd, J=9.0, 13.0 Hz), 2.05 (1H, dd, J=9.0, 13.0 Hz), 1.36 (3H, s), 1.24 (3H, t, J=7.0 Hz); $^{13}$C-NMR (125 MHz, CDCl$_3$): δ/ppm 174.7 (C), 173.4 (C), 156.3 (C), 131.1 (CH), 130.4 (CH), 129.4 (C), 112.7 (C), 112.0 (CH), 66.8 (CH), 61.0 (CH$_2$), 59.0 (CH$_3$), 55.4 (CH$_3$), 54.5 (C), 51.3 (CH), 41.7 (CH$_2$), 22.8 (CH$_3$), 14.2 (CH$_3$). IR (film): v/cm$^{-1}$ 3366, 2980, 2938, 2839, 2236, 1736, 1486, 1252, 1202, 1134, 1028, 809. LR-MS: 389.0 (M+Na$^+$); HR-MS (ESI) calculated for C$_{16}$H$_{19}$N$_2$O$_3$BrNa: 389.0477 (M+Na$^+$), found: 389.0471.

4-(tert-Butyl) 2-Ethyl rac-(2S,4S,5S)-5-(4-Fluorophenyl)-4-methylpyrrolidine-2,4-dicarboxylate

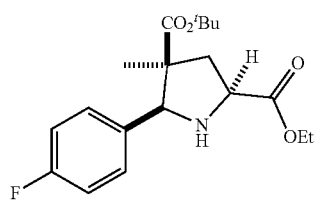

Chemical Formula: C$_{19}$H$_{26}$FNO$_4$
Exact Mass: 351.18

Isolated as yellow oil (dr>9:1). $^1$H-NMR (500 MHz, CDCl$_3$): δ/ppm 7.37 (2H, dd, J=5.5, 8.0 Hz), 7.04 (2H, app. t, J=8.0 Hz), 4.31 (2H, q, J=7.0 Hz), 4.08 (1H, s), 4.03 (1H, t, J=8.5 Hz), 2.69 (1H, br. s), 2.66 (1H, dd, J=9.0, 13.0 Hz), 2.12 (1H, dd, J=8.5, 13.0 Hz), 1.49 (3H, s), 1.36 (3H, t, J=7.0 Hz), 1.13 (9H, s); $^{13}$C-NMR (125 MHz, CDCl$_3$): δ/ppm 173.7 (C), 173.4 (C), 162.3 (C, d, J=244 Hz), 135.9 (C), 128.9 (2CH, d, J=8 Hz), 114.9 (2CH, d, J=21 Hz), 80.8 (C), 72.3 (CH), 61.2 (CH$_2$), 58.9 (CH), 55.1 (C), 41.9 (CH$_2$), 27.6 (3CH$_3$), 24.3 (CH$_3$), 14.3 (CH$_3$). IR (film): ν/cm$^{-1}$ 3368, 2979, 2935, 1724, 1511, 1369, 1224, 1154. LR-MS: 352.2 M+H$^+$; HR-MS (ESI) calculated for C$_{19}$H$_{26}$NO$_4$FNa: 374.1743 (M+Na$^+$), found: 374.1742.

Ethyl rac-(2S,4S,5S)-4-Cyano-4-methyl-5-phenylpyrrolidine-2-carboxylate

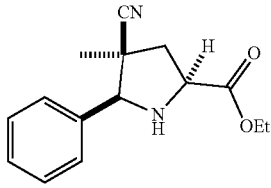

Chemical Formula: C$_{15}$H$_{18}$N$_2$O$_2$
Exact Mass: 258.1368

$^1$H-NMR (500 MHz, CDCl$_3$): δ/ppm 7.52 (2H, d, J=7.1 Hz), 7.41-7.34 (3H, m), 4.34-4.24 (2H, m), 3.98 (1H, dd, J=4.2, 9.7 Hz), 3.93 (1H, s), 2.90 (1H, s), 2.82 (1H, dd, J=4.2, 13.6 Hz), 2.29 (1H, dd, J=9.6, 13.6 Hz), 1.42 (3H, s), 1.34 (3H, t, J=7.1 Hz); $^{13}$C-NMR (125 MHz, CDCl$_3$): δ/ppm 173.0 (C), 136.5 (C), 128.9 (CH), 128.6 (2CH), 127.6 (2CH), 121.9 (C), 72.4 (CH), 61.7 (CH$_2$), 57.3 (CH), 44.1 (C), 42.5 (CH$_2$), 22.0 (CH$_3$), 14.2 (CH$_3$); IR (film): ν/cm$^{-1}$ 3348, 2980, 2234, 1734, 1454; LR-MS: 281.1 [M+Na]$^+$; HR-MS (ESI) calculated for C$_{15}$H$_{18}$N$_2$O$_2$Na: 281.1266, found: 281.1263.

Ethyl rac-(2S,4S,5S)-4-Cyano-5-(4-fluorophenyl)-4-methylpyrrolidine-2-carboxylate

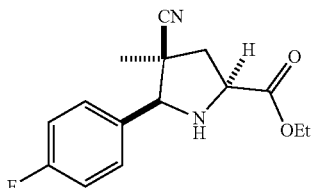

Chemical Formula: C$_{15}$H$_{17}$FN$_2$O$_2$
Exact Mass: 276.1274

$^1$H-NMR (500 MHz, CDCl$_3$): δ/ppm 7.52 (2H, dd, J=5.4, 8.7 Hz), 7.09 (2H, t, J=8.7 Hz), 4.34-4.24 (2H, m), 4.00 (1H, dd, J=4.2, 9.6 Hz), 3.95 (1H, s), 2.83 (1H, dd, J=4.2, 13.7 Hz), 2.82 (1H, s), 2.30 (1H, dd, J=9.6, 13.7 Hz), 1.41 (3H, s), 1.34 (3H, t, J=7.1 Hz); $^{13}$C-NMR (125 MHz, CDCl$_3$): δ/ppm 172.9 (C), 163.2 (C, d, J=246 Hz), 132.4 (C), 129.4 (2CH, d, J=8 Hz), 121.8 (C), 115.7 (2CH, d, J=22 Hz), 71.7 (CH), 61.9 (CH$_2$), 57.3 (CH), 44.0 (C), 42.2 (CH$_2$), 22.0 (CH$_3$), 14.3 (CH$_3$); IR (film): ν/cm$^{-1}$ 3348, 2982, 2235, 1736, 1605, 1510; LR-MS: 299.1 [M+Na]$^+$; HR-MS (ESI) calculated for C$_{15}$H$_{17}$FN$_2$O$_2$Na: 299.1172, found: 299.1177.

Ethyl rac-(2S,4S,5S)-5-(Benzo[d][1,3]dioxol-5-yl)-4-cyano-4-methylpyrrolidine-2-carboxylate

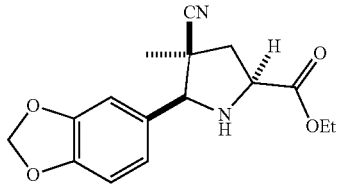

Chemical Formula: C$_{16}$H$_{18}$N$_2$O$_4$
Exact Mass: 302.1267

Isolated as brown oil (dr=3:2). $^1$H-NMR (500 MHz, CDCl$_3$): δ/ppm 7.12 (1H, s), 6.98 (1H, d, J=8.5 Hz), 6.83 (1H, d, J=8.5 Hz), 5.99 (2H, s), 4.31 (2H, q, J=7.0 Hz), 3.98 (1H, dd, J=4.5, 9.5 Hz), 3.89 (1H, s), 2.83 (1H, dd, J=4.0, 13.5 Hz), 2.75 (1H, br. s), 2.29 (1H, dd, J=9.5, 13.5 Hz), 1.44 (3H, s), 1.36 (3H, t, J=7.0 Hz); $^{13}$C-NMR (125 MHz, CDCl$_3$): δ/ppm 173.0 (C), 148.0 (C), 147.9 (C), 130.6 (C), 122.1 (C), 121.1 (CH), 108.2 (CH), 107.9 (CH), 101.3 (CH$_2$), 72.1 (CH), 61.6 (CH$_2$), 57.0 (CH), 43.8 (C), 42.1 (CH$_2$), 22.1 (CH$_3$), 14.2 (CH$_3$). IR (film): ν/cm$^{-1}$ 3361, 2984, 2900, 2254, 1734, 1490, 1447, 1265, 1041, 909. LR-MS: 325.1 M+Na$^+$; HR-MS (ESI) calculated for C$_{16}$H$_{18}$N$_2$O$_4$Na: 325.1164 (M+Na$^+$), found: 325.1161.

Ethyl rac-(2S,4S,5R)-5-(6-Bromobenzo[d][1,3]dioxol-5-yl)-4-cyano-4-methylpyrrolidine-2-carboxylate

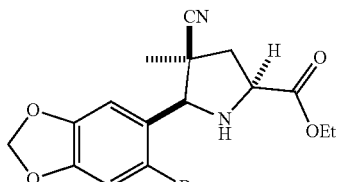

Chemical Formula: C$_{16}$H$_{17}$BrN$_2$O$_4$
Exact Mass: 380.0372

Isolated as brown oil (single diastereomer). $^1$H-NMR (500 MHz, CDCl$_3$): δ/ppm 7.48 (1H, s), 6.96 (1H, s), 5.97 (1H, s), 5.92 (1H, s), 4.56 (1H, s), 4.20 (2H, q, J=7.0 Hz), 4.00 (1H, m), 2.67 (1H, dd, J=6.0, 8.0 Hz), 2.65 (1H, broad s), 2.27 (1H, dd, J=9.0, 13.5 Hz), 1.53 (3H, s), 1.27 (3H, t, J=7.0 Hz); $^{13}$C-NMR (125 MHz, CDCl$_3$): δ/ppm 172.8 (C), 148.3 (C), 147.6 (C), 130.9 (C), 122.0 (C), 114.5 (C), 112.4 (CH), 109.4 (CH), 102.0 (CH$_2$), 68.5 (CH), 61.4 (CH$_2$), 57.1 (CH), 44.3 (C), 41.4 (CH$_2$), 23.3 (CH$_3$), 14.2 (CH$_3$). IR (film): ν/cm$^{-1}$ 3366, 2981, 2904, 2237, 1737, 1504, 1477, 1408, 1241, 1205, 1117, 1037, 931, 846. LR-MS: 381.2 M+Na$^+$.

Ethyl rac-(2S,4S,5R)-5-(5-Bromo-2-methoxyphenyl)-4-cyano-4-methylpyrrolidine-2-carboxylate

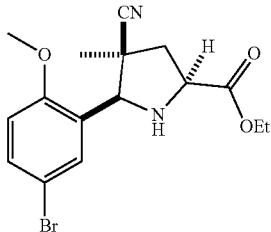

Chemical Formula: $C_{16}H_{19}BrN_2O_3$
Exact Mass: 366.0579

Isolated as brown oil (single diastereomer). $^1$H-NMR (500 MHz, CDCl$_3$): δ/ppm 7.89 (1H, d, J=2.5 Hz), 7.37 (1H, dd, J=2.5, 9.0 Hz), 6.77 (1H, d, J=9.0 Hz), 4.47 (1H, s), 4.27 (2H, q, J=7.5 Hz), 3.98 (1H, t, J=7.5 Hz), 3.83 (3H, s), 2.71 (1H, br s), 2.62 (1H, dd, J=7.0, 13.0 Hz), 2.26 (1H, dd, J=8.5, 13.0 Hz), 1.49 (3H, s), 1.34 (3H, t, J=7.5 Hz); $^{13}$C-NMR (125 MHz, CDCl$_3$): δ/ppm 172.7 (C), 156.4 (C), 131.9 (CH), 131.1 (CH), 129.1 (C), 122.3 (C), 113.1 (C), 112.2 (CH), 64.5 (CH), 61.5 (CH$_2$), 57.7 (CH), 55.5 (CH$_3$), 43.9 (C), 41.8 (CH$_2$), 23.6 (CH$_3$), 14.3 (CH$_3$). IR (film): v/cm$^{-1}$ 3366, 2980, 2938, 2904, 2839, 2236, 1736, 1486, 1463, 1252, 1202, 1134, 1028, 809. LR-MS: 389.0 M+Na$^+$; HR-MS (ESI) calculated for $C_{16}H_{19}N_2O_3Na$: 389.0477, found: 389.0471.

Ethyl rac-(2S,4S,5S)-4-Cyano-5-(2,2-difluorobenzo[d][1,3]dioxol-5-yl)-4-methylpyrrolidine-2-carboxylate

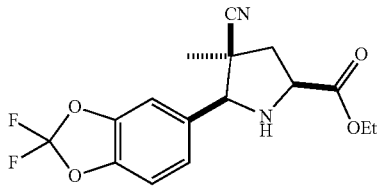

Chemical Formula: $C_{16}H_{16}F_2N_2O_4$
Exact Mass: 338.1078

Isolated as yellow oil (dr=4:1). $^1$H-NMR (500 MHz, CDCl$_3$): δ/ppm 7.38 (1H, s), 7.22 (1H, d, J=8.5 Hz), 7.06 (1H, d, J=8.5 Hz), 4.24-4.34 (2H, m), 3.97 (1H, s), 3.95-4.01 (1H, m), 2.84 (1H, dd, J=4.5, 9.0 Hz), 2.68 (1H, s), 2.29 (1H, dd, J=4.5, 8.5 Hz), 1.44 (3H, s), 1.33 (3H, t, J=9.0 Hz); $^{13}$C-NMR (125 MHz, CDCl$_3$): δ/ppm 172.7 (C), 144.1 (C), 133.7 (C), 133.3 (C), 131.8 (C, t, J=250 Hz), 123.1 (CH), 121.6 (C), 109.3 (CH), 109.1 (CH), 71.9 (CH), 61.8 (CH$_2$), 57.0 (CH), 43.9 (C), 41.8 (CH$_2$), 22.1 (CH$_3$), 14.2 (CH$_3$). IR (film): v/cm$^{-1}$ 3351, 3078, 2983, 2236, 1738, 1497, 1448, 1382, 1239, 1148, 1034, 818, 703.

Ethyl rac-(2S,4S,5S)-5-(3,4-Bis(allyloxy)phenyl)-4-cyano-4-methylpyrrolidine-2-carboxylate

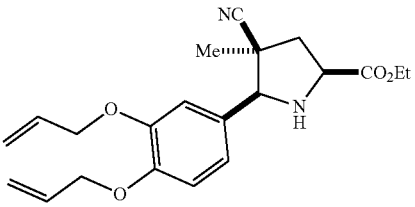

Chemical Formula: $C_{21}H_{26}N_2O_4$
Exact Mass: 370.1893
Molecular Weight: 370.4490

Isolated as yellow oil (dr=4:1). $^1$H-NMR (500 MHz, CDCl$_3$) δ/ppm 7.17 (d, J=1.5 Hz, 1H), 7.01-6.99 (m, 1H), 6.89 (d, J=8.2 Hz, 1H), 6.13-6.04 (m, 2H), 5.47-5.40 (m, 2H), 5.31-5.26 (m, 2H), 4.66-4.60 (m, 4H), 4.33-4.26 (m, 2H), 3.96 (dd, J=9.6, 3.9 Hz, 1H), 3.85 (s, 1H), 2.82 (dd, J=13.6, 4.1 Hz, 1H), 2.75 (broad s, 1H), 2.27 (dd, J=13.6, 9.7 Hz, 1H), 1.40 (s, 3H), 1.33 (t, J=7.6 Hz, 3H) ppm; $^{13}$C-NMR (126 MHz, CDCl$_3$) δ/ppm 173.2 (C), 149.1 (C), 148.6 (C), 133.5 (2×CH), 129.4 (C), 122.2 (C), 120.5 (CH), 118.0 (CH$_2$), 117.8 (CH$_2$), 113.8 (CH), 113.4 (CH), 72.4 (CH), 70.2 (CH$_2$), 70.0 (CH$_2$), 61.8 (CH$_2$), 57.3 (CH), 44.0 (C), 42.5 (CH$_2$), 22.1 (CH$_3$), 14.3 (CH$_3$) ppm; IR (film) v/cm$^{-1}$ 2982, 2936, 1735, 1649, 1513, 1454, 1426, 1378, 1265, 1217, 1138, 1021, 997, 929, 810 cm$^{-1}$; HRMS (ESI) calcd for $C_{21}H_{26}N_2O_4Na^+$ (M+Na) 393.1790, found 393.1796.

Ethyl rac-(2S,4S,5S)-4-Cyano-5-(7-methoxybenzo[d][1,3]dioxol-5-yl)-4-methylpyrrolidine-2-carboxylate

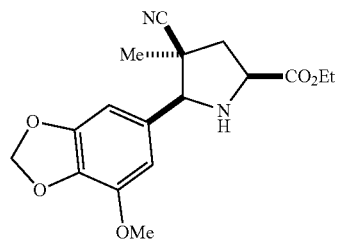

Chemical Formula: $C_{17}H_{20}N_2O_5$
Exact Mass: 332.1372
Molecular Weight: 332.3560

Isolated as yellow oil (dr=3:2). $^1$H-NMR (500 MHz, CDCl$_3$) δ/ppm 6.78 (s, 1H), 6.67 (s, 1H), 5.96 (s, 2H), 4.29-4.22 (m, 2H), 3.93 (dd, J=9.5, 4.3 Hz, 1H), 3.91 (s, 3H), 3.82 (s, 1H), 2.78 (dd, J=13.6, 4.3 Hz, 1H), 2.68 (broad s, 1H), 2.24 (dd, J=13.6, 9.6 Hz, 1H), 1.40 (s, 3H), 1.31 (t, J=7.2 Hz, 3H) ppm; $^{13}$C-NMR (126 MHz, CDCl$_3$) δ/ppm 172.9 (C), 148.8 (C), 143.6 (C), 135.6 (C), 131.4 (C), 122.0 (C), 107.1 (CH), 101.9 (CH), 101.7 (CH$_2$), 72.3 (CH), 61.7 (CH$_2$), 57.1 (CH$_3$), 56.7 (CH), 43.9 (C), 42.1 (CH$_2$), 22.2 (CH$_3$), 14.2 (CH$_3$) ppm; IR (film) v/cm$^{-1}$ 2979, 2235, 1735, 1635, 1510, 1452, 1381, 1323, 1291, 1202, 1138, 1094, 1043, 929, 855, 831, 733 cm$^{-1}$; HRMS (ESI) calcd for $C_{17}H_{20}N_2O_5Na^+$ (M+Na) 355.1270, found 355.1261.

Ethyl rac-(2S,4S,5S)-4-Cyano-5-(2,3-dihydro-1H-inden-5-yl)-4-methylpyrrolidine-2-carboxylate

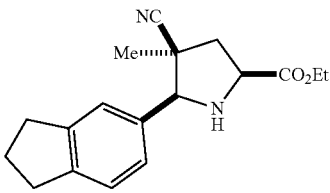

Chemical Formula: $C_{18}H_{22}N_2O_2$
Exact Mass: 298.1681
Molecular Weight: 298.3860

Isolated as yellow oil (dr=1:1). $^1$H-NMR (500 MHz, CDCl$_3$) δ 7.40 (s, 1H), 7.27-7.23 (m, 2H), 4.34-4.26 (m, 2H), 3.98 (dd, J=9.6, 3.9 Hz, 1H), 3.90 (s, 1H), 2.97-2.89 (m, 4H), 2.83 (dd, J=13.8, 4.2 Hz, 1H), 2.30 (dd, J=13.8, 9.7 Hz, 1H), 2.09 (app. quintet, J=7.4 Hz, 2H), 1.62 (broad s, 1H), 1.42 (s, 3H), 1.35 (t, J=7.3 Hz, 3H) ppm; $^{13}$C-NMR (126 MHz, CDCl$_3$) δ 173.2 (C), 145.3 (C), 144.8 (C), 134.3 (C), 125.6 (CH), 124.5 (CH), 123.4 (CH), 122.2 (C), 72.8 (CH), 61.8 (CH$_2$), 57.5 (CH), 44.2 (C), 42.8 (CH$_2$), 33.0 (CH$_2$), 32.8 (CH$_2$), 25.6 (CH$_2$), 22.1 (CH$_3$), 14.4 (CH$_3$) ppm; IR (film) v/cm$^{-1}$ 2940, 2234, 1735, 1447, 1378, 1209, 1139, 1097, 1032, 826 cm$^{-1}$; HRMS (ESI) calcd for $C_{18}H_{22}N_2O_2Na^+$ (M+Na) 321.1579, found 321.1577.

Ethyl rac-(2S,4S,5S)-4-Cyano-4-methyl-5-(1-(phenylsulfonyl)-1H-indol-3-yl)pyrrolidine-2-carboxylate

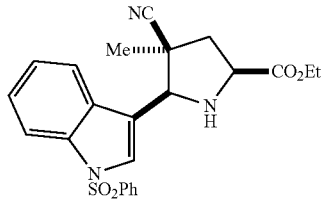

Chemical Formula: $C_{23}H_{23}N_3O_4S$
Exact Mass: 437.1409
Molecular Weight: 437.5140

Isolated as a yellow, highly viscous oil. $^1$H-NMR (500 MHz, CDCl$_3$) δ 7.98 (d, J=6.4 Hz, 2H), 7.93 (d, J=8.3 Hz, 2H), 7.59 (d, J=7.9 Hz, 1H), 7.52 (t, J=7.4 Hz, 1H), 7.43 (t, J=7.8 Hz, 2H), 7.32 (t, J=7.7 Hz, 1H), 7.23 (t, J=7.6 Hz, 1H), 4.35-4.28 (m, 2H), 4.27 (d, J=5.6 Hz, 1H), 4.04-4.00 (m, 1H), 2.88 (dd, J=13.7, 4.3 Hz, 1H), 2.81 (broad s, 1H), 2.33 (dd, J=13.7, 9.8 Hz, 1H), 1.46 (s, 3H), 1.37 (t, J=7.1 Hz, 3H) ppm; $^{13}$C-NMR (126 MHz, CDCl$_3$) δ 172.7 (C), 137.9 (C), 135.1 (C), 134.0 (CH), 129.8 (C), 129.4 (CH), 127.2 (CH), 125.2 (CH), 125.1 (CH), 123.4 (CH), 122.2 (C), 119.8 (CH), 119.1 (C), 113.9 (CH), 64.6 (CH), 61.9 (CH$_2$), 57.4 (CH), 44.6 (C), 42.6 (CH$_2$), 22.4 (CH$_3$), 14.3 (CH$_3$) ppm; IR (film) v/cm$^{-1}$ 2980, 2235, 1735, 1606, 1447, 1369, 1273, 1212, 1176, 1125, 1092, 1024, 979, 858, 750, 722 cm$^{-1}$; HRMS (ESI) calcd for $C_{23}H_{23}N_3O_4SNa^+$ (M+Na) 460.1307, found 460.1305.

Example 3

General Procedure for Forming Diketopiperazines by Sequential Reaction of Pyrrolidine Esters with 2-Chloroalkanonyl Chlorides and Amines Methyl rac-(3R,6S,7S,8aS)-6-(4-Fluorophenyl)-2,3,7-trimethyl-1,4-dioxooctahydropyrrolo[1,2-a]pyrazine-7-carboxylate

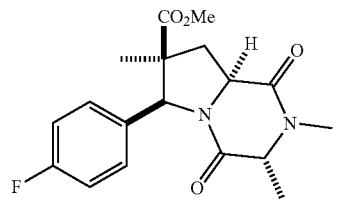

Chemical Formula: $C_{18}H_{21}FN_2O_4$
Exact Mass: 348.1485

The corresponding pyrrolidine (1.0 equiv) was dissolved in 10 mL of CH$_2$Cl$_2$ and cooled to 0° C. with an ice-bath. Triethylamine (1.2 equiv) was added, followed by dropwise addition of a solution of 2-chloropropionyl chloride (1.2 equiv, 50% v/v in CH$_2$Cl$_2$). This mixture was stirred for 1 h with cooling, followed by 1 h after removal of the ice-bath. The intermediate α-chloroamide is then directly extracted (3×CH$_2$Cl$_2$) and isolated as brownish foam after removal of the volatiles in vacuo. The corresponding amide was re-dissolved in 10 mL of CH$_2$Cl$_2$ and combined with the equivalent volume of 40% aq MeNH$_2$ solution to give a biphasic mixture, which was stirred at rt for 12-16 h. Extraction of this mixture gives the crude diketopiperazine (DKP) product as yellow foam (purity 50-80%). This residue was stirred with MeOH (1 M) for 1 h, whereupon a colorless solid was obtained ~70% yield. Trituration of this material from a methanolic solution in CH$_2$Cl$_2$ (often accelerated by vigorous stirring) gave the major DKP stereoisomer as a colorless solid after filtration and drying under high vacuum. Either the pure DKP steroisomer, or the solid 5:1 mixture of DKP isomers, could be employed in the subsequent sulfidation step.

$^1$H-NMR (500 MHz, CDCl$_3$): δ/ppm 7.00-7.10 (2H, m), 6.91 (2H, t, J=8.5 Hz), 4.81 (1H, s), 4.36 (1H, dd, J=6.5, 11.5 Hz), 3.81 (1H, q, J=9.0 Hz), 3.22 (3H, s), 2.94 (3H, s), 2.90-2.95 (1H, m), 2.16 (1H, dd, J=6.5, 14.0 Hz), 1.53 (3H, s), 1.44 (3H, d, J=9.0 Hz); $^{13}$C-NMR (125 MHz, CDCl$_3$): δ/ppm 172.1 (C), 167.3 (C), 166.9 (C), 162.3 (C, d, J=249 Hz), 133.6 (C, d, J=3 Hz), 128.3 (2 CH, d, J=8 Hz), 115.2 (2 CH, d, J=21 Hz), 69.4 (CH), 60.9 (CH), 56.9 (CH), 53.3 (C), 51.9 (CH$_3$), 34.4 (CH$_2$), 32.0 (CH$_3$), 24.2 (CH$_3$), 15.3 (CH$_3$). IR (film): v/cm$^{-1}$ 2975, 2929, 1736, 1677, 1605, 1509, 1433, 1401, 1299, 1248, 1225, 1126, 1158, 849. LR-MS: 371.07 (M+Na$^+$); HR-MS (ESI) calculated for $C_{18}H_{22}N_2O_4F$: 349.1564 (M+H$^+$), found: 349.1570.

tert-Butyl rac-(3R,6S,7S,8aS)-6-(4-Fluorophenyl)-2,3,7-trimethyl-1,4-dioxooctahydropyrrolo[1,2-a]pyrazine-7-carboxylate

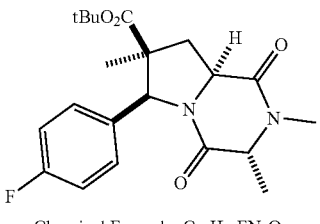

Chemical Formula: $C_{21}H_{27}FN_2O_4$
Exact Mass: 390.1955

$^1$H-NMR (500 MHz, CDCl$_3$): δ/ppm 7.06-7.13 (2H, m), 6.91-6.95 (2H, m), 4.76 (1H, s), 4.34 (1H, dd, J=7.0, 12.0 Hz), 3.79 (1H, q, J=7.0 Hz), 3.00 (3H, s), 2.92-3.00 (1H, m), 2.17 (1H, dd, J=6.5, 14.0 Hz), 1.51 (3H, s), 1.45 (3H, d, J=7.0 Hz), 1.05 (9H, s); $^{13}$C-NMR (125 MHz, CDCl$_3$): δ/ppm 170.8 (C), 167.3 (C), 166.7 (C), 162.3 (C, d, J=250 Hz), 134.2 (C), 129.2 (2CH), 115.1 (2CH, d, J=21 Hz), 81.4 (C), 69.3 (CH), 60.8 (CH), 56.7 (CH), 53.4 (C), 34.8 (CH$_2$), 31.9 (CH$_3$), 27.3 (3CH$_3$), 25.2 (CH$_3$), 15.2 (CH$_3$). IR (film): ν/cm$^{-1}$ 2977, 2934, 1724, 1673, 1510, 1452, 1430, 1401, 1369, 1304, 1250, 1228, 1167, 1124, 848, 734. LR-MS: 413.2 (M+Na$^+$); HR-MS (ESI) calculated for C$_{21}$H$_{27}$N$_2$O$_4$FNa: 413.1852 (M+Na$^+$), found: 413.1846.

Methyl rac-(3R,6S,7S,8aS)-6-(Benzo[d][1,3]dioxol-5-yl)-2,3,7-trimethyl-1,4-dioxooctahydropyrrolo[1,2-a]pyrazine-7-carboxylate

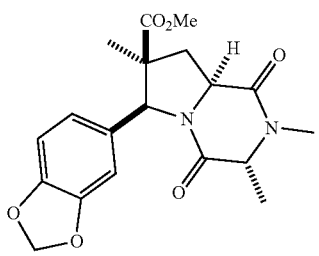

Chemical Formula: $C_{19}H_{22}N_2O_6$
Exact Mass: 374.1478

Isolated as an 8:1 mixture of diastereomers, data for the major isomer is reported. $^1$H-NMR (500 MHz, CDCl$_3$): δ/ppm 6.68 (1H, d, J=8.0 Hz), 6.54 (1H, d, J=8.0 Hz), 6.51 (1H, s), 5.90 (2H, s), 4.78 (1H), 4.36 (1H, dd, J=6.5, 11.5 Hz), 3.85 (1H, app. t, J=7.0 Hz), 3.32 (3H, s), 3.03 (3H, s), 2.90-3.00 (1H, m), 2.16 (1H, dd, J=6.5, 8.5 Hz), 1.53 (3H, s), 1.41 (3H, s); $^{13}$C-NMR (125 MHz, CDCl$_3$): δ/ppm 172.09 (C), 167.2 (C), 166.8 (C), 147.5 (C), 147.3 (C), 131.4 (C), 120.3 (CH), 108.0 (CH), 106.9 (CH), 101.1 (CH$_2$), 69.8 (CH), 60.8 (CH), 56.8 (CH$_3$), 53.2 (C), 51.9 (CH), 34.2 (CH$_2$), 32.0 (CH$_3$), 24.1 (CH$_3$), 15.2 (CH$_3$). LR-MS: 416.1 M+Na+; IR (film): ν/cm$^{-1}$ 2953, 2949, 1735, 1672, 1490, 1432, 1294, 1245, 1122, 1037. HR-MS (ESI) calculated for C$_{19}$H$_{22}$N$_2$O$_6$Na: 397.1375 (M+Na$^+$), found: 397.1367.

Rac-(3R,6S,7S,8aS)-2,3,7-trimethyl-1,4-dioxo-6-phenyloctahydropyrrolo-[1,2-a]pyrazine-7-carbonitrile

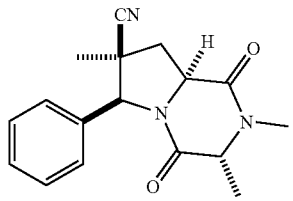

Chemical Formula: $C_{17}H_{19}N_3O_2$
Exact Mass: 297.1477

$^1$H-NMR (600 MHz, CDCl$_3$): δ/ppm 7.39-7.33 (3H, m), 7.12 (2H, d, J=7.2 Hz), 4.91 (1H, s), 4.40 (1H, dd, J=6.6, 11.4 Hz), 3.91 (1H, q, J=3.6, 7.2 Hz), 3.05 (3H, s), 2.79 (1H, t, J=11.4 Hz), 2.46 (1H, dd, J=6.6, 13.2 Hz), 1.69 (3H, s), 1.48 (3H, d, J=7.2 Hz); $^{13}$C-NMR (125 MHz, CDCl$_3$): δ/ppm 166.7 (C), 166.2 (C), 136.9 (C), 129.2 (2CH), 129.1 (2CH), 126.1 (CH), 119.9 (C), 69.8 (CH), 60.9 (CH), 56.3 (CH), 42.6 (C), 36.7 (CH$_2$), 32.2 (CH$_3$), 25.3 (CH$_3$), 15.4 (CH$_3$); IR (film): ν/cm$^{-1}$ 2981, 2937, 2244, 1673; LR-MS: 320.1 [M+Na]$^+$; HR-MS (ESI) calculated for C$_{17}$H$_{19}$N$_3$O$_2$Na: 320.1375, found: 320.1380.

Rac-(3R,6S,7S,8aS)-6-(4-fluorophenyl)-2,3,7-trimethyl-1,4-dioxooctahydropyrrolo-[1,2-a]pyrazine-7-carbonitrile

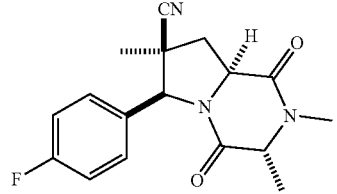

Chemical Formula: $C_{17}H_{18}FN_3O_2$
Exact Mass: 315.1383

$^1$H-NMR (500 MHz, CDCl$_3$): δ/ppm 7.13-7.05 (4H, m), 4.90 (1H, s), 4.39 (1H, dd, J=6.5, 11.0 Hz), 3.90 (1H, q, J=7.0 Hz), 3.06 (3H, s), 2.76 (1H, t, J=12.0 Hz), 2.47 (1H, dd, J=6.5, 13.5 Hz), 1.69 (3H, s), 1.49 (3H, d, J=7.5 Hz); $^{13}$C-NMR (125 MHz, CDCl$_3$): δ/ppm 166.8 (C), 166.1 (C), 163.0 (C, d, J=247 Hz), 132.8 (C, d, J=3 Hz), 127.9 (2CH, d, J=8 Hz), 119.8 (C), 116.2 (2CH, d, J=22 Hz), 69.2 (CH), 60.9 (CH), 56.3 (CH), 42.6 (C), 36.8 (CH$_2$), 32.2 (CH$_3$), 25.3 (CH$_3$), 15.4 (CH$_3$); IR (film): ν/cm$^{-1}$ 2989, 2940, 2241, 1681; LR-MS: 338.1 [M+Na]$^+$; HR-MS (ESI) calculated for C$_{17}$H$_{18}$FN$_3$O$_2$Na: 338.1281, found: 338.1283.

113

Rac-(3R,6S,7S,8aS)-6-(Benzo[d][1,3]dioxol-5-yl)-2,3,7-trimethyl-1,4-dioxooctahydropyrrolo[1,2-a]-pyrazine-7-carbonitrile

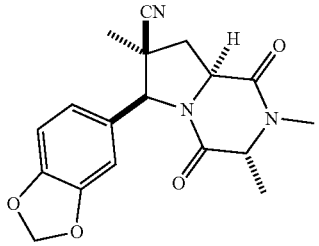

Chemical Formula: $C_{18}H_{19}N_3O_4$
Exact Mass: 341.1376

$^1$H-NMR (500 MHz, CDCl$_3$): δ/ppm 6.79 (1H, d, J=9.0 Hz), 6.63 (1H, d, J=9.0 Hz), 6.57 (1H, s), 5.96 (2H, s), 4.82 (1H, s), 4.36 (1H, dd, J=6.5, 11.0 Hz), 3.90 (1H, app q, J=7.0 Hz), 3.04 (3H, s), 2.76 (1H, app t, J=7.0 Hz), 2.45 (1H, dd, J=6.5, 13.5 Hz), 1.66 (3H, s), 1.47 (3H, d, J=7.0 Hz); $^{13}$C-NMR (125 MHz, CDCl$_3$): δ/ppm 166.6 (C), 166.0 (C), 148.2 (C), 148.1 (C), 130.8 (C), 119.9 (CH), 119.8 (C), 108.6 (CH), 106.2 (CH), 101.4 (CH$_2$), 69.6 (CH), 60.8 (CH), 56.1 (CH), 42.6 (C), 36.7 (CH$_2$), 32.0 (CH$_3$), 25.1 (CH$_3$), 15.3 (CH$_3$). LR-MS: 364.0 M+Na$^+$; IR (film) ν/cm$^{-1}$: 2982, 2917, 2244, 1671, 1491, 1447, 1246, 1037, 925, 721 ν/cm$^{-1}$. HR-MS (ESI) calculated for $C_{18}H_{19}N_3O_4Na$: 364.1273 (M+Na$^+$), found: 364.1273.

Rac-(6R,7S,8aS)-2,3,7-Trimethyl-1,4-dioxo-6-(thiophen-2-yl)octahydropyrrolo[1,2-a]pyrazine-7-carbonitrile

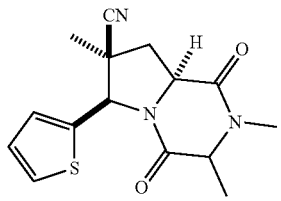

Chemical Formula: $C_{15}H_{17}N_3O_2S$
Exact Mass: 303.1041

$^1$H-NMR (500 MHz, CDCl$_3$): δ/ppm 7.31 (1H, m), 7.11 (1H, s), 7.06 (1H, m), 5.27 (1H, s), 4.39 (1H, dd, J=6.5, 11.0 Hz), 3.95 (1H, q, J=7.5 Hz), 3.08 (3H, s), 3.00 (1H, app t, J=13.0 Hz), 2.56 (1H, dd, J=6.5, 13.0 Hz), 1.72 (3H, s), 1.52 (3H, d, J=7.5 Hz); $^{13}$C-NMR (125 MHz, CDCl$_3$): δ/ppm 166.9 (C), 166.0 (C), 140.4 (C), 127.5 (CH), 127.0 (CH), 125.5 (CH), 119.6 (C), 65.3 (CH), 60.8 (CH), 55.8 (CH), 42.9 (C), 36.8 (CH$_2$), 32.2 (CH$_3$), 24.5 (CH$_3$), 15.4 (CH$_3$). IR (film): ν/cm$^{-1}$ 2981, 2935, 2246, 1672, 1447, 1428, 1402, 1301, 1229, 1065, 915, 722. LR-MS: 326.0 M+Na$^+$. HR-MS (ESI) calculated for $C_{15}H_{17}N_3O_2SNa$: 326.0939 (M+Na$^+$), found: 326.0942.

114

Rac-(6S,7S,8aS)-6-(4-Chlorophenyl)-2,3,7-trimethyl-1,4-dioxooctahydropyrrolo[1,2-a]pyrazine-7-carbonitrile

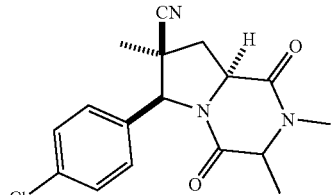

Chemical Formula: $C_{17}H_{18}ClN_3O_2$
Exact Mass: 331.1088

$^1$H-NMR (500 MHz, CDCl$_3$): δ/ppm 7.35 (2H, d, J=8.5 Hz), 7.07 (2H, d, J=8.5 Hz), 4.88 (1H, s), 4.39 (1H, dd, J=6.5, 11.5 Hz), 3.90 (1H, q, J=7.5 Hz), 3.06 (3H, s), 2.76 (1H, app t, J=12.0 Hz), 2.48 (1H, dd, J=6.5, 8.5 Hz), 1.70 (3H, s), 1.49 (3H, d, J=7.5 Hz); $^{13}$C-NMR (125 MHz, CDCl$_3$): δ/ppm 166.7 (C), 166.0 (C), 135.4 (C), 135.1 (C), 129.4 (2CH), 127.5 (2CH), 119.7 (C), 69.2 (CH), 60.9 (CH), 56.3 (CH), 42.4 (C), 36.8 (CH$_2$), 32.2 (CH$_3$), 25.3 (CH$_3$), 15.4 (CH$_3$). IR (film): ν/cm$^{-1}$ 2981, 2919, 2852, 2246, 1673, 1490, 1430, 1303, 1235, 1093, 731. LR-MS: 354.0 M+Na$^+$. HR-MS (ESI) calculated for $C_{17}H_{18}N_3O_2ClNa$: 354.0985 (M+Na$^+$), found: 354.0981.

Rac-(3R,6S,7S,8aS)-6-(Benzo[d][1,3]dioxol-5-yl)-2-(3-(dimethylamino)propyl)-3,7-dimethyl-1,4-dioxooctahydropyrrolo[1,2-a]pyrazine-7-carbonitrile

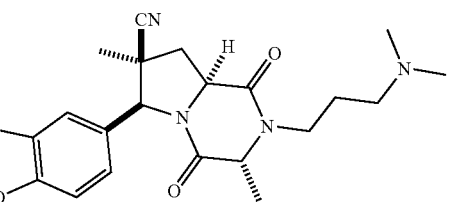

Chemical Formula: $C_{22}H_{28}N_4O_4$
Exact Mass: 412.2111

Isolated as an 8:1 mixture of diastereomers, data for the major isomer is reported. $^1$H-NMR (500 MHz, CDCl$_3$): δ/ppm 6.74 (1H, d, J=8.0 Hz), 6.56 (1H, d, J=8.0 Hz), 6.52 (1H, s), 5.91 (2H, s), 4.80 (1H, s), 4.35 (1H, dd, J=6.5, 11.0 Hz), 4.02 (1H, q, J=7.5 Hz), 3.83 (1H, dt, J=7.5, 13.5 Hz), 3.00 (1H, dt, J=7.5, 13.5 Hz), 2.74 (1H, app t, J=12.0 Hz), 2.40 (1H, dd, J=6.5, 13.5 Hz), 2.20-2.30 (2H, m), 2.14 (6H, s), 1.70-1.80 (2H, m), 1.62 (3H, s), 1.43 (3H, d, J=6.5 Hz); $^{13}$C-NMR (125 MHz, CDCl$_3$): δ/ppm 167.1 (C), 166.3 (C), 148.3 (C), 148.2 (C), 131.0 (C), 119.9 (C), 119.7 (CH), 108.6 (CH), 106.3 (CH), 101.5 (CH$_2$), 69.4 (CH), 59.3 (CH), 56.3 (CH$_2$), 56.2 (CH), 45.4 (2CH$_3$), 43.3 (C), 42.7 (CH$_2$), 36.6 (CH$_2$), 25.9 (CH$_2$), 25.1 (CH$_3$), 16.0 (CH$_3$). IR (film): ν/cm$^{-1}$ 2979, 2943, 2822, 2781, 2244, 1672, 1491, 1448, 1427, 1245, 1037, 929, 811, 735. LR-MS: 435.3 M+Na$^+$. HR-MS (ESI) calculated for $C_{22}H_{28}N_4O_4Na$: 435.2008 (M+Na$^+$), found: 435.2015.

115

Rac-(3R,6R,7S,8aS)-6-(6-Bromobenzo[d][1,3]di-oxol-5-yl)-2,3,7-trimethyl-1,4-dioxooctahydro-pyrrolo[1,2-a]pyrazine-7-carbonitrile

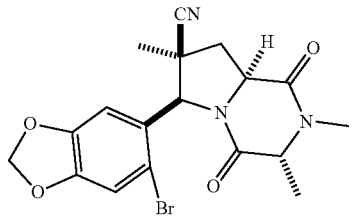

Chemical Formula: $C_{18}H_{18}BrN_3O_4$
Exact Mass: 419.0481

Isolated as a 3:1 mixture of diastereomers, data for the major isomer is reported. $^1$H-NMR (500 MHz, CDCl$_3$): δ/ppm 7.07 (1H, s), 6.34 (1H, s), 5.98 (2H, s), 5.34 (1H, s), 4.36 (1H, dd, J=6.5, 12.0 Hz), 3.92 (1H, q, J=7.0 Hz), 3.04 (3H, s), 2.66 (1H, app t, J=13.0 Hz), 2.48 (1H, dd, J=6.5, 13.0 Hz), 1.74 (3H, s), 1.47 (3H, d, J=7.0 Hz); $^{13}$C-NMR (125 MHz, CDCl$_3$): δ/ppm 166.5 (C), 166.0 (C), 148.7 (C), 148.1 (C), 129.1 (C), 119.7 (C), 115.0 (C), 113.5 (CH), 105.0 (CH), 102.3 (CH$_2$), 68.2 (CH), 60.8 (CH), 56.4 (CH), 42.2 (C), 37.4 (CH$_2$), 31.8 (CH$_3$), 24.9 (CH$_3$), 15.5 (CH$_3$). IR (film): ν/cm$^{-1}$ 2982, 2246, 1675, 1503, 1478, 1429, 1402, 1307, 1248, 1120, 1036, 928. LR-MS: 435.3 HR-MS (ESI) calculated for $C_{18}H_{18}BrN_3O_4Na$: 442.0378 (M+Na$^+$), found: 442.0369.

Rac-(3R,6S,7S,8aS)-2,3,7-Trimethyl-1,4-dioxo-6-(p-tolyl)octahydropyrrolo[1,2-a]pyrazine-7-carbonitrile

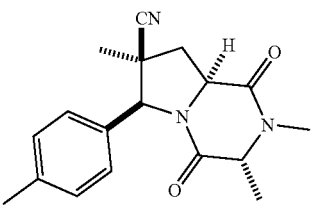

Chemical Formula: $C_{18}H_{21}N_3O_2$
Exact Mass: 311.1634

$^1$H-NMR (500 MHz, CDCl$_3$): δ/ppm 7.17 (2H, d, J=7.5 Hz), 7.01 (2H, d, J=7.5 Hz), 4.88 (1H, s), 4.38 (1H, dd, J=7.0, 11.0 Hz), 3.89 (1H, q, J=7.0 Hz), 3.04 (3H, s), 2.79 (1H, app t, J=12.5 Hz), 2.44 (1H, dd, J=6.5, 12.5 Hz), 2.32 (3H, s), 1.67 (3H, s), 1.47 (3H, d, J=7.0 Hz); $^{13}$C-NMR (125 MHz, CDCl$_3$): δ/ppm 166.7 (C), 166.2 (C), 138.9 (C), 134.0 (C), 129.8 (2CH), 125.9 (2CH), 120.0 (C), 69.6 (CH), 60.9 (CH), 56.2 (CH), 42.6 (C), 36.7 (CH$_2$), 32.1 (CH$_3$), 25.2 (CH$_3$), 21.3 (CH$_3$), 15.4 (CH$_3$). IR (film): ν/cm$^{-1}$ 3054, 2982, 2935, 2877, 2243, 1681, 1515, 1452, 1430, 1402, 1306, 1246, 1230, 1063, 804, 734. LR-MS: 334.0 M+Na$^+$. HR-MS (ESI) calculated for $C_{18}H_{21}N_3O_2Na$: 334.1531, found: 334.1536. The structure and relative configuration of this sample was confirmed by single-crystal X-ray analysis.

116

Rac-(3R,6S,7S,8aS)-6-(2,3-Dihydrobenzo[b][1,4]dioxin-6-yl)-2,3,7-trimethyl-1,4-dioxooctahydro-pyrrolo[1,2-a]pyrazine-7-carbonitrile

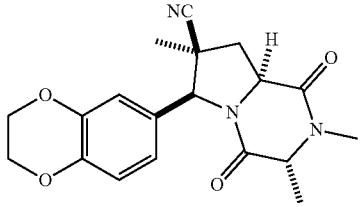

Chemical Formula: $C_{19}H_{21}N_3O_4$
Exact Mass: 355.1532

$^1$H-NMR (500 MHz, 1:1 d$_4$-MeOD/CDCl$_3$): δ/ppm 6.61 (1H, d, J=7.0 Hz), 6.38 (2H, m), 4.59 (1H, s), 4.28 (1H, m), 4.00 (4H, m), 3.69 (1H, q, J=9.0 Hz), 2.82 (3H, s), 2.48 (1H, app t, J=12.0 Hz), 2.23 (1H, dd, J=8.5, 12.0 Hz), 1.45 (3H, s), 1.26 (3H, d, J=9.0 Hz); $^{13}$C-NMR (125 MHz, CDCl$_3$): δ/ppm 167.3 (C), 166.6 (C), 144.0 (C), 143.7 (C), 130.2 (C), 120.0 (C), 119.1 (CH), 117.6 (CH), 114.9 (CH), 69.3 (CH), 64.3 (2CH$_2$), 60.8 (CH), 56.1 (CH), 42.7 (C), 36.5 (CH$_2$), 31.9 (CH$_3$), 24.7 (CH$_3$), 14.9 (CH$_3$). IR (film): ν/cm$^{-1}$ 3056.3, 2982.2, 2936.7, 2878.2, 2244.2, 1672.0, 1509.0, 1450.8, 1432.5, 1307.3, 1287.9, 1067.0, 886.5. LR-MS: 378.1 M+Na$^+$. HR-MS (ESI) calculated for $C_{19}H_{21}N_3O_4Na$: 378.1430, found: 378.1433.

Rac-(3R,6S,7S,8aS)-6-(Benzo[d][1,3]dioxol-5-yl)-3,7-dimethyl-2-(2-morpholinoethyl)-1,4-dioxooctahydropyrrolo[1,2-a]pyrazine-7-carbonitrile

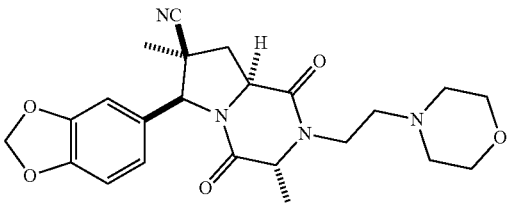

Chemical Formula: $C_{23}H_{28}N_4O_5$
Exact Mass: 440.2060

$^1$H-NMR (500 MHz, 1:1 d$_4$-MeOD/CDCl$_3$): δ/ppm 6.61 (1H, d, J=9.5 Hz), 6.49 (1H, d, J=9.5 Hz), 6.36 (1H, s), 5.77 (2H, s), 4.67 (1H, s), 4.31 (1H, dd, J=6.5, 11.0 Hz), 3.88 (1H, q, J=9.0 Hz), 3.80 (1H, m), 3.44-3.50 (4H, m), 2.88-2.95 (1H, m), 2.55 (1H, app t, J=6.5 Hz), 2.20-2.45 (7H, m), 1.49 (3H, s), 1.31 (3H, d, J=9.0 Hz); $^{13}$C-NMR (125 MHz, CDCl$_3$): δ/ppm 167.4 (C), 166.5 (C), 148.2 (C), 148.1 (C), 131.0 (C), 120.2 (CH), 120.0 (CH), 108.5 (CH), 105.8 (CH), 101.5 (CH$_2$), 69.4 (CH), 66.9 (2CH$_2$), 59.7 (CH), 56.4 (CH$_2$), 56.1 (CH), 53.7 (2CH$_2$), 42.8 (C), 41.6 (CH$_2$), 36.5 (CH$_2$), 24.8 (CH$_3$), 15.6 (CH$_3$). IR (film): ν/cm$^{-1}$ 2955.4, 2858.2, 2812.5, 2243.7, 1672.0, 1491.0, 1448.4, 1426.9, 1295.8, 1245.8, 1115.3, 1036.5, 922.1. LR-MS: 441.3 M+H$^+$. HR-MS (ESI) calculated for $C_{23}H_{28}N_4O_5Na$: 463.1957, found 463.1946.

Rac-(3R,6S,7S,8aS)-6-(2,2-Difluorobenzo[d][1,3]dioxol-5-yl)-2,3,7-trimethyl-1,4-dioxooctahydropyrrolo[1,2-a]pyrazine-7-carbonitrile

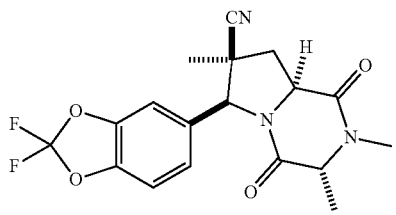

Chemical Formula: $C_{18}H_{17}F_2N_3O_4$
Exact Mass: 377.3478

$^1$H-NMR (500 MHz, CDCl$_3$): δ/ppm 7.07 (1H, d, J=8.0 Hz), 6.90 (1H, d, J=8.0 Hz), 6.83 (1H, s), 4.88 (1H, s), 4.36-4.43 (1H, dd, J=6.5, 11.5 Hz), 3.92 (1H, q, J=7.0 Hz), 3.07 (3H, s), 2.76 (1H, app t, J=12.0 Hz), 2.51 (1H, dd, J=6.5, 13.5 Hz), 1.71 (3H, s), 1.50 (3H, d, J=7.0 Hz); $^{13}$C-NMR (125 MHz, CDCl$_3$): δ/ppm 166.8 (C), 165.9 (C), 144.2 (C), 144.1 (C), 133.3 (C), 131.7 (CF$_2$, t, J=255 Hz), 121.9 (CH), 119.6 (C), 110.0 (CH), 107.4 (CH), 69.4 (CH), 60.5 (CH), 56.3 (CH), 42.6 (C), 36.9 (CH$_2$), 32.2 (CH$_3$), 25.3 (CH$_3$), 15.4 (CH$_3$). IR (film): ν/cm$^{-1}$ 2984, 2939, 2246, 1674, 1500, 1452, 1429, 1403, 1241, 1150, 912, 732. LR-MS: 400.2 (M+Na$^+$); HR-MS (ESI) calculated for $C_{18}H_{17}N_3O_4F_2Na$: 400.1085, found: 400.1092.

Rac-(3R,6S,7R,8aS)-6-(Benzo[d][1,3]dioxol-5-yl)-7-(((tert-butyldimethylsilyl)oxy)methyl)-2,3-dimethyl-1,4-dioxooctahydropyrrolo[1,2-a]pyrazine-7-carbonitrile

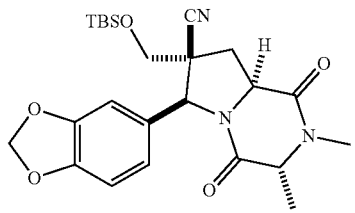

Chemical Formula: $C_{24}H_{33}N_3O_5Si$
Molecular Weight: 471.6290

$^1$H-NMR (500 MHz, CDCl$_3$): δ/ppm 6.73 (1H, d, J=9.0 Hz), 6.2-7.0 (2H, br s), 5.95 (2H, d, J=9.0 Hz), 5.35 (1H, s), 4.62 (1H, 1H, m), 3.88 (1H, q, J=7.5 Hz), 3.29 (1H, d, J=9.5 Hz), 3.21 (1H, d, J=9.5 Hz), 3.05 (3H, s), 2.58-2.62 (1H, m), 2.26 (1H, app t, J=12.0 Hz), 1.52 (3H, d, J=7.5 Hz), 0.88 (9H, s), 0.01 (3H, s), −0.02 (3H, s); $^{13}$C-NMR (125 MHz, CDCl$_3$): δ/ppm 166.4 (C), 166.2 (C), 148.0 (2C), 128.2 (C), 121.7 (C), 108.5 (CH), 101.5 (CH$_2$), 66.6 (CH), 63.5 (CH$_2$), 61.1 (CH), 57.0 (CH), 49.2 (C), 33.1 (CH$_2$), 32.1 (CH$_3$), 25.7 (3CH$_3$), 18.2 (C), 15.4 (CH$_3$), −5.6 (2CH$_3$), 2 aromatic CH not seen. IR (film): ν/cm$^{-1}$ 2930, 2884, 2857, 2240, 1678, 1490, 1448, 1402, 1245, 1105, 1039, 928, 840, 780, 732. LR-MS: 494.3 (M+Na$^+$); HR-MS (ESI) calculated for $C_{24}H_{33}N_3O_5SiNa$: 494.2087, found: 494.2068.

Rac-(3R,6S,7R,8aS)-6-(Benzo[d][1,3]dioxol-5-yl)-7-(methoxymethyl)-2,3-dimethyl-1,4-dioxo-octahydropyrrolo[1,2-a]pyrazine-7-carbonitrile

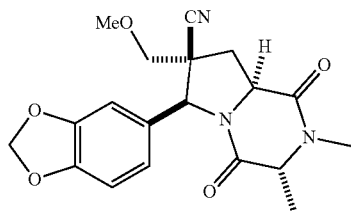

Chemical Formula: $C_{19}H_{21}N_3O_5$
Molecular Weight: 371.3930

$^1$H-NMR (500 MHz, CDCl$_3$): δ/ppm 6.78 (1H, d, J=8.0 Hz), 6.65 (1H, d, J=8.0 Hz), 6.59 (1H, s), 5.95 (2H, s), 5.03 (1H, s), 4.36 (1H, dd, J=7.0, 11.0 Hz), 3.88 (1H, q, J=7.0 Hz), 3.62 (2H, s), 3.48 (3H, s), 3.02 (3H, s), 2.74 (1H, app t, J=11.5 Hz), 2.67 (1H, dd, J=7.5, 14.0 Hz), 1.44 (3H, d, J=7.0 Hz); $^{13}$C-NMR (125 MHz, CDCl$_3$): δ/ppm 166.7 (C), 166.2 (C), 148.3 (C), 148.2 (C), 130.8 (C), 120.0 (CH), 118.3 (C), 108.8 (CH), 106.4 (CH), 101.5 (CH$_2$), 74.8 (CH$_2$), 65.4 (CH), 60.8 (CH), 59.8 (CH$_3$), 56.8 (CH), 48.7 (C), 33.7 (CH$_2$), 32.1 (CH$_3$), 15.3 (CH$_3$).

Rac-(3R,6R,7S,8aS)-6-(Benzo[d][1,3]dioxol-4-yl)-2,3,7-trimethyl-1,4-dioxooctahydropyrrolo[1,2-a]pyrazine-7-carbonitrile

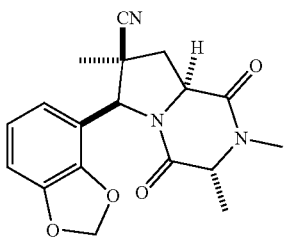

Chemical Formula: $C_{18}H_{19}N_3O_4$
Molecular Weight: 341.3670

$^1$H-NMR (500 MHz, d$_6$-DMSO, 390K): δ/ppm 6.85 (2H, br s), 6.65 (1H, br s), 6.00 (1H, s), 5.92 (1H, s), 4.96 (1H, s), 4.67 (1H, dd, J=6.5, 10.5 Hz), 3.95 (1H, q, J=7.0 Hz), 2.97 (3H, s), 2.58-2.67 (1H, m), 2.44-2.55 (1H, m), 1.72 (3H, s), 1.46 (3H, d, J=7.0 Hz); $^{13}$C-NMR (125 MHz, d$_6$-DMSO, 390K): δ/ppm 166.8 (C), 166.6 (C), 147.9 (C), 145.0 (C), 122.1 (CH), 121.1 (C), 120.5 (CH), 108.7 (CH), 101.4 (CH$_2$), 65.6 (CH), 60.6 (CH), 56.4 (CH), 42.7 (C), 38.1 (CH$_2$), 31.8 (CH$_3$), 25.0 (CH$_3$), 15.6 (CH$_3$). IR (film): ν/cm$^{-1}$ 3056, 2981, 2895, 2244, 1672, 1460, 1432, 1402, 1251, 1066, 928, 731. LR-MS: 342.1 (M+H$^+$); HR-MS (ESI) calculated for $C_{18}H_{19}N_3O_4Na$: 364.1273, found: 364.1267.

Rac-(3R,6S,7S,8aS)-6-(benzo[d][1,3]dioxol-5-yl)-2-butyl-3,7-dimethyl-1,4-dioxo-octahydropyrrolo[1,2-a]pyrazine-7-carbonitrile

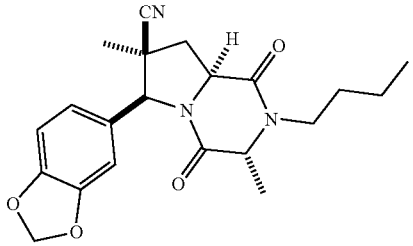 [SMILES: CCCCN1C(=O)[C@@H]2C[C@](C)(C#N)[C@H](c3ccc4c(c3)OCO4)N2C(=O)[C@H]1C]

$^1$H-NMR (500 MHz, CDCl$_3$): δ/ppm 6.79 (1H, d, J=9.0 Hz), 6.60 (1H, d, J=9.0 Hz), 6.55 (1H, s), 5.96 (2H, s), 4.82 (1H, s), 4.38 (1H, dd, J=6.5, 11.0 Hz), 3.95 (1H, app q, J=7.0 Hz), 2.99 (1H, m), 2.81 (1H, app t, J=7.0 Hz), 2.43 (1H, dd, J=6.5, 13.5 Hz), 1.60 (2H, m), 1.56 (3H, s), 1.45 (3H, d, J=7.0 Hz) 1.38 (2H, m), 0.96 (3H, t, J=7.2 Hz); $^{13}$C-NMR (125 MHz, CDCl$_3$): δ/ppm 167.2 (C), 166.3 (C), 148.6 (C), 148.4 (C), 131.1 (C), 120.0 (CH), 119.9 (C), 108.8 (CH), 106.4 (CH), 101.7 (CH$_2$), 69.7 (CH), 59.0 (CH), 56.5 (CH), 44.8 (C), 42.9 (CH$_2$), 36.9 (CH$_2$), 30.0 (CH$_2$), 25.4 (CH$_3$), 20.2 (CH$_2$), 16.2 (CH$_3$). 13.9 (CH$_3$), LR-MS: 406.2 M+Na$^+$; IR (film): v/cm$^{-1}$ 2982, 2917, 2244, 1671, 1491, 1447, 1246, 1037, 925, 721 v/cm$^{-1}$. HR-MS (ESI) calculated for C$_{21}$H$_{25}$N$_3$O$_4$Na: 406.1713 (M+Na$^+$), found: 406.1730.

Rac-(3R,6S,7S,8aS)-6-(4-methoxyphenyl)-2,3,7-trimethyl-1,4-dioxooctahydropyrrolo[1,2-a]pyrazine-7-carbonitrile

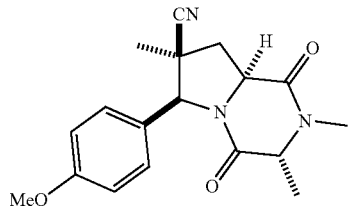 [SMILES: COc1ccc([C@@H]2N3C(=O)[C@@H](C)N(C)C(=O)[C@@H]3C[C@]2(C)C#N)cc1]

$^1$H-NMR (500 MHz, CDCl$_3$): δ/ppm 7.05 (2H, d, J=8.5 Hz), 6.88 (2H, d, J=8.5 Hz), 4.88 (1H, s), 4.39 (1H, dd, J=6.5, 11.5 Hz), 3.90 (1H, q, J=7.5 Hz), 3.79 (3H, s), 3.05 (3H, s), 2.80 (1H, app t, J=12.0 Hz), 2.46 (1H, dd, J=6.5, 8.5 Hz), 1.70 (3H, s), 1.48 (3H, d, J=7.5 Hz); $^{13}$C-NMR (125 MHz, CDCl$_3$): δ/ppm 166.6 (C), 166.2 (C), 159.9 (C), 128.9 (C), 127.2 (2CH), 119.9 (C), 114.4 (2CH), 69.3 (CH), 60.9 (CH), 56.1 (CH), 55.2 (CH$_3$), 42.6 (C), 36.6 (CH$_2$), 32.1 (CH$_3$), 25.1 (CH$_3$), 15.3 (CH$_3$). IR (film): v/cm$^{-1}$ 2981, 2919, 2852, 2246, 1673, 1490, 1303, 1235, 1093, 756. HR-MS (ESI) calculated for C$_{18}$H$_{21}$N$_3$O$_3$Na: 350.1475 (M+Na$^+$), found: 350.1465.

Rac-(3R,6S,7S,8aS)-6-(benzo[d][1,3]dioxol-5-yl)-3-ethyl-2,7-dimethyl-1,4-dioxo-octahydropyrrolo[1,2-a]pyrazine-7-carbonitrile

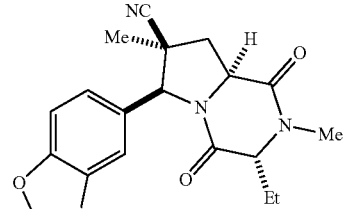

Chemical Formula: C$_{19}$H$_{21}$N$_3$O$_4$
Exact Mass: 355.1532
Molecular Weight: 355.3940

Prepared from the corresponding pyrrolidine ester and 2-chlorobutanoyl chloride by conducting the reaction with methylamine at 60° C. overnight. Isolated as a 9:1 mixture of diastereomers; NMR data for the major isomer is reported. $^1$H-NMR (600 MHz, CDCl$_3$) δ 6.79 (d, J=8.0 Hz, 1H), 6.63 (dd, J=8.0, 1.9 Hz, 1H), 6.56 (t, J=1.9 Hz, 1H), 5.96 (s, 2H), 4.83 (s, 1H), 4.41 (dd, J=8.0, 1.9 Hz, 1H), 3.77 (dd, J=7.5, 6.3 Hz, 1H), 3.08 (s, 3H), 2.76 (dd, J=13.0, 11.7 Hz, 1H), 2.45 (dd, J=13.2, 6.7 Hz, 1H), 1.95-1.92 (m, 1H), 1.91-1.85 (m, 1H), 1.66 (s, 3H), 1.07 (t, J=7.4 Hz, 3H) ppm; $^{13}$C-NMR (126 MHz, CDCl$_3$) δ 166.4 (C), 166.2 (C), 148.4 (C), 148.3 (C), 131.0 (C), 120.0 (CH), 119.9 (C), 108.8 (CH), 106.3 (CH), 101.6 (CH$_2$), 69.9 (CH), 66.8 (CH), 56.3 (CH), 42.7 (C), 37.0 (CH$_2$), 33.5 (CH$_3$), 25.4 (CH$_3$), 24.4 (CH$_2$), 10.6 (CH$_3$) ppm; IR (film) v/cm$^{-1}$ 2929, 2245, 1672, 1491, 1446, 1402, 1246, 1038, 916, 821, 730 cm$^{-1}$; HRMS (ESI) calcd for C$_{19}$H$_{21}$N$_3$O$_4$Na$^+$ (M+Na) 378.1430, found 378.1433.

Rac-(3R,6S,7S,8aS)-2-allyl-6-(benzo[d][1,3]dioxol-5-yl)-3,7-dimethyl-1,4-dioxo-octahydropyrrolo[1,2-a]pyrazine-7-carbonitrile

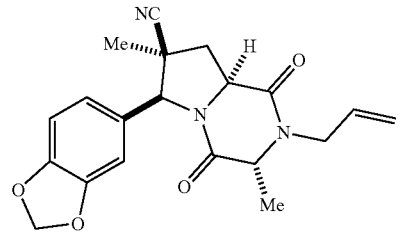

Chemical Formula: C$_{20}$H$_{21}$N$_3$O$_4$
Exact Mass: 367.1532
Molecular Weight: 367.4050

The cyclization to the diketopiperazine was performed in a THF/H$_2$O (1:1) solvent mixture at 80° C., overnight. $^1$H-NMR (600 MHz, CDCl$_3$) δ 6.80-6.78 (m, 1H), 6.63-6.61 (m, 1H), 6.56 (d, J=1.6 Hz, 1H), 5.98-5.96 (m, 2H), 5.81-5.74 (m, 1H), 5.27 (dd, J=10.2, 1.1 Hz, 1H), 5.24 (dd, J=17.0, 1.1 Hz, 1H), 4.84 (s, 1H), 4.50 (ddt, J=15.3, 5.3, 1.4 Hz, 1H), 4.41 (dd, J=11.7, 6.7 Hz, 1H), 3.97 (q, J=7.4 Hz, 1H), 3.68 (dd, J=15.2, 6.8 Hz, 1H), 2.82 (dd, J=13.3, 11.5 Hz, 1H), 2.46 (dd, J=13.3, 6.8 Hz, 1H), 1.68 (s, 3H), 1.48 (d, J=7.4 Hz, 3H) ppm; $^{13}$C-NMR (126 MHz, CDCl$_3$) δ 167.0 (C), 166.1 (C), 148.4 (C), 148.3 (C), 131.8 (CH), 131.0 (C), 119.9 (CH), 119.3 (CH$_2$), 108.8 (CH), 106.3 (CH), 101.6 (CH$_2$), 69.6 (CH), 58.2 (CH), 56.3 (CH), 54.7 (C), 47.1 (CH$_2$), 42.8 (C), 36.7 (CH$_2$), 25.4 (CH$_3$), 16.0 (CH$_3$) ppm; IR (film) ν/cm$^{-1}$ 2924, 2853, 2244, 1674, 1505, 1448, 1427, 1294, 1246, 1184, 1101, 1038, 933, 859, 809, 735 cm$^{-1}$; HRMS (ESI) calcd for C$_{20}$H$_{21}$N$_3$O$_4$Na$^+$ (M+Na) 390.1430, found 390.1438.

Rac-(3R,6S,7S,8aS)-6-(benzo[d][1,3]dioxol-5-yl)-2-cyclopropyl-3,7-dimethyl-1,4-dioxooctahydropyrrolo[1,2-a]pyrazine-7-carbonitrile

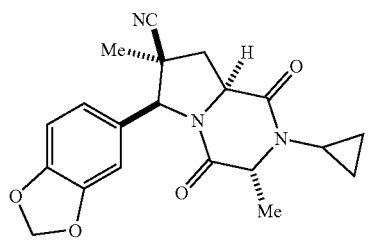

Chemical Formula: C$_{20}$H$_{21}$N$_3$O$_4$
Exact Mass: 367.1532
Molecular Weight: 367.4050

Cyclization to the diketopiperazine was performed using cyclopropylamine (3.5 equiv) in a THF/H$_2$O (1:1) solvent mixture that was heated from 80-100° C. over 2 d. $^1$H-NMR (500 MHz, CDCl$_3$) δ 6.76 (d, J=8.0 Hz, 1H), 6.56 (d, J=8.0 Hz, 1H), 6.47 (s, 1H), 5.95 (s, 2H), 4.80 (s, 1H), 4.38 (dd, J=11.3, 6.7 Hz, 1H), 3.98 (q, J=7.3 Hz, 1H), 2.74-2.69 (m, 2H), 2.45 (dd, J=13.3, 6.7 Hz, 1H), 1.65 (s, 3H), 1.49 (d, J=7.3 Hz, 3H), 1.09 (dq, J=9.5, 6.6 Hz, 1H), 0.88-0.83 (m, 1H), 0.79 (dq, J=9.5, 6.5 Hz, 1H), 0.58 (dq, J=10.4, 5.2 Hz, 1H) ppm; $^{13}$C-NMR (126 MHz, CDCl$_3$) δ 168.2 (C), 167.2 (C), 148.3 (C), 148.2 (C), 130.9 (C), 119.9 (CH), 119.8 (CH), 108.7 (CH), 106.1 (CH), 101.5 (CH$_2$), 69.4 (CH), 59.8 (CH), 56.7 (CH), 42.7 (C), 36.7 (CH$_2$), 28.0 (CH), 25.2 (CH$_3$), 16.2 (CH$_3$), 8.7 (CH$_2$), 5.7 (CH$_2$) ppm; IR (film) ν/cm$^{-1}$ 2984, 1675, 1490, 1424, 1376, 1245, 1189, 1036, 932, 733 cm$^{-1}$; HRMS (ESI) calcd for C$_{20}$H$_{21}$N$_3$O$_4$Na$^+$ (M+Na) 390.1430, found 390.1433.

Rac-(3R,6S,7S,8aS)-6-(3,4-bis(allyloxy)phenyl)-2,3,7-trimethyl-1,4-dioxooctahydro-pyrrolo[1,2-a]pyrazine-7-carbonitrile

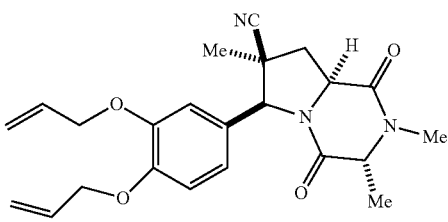

Chemical Formula: C$_{23}$H$_{27}$N$_3$O$_4$
Exact Mass: 409.2002
Molecular Weight: 409.4860

$^1$H-NMR (500 MHz, CDCl$_3$) δ 6.86 (d, J=8.2 Hz, 1H), 6.65-6.63 (m, 2H), 6.09-6.01 (m, 2H), 5.39 (dd, J=17.2 Hz, 1.1 Hz, 1H), 5.37 (dd, J=17.3 Hz, 1.2 Hz, 1H), 5.26 (app. dt, J=10.6, 0.2 Hz, 2H), 4.85 (s, 1H), 4.60-4.57 (m, 4H), 4.37 (dd, J=11.3, 6.8 Hz, 1H), 3.91 (q, J=7.2 Hz, 1H), 3.06 (s, 3H), 2.78 (app t, J=12.2 Hz, 1H), 2.44 (dd, J=13.3, 6.8 Hz, 1H), 1.68 (s, 3H), 1.49 (d, J=7.2 Hz, 3H) ppm; $^{13}$C-NMR (126 MHz, CDCl$_3$) δ 166.8 (C), 166.3 (C), 149.2 (C), 148.7 (C), 133.4 (CH), 133.4 (CH), 129.6 (C), 119.9 (C), 118.7 (CH), 117.9 (CH$_2$), 117.9 (CH$_2$), 113.9 (CH), 112.4 (CH), 70.2 (CH$_2$), 69.9 (CH$_2$), 69.5 (CH), 61.1 (CH), 56.2 (CH), 42.7 (C), 36.7 (CH$_2$), 32.3 (CH$_3$), 25.3 (CH$_3$), 15.4 (CH$_3$) ppm; IR (film) ν/cm$^{-1}$ 2983, 1672, 1515, 1451, 1426, 1306, 1259, 1224, 1206, 1139, 1017, 996, 924, 806, 732 cm$^{-1}$; HRMS (ESI) calcd for C$_{23}$H$_{27}$N$_3$O$_4$Na$^+$ (M+Na) 432.1899, found 432.1888.

Rac-(3R,6S,7S,8aS)-6-(7-methoxybenzo[d][1,3]dioxol-5-yl)-2,3,7-trimethyl-1,4-dioxooctahydropyrrolo[1,2-a]pyrazine-7-carbonitrile

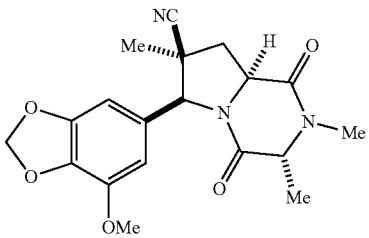

Chemical Formula: C$_{19}$H$_{21}$N$_3$O$_5$
Exact Mass: 371.1481
Molecular Weight: 371.3930

Isolated as an 8:1 mixture of diastereomers; NMR data for the major isomer is reported. $^1$H-NMR (500 MHz, CDCl$_3$) δ 6.34 (s, 1H), 6.24 (s, 1H), 5.97 (s, 2H), 4.81 (s, 1H), 4.36 (dd, J=11.3, 6.6 Hz, 1H), 3.92 (q, J=7.3 Hz, 1H), 3.89 (s, 3H), 3.05 (s, 3H), 2.78 (app. t, J=12.4 Hz, 1H), 2.46 (dd, J=13.3, 6.6 Hz, 1H), 1.68 (s, 3H), 1.49 (d, J=7.3 Hz, 3H) ppm; $^{13}$C-NMR (126 MHz, CDCl$_3$) δ 166.9 (C), 166.2 (C), 149.5 (C), 143.8 (C), 135.9 (C), 131.6 (C), 119.9 (C), 107.0 (CH), 102.0 (CH$_2$), 99.7 (CH), 69.8 (CH), 61.0 (CH), 56.8 (CH$_3$), 56.3 (CH), 42.8 (C), 36.8 (CH$_2$), 32.3 (CH$_3$), 25.4 (CH$_3$), 15.5 (CH$_3$) ppm; IR (film) ν/cm$^{-1}$ 2981, 1143, 1673, 1512, 1452, 1433, 1402, 1324, 1240, 1199, 1135, 1093, 1043, 927, 735 cm$^{-1}$; HRMS (ESI) calcd for C$_{19}$H$_{21}$N$_3$O$_5$Na$^+$ (M+Na) 394.1379, found 394.1371.

Rac-(3R,6S,7S,8aS)-6-(2,3-dihydro-1H-inden-5-yl)-2,3,7-trimethyl-1,4-dioxooctahydro-pyrrolo[1,2-a]pyrazine-7-carbonitrile

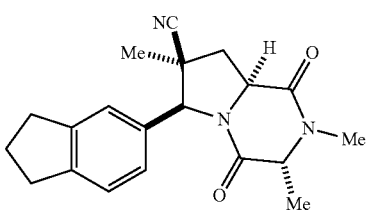

Chemical Formula: C$_{20}$H$_{23}$N$_3$O$_2$
Exact Mass: 337.1790
Molecular Weight: 337.4230

¹H-NMR (500 MHz, CDCl₃) D 7.19 (d, J=7.7 Hz, 1H), 6.96 (s, 1H), 6.93 (d, J=7.7 Hz, 1H), 4.89 (s, 1H), 4.38 (dd, J=11.6, 6.7 Hz, 1H), 3.91 (q, J=7.3 Hz, 1H), 3.07 (s, 3H), 2.90-2.80 (m, 5H), 2.45 (dd, J=13.3, 6.6 Hz, 1H), 2.05 (app. quintett, J=7.5 Hz, 2H), 1.69 (s, 3H), 1.49 (d, J=7.3 Hz, 3H) ppm; ¹³C-NMR (126 MHz, CDCl₃) δ 166.8 (C), 166.3 (C), 145.5 (C), 145.2 (C), 134.8 (C), 125.0 (CH), 123.9 (CH), 122.1 (CH), 120.1 (C), 70.1 (CH), 61.0 (CH), 56.3 (CH), 42.8 (C), 36.8 (CH₂), 33.0 (CH₂), 32.8 (CH₂), 32.2 (CH₂), 25.4 (CH₃), 25.4 (CH₂), 15.5 (CH₂) ppm; IR (film) v/cm⁻¹ 1940, 1673, 1431, 1402, 1306, 1239, 1062, 814, 733 cm⁻¹; HRMS (ESI) calcd for C₂₀H₂₃N₃O₂Na⁺ (M+Na) 360.1688, found 360.1684.

Rac (3R,6S,7S,8aS)-2,3,7-trimethyl-1,4-dioxo-6-(1-(phenylsulfonyl)-1H-indol-3-yl)octahydropyrrolo[1,2-a]pyrazine-7-carbonitrile

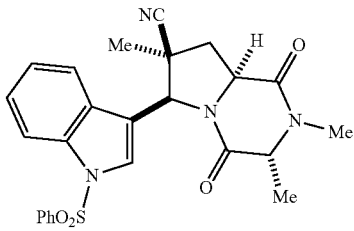

Chemical Formula: C₂₅H₂₄N₄O₄S
Exact Mass: 476.1518
Molecular Weight: 476.5510

Isolated as an 7:1 mixture of diasteromers; NMR data for the major isomer is reported. ¹H-NMR (500 MHz, CDCl₃) δ 7.89 (d, J=8.2 Hz, 1H), 7.77 (d, J=7.5 Hz, 2H), 7.51 (app. t, J=7.3 Hz, 1H), 7.46-7.39 (m, 4H), 7.31 (app. t, J=7.3 Hz, 1H), 7.25 (app. t, J=7.3 Hz, 1H), 5.18 (s, 1H), 4.40 (dd, J=12.4, 6.3 Hz, 1H), 3.92 (q, J=7.4 Hz, 1H), 3.09 (s, 3H), 2.83 (app. t, J=11.9 Hz, 1H), 2.57 (dd, J=13.3, 6.3 Hz, 1H), 1.73 (s, 3H), 1.49 (s, 3H) ppm; ¹³C-NMR (126 MHz, CDCl₃) δ 166.7 (C), 166.0 (C), 137.9 (C), 135.4 (C), 134.1 (CH), 129.5 (CH), 126.8 (CH), 125.6 (CH), 124.1 (CH), 123.9 (CH), 119.9 (CH), 119.6 (C), 119.5 (C), 119.4 (C), 114.1 (CH), 62.4 (CH), 60.9 (CH), 56.2 (CH), 42.2 (C), 38.1 (CH₂), 32.3 (CH₃), 25.1 (CH₃), 15.7 (CH₃) ppm; IR (film) v/cm⁻¹ 2982, 1675, 1448, 1367, 1307, 1175, 1124, 1095, 977, 748, 725 cm⁻¹; HRMS (ESI) calcd for C₂₅H₂₄N₄O₄SNa⁺ (M+Na) 499.1416, found 499.1412.

Alternate Procedure for Forming Diketopiperazines from Substituted Prolidine Esters and Protected α-Amino Acids Rac-(3R,6S,7S,8aS)-6-(benzo[d][1,3]dioxol-5-yl)-3-benzyl-2,7-dimethyl-1,4-dioxooctahydropyrrolo[1,2-a]pyrazine-7-carbonitrile

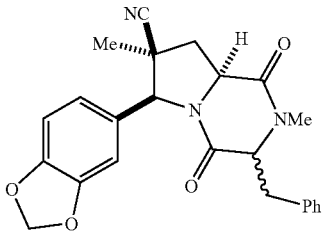

Chemical Formula: C₂₄H₂₃N₃O₄
Exact Mass: 417.1689
Molecular Weight: 417.4650

To a solution of N-Boc-phenylalanine (263 mg, 1.00 mmol, 1.5 equiv) in dry CH₂Cl₂ (2 mL) at 0° C. was added N,N-diisopropylethylamine (0.12 mL, 0.66 mmol, 1 equiv) and BOPCl (253 mg, 1.00 mmol, 1.5 equiv) and the reaction was allowed to warm to room temperature over 1 h. After recooling to 0° C. additional N,N-diisopropylethylamine (0.23 mL, 1.3 mmol, 2 equiv) was added, followed by the dropwise addition of a solution of the corresponding pyrrolidine ester (200 mg, 0.66 mmol, 1 equiv) in CH₂Cl₂ (1.3 mL). The reaction was allowed to warm to room temperature overnight, after which time TLC analysis showed full conversion of the starting material. After an extractive work-up (CH₂Cl₂/water), the crude product was filtered through a silica gel plug using hexanes/ethyl acetate (1:1) as the eluent and the volatiles were removed in vacuo. The crude acylated pyrrolidine ester was dissolved in dry CH₂Cl₂ (2.1 mL) and cooled to 0° C. Trifluoroacetic acid (0.8 mL) was added, the reaction allowed to warm to rt over 3 h, and the volatiles were removed under reduced pressure. The resulting residue was dissolved in a 4:1 mixture i-BuOH/toluene (18 mL) containing N,N-diisopropylethylamine (0.46 mL, 2.65 mmol, 4 equiv). The vial was sealed with a teflon cap and heated to 100° C. overnight. After an extractive work up (CH₂Cl₂/water) and concentration, two diastereomeric DKPs were separated by silica gel chromatography (eluent: hexanes/EtOAc 1:3).

NMR data for diastereomer A: ¹H-NMR (600 MHz, CDCl₃) δ 7.38-7.35 (m, 3H), 7.26-7.25 (m, 2H), 7.00 (d, J=3.7 Hz, 1H), 6.78 (d, J=8.0 Hz, 1H), 6.63 (d, J=7.2 Hz, 1H), 6.55 (s, 1H), 5.92 (s, 2H), 4.71 (s, 1H), 4.29 (app. q, J=4.2 Hz, 1H), 3.31 (dd, J=13.9, 4.6 Hz, 1H), 2.95 (dd, J=13.9, 4.4 Hz, 1H), 2.64 (dd, J=11.9, 6.2 Hz, 1H), 2.44 (app. t, J=12.5 Hz, 1H), 2.05 (dd, J=13.0, 6.3 Hz, 1H), 1.32 (s, 3H) ppm. NMR data for diastereomer B: ¹H-NMR (600 MHz, CDCl₃) δ 7.37-7.34 (m, 2H), 7.32-7.29 (m, 1H), 7.22-7.19 (m, 2H), 6.81 (d, J=8.0 Hz, 1H), 6.64 (dd, J=8.8, 1.7 Hz, 1H), 6.60 (d, J=1.8 Hz, 1H), 6.00 (d, J=1.5 Hz, 1H), 5.99 (d, J=1.5 Hz, 1H), 5.69 (broad s, 1H), 4.91 (s, 1H), 4.40 (dd, J=11.3, 6.9 Hz, 1H), 4.32 (dd, J=10.2, 4.2 Hz, 1H), 3.51 (dd, J=14.7, 3.9 Hz, 1H), 2.79 (dd, J=11.5, 4.1 Hz, 1H), 2.77 (dd, J=10.3, 4.4 Hz, 1H), 2.40 (dd, J=13.4, 6.8 Hz, 1H), 1.68 (s, 3H) ppm.

Both DKP products were individually methylated in a separate reaction vessel by the following procedure: To the intermediate DKP (91 mg, 0.23 mmol, 1 equiv) in acetone (2.8 mL) was added K₂CO₃ (620 mg, 4.5 mmol, 20 equiv) and MeI (1.4 mL, 23 mmol, 100 equiv) and the reaction was stirred for 2 d at room temperature with the exclusion of light. After an extractive work up (CH₂Cl₂/water), each diasteromeric DKP was obtained as amorphous solid.

Diastereomer A: ¹H-NMR (500 MHz, CDCl₃) δ 7.34-7.31 (m, 3H), 7.18-7.13 (m, 2H), 6.77 (d, J=7.8 Hz, 1H), 6.59 (d, J=7.8 Hz, 1H), 6.51 (s, 1H), 5.95 (s, 2H), 4.65 (s, 1H), 4.18 (t, J=4.1 Hz, 1H), 3.28 (dd, J=14.1, 3.9 Hz, 1H), 3.14-3.10 (m, 4H), 2.40-2.39 (m, 2H), 2.04-2.01 (m, 1H), 1.26 (s, 3H) ppm; ¹³C-NMR (126 MHz, CDCl₃) δ 166.5 (C), 165.5 (C), 148.3 (C), 148.2 (C), 135.4 (C), 131.1 (C), 129.9 (CH), 129.2 (CH), 128.1 (CH), 120.0 (C), 119.9 (CH), 108.8 (CH), 106.1 (CH), 101.5 (CH₂), 69.5 (CH), 66.4 (CH), 55.4 (CH), 42.3 (C), 36.8 (CH₂), 36.4 (CH₂), 32.4 (CH₃), 24.8 (CH₃) ppm; IR (film) v/cm⁻¹ 2934, 2247, 1673, 1505, 1491, 1446, 1403, 1304, 1247, 1102, 1053 cm⁻¹; HRMS (ESI) calcd for C₂₄H₂₃N₃O₄Na⁺ (M+Na) 440.1586, found 440.1580. Diastereomer B: ¹H-NMR (500 MHz, CDCl₃) δ 7.26-7.19 (m, 3H), 7.14-7.11 (m, 2H), 6.76 (d, J=8.0 Hz, 1H), 6.55 (d, J=8.4 Hz, 1H), 6.52 (s, 1H), 5.99-5.96 (m, 2H), 4.82 (s, 1H), 4.43 (t, J=5.2 Hz, 1H), 4.37 (dd, J=11.3, 6.8 Hz, 1H), 3.48 (dd, J=16.0, 5.6 Hz, 1H), 3.42 (dd, J=16.0, 5.5 Hz, 1H), 3.04

(s, 3H), 2.81 (dd, J=13.1, 11.5 Hz, 1H), 2.46 (dd, J=13.4, 6.6 Hz, 1H), 1.66 (s, 3H) ppm; $^{13}$C-NMR (126 MHz, CDCl$_3$) δ 168.1 (C), 165.8 (C), 148.3 (2×C), 136.5 (C), 130.8 (C), 129.0 (CH), 128.8 (CH), 127.1 (CH), 120.1 (C), 120.0 (CH), 108.8 (CH), 106.7 (CH), 101.2 (CH$_2$), 69.8 (CH), 61.3 (CH), 57.4 (CH), 42.8 (C), 37.0 (CH$_2$), 33.5 (CH$_2$), 30.9 (CH$_3$), 25.6 (CH$_3$) ppm; IR (film) v/cm$^{-1}$ 1675, 1504, 1491, 1448, 1390, 1306, 1244, 1039, 912, 733, 700 cm'; HRMS (ESI) calcd for C$_{24}$H$_{23}$N$_3$O$_4$Na$^+$ (M+Na) 440.1586, found 440.1577.

Example 4

General Procedure for Synthesis of Epidithiodiketopiperazines

Methyl Rac-(3S,6S,7S,8aS)-6-(4-fluorophenyl)-2,3,7-trimethyl-1,4-dioxohexahydro-6H-3,8a-epidithio-pyrrolo[1,2-a]pyrazine-7-carboxylate

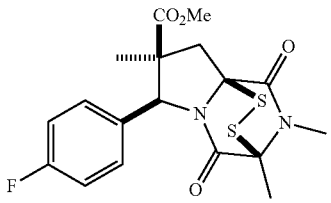

Chemical Formula: C$_{18}$H$_{19}$FN$_2$O$_4$S$_2$
Exact Mass: 410.0770

To a suspension of elemental sulfur (32 mg, 1.0 mmol) in dry THF (5 mL) was added a solution of NaHMDS (0.25 mL, 2 M in THF) at room temperature. After 1 min, a solution of the diketopiperazine (70 mg, 0.2 mmol, in 2 mL THF) was added, followed by a second aliquot of NaHMDS (0.25 mL, 2 M in THF) within another 2 min. The resulting orange-brown solution was stirred for 30 min at rt, cooled to 0° C. and quenched by addition of aqueous NH$_4$Cl. After extractive work-up (CH$_2$Cl$_2$/water) and evaporation of the solvent, a yellow residue was obtained. This residue was re-dissolved in a mixture of MeOH/THF (5 mL) to which NaBH$_4$ (350 mg, 1 mmol) was added portionwise at 0° C. After stirring for 30 min, this mixture was quenched with aqueous NH$_4$Cl, extracted (CH$_2$Cl$_2$/water) and the extract was dried over Na$_2$SO$_4$. After evaporation of the solvent, a yellow residue was obtained, which was subsequently dissolved in EtOAc (10 mL). A solution of KI$_3$ (0.5 M, 2 mL) in water was added and the biphasic system was stirred at rt for 15 min, after which time 3 mL of saturated aqueous Na$_2$S$_2$O$_3$ was added to give a pale yellow EtOAc layer. Aqueous extraction and evaporation of the organic phase gives a yellow oil, which was purified by preparative TLC (Et$_2$O/CH$_2$Cl$_2$) to give the title compound as a yellow oil.

$^1$H-NMR (500 MHz, CDCl$_3$): δ/ppm 7.41 (2H, m), 7.03 (2H, t, J=9.0 Hz), 5.09 (1H, s), 3.36 (3H, s), 3.34 (1H, d, J=14.5 Hz), 3.25 (1H, d, J=14.5 Hz), 3.11 (3H, s), 1.97 (3H, s), 1.55 (3H, s); $^{13}$C-NMR (125 MHz, CDCl$_3$): δ/ppm 171.89 (C), 166.2 (C), 163.1 (C), 162.6 (C, d, J=250 Hz), 131.8 (C), 129.4 (2CH, d, J=8 Hz), 115.5 (2CH, d, J=22 Hz), 74.6 (C), 73.4 (C), 72.4 (CH), 55.1 (C), 52.3 (CH$_3$), 38.9 (CH$_2$), 27.8 (CH$_3$), 25.5 (CH$_3$), 18.4 (CH$_3$). IR (film): v/cm$^{-1}$ 2951, 1736, 1692, 1606, 1511, 1255, 1228, 1161, 1129, 848, 733.

LR-MS: 432.85 (M+Na$^+$); HR-MS (ESI) calculated for C$_{18}$H$_{19}$N$_2$O$_4$FS$_2$Na: 433.0668, found: 433.0660.

Example 5

Alternate Simplified General Procedure for Synthesis of Epidithiodiketopiperazines Rac-(3S,6S,7S,8aS)-6-(benzo[d][1,3]dioxol-5-yl)-3-ethyl-2,7-dimethyl-1,4-dioxohexahydro-6H-3,8a-epidithiopyrrolo[1,2-a]pyrazine-7-carbonitrile To a suspension of S$_8$ (83 mg, 0.32 mmol) in dry THF (3.4 mL) was added a solution of NaHMDS (1.7 mL, 0.93 mmol, 3.3 equiv, 2 M in THF) at room temperature over 40 sec. After 1 min, a solution of the diketopiperazine (100 mg, 0.28 mmol, in 2.6 mL THF) was added dropwise, followed by a second aliquot of NaHMDS (1.1 mL, 0.62 mmol, 2.2 equiv, 2 M in THF) within another 30-40 sec. The resulting orange-yellow solution was stirred for 50 min at rt and quenched by addition of saturated aqueous NH$_4$Cl. After extractive work-up (CH$_2$Cl$_2$/water) and evaporation of the solvent, a yellow-brown amorphous residue was obtained. This residue was evaporated onto 2.2 g SiO$_2$ and placed on top of a filter frit containing 12 g SiO$_2$. Washing of this SiO$_2$ plug with 150 mL of hexanes removes the majority of HMDS-related material. Subsequent washing with 150 mL of MeCN elutes the sulfidated products as a mixture of epidi- and epitrisulfide products (epidi:epitri usually ~9:1). These products were separated by preparative TLC (2-4% EtOAc/CH$_2$Cl$_2$). The desired epidisulfide product (R$_f$~0.3) was isolated as an off-white solid (purity ~95%) after removal of the volatiles in vacuo.

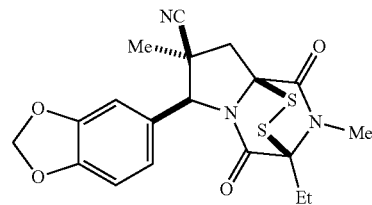

Chemical Formula: C$_{19}$H$_{19}$N$_3$O$_4$S$_2$
Exact Mass: 417.0817
Molecular Weight: 417.4980

$^1$H-NMR (600 MHz, CDCl$_3$) δ 6.88 (s, 1H), 6.84 (app. s, 2H), 5.99 (app. m, 2H), 4.83 (s, 1H), 3.28 (d, J=15.0 Hz, 1H), 3.10 (s, 3H), 3.01 (d, J=15.0 Hz, 1H), 2.39 (m, 1H), 2.30 (m, 1H), 1.68 (s, 3H), 1.25 (t, J=7.2 Hz, 3H) ppm; $^{13}$C-NMR (126 MHz, CDCl$_3$) δ 166.6 (C), 161.0 (C), 148.6 (C), 148.3 (C), 127.5 (C), 120.8 (CH), 120.4 (C), 108.6 (CH), 107.3 (CH), 101.6 (CH$_2$), 78.0 (C), 73.5 (C), 72.6 (CH), 44.5 (C), 42.9 (CH$_2$), 28.8 (CH$_3$), 25.4 (CH$_2$), 24.9 (CH$_3$), 9.9 (CH$_3$) ppm; IR (film) v/cm$^{-1}$ 2917, 1685, 1558, 1506, 1491, 1357, 1249, 1001, 928 cm$^{-1}$; HRMS (ESI) calcd for C$_{19}$H$_{19}$N$_3$O$_4$S$_2$Na$^+$ (M+Na) 440.0715, found 440.0718.

At the end of the concentration process, MeOH (1-2 mL) and CH$_2$Cl$_2$ (1-2 mL) can be added and then again removed in vacuo to facilitate the formation of a colorless powder. In other cases, the epidi- and epitrisulfide products can be separated by column chromatography on silica gel using a mixtures of CH$_2$Cl$_2$ and EtOAc as the eluent. Generally either of the two procedures described above can be used to prepare the epidithiodiketopiperazine products.

tert-Butyl Rac-(3S,6S,7S,8aS)-6-(4-fluorophenyl)-2,3,7-trimethyl-1,4-dioxohexahydro-6H-3,8a-epidithiopyrrolo[1,2-a]pyrazine-7-carboxylate

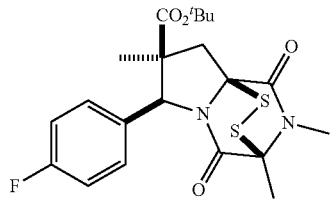

Chemical Formula: $C_{21}H_{25}FN_2O_4S_2$
Exact Mass: 452.1240

$^1$H-NMR (500 MHz, CDCl$_3$): δ/ppm 7.52-7.55 (2H, m), 7.09 (2H, t, J=8.5 Hz), 5.04 (1H, s), 3.36 (1H, d, J=14.5 Hz), 3.31 (1H, d, J=14.5 Hz), 3.14 (3H, s), 1.99 (3H, s), 1.56 (3H, s), 1.17 (9H, s); $^{13}$C-NMR (125 MHz, CDCl$_3$): δ/ppm 170.4 (C), 166.3 (C), 163.0 (C), 161.7 (C, d, J=247 Hz), 132.3 (C), 130.4 (2CH, d, J=8 Hz), 115.5 (2CH, d, J=22 Hz), 82.2 (C), 74.4 (C), 73.5 (C), 72.2 (CH), 55.0 (C), 39.4 (CH$_2$), 27.8 (CH$_3$), 27.5 (3CH$_3$), 26.6 (CH$_3$), 18.3 (CH$_3$). IR (film): ν/cm$^{-1}$ 2977, 2935, 1693, 1511, 1367, 1310, 1229, 1132, 847. LR-MS: 475.1 (M+Na); HR-MS (ESI) calculated for $C_{21}H_{25}N_2O_4FS_2Na$: 475.1137, found: 475.1132.

Methyl Rac-(3S,6S,7S,8aS)-6-(benzo[d][1,3]dioxol-5-yl)-2,3,7-trimethyl-1,4-dioxohexahydro-6H-3,8a-epidithiopyrrolo[1,2-a]pyrazine-7-carboxylate

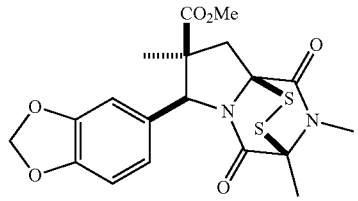

Chemical Formula: $C_{19}H_{20}N_2O_6S_2$
Exact Mass: 436.0763

$^1$H-NMR (500 MHz, CDCl$_3$): δ/ppm 6.98 (1H, s), 6.87 (1H, d, J=8.0 Hz), 6.76 (1H, d, J=8.0 Hz), 5.96 (2H, s), 5.03 (1H, s), 3.42 (3H, s), 3.34 (1H, d, J=14.0 Hz), 3.22 (1H, d, J=14.0 Hz), 3.10 (3H, s), 1.96 (3H, s), 1.52 (3H); $^{13}$C-NMR (125 MHz, CDCl$_3$): δ/ppm 171.6 (C), 166.3 (C), 163.1 (C), 147.9 (C), 147.6 (C), 129.6 (C), 121.3 (CH), 108.2 (CH), 108.0 (CH), 101.3 (CH$_2$), 74.6 (C), 73.4 (C), 72.9 (CH), 55.1 (C), 52.3 (CH$_3$), 38.8 (CH$_2$), 27.8 (CH$_3$), 25.4 (CH$_3$), 18.4 (CH$_3$). IR (film): ν/cm$^{-1}$ 2953, 1736, 1692, 1490, 1447, 1356, 1250, 1038. LR-MS: 459.2 M+Na$^+$; HR-MS (ESI) calculated for $C_{19}H_{20}N_2O_6S_2Na$: 459.0660, found: 459.0652.

Methyl Rac-(3S,6S,7S,8aS)-6-(5-bromo-2-methoxyphenyl)-2,3,7-trimethyl-1,4-dioxohexahydro-6H-3,8a-epidithiopyrrolo[1,2-a]pyrazine-7-carboxylate

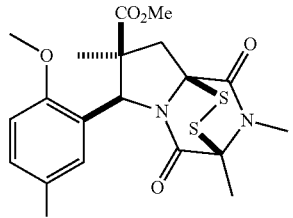

Chemical Formula: $C_{19}H_{21}BrN_2O_5S_2$
Exact Mass: 500.0075

$^1$H-NMR (500 MHz, CDCl$_3$): δ/ppm 7.54 (1H, s), 7.34 (1H, d, J=9.0 Hz), 6.70 (1H, d, J=9.0 Hz), 5.52 (1H, s), 3.78 (3H, s), 3.33 (3H, s), 3.26 (1H, d, J=14.5 Hz), 3.21 (1H, d, J=14.5 Hz), 3.09 (3H, s), 1.96 (3H, s), 1.52 (3H, s); $^{13}$C-NMR (125 MHz, CDCl$_3$): δ/ppm 171.7 (C), 166.3 (C), 162.8 (C), 155.5 (C), 132.1 (CH), 130.9 (CH), 126.9 (C), 113.2 (C), 111.8 (CH), 74.8 (C), 73.3 (C), 67.2 (CH), 55.7 (CH$_3$), 54.4 (C), 52.2 (CH$_3$), 40.6 (CH$_2$), 27.8 (CH$_3$), 25.0 (CH$_3$), 18.4 (CH$_3$). IR (film): ν/cm$^{-1}$ 2939, 1734, 1692, 1489, 1356, 1253, 1129, 1028, 914. LR-MS: 523.2 (M+Na$^+$); HR-MS (ESI) calculated for $C_{19}H_{21}N_2O_5S_2BrNa$: 522.9973 (M+Na$^+$), found: 522.9972.

Methyl Rac-(3S,6S,7S,8aS)-2,3,7-trimethyl-1,4-dioxo-6-(pyridin-3-yl)hexahydro-6H-3,8a-epidithiopyrrolo[1,2-a]pyrazine-7-carboxylate

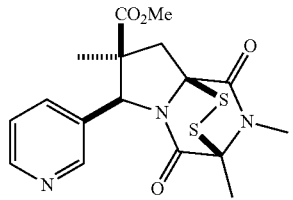

Chemical Formula: $C_{17}H_{19}N_3O_4S_2$
Exact Mass: 393.0817

Isolated as a 4:1 mixture of diastereomers, data for the major isomer is reported. $^1$H-NMR (500 MHz, CDCl$_3$): δ/ppm 8.63 (1H, d, J=2.0 Hz), 8.54 (1H, dd, J=2.0, 5.0 Hz), 7.81 (1H, d, J=8.0 Hz), 7.27-7.30 (1H, m), 5.10 (1H, s), 3.36 3H, s), 3.25-3.34 (2H, m), 3.10 (3H, s), 1.96 (3H, s), 1.57 (3H, s); $^{13}$C-NMR (125 MHz, CDCl$_3$): δ/ppm 171.4 (C), 166.2 (C), 163.1 (C), 149.8 (CH), 149.2 (CH), 135.1 (CH), 131.8 (C), 123.5 (CH), 74.6 (C), 73.4 (C), 70.5 (CH), 55.1 (C), 52.5 (CH$_3$), 39.1 (CH$_2$), 27.8 (CH$_3$), 25.5 (CH$_3$), 18.3 (CH$_3$). IR (film): ν/cm$^{-1}$ 2927, 1735, 1690, 1354, 1309, 1261, 1129, 916. LR-MS: 416.1 (M+Na$^+$); HR-MS (ESI) calculated for $C_{17}H_{19}N_3O_4S_2Na$: 416.0715 (M+Na$^+$), found: 416.0715.

129
Rac-(3S,6S,7S,8aS,9S)-2,3,7-trimethyl-1,4-dioxo-6-phenylhexahydro-6H-3,8a-epidithiopyrrolo[1,2-a]pyrazine-7-carbonitrile

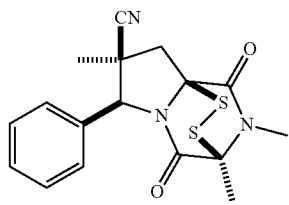

Chemical Formula: $C_{17}H_{17}N_3O_2S_2$
Exact Mass: 359.0762

$^1$H-NMR (500 MHz, CDCl$_3$): δ/ppm 7.46-7.38 (5H, m), 4.91 (1H, s), 3.32 (1H, d, J=14.5 Hz), 3.09 (3H, s), 3.00 (1H, d, J=14.9 Hz), 1.94 (3H, s), 1.69 (3H, s); $^{13}$C-NMR (125 MHz, CDCl$_3$): δ/ppm 165.7 (C), 162.2 (C), 133.8 (C), 129.6 (CH), 129.1 (2CH), 126.9 (2CH), 120.2 (C), 73.4 (C), 72.5 (CH), 44.5 (C), 43.0 (CH$_2$) 29.8 (C), 27.9 (CH$_3$), 24.9 (CH$_3$), 18.2 (CH$_3$); IR (film): ν/cm$^{-1}$ 2917, 2849, 2361, 2341, 2241, 1705, 1680; LR-MS: 382.0 [M+Na]$^+$; HR-MS (ESI) calculated for $C_{17}H_{17}N_3O_2S_2$Na: 382.0660, found: 382.0671.

Rac (3S,6S,7S,8aS,9S)-6-(4-fluorophenyl)-2,3,7-trimethyl-1,4-dioxohexahydro-6H-3,8a-epidithiopyrrolo[1,2-a]pyrazine-7-carbonitrile

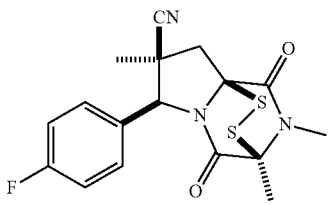

Chemical Formula: $C_{17}H_{16}FN_3O_2S_2$
Exact Mass: 377.0668

$^1$H-NMR (500 MHz, CDCl$_3$): δ/ppm 7.37 (2H, dd, J=5.4, 8.4 Hz), 7.13 (2H, t, J=8.7 Hz), 4.89 (1H, s), 3.31 (1H, d, J=14.7 Hz), 3.08 (3H, s), 2.99 (1H, d, J=15.0 Hz), 1.94 (3H, s), 1.68 (3H, s); $^{13}$C-NMR (125 MHz, CDCl$_3$): δ/ppm 165.6 (C), 163.4 (C, d, J=247 Hz), 162.2 (C), 129.6 (C, d, J=3 Hz), 128.8 (2CH, d, J=8 Hz), 120.2 (C), 116.2 (2CH, d, J=22 Hz), 73.52 (C), 73.46 (C), 71.9 (CH), 44.5 (C), 42.9 (CH$_2$), 27.9 (CH$_3$), 24.7 (CH$_3$), 18.2 (CH$_3$); IR (film): ν/cm$^{-1}$ 2991, 2356, 2239, 1706, 1682, 1512; LR-MS: 400.0 [M+Na]$^+$; HR-MS (ESI) calculated for $C_{17}H_{16}FN_3O_2S_2$: 400.0566, found: 400.0582.

130
Rac-(3S,6S,7S,8aS)-6-(Benzo[d][1,3]dioxol-5-yl)-2,3,7-trimethyl-1,4-dioxohexahydro-6H-3,8a-epidithiopyrrolo[1,2-a]pyrazine-7-carbonitrile

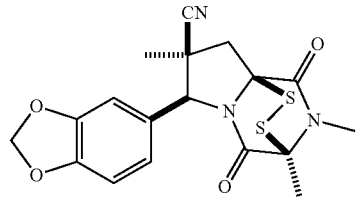

Chemical Formula: $C_{18}H_{17}N_3O_4S_2$
Exact Mass: 403.0660

Major ETP stereoisomer. $^1$H-NMR (500 MHz, CDCl$_3$): δ/ppm 6.96 (1H, s), 6.91 (2H, app. s), 6.06 (2H, s), 4.89 (1H, s), 3.36 (1H, d, J=14.5 Hz), 3.14 (3H, s), 3.06 (1H, d, J=14.5 Hz), 2.00 (3H, s), 1.73 (3H, s); $^{13}$C-NMR (125 MHz, CDCl$_3$): δ/ppm 165.6 (C), 162.1 (C), 148.6 (C), 148.3 (C), 127.5 (C), 120.7 (CH), 120.3 (C), 108.6 (CH), 107.2 (CH), 101.6 (CH$_2$), 73.4 (C), 73.3 (C), 72.4 (CH), 44.4 (C), 42.8 (CH$_2$), 27.8 (CH$_3$), 24.8 (CH$_3$), 18.1 (CH$_3$). IR (film): ν/cm$^{-1}$ 2984, 2902, 2250, 1688, 1491, 1446, 1358, 1250, 1038, 731. LR-MS: 426.1 M+Na$^+$; HR-MS (ESI) calculated for $C_{18}H_{17}N_3O_4S_2$Na: 426.0558, found: 426.0555. The constitution and relative configuration of this product was confirmed by single-crystal X-ray analysis.

Rac-(3R,6S,7S,8aR)-6-(Benzo[d][1,3]dioxol-5-yl)-2,3,7-trimethyl-1,4-dioxohexahydro-6H-3,8a-epidithiopyrrolo[1,2-a]pyrazine-7-carbonitrile

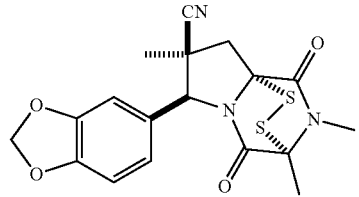

Chemical Formula: $C_{18}H_{17}N_3O_4S_2$
Exact Mass: 403.0660

Minor ETP stereoisomer. $^1$H-NMR (500 MHz, CDCl$_3$): δ/ppm 6.80 (1H, d, J=8.0 Hz), 6.60 (1H, d, J=8.0 Hz), 6.55 (1H, s), 5.99 (2H, s), 5.03 (1H, s), 3.80 (1H, d, J=15.0 Hz), 3.12 (3H, s), 2.51 (1H, d, J=15.0 Hz), 1.99 (3H, s), 1.94 (3H, s); $^{13}$C-NMR (125 MHz, CDCl$_3$): δ/ppm 165.3 (C), 162.4 (C), 148.6 (C), 148.5 (C), 129.4 (C), 120.1 (CH), 119.6 (C), 108.9 (CH), 106.3 (CH), 101.6 (CH$_2$), 73.8 (C), 73.7 (C), 71.6 (CH), 43.8 (C), 42.3 (CH$_2$), 27.9 (CH$_3$), 27.2 (CH$_3$), 18.3 (CH$_3$). IR (film): ν/cm$^{-1}$ 2988, 2940, 2900, 2249, 1694, 1504, 1448, 1355, 1248, 1111, 1038, 912, 731. LR-MS: 426.0 M+Na$^+$; HR-MS (ESI) calculated for $C_{18}H_{17}N_3O_4S_2$Na: 426.0558, found: 426.0553.

Rac-(3S,6R,7S,8aS)-6-(5-Bromo-2-methoxyphenyl)-2,3,7-trimethyl-1,4-dioxohexahydro-6H-3,8a-epidithiopyrrolo[1,2-a]pyrazine-7-carbonitrile

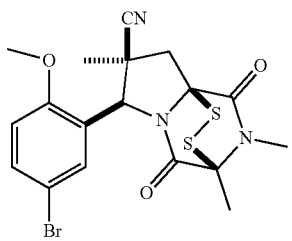

Chemical Formula: $C_{18}H_{18}BrN_3O_3S_2$
Exact Mass: 466.9973

$^1$H-NMR (500 MHz, CDCl$_3$): δ/ppm 7.50 (1H, s), 7.45 (1H, dd, J=2.0, 8.5 Hz), 6.83 (1H, d, J=8.5 Hz), 5.49 (1H, s), 3.90 (3H, s), 3.45 (1H, d, J=14.5 Hz), 3.10 (3H, s), 2.91 (1H, d, J=14.5 Hz), 1.98 (3H, s), 1.65 (3H, s); $^{13}$C-NMR (125 MHz, CDCl$_3$): δ/ppm 165.7 (C), 162.7 (C), 155.8 (C), 133.2 (CH), 129.9 (CH), 120.0 (C), 113.4 (C), 112.5 (CH), 73.7 (C), 73.3 (C), 65.5 (CH), 55.6 (CH$_3$), 43.5 (C), 41.9 (CH$_2$), 27.9 (CH$_3$), 25.7 (CH$_3$), 18.3 (CH$_3$). IR (film): ν/cm$^{-1}$ 2937, 2359, 1692, 1488, 1359, 1252, 729. LR-MS: 490.0 (M+Na); HR-MS (ESI) calculated for $C_{18}H_{18}N_3O_3BrS_2Na$: 489.9871, found: 489.9862.

Rac-(3S,6R,7S,8aS)-2,3,7-Trimethyl-1,4-dioxo-6-(thiophen-2-yl)hexahydro-6H-3,8a-epidithiopyrrolo[1,2-a]pyrazine-7-carbonitrile

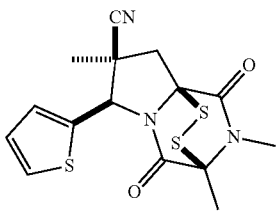

Chemical Formula: $C_{15}H_{15}N_3O_2S_3$
Exact Mass: 365.0326

$^1$H-NMR (500 MHz, CDCl$_3$): δ/ppm 7.36 (1H, d, J=4.5 Hz), 7.30 (1H, br. s), 7.07 (1H, t, J=4.5 Hz), 5.30 (1H, s), 3.43 (1H, d, J=14.5 Hz), 3.00-3.15 (4H, m), 1.96 (3H, s), 1.66 (3H, s); $^{13}$C-NMR (125 MHz, CDCl$_3$): δ/ppm 165.5 (C), 162.2 (C), 136.2 (C), 127.7 (CH), 127.6 (CH), 126.8 (CH), 119.6 (C), 73.4 (C), 72.9 (C), 67.3 (CH), 44.3 (C), 42.0 (CH$_2$), 27.9 (CH$_3$), 25.2 (CH$_3$), 18.2 (CH$_3$). IR (film): ν/cm$^{-1}$ 2917, 2361, 1699, 1403, 1360, 1251, 1068, 848. LR-MS: 388.1 (M+Na$^+$); HR-MS (ESI) calculated for $C_{15}H_5N_3O_2S_3Na$: 388.0224, found: 388.0221.

Rac-(3S,6S,7S,8aS)-6-([1,1'-Biphenyl]-4-yl)-2,3,7-trimethyl-1,4-dioxohexahydro-6H-3,8a-epidithiopyrrolo[1,2-a]pyrazine-7-carbonitrile

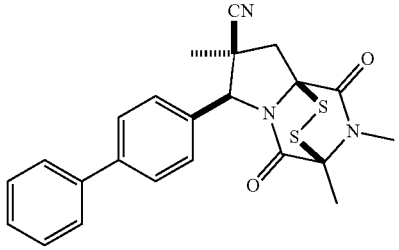

Chemical Formula: $C_{23}H_{21}N_3O_2S_2$
Exact Mass: 435.1075

$^1$H-NMR (500 MHz, CDCl$_3$): δ/ppm 7.72 (2H, d, J=8.5 Hz), 7.66 (2H, d, J=8.5 Hz), 7.45-7.53 (4H, m), 7.41 (1H, t, J=7.5 Hz), 5.02 (1H, s), 3.41 (1H, d, J=15.0 Hz), 3.16 (3H, s), 3.09 (1H, d, J=15.0 Hz), 2.02 (3H, s), 1.78 (3H, s); $^{13}$C-NMR (125 MHz, CDCl$_3$): δ/ppm 165.6 (C), 162.2 (C), 142.3 (C), 140.4 (C), 132.6 (C), 128.8 (2CH), 127.7 (2CH), 127.6 (2CH), 127.2 (CH+2CH), 120.2 (C), 73.5 (C), 73.4 (C), 72.2 (CH), 44.4 (C), 42.9 (CH$_2$), 27.8 (CH$_3$), 24.8 (CH$_3$), 18.1 (CH$_3$). IR (film): ν/cm$^{-1}$ 2935, 2250, 1689, 1488, 1448, 1414, 1358, 1252, 910. LR-MS: 458.2 (M+Na$^+$); HR-MS (ESI) calculated for $C_{23}H_{21}N_3O_2S_2Na$: 458.0973, found: 458.0972.

Rac-(3S,6S,7S,8aS)-2,3,7-Trimethyl-1,4-dioxo-6-(p-tolyl)hexahydro-6H-3,8a-epidithiopyrrolo[1,2-a]pyrazine-7-carbonitrile

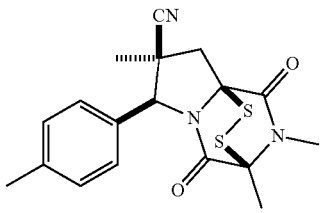

Chemical Formula: $C_{18}H_{19}N_3O_2S_2$
Exact Mass: 373.0919

$^1$H-NMR (500 MHz, CDCl$_3$): δ/ppm 7.28-7.35 (4H, m), 4.94 (1H, s), 3.37 (1H, d, J=15.0 Hz), 3.14 (3H, s), 3.06 (1H, d, J=15.0 Hz), 2.43 (3H, s), 2.00 (3H, s), 1.74 (3H, s), $^{13}$C-NMR (125 MHz, CDCl$_3$): δ/ppm 165.7 (C), 162.1 (C), 139.3 (C), 130.7 (C), 129.7 (2CH), 126.7 (2CH), 120.3 (C), 73.5 (C), 73.3 (C), 72.4 (CH), 44.5 (C), 42.9 (CH$_2$), 27.8 (CH$_3$), 24.7 (CH$_3$), 21.4 (CH$_3$), 18.1 (CH$_3$). IR (film): ν/cm$^{-1}$ 2990, 2921, 2245, 1685, 1516, 1358, 1253, 816. LR-MS: 396.2 (M+Na$^+$); HR-MS (ESI) calculated for $C_{18}H_{19}N_3O_2S_2Na$: 396.0816, found: 396.0800. The constitution and relative configuration of this product was confirmed by single-crystal X-ray analysis.

133

Rac-(3S,6S,7S,8aS)-6-(2,3-Dihydrobenzo[b][1,4]dioxin-6-yl)-2,3,7-trimethyl-1,4-dioxohexahydro-6H-3,8a-epidithiopyrrolo[1,2-a]pyrazine-7-carbonitrile

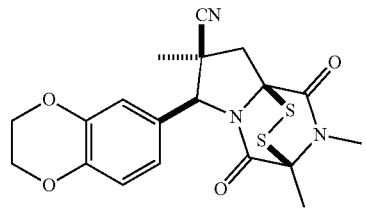

Chemical Formula: $C_{19}H_{19}N_3O_4S_2$
Exact Mass: 417.0817

$^1$H-NMR (500 MHz, CDCl$_3$): δ/ppm 6.90-7.00 (3H, m), 4.88 (1H, s), 4.32 (4H, m), 3.36 (1H, d, J=14.5 Hz), 3.14 (3H, s), 3.05 (1H, d, J=14.5 Hz), 2.00 (3H, s), 1.72 (3H, s); $^{13}$C-NMR (125 MHz, CDCl$_3$): δ/ppm 165.7 (C), 162.2 (C), 144.4 (C), 143.7 (C), 126.9 (C), 120.2 (C), 119.9 (CH), 117.9 (CH), 115.9 (CH), 73.4 (C), 73.3 (C), 72.0 (CH), 64.3 (2CH$_2$), 44.4 (C), 42.7 (CH$_2$), 27.8 (CH$_3$), 24.9 (CH$_3$), 18.1 (CH$_3$). IR (film): ν/cm$^{-1}$ 2984, 2938, 2251, 1690, 1592, 1509, 1360, 1288, 1260, 1067, 912. LR-MS: 439.9 (M+Na$^+$); HR-MS (ESI) calculated for $C_{19}H_{19}N_3O_4S_2Na$: 440.0715, found: 440.0728.

Rac-(3S,6S,7S,8aS)-6-(4-Chlorophenyl)-2,3,7-trimethyl-1,4-dioxohexahydro-6H-3,8a-epidithiopyrrolo[1,2-a]pyrazine-7-carbonitrile

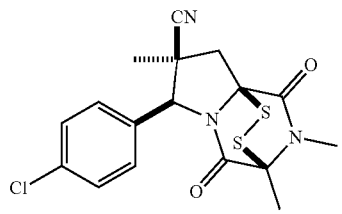

Chemical Formula: $C_{17}H_{16}ClN_3O_2S_2$
Exact Mass: 393.0372

$^1$H-NMR (500 MHz, CDCl$_3$): δ/ppm 7.42 (2H, d, J=8.5 Hz), 7.32 (2H, d, J=8.5 Hz), 4.87 (1H, s), 3.32 (1H, d, J=15.0 Hz), 3.08 (3H, s), 2.99 (1H, d, J=15.0 Hz), 1.94 (3H, s), 1.68 (3H, s); $^{13}$C-NMR (125 MHz, CDCl$_3$): δ/ppm 165.5 (C), 162.1 (C), 135.5 (C), 132.2 (C), 129.3 (2CH), 128.2 (2CH), 120.0 (C), 73.5 (C), 73.4 (C), 71.8 (CH), 44.3 (C), 42.9 (CH$_2$), 27.8 (CH$_3$), 24.7 (CH$_3$), 18.1 (CH$_3$). IR (film): ν/cm$^{-1}$ 2992, 2941, 2246, 1690, 1493, 1359, 1255, 1090, 825. LR-MS: 416.2 (M+Na$^+$); HR-MS (ESI) calculated for $C_{17}H_{16}N_3O_2ClS_2Na$: 416.0270, found: 416.0261.

134

Rac-(3S,6S,7S,8aS)-6-(3,4-Dichlorophenyl)-2,3,7-trimethyl-1,4-dioxohexahydro-6H-3,8a-epidithiopyrrolo[1,2-a]pyrazine-7-carbonitrile

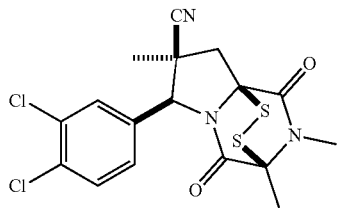

Chemical Formula: $C_{17}H_{15}Cl_2N_3O_2S_2$
Exact Mass: 426.9983

$^1$H-NMR (500 MHz, CDCl$_3$): δ/ppm 7.53 (1H, d, J=8.0 Hz), 7.46 (1H, s), 7.25 (1H, d, J=8.0 Hz), 4.85 (1H, s), 3.33 (1H, d, J=15.0 Hz), 3.09 (3H, s), 3.00 (1H, d, J=15.0 Hz), 1.95 (3H, s), 1.70 (3H, s); $^{13}$C-NMR (125 MHz, CDCl$_3$): δ/ppm 165.4 (C), 162.0 (C), 133.9 (2C), 133.2 (C), 131.2 (CH), 129.0 (CH), 126.2 (CH), 119.8 (C), 73.4 (2C), 71.2 (CH), 44.2 (C), 42.9 (CH$_2$), 27.9 (CH$_3$), 24.8 (CH$_3$), 18.1 (CH$_3$). IR (film): ν/cm$^{-1}$ 2936, 2250, 1696, 1472, 1359, 1252, 1136, 1031, 912, 730. LR-MS: 449.9 (M+Na$^+$); HR-MS (ESI) calculated for $C_{17}H_{15}N_3O_2Cl_2S_2Na$: 449.9880, found: 449.9853.

Rac-(3S,6R,7S,8aS)-6-(6-Bromobenzo[d][1,3]dioxol-5-yl)-2,3,7-trimethyl-1,4-dioxohexahydro-6H-3,8a-epidithiopyrrolo[1,2-a]pyrazine-7-carbonitrile

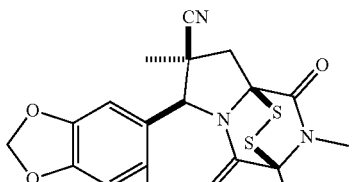

Chemical Formula: $C_{18}H_{16}BrN_3O_4S_2$
Exact Mass: 480.9766

$^1$H-NMR (500 MHz, CDCl$_3$): δ/ppm 7.07 (1H, s), 7.05 (1H, s), 6.02 (2H, s), 5.22 (1H, s), 3.41 (1H, d, J=15.0 Hz), 3.08 (3H, s), 2.98 (1H, d, J=15.0 Hz), 1.95 (3H, s), 1.75 (3H, s); $^{13}$C-NMR (125 MHz, CDCl$_3$): δ/ppm 165.5 (C), 162.2 (C), 149.1 (C), 148.3 (C), 126.8 (C), 120.0 (C), 114.4 (C), 113.2 (CH), 108.0 (CH), 102.3 (CH$_2$), 73.6 (C), 73.3 (C), 71.0 (CH), 44.2 (C), 42.8 (CH$_2$), 27.8 (CH$_3$), 25.5 (CH$_3$), 18.1 (CH$_3$). IR (film): ν/cm$^{-1}$ 3043, 2986, 2913, 2243, 1694, 1504, 1480, 1355, 1242, 1118, 1037, 931, 734. LR-MS: 504.1 (M+Na$^+$); HR-MS (ESI) calculated for $C_{18}H_{16}N_3O_4BrS_2Na$: 503.9663, found: 503.9647.

Rac-(3S,6S,7R,8aS)-6-(Benzo[d][1,3]dioxol-5-yl)-7-((dimethylamino)methyl)-2,3,7-trimethyl-tetrahydro-6H-3,8a-epidithiopyrrolo[1,2-a]pyrazine-1,4-dione

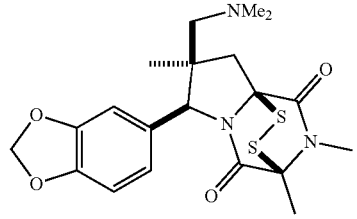

Chemical Formula: $C_{20}H_{25}N_3O_4S_2$
Exact Mass: 435.1286

Prepared from rac-(3R,6S,7S,8aS)-6-(Benzo[d][1,3]dioxol-5-yl)-2,3,7-trimethyl-1,4-dioxo-octahydropyrrolo[1,2-a]-pyrazine-7-carbonitrile by conventional $NiCl_2/NaBH_4$ reduction of the nitrile, Eschweiler-Clarke dimethylation of the resulting primary amine and sulfidation.

H-NMR (500 MHz, $CDCl_3$): δ/ppm 6.91 (1H, s), 6.76-6.83 (2H, m), 5.97 (2H, s), 4.77 (1H, s), 3.18 (1H, d, J=14.5 Hz), 3.07 (3H, s), 2.55 (1H, d, J=14.5 Hz), 2.15 (6H, s), 1.97 (2H, s), 1.94 (3H, s), 1.27 (3H, s); $^{13}$C-NMR (125 MHz, $CDCl_3$): δ/ppm 166.6 (C), 163.1 (C), 148.0 (C), 147.3 (C), 130.0 (C), 121.3 (CH), 108.4 (CH), 108.1 (CH), 101.3 ($CH_2$), 74.9 (C), 74.2 (CH), 73.5 (C), 66.1 ($CH_2$), 8.2 (2$CH_3$), 47.8 (C), 41.8 ($CH_2$), 27.7 ($CH_3$), 26.5 ($CH_3$), 18.4 ($CH_3$). IR (film): ν/cm$^{-1}$ 2940, 2821, 2770, 1690, 1490, 1445, 1379, 1353, 1249, 1104, 1038, 932, 734. LR-MS: 458.2 (M+Na$^+$); HR-MS (ESI) calculated for $C_{20}H_{25}N_3O_4S_2Na$: 458.1184, found: 458.1185.

Rac-(3S,6R,7S,8aS)-6-(4-Methoxybenzo[d][1,3]dioxol-5-yl)-2,3,7-trimethyl-1,4-dioxohexahydro-6H-3,8a-epidithiopyrrolo[1,2-a]pyrazine-7-carbonitrile

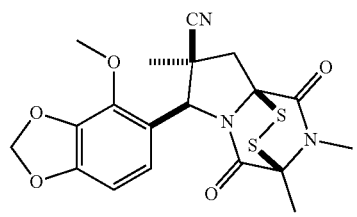

Chemical Formula: $C_{19}H_{19}N_3O_5S_2$
Molecular Weight: 433.4970

$^1$H-NMR (500 MHz, $CDCl_3$): δ/ppm 6.52-6.62 (2H, m), 6.01 (2H, s), 4.84 (1H, s), 3.89 (3H, s), 3.31 (1H, d, J=15.0 Hz), 3.09 (3H, s), 3.01 (1H, d, J=15.0 Hz), 1.96 (3H, s), 1.68 (3H, s); $^{13}$C-NMR (125 MHz, $CDCl_3$): δ/ppm 165.5 (C), 162.0 (C), 149.2 (C), 143.8 (C), 136.0 (C), 128.1 (C), 120.2 (C), 106.1 (CH), 102.1 ($CH_2$), 101.2 (CH), 73.6 (C), 73.5 (C), 72.4 (CH), 56.6 ($CH_3$), 44.5 (C), 42.7 ($CH_2$), 27.9 ($CH_3$), 25.1 ($CH_3$), 18.2 ($CH_3$). IR (film): ν/cm$^{-1}$ 2940, 2902, 2241, 1696, 1636, 1513, 1453, 1358, 1250, 1201, 1130, 1093, 1044, 874, 734. LR-MS: 456.0 M+Na$^+$; HR-MS (ESI) calculated for $C_{19}H_{19}N_3O_5S_2Na$: 456.0664, found: 456.0653.

Rac-(3S,6S,7R,8aS)-6-(Benzo[d][1,3]dioxol-5-yl)-7-(methoxymethyl)-2,3-dimethyl-1,4-dioxohexahydro-6H-3,8a-epidithiopyrrolo[1,2-a]pyrazine-7-carbonitrile

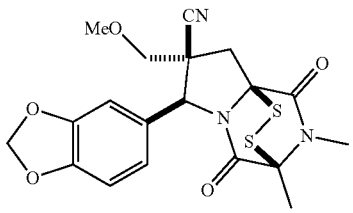

Chemical Formula: $C_{19}H_{19}N_3O_5S_2$
Molecular Weight: 433.4970

$^1$H-NMR (500 MHz, $CDCl_3$): δ/ppm 6.91 (1H, s), 6.80-6.88 (2H, m), 5.99 (2H, s), 5.26 (1H, s), 3.61 (1H, d, J=9.5 Hz), 3.58 (1H, d, J=15.0 Hz), 3.54 (1H, d, J=9.5 Hz), 3.47 (3H, s), 3.08 (3H, s), 2.88 (1H, d, J=15.0 Hz), 1.94 (3H, s); $^{13}$C-NMR (125 MHz, $CDCl_3$): δ/ppm 165.5 (C), 162.0 (C), 148.4 (C), 148.3 (C), 128.0 (C), 120.9 (CH), 118.4 (C), 108.7 (CH), 107.4 (CH), 101.5 ($CH_2$), 73.8 (C), 73.5 (C), 73.0 ($CH_2$), 67.2 (CH), 59.7 ($CH_3$), 49.6 (C), 38.5 ($CH_2$), 27.8 ($CH_3$), 18.1 ($CH_3$). IR (film): ν/cm$^{-1}$ 2993, 2928, 2898, 2250, 1693, 1497, 1491, 1447, 1358, 1250, 1118, 1038, 914, 731. LR-MS: 456.0 M+Na$^+$; HR-MS (ESI) calculated for $C_{19}H_{19}N_3O_5S_2Na$: 456.0664, found: 456.0650.

Rac-(3S,6S,7S,8aS)-6-(2,2-Difluorobenzo[d][1,3]dioxol-5-yl)-2,3,7-trimethyl-1,4-dioxohexahydro-6H-3,8a-epidithiopyrrolo[1,2-a]pyrazine-7-carbonitrile

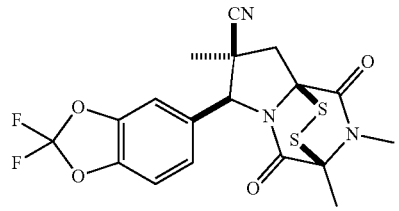

Chemical Formula: $C_{18}H_{15}F_2N_3O_4S_2$
Molecular Weight: 439.4518

$^1$H-NMR (500 MHz, $CDCl_3$): δ/ppm 7.09-7.15 (3H, m), 4.89 (1H, s), 3.33 (1H, d, J=14.5 Hz), 3.08 (3H, s), 3.00 (1H, d, J=14.5 Hz), 1.95 (3H, s), 1.69 (3H, s); $^{13}$C-NMR (125 MHz, $CDCl_3$): δ/ppm 165.4 (C), 162.1 (C), 144.4 (C), 144.2 (C), 131.7 (C, t, J=255 Hz), 130.0 (C), 122.6 (CH), 119.9 (C), 109.8 (CH), 108.3 (CH), 77.3 (C), 73.4 (C), 72.0 (CH), 44.4 (C), 42.9 ($CH_2$), 27.9 ($CH_3$), 24.8 ($CH_3$), 18.1 ($CH_3$). IR (film): ν/cm$^{-1}$ 2986, 2942, 2253, 1697, 1501, 1450, 1358, 1240, 1154, 1034, 903, 731. LR-MS: 462.0 M+Na$^+$; HR-MS (ESI) calculated for $C_{18}H_{15}N_3O_4F_2S_2Na$: 462.0370, found: 462.0377.

137

Rac-(3R,6R,7S,8aR)-6-(5-Bromobenzo[d][1,3]di-
oxol-4-yl)-2,3,7-trimethyl-1,4-dioxohexahydro-6H-
3,8a-epidithiopyrrolo[1,2-a]pyrazine-7-carbonitrile

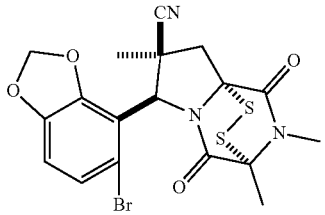

Chemical Formula: $C_{18}H_{16}BrN_3O_4S_2$
Molecular Weight: 482.3670

$^1$H-NMR (500 MHz, CDCl$_3$): δ/ppm 7.13 (1H, d, J=8.5 Hz), 6.69 (1H, d, J=8.5 Hz), 5.90 (1H, s), 5.80 (1H, s), 5.65 (1H, s), 3.88 (1H, d, J=15.5 Hz), 3.06 (3H, s), 2.57 (1H, d, J=15.5 Hz), 2.12 (3H, s), 1.95 (3H, s); $^{13}$C-NMR (125 MHz, CDCl$_3$): δ/ppm 165.5 (C), 161.6 (C), 147.6 (C), 145.1 (C), 126.4 (CH), 119.6 (C), 117.7 (C), 114.9 (C), 110.5 (CH), 102.1 (CH$_2$), 74.6 (C), 73.7 (C), 68.5 (CH), 44.3 (CH$_2$), 43.1 (C), 27.6 (CH$_3$), 27.5 (CH$_3$), 18.3 (CH$_3$). IR (film): v/cm$^{-1}$ 2986, 2880, 2250, 1695, 1457, 1357, 1242, 1059, 1035, 932, 731. LR-MS: 503.9 M+Na$^+$; HR-MS (ESI) calculated for $C_{18}H_{16}N_3O_4S_2$BrNa: 503.9663, found: 503.9655. The constitution and relative configuration of this product was confirmed by single-crystal X-ray analysis.

Rac-(3S,6R,7S,8aS)-6-(Benzo[d][1,3]dioxol-4-yl)-2,
3,7-trimethyl-1,4-dioxohexahydro-6H-3,8a-epidith-
iopyrrolo[1,2-a]pyrazine-7-carbonitrile

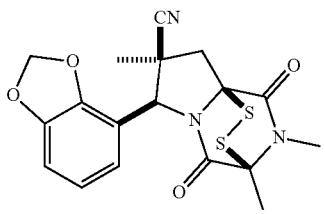

Chemical Formula: $C_{18}H_{17}N_3O_4S_2$
Molecular Weight: 403.4710

$^1$H-NMR (500 MHz, CDCl$_3$): δ/ppm 6.80-6.96 (3H, m), 6.02 (1H, s), 6.00 (1H, s), 5.22 (1H, s), 3.35 (1H, d, J=15.0 Hz), 3.08 (3H, s), 2.98 (1H, d, J=15.0 Hz), 1.95 (3H, s), 1.70 (3H, s); $^{13}$C-NMR (125 MHz, CDCl$_3$): δ/ppm 165.6 (C), 162.2 (C), 147.6 (C), 145.2 (C), 122.3 (CH), 120.1 (C), 119.5 (CH), 115.7 (C), 109.5 (CH), 101.3 (CH$_2$), 73.6 (C), 73.3 (C), 66.2 (CH), 44.1 (C), 42.7 (CH$_2$), 27.8 (CH$_3$), 25.1 (CH$_3$), 18.2 (CH$_3$). IR (film): v/cm$^{-1}$ 2991, 2905, 2241, 1697, 1462, 1357, 1249, 1063, 1029, 931, 731. LR-MS: 426.0 M+Na$^+$; HR-MS (ESI) calculated for $C_{18}H_{17}N_3O_4S_2$Na: 426.0558, found: 426.0552. The constitution and relative configuration of this product was confirmed by single-crystal X-ray analysis.

138

Rac-(3S,6S,7R,8aS)-6-(Benzo[d][1,3]dioxol-5-yl)-2,
3-dimethyl-7-(morpholinomethyl)-1,4-dioxohexa-
hydro-6H-3,8a-epidithiopyrrolo[1,2-a]pyrazine-7-
carbonitrile

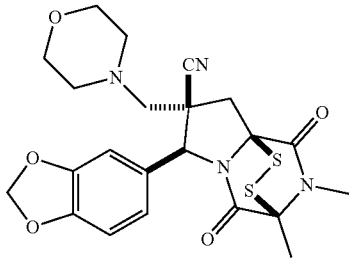

Chemical Formula: $C_{22}H_{24}N_4O_5S_2$
Molecular Weight: 488.5770

$^1$H-NMR (500 MHz, CDCl$_3$): δ/ppm 6.96 (1H, s), 6.91 (1H, d, J=8.0 Hz), 6.84 (1H, d, J=7.0 Hz), 5.99 (2H, s), 5.17 (1H, s), 3.65-3.74 (4H, m), 3.56 (1H, d, J=14.5 Hz), 3.04 (3H, s), 2.92 (1H, d, J=14.5 Hz), 2.70-2.80 (2H, m), 2.60-2.75 (4H, m), 1.94 (3H, s); $^{13}$C-NMR (125 MHz, CDCl$_3$): δ/ppm 165.6 (C), 162.2 (C), 148.4 (C), 148.3 (C), 128.2 (C), 121.1 (CH), 119.7 (C), 108.7 (CH), 107.6 (CH), 101.5 (CH$_2$), 73.7 (C), 73.5 (C), 68.7 (CH), 67.1 (2CH$_2$), 63.4 (CH$_2$), 55.3 (2CH$_2$), 49.6 (C), 39.5 (CH$_2$), 27.9 (CH$_3$), 18.2 (CH$_3$). IR (film): v/cm$^{-1}$ 2958, 2855, 2816, 2248, 1688, 1491, 1447, 1356, 1260, 1116, 1037, 914, 864, 730. LR-MS: 511.1 M+Na$^+$; HR-MS (ESI) calculated for $C_{22}H_{24}N_4O_5S_2$Na: 511.1086, found: 511.1068.

Rac-(3S,6S,7S,8aS)-6-(benzo[d][1,3]dioxol-5-yl)-2-
butyl-3,7-dimethyl-1,4-dioxohexahydro-1H-3,8a-
epidithiopyrrolo[1,2-a]pyrazine-7-carbonitrile

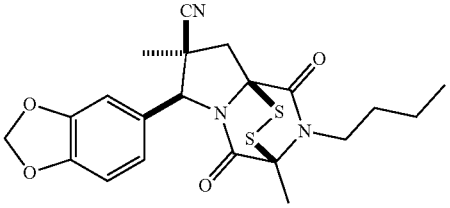

$^1$H-NMR (500 MHz, CDCl$_3$): δ/ppm 6.88 (1H, s), 6.82 (2H, app. s), 5.99 (2H, s), 4.81 (1H, s), 3.78, (1H, m), 3.30 (1H, d, J=14.5 Hz), 2.99 (1H, d, J=14.5 Hz), 1.98 (3H, s), 1.66 (3H, s), 1.62 (2H, m), 1.38 (2H, m), 0.96 (3H, t, J=7.2 Hz); $^{13}$C-NMR (125 MHz, CDCl$_3$): δ/ppm 165.2 (C), 162.4 (C), 148.7 (C), 148.4 (C), 127.7 (C), 120.8 (CH), 120.5 (C), 108.7 (CH), 107.4 (CH), 101.7 (CH$_2$), 73.8 (C), 73.0 (C), 72.5 (CH), 44.6 (C), 43.3 (CH$_2$), 43.0 (CH$_2$), 29.9 (CH$_2$), 25.0 (CH$_3$), 24.8 (CH$_2$), 20.4 (CH$_2$), 17.8 (CH$_3$), 14.0 (CH$_3$). IR (film): v/cm$^{-1}$ 2984, 2902, 2250, 1688, 1491, 1446, 1358, 1250, 1038, 731. HR-MS (ESI) calculated for $C_{21}H_{23}N_3O_4S_2$Na: 468.1022, found: 468.1018.

Rac-(3S,6S,7S,8aS)-6-(4-methoxyphenyl)-2,3,7-trimethyl-1,4-dioxohexahydro-1H-3,8a-epidithiopyrrolo[1,2-a]pyrazine-7-carbonitrile

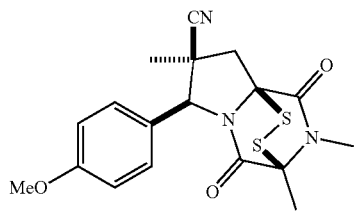

$^1$H-NMR (500 MHz, CDCl$_3$): δ/ppm 7.30 (2H, d, J=8.5 Hz), 6.96 (2H, d, J=8.5 Hz), 4.85 (1H, s), 3.79 (3H, s), 3.28 (1H, d, J=15.0 Hz), 3.08 (3H, s), 2.99 (1H, d, J=15.0 Hz), 1.94 (3H, s), 1.66 (3H, s); $^{13}$C-NMR (125 MHz, CDCl$_3$): δ/ppm 165.0 (C), 162.3 (C), 159.9 (C), 128.7 (C), 127.3 (2CH), 117.8 (C), 114.7 (2CH), 73.6 (C), 73.4 (C), 72.0 (CH), 55.2 (CH$_3$), 44.2 (C), 42.7 (CH$_2$), 27.7 (CH$_3$), 24.8 (CH$_3$), 18.0 (CH$_3$). IR (film): ν/cm$^{-1}$ 2988, 2940, 2246, 1690, 1493, 1359, 1255, 1093, 756. HR-MS (ESI) calculated for C$_{18}$H$_{19}$N$_3$O$_3$S$_2$Na: 412.0760, found: 412.0753.

Rac-(3S,6S,7S,8aS)-6-(benzo[d][1,3]dioxol-5-yl)-3-benzyl-2,7-dimethyl-1,4-dioxohexahydro-6H-3,8a-epidithiopyrrolo[1,2-a]pyrazine-7-carbonitrile

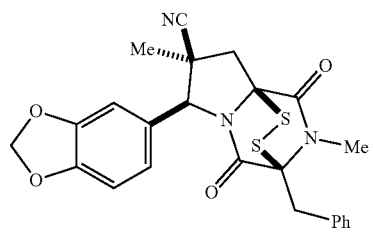

Chemical Formula: C$_{24}$H$_{21}$N$_3$O$_4$S$_2$
Exact Mass: 479.0973
Molecular Weight: 479.5690

$^1$H-NMR (500 MHz, CDCl$_3$) δ 7.33-7.31 (m, 2H), 7.29-7.24 (m, 3H), 6.86 (s, 1H), 6.82-6.81 (m, 2H), 5.99-5.98 (m, 2H), 4.90 (s, 1H), 3.82 (d, J=15.3 Hz, 1H), 3.75 (d, J=15.3 Hz, 1H), 3.32 (d, J=14.9 Hz, 1H), 3.07 (s, 3H), 3.02 (d, J=14.9 Hz, 1H), 1.70 (s, 3H) ppm; $^{13}$C-NMR (126 MHz, CDCl$_3$) δ 166.4 (C), 161.4 (C), 148.6 (C), 148.3 (C), 133.6 (C), 129.9 (CH), 128.7 (CH), 127.8 (CH), 127.4 (C), 120.8 (CH), 120.3 (C), 108.7 (CH), 107.4 (CH), 101.6 (CH$_2$), 77.8 (C), 73.5 (C), 72.7 (CH), 44.5 (C), 42.9 (CH$_2$), 36.6 (CH$_2$), 29.4 (CH$_3$), 25.0 (CH$_3$) ppm; IR (film) ν/cm$^{-1}$ 2917, 1695, 1491, 1447, 1357, 1249, 1190, 1037, 931, 817 cm$^{-1}$; HRMS (ESI) calcd for C$_{24}$H$_{21}$N$_3$O$_4$S$_2$Na$^+$ (M+Na) 502.0871, found 502.0867.

Rac-(3S,6S,7S,8aS)-2-allyl-6-(benzo[d][1,3]dioxol-5-yl)-3,7-dimethyl-1,4-dioxohexahydro-6H-3,8a-epidithiopyrrolo[1,2-a]pyrazine-7-carbonitrile

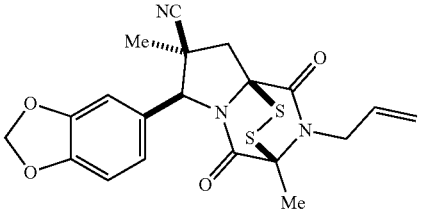

Chemical Formula: C$_{20}$H$_{19}$N$_3$O$_4$S$_2$
Exact Mass: 429.0817
Molecular Weight: 429.5090

$^1$H-NMR (500 MHz, CDCl$_3$) δ 6.88 (s, 1H), 6.84 (app. s, 2H), 5.99 (s, 2H), 5.89-5.82 (m, 1H), 5.28 (d, J=17.6 Hz, 1H), 5.25 (d, J=10.6 Hz, 1H), 4.83 (s, 1H), 4.41-4.37 (m, 1H), 4.02 (dd, J=16.2, 5.6 Hz 1H), 3.30 (d, J=14.9 Hz, 1H), 3.01 (d, J=14.9 Hz, 1H), 1.98 (s, 3H), 1.66 (s, 3H) ppm; $^{13}$C-NMR (126 MHz, CDCl$_3$) δ 165.1 (C), 162.2 (C), 148.6 (C), 148.3 (C), 131.5 (CH), 127.6 (C), 120.7 (CH), 120.4 (C), 118.4 (CH$_2$), 108.6 (CH), 107.2 (CH), 101.6 (CH$_2$), 73.6 (C), 73.1 (C), 72.4 (CH), 45.2 (CH$_2$), 44.5 (C), 42.9 (CH$_2$), 24.8 (CH$_3$), 17.5 (CH$_3$) ppm; IR (film) ν/cm$^{-1}$ 1688, 1491, 1446, 1359, 1249, 1191, 1103, 1038, 929 cm$^{-1}$; HRMS (ESI) calcd for C$_{20}$H$_{19}$N$_3$O$_4$S$_2$Na$^+$ (M+Na) 452.0715, found 452.0719.

Rac-(3S,6S,7S,8aS)-6-(benzo[d][1,3]dioxol-5-yl)-2-cyclopropyl-3,7-dimethyl-1,4-dioxohexahydro-6H-3,8a-epidithiopyrrolo[1,2-a]pyrazine-7-carbonitrile

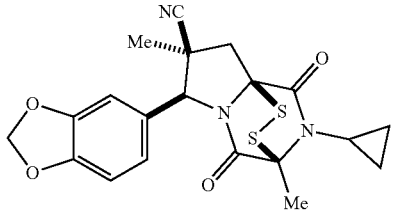

Chemical Formula: C$_{20}$H$_{19}$N$_3$O$_4$S$_2$
Exact Mass: 429.0817
Molecular Weight: 429.5090

$^1$H-NMR (500 MHz, CDCl$_3$) δ 6.87 (s, 1H), 6.84-6.81 (app. s, 2H), 5.99 (s, 2H), 4.80 (s, 1H), 3.27 (d, J=14.9 Hz, 1H), 2.93 (d, J=14.9 Hz, 1H), 2.57-2.53 (m, 1H), 2.12 (s, 3H), 1.66 (s, 3H), 1.29-1.24 (m, 1H), 1.06-0.97 (m, 2H), 0.96-0.90 (m, 1H) ppm; $^{13}$C-NMR (126 MHz, CDCl$_3$) δ 165.7 (C), 162.3 (C), 148.6 (C), 148.3 (C), 127.6 (C), 120.7 (CH), 120.4 (C), 108.6 (CH), 107.2 (CH), 101.6 (CH$_2$), 74.4 (C), 74.1 (C), 72.4 (CH), 44.5 (C), 42.9 (CH$_2$), 25.8 (CH), 24.8 (CH$_3$), 17.8 (CH$_3$), 8.2 (CH$_2$), 7.7 (CH$_2$) ppm; IR (film) ν/cm$^{-1}$ 1696, 1491, 1446, 1348, 1248, 1189, 1037, 930, 735 cm$^{-1}$; HRMS (ESI) calcd for C$_{20}$H$_{19}$N$_3$O$_4$S$_2$Na$^+$ (M+Na) 452.0715, found 452.0702.

141

Rac-(3S,6S,7S,8aS)-6-(3,4-bis(allyloxy)phenyl)-2,3,7-trimethyl-1,4-dioxohexahydro-6H-3,8a-epidithiopyrrolo[1,2-a]pyrazine-7-carbonitrile

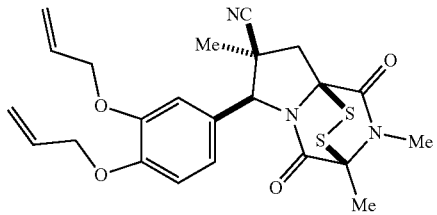

Chemical Formula: C₂₃H₂₅N₃O₄S₂
Exact Mass: 471.1286
Molecular Weight: 471.5900

$^1$H-NMR (500 MHz, CDCl₃) δ 6.95 (s, 1H), 6.92-6.88 (m, 2H), 6.11-6.03 (m, 2H), 5.45-5.38 (m, 2H), 5.29-5.24 (m, 2H), 4.87 (s, 1H), 4.63-4.60 (m, 4H), 3.31 (d, J=14.8 Hz, 1H), 3.08 (s, 3H), 2.98 (d, J=14.8 Hz, 1H), 1.95 (s, 3H), 1.66 (s, 3H) ppm; $^{13}$C-NMR (126 MHz, CDCl₃) δ165.6 (C), 162.2 (C), 149.3 (C), 148.8 (C), 133.4 (CH), 133.3 (CH), 126.5 (C), 120.3 (CH), 119.8, 117.9 (CH₂), 117.8 (CH₂), 113.7 (CH), 112.2 (CH), 73.8 (C), 73.6 (C), 72.4 (C), 70.0 (CH₂), 69.9 (CH₂), 44.5 (C), 42.8 (CH₂), 27.9 (CH₃), 25.1 (CH₃), 18.3 (CH₃) ppm; IR (film) ν/cm⁻¹ 1695, 1607, 1593, 1516, 1424, 1380, 1360, 1262, 1218, 1141, 996, 919, 731 cm⁻¹; HRMS (ESI) calcd for C₂₃H₂₅N₃O₄S₂Na⁺ (M+Na) 494.1184, found 494.1188.

Rac-(3S,6S,7S,8aS)-6-(7-methoxybenzo[d][1,3]dioxol-5-yl)-2,3,7-trimethyl-1,4-dioxohexa-hydro-6H-3,8a-epidithiopyrrolo[1,2-a]pyrazine-7-carbonitrile

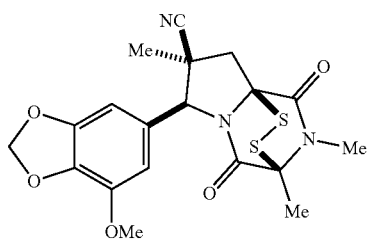

Chemical Formula: C₁₉H₁₉N₃O₅S₂
Exact Mass: 433.0766
Molecular Weight: 433.4970

$^1$H-NMR (500 MHz, CDCl₃) δ 6.60 (s, 1H), 6.58 (s, 1H), 6.00 (m, 2H), 4.84 (s, 1H), 3.89 (s, 3H), 3.31 (d, J=14.8 Hz, 1H), 3.08 (s, 3H), 2.99 (d, J=14.8 Hz, 1H), 1.95 (s, 3H), 1.67 (s, 3H) ppm; $^{13}$C-NMR (126 MHz, CDCl₃) δ 165.5 (C), 162.1 (C), 149.3 (C), 143.9 (C), 136.1 (C), 128.2 (C), 120.2 (C), 106.5 (CH), 102.0 (CH₂), 101.3 (CH), 73.7 (C), 73.6 (C), 72.5 (C), 56.7 (CH₃), 44.5 (C), 42.8 (CH₂), 27.9 (CH₃), 25.2 (CH₃), 18.2 (CH₃) ppm; IR (film) ν/cm⁻¹ 2984, 2250, 1696, 1637, 1512, 1453, 1358, 1246, 1201, 1129, 1093, 1044, 913, 731 cm⁻¹; HRMS (ESI) calcd for C₁₉H₁₉N₃O₅S₂Na⁺ (M+Na) 456.0664, found 456.0648.

142

Rac-(3S,6S,7S,8aS)-6-(2,3-dihydro-1H-inden-5-yl)-2,3,7-trimethyl-1,4-dioxohexahydro-6H-3,8a-epidithiopyrrolo[1,2-a]pyrazine-7-carbonitrile

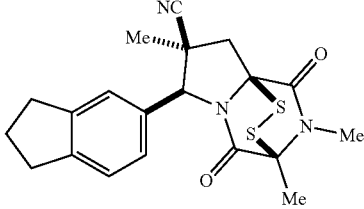

Chemical Formula: C₂₀H₂₁N₃O₂S₂
Exact Mass: 399.1075
Molecular Weight: 399.5270

$^1$H-NMR (500 MHz, CDCl₃) δ 7.26 (d, J=7.2 Hz, 1H), 7.20 (s, 1H), 7.15 (d, J=7.2 Hz, 1H), 4.87 (s, 1H), 3.30 (d, J=14.9 Hz, 1H), 3.07 (s, 3H), 3.00 (d, J=14.9 Hz, 1H), 2.94-2.89 (m, 4H), 2.08 (app. quintet, J=7.5 Hz, 2H), 1.93 (s, 3H), 1.67 (s, 3H) ppm; $^{13}$C-NMR (126 MHz, CDCl₃) δ 165.8 (C), 162.2 (C), 145.8 (C), 145.0 (C), 131.5 (C), 124.9 (CH), 124.8 (CH), 122.9 (CH), 120.5 (C), 73.6 (C), 73.4 (C), 72.8 (CH), 44.6 (C), 43.0 (CH₂), 33.0 (CH₂), 32.8 (CH₂), 27.9 (CH₃), 25.4 (CH₂), 24.8 (CH₃), 18.2 (CH₃) ppm; IR (film) ν/cm⁻¹ 2941, 2251, 1696, 1440, 1359, 1254, 1202, 1145, 1112, 1067, 1030, 911, 731 cm⁻¹; HRMS (ESI) calcd for C₂₀H₂₁N₃O₂S₂Na⁺ (M+Na) 422.0973, found 422.0965.

Rac-(3S,6S,7S,8aS)-2,3,7-trimethyl-1,4-dioxo-6-(1-(phenylsulfonyl)-1H-indol-3-yl)hexahydro-6H-3,8a-epidithiopyrrolo[1,2-a]pyrazine-7-carbonitrile

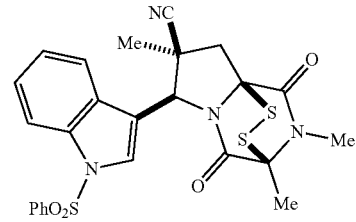

Chemical Formula: C₂₅H₂₂N₄O₄S₃
Exact Mass: 538.0803
Molecular Weight: 538.6550

$^1$H-NMR (500 MHz, CDCl₃) δ 7.96 (d, J=8.4 Hz, 1H), 7.86-7.84 (m, 3H), 7.55 (d, J=8.0 Hz, 1H), 7.52 (d, J=8.0 Hz, 1H), 7.42 (t, J=7.8 Hz, 2H), 7.34 (t, J=7.7 Hz, 1H), 7.28 (d, J=7.8 Hz, 1H), 5.29 (s, 1H), 3.43 (d, J=14.7 Hz, 1H), 3.10 (s, 3H), 3.05 (d, J=14.7 Hz, 1H), 1.96 (s, 3H), 1.70 (s, 3H) ppm; $^{13}$C-NMR (126 MHz, CDCl₃) δ 165.5 (C), 162.0 (C), 137.8 (C), 135.3 (C), 134.2 (CH), 129.4 (CH), 128.9 (C), 127.1 (CH), 125.8 (CH), 125.5 (CH), 123.8 (CH), 120.1 (C), 119.5 (CH), 116.6 (C), 114.1 (CH), 73.6 (C), 73.3 (C), 64.2 (CH), 43.8 (C), 42.8 (CH₂), 28.0 (CH₃), 25.2 (CH₃), 18.3 (CH₃) ppm; IR (film) ν/cm⁻¹ 2360, 1696, 1447, 1361, 1214, 1176, 1120, 1095, 974, 747, 725, 684 cm⁻¹; HRMS (ESI) calcd for C₂₅H₂₂N₄O₄S₃Na⁺ (M+Na) 561.0701, found 561.0703.

Example 6

Separation of Enantiomers of ETP Products

Isolation of (3S,6S,7S,8aS)- and (3R,6R,7R,8aR)-6-(benzo[d][1,3]dioxol-5-yl)-2,3,7-trimethyl-1,4-dioxohexahydro-6H-3,8a-epidithiopyrrolo[1,2-a]pyrazine-7-carbonitriles

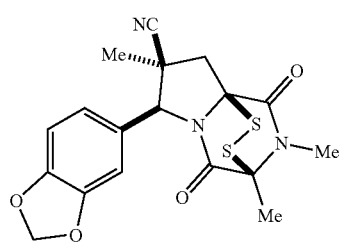

LEO-13-1721

Chemical Formula: $C_{18}H_{17}N_3O_4S_2$
Exact Mass: 403.0660
Molecular Weight: 403.4710

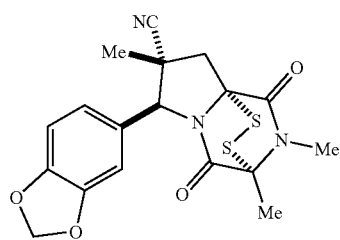

LEO-13-1722

Chemical Formula: $C_{18}H_{17}N_3O_4S_2$
Exact Mass: 403.0660
Molecular Weight: 403.4710

The two enantiomers were separated by preparative chiral HPLC (stationary phase: CHIRALPAK IA (250×50 mm i.d., 5 micron), mobile phase: reagent alcohol 100%), flow rate 2.5 mL/min). The enantiomeric excess was determined by means of analytical chiral HPLC (stationary phase CHIRALPAK IA-3 (50×4.6 mm i.d., 3 micron), mobile phase: reagent alcohol 100%, flow rate 1 mL/min, 254 nm): (3S,6S,7S,8aS)-enantiomer: $t_{ret}$=1.40 min; (3R,6R,7R,8aR)-enantiomer: $t_{ret}$=2.11 min.

Figure 36:
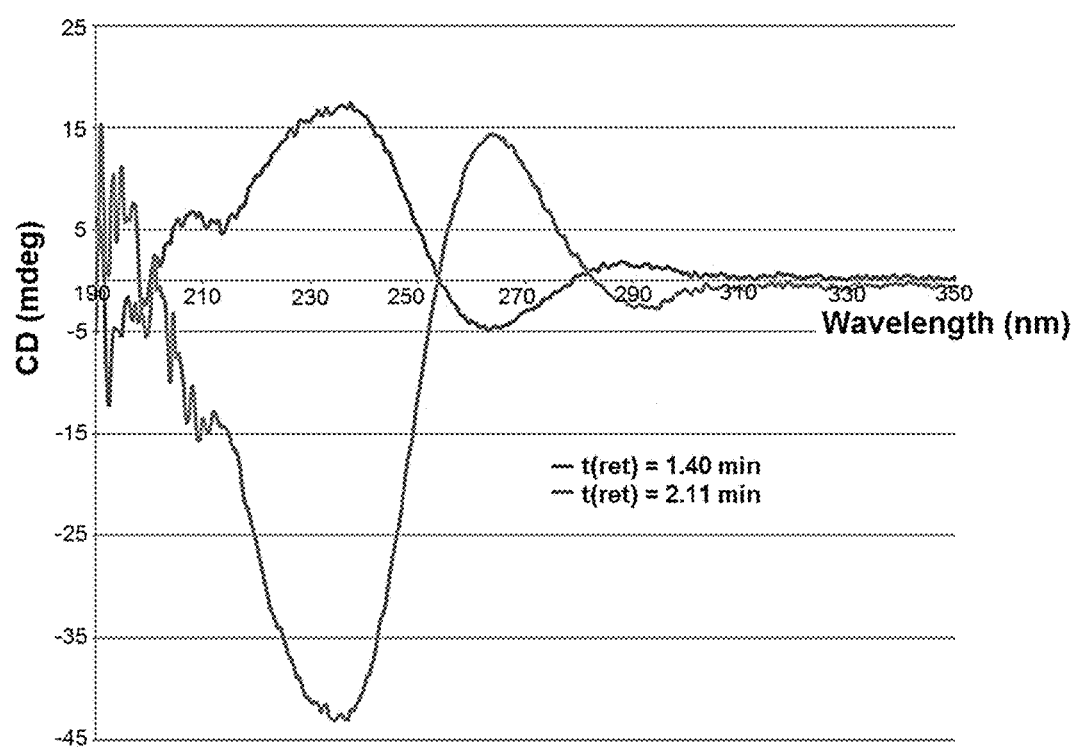
FIG. 36: CD Data for the two enantiomers of ETP69: (3S,6S,7S,8aS): $t_{ret}$=1.40 min (red); (3R,6R,7R,8aR): $t_{ret}$=2.11 min (blue) in EtOH (c≈$10^{-4}$ M). See text for details.

Absolute configuration was assigned on the basis of CD data (FIG. 36) and existing precedent [Carmack, M.; Neubert, L. A. *J. Am. Chem. Soc.* 1967, 89, 7134-7136. Hauser, D.; Weber, H. P.; Sigg, H. *P. Helv. Chim. Acta* 1970, 53, 1061-1073. Minato, H.; Matsumoto, M.; Katayama, T. *J. Chem. Soc. D.* 1971, 44-45. Nagarajan, R.; Woody, R. W. *J. Am. Chem. Soc.* 1973, 95, 7212-7222. Woody, R. W. *Tetrahedron* 1973, 29, 1273-1283].

Example 7

Cell Culture

HT1080, 293T cells and the pancreatic cancer cell lines Panel, BxPC3, SU.86.86 were obtained from ATCC (Manassas, Va.). Panel, HT1080 and 293T cells were maintained in DMEM medium (Mediatech, Manassas, Va.) supplemented with 10% heat inactivated FBS (Gemini Bio-products, West Sacramento, Calif.). BxPC3 and SU.86.86 cells were maintained in RPMI-1640 medium (Mediatech) supplemented with 10% heat inactivated FBS.

Mts Assay:

Panel, BxPC3, or SU.86.86 cells were seeded in a 96-well plate at a density of 7500 cells/well prior to treatment with increasing amounts of ETP69 or DMSO vehicle control. Forty-eight hours post treatment cells were incubated with the MTS substrate (CellTiter 96 AQueous One Solution Cell Proliferation Assay, Promega, Madison, Wis.) according to the manufacturer's instructions. The absorbance was measured at 490 nm using a 96-well plate reader (Synergy 4, Biotek), and the data were normalized to the absorbance of DMSO-treated cells. $IC_{50}$ values were determined using GraphPad Prism's non-linear regression function. See FIGS. 11, 21, 22A, 22B, 23, 24A, 24B, 24C, 25A and 25B.

Figure 26:
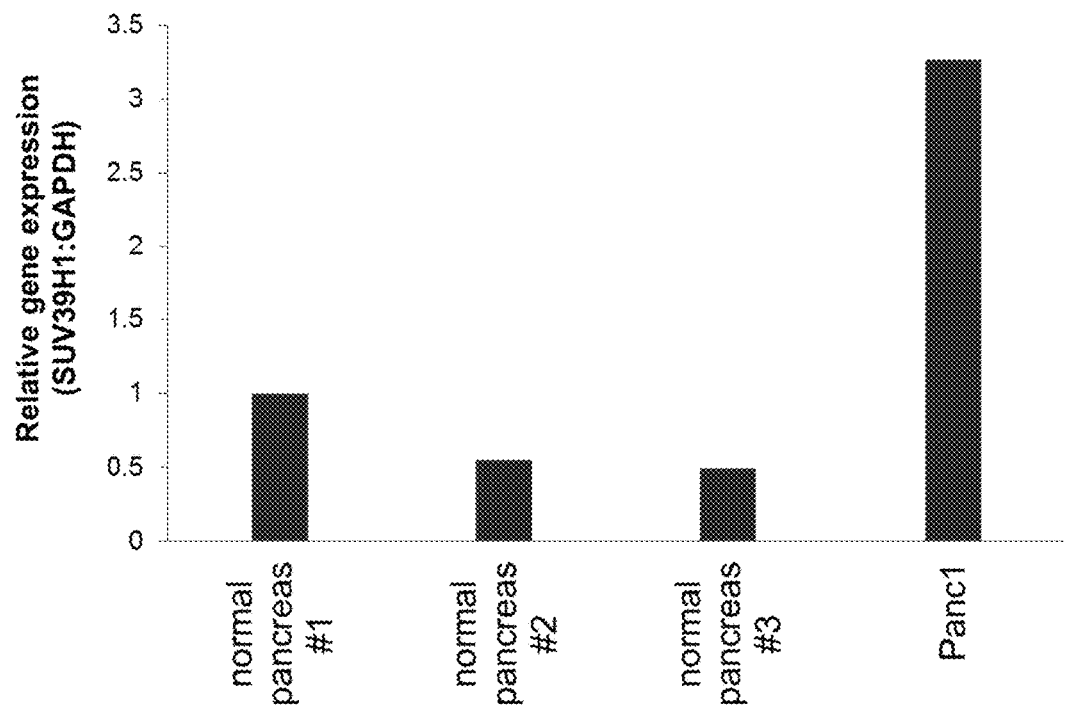
FIG. 26: SUV39H1 expression levels in normal pancreas and Panc1 cancer cells: normal pancrease cells express less SUV39H1 than the Panc1 cancer cell line.
Figure 27:
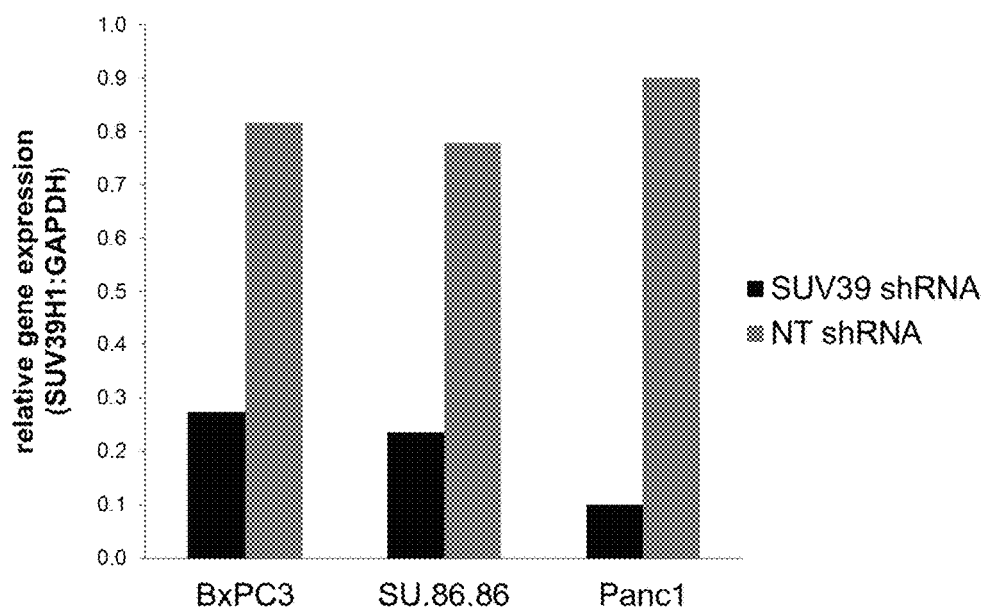
FIG. 27: Stable SUV39H1 Knockdown in Pancreatic Cancer Cells: SUV39H1 expression levels of BxPC3, SU.86.86 and Panc1 cells expressing SUV39H1 shRNA are reduced by 73%, 77% and 90%, respectively, compared to unmodified cells. Cell lines expressing a non-targeting control shRNA (NT) were generated as controls.
Figure 28:
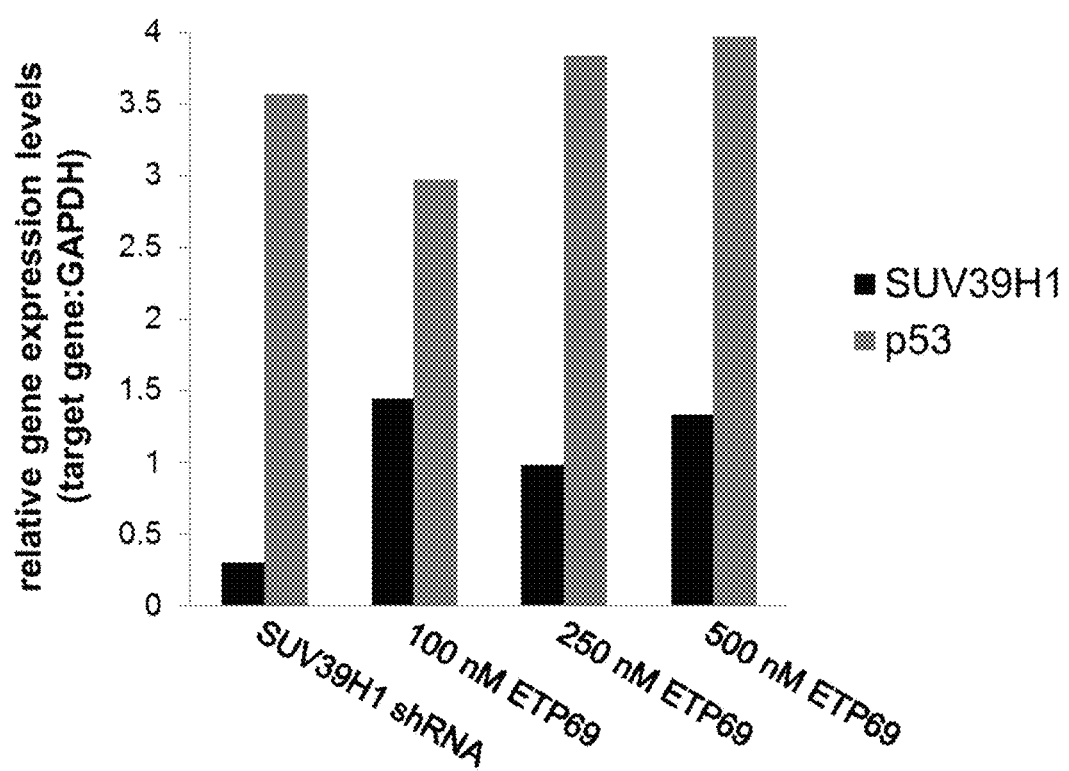
FIG. 28: p53 Up-Regulation Following SUV39H1 Knockdown or Treatment with ETP69 in Panc1 cells: Treatment with increasing concentrations (100 nM-500 nM) of ETP69 or shRNA-mediated knockdown of SUV39H1 leads to ≥3-fold up-regulation of p53 in Panc1 cells.

Lentiviral Vector Production:

293T cells were plated at a density of $4 \times 10^6$ cells per 10-cm culture dish. Cells were co-transfected by calcium phosphate co-precipitation with either 20 al of pPACK packaging plasmid mix (SBI, Mountain View, Calif.) and 15 μg of pLKO.1-SUV39H1 shRNA (TRCN0000275322, Sigma St. Louis, Mo.) or pLKO.1-non-silencing shRNA (Sigma). The culture medium was replaced with fresh medium after 6 h. Supernatant was collected 24 h and 48 h after transfection. To determine the viral titers, $10^5$ HT1080 cells were seeded in a six-well plate and transduced with various dilutions of the vector in the presence of 4 μg of Polybrene/ml (Sigma, St. Louis, Mo.). The culture medium was replaced 48 h later with fresh medium containing puromycin (Sigma) at a concentration of 1.5 μg/ml. Puromycin-resistant colonies were counted 10 days after transduction. The pancreatic cancer cells (Panc1, BxPC3 and SU.86.86) were transduced with the viral vectors at a MOI of 0.5. Transduced cells were selected with puromycin (1.5 μg/ml for BxPC3 and SU.86.86; 2 μg/ml for Panc1). See FIGS. 24-26.

QPCR:

Total RNA was isolated from cells using the RNeasy kit (Qiagen). The Tetro cDNA kit (Bioline) and SensiFast Probe kit (Bioline) were used to reverse-transcribe and amplify total RNA according to the manufacturer's protocol. The ProbeFinder software (Roche Applied Science) was used to design the primer sets for SUV39H1, p53 and GAPDH and to select the respective probes from the Universal ProbeLibrary (Roche Applied Science). Probe #13 and the following primers were used for the SUV39H1 assay: 5' gtcatggag-tacgtgggagag (SEQ ID NO: 1) and 5' cctgacggtcgtagatctgg (SEQ ID NO:2). Probe #21 and the following primers were used for the p53 assay: 5' tagtgtggtggtgccctatg (SEQ ID NO:3) and 5'cacatgtagttgtagtggatggtg (SEQ ID NO:4). Probe #60 and the following primers were used for the GAPDH assay: 5' agccacatcgctcagacac (SEQ ID NO:5) and 5' gcccaatacgaccaaatcc (SEQ ID NO:6). All samples were run in triplicates. Amplifications were performed on a Bio-Rad CFX96 Touch Multiple-Color Real-time PCR Detection System. The data were normalized to the GAPDH expression and the relative expression levels were calculated using the $2^{-\Delta\Delta Ct}$ method.

Figure 29:
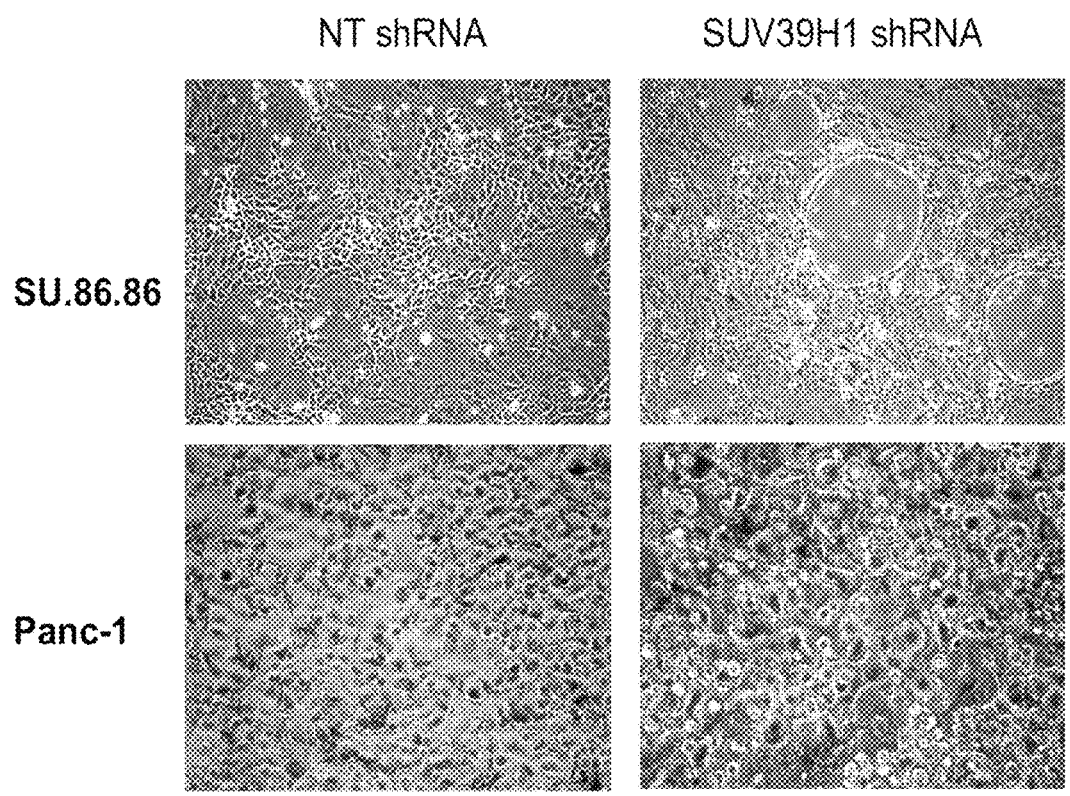
FIG. 29: SUV39H1 knockdown increases senescence in pancreatic cancer cells Senescence-associated b-galactosidase activity: SU.86.86 and Panc-1 cells expressing SUV39H1shRNA show increased senescence-associated beta-galactosidase activity, as evidenced by the stain. No senescence-associated beta-galactosidase activity was detected in the control cells expressing a non-targeting (NT) shRNA.
Figure 30:
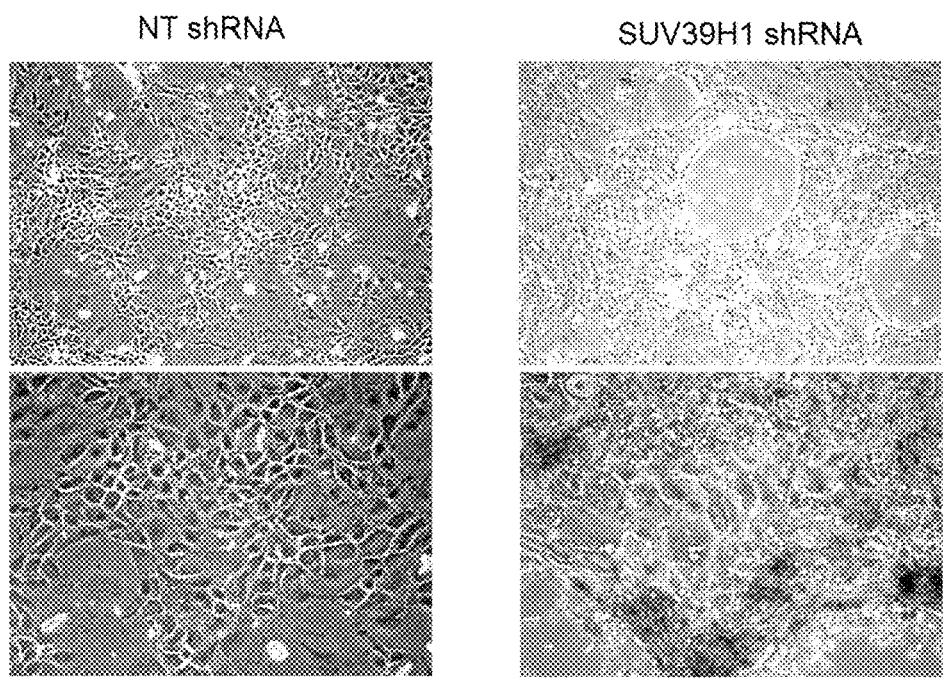
FIG. 30: SUV39H1 Knockdown Increases Senescence in SU.86.86: SU.86.86 cells expressing SUV39H1shRNA show increased senescence-associated beta-galactosidase activity, as evidenced by the blue stain. No senescence-associated beta-galactosidase activity was detected in the control cells expressing a non-targeting (NT) shRNA.
Figure 31:
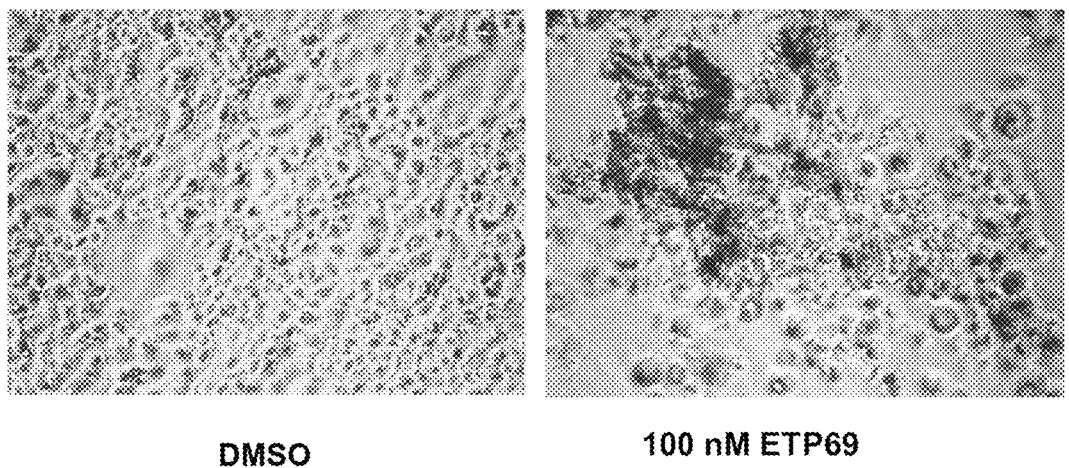
FIG. 31: ETP69 induces senescence in Panc1 cancer cells in senescence-associate beta-galactosidase activity: Panc1 pancreatic cancer cells treated with ETP69 for 5 days show increased senescence-associated beta-galactosidase activity (blue stain) compared to Panc1 cells treated with DMSO (vehicle control).

Senescence Assay:

Panc cells were seeded at a density of $3 \times 10^4$ cells per well in a 24-well plate. The cells were then treated with 100 nM ETP69 or 0.3% DMSO (vehicle control). Panc-1 and SU.86.86 cells expressing SUV39H1 shRNA or a non-targeting (NT) control shRNA were also seeded in 24-well plates at a density of $3 \times 10^4$ cells/well and $5 \times 10^4$ cells/well, respectively. After 5 days, cells were washed with PBS, fixed with 3% formaldehyde/PBS, and stained over night at 37° C. with a freshly prepared staining solution (1 mg/ml 5-bromo-4-chloro-3-indolyl b-D-galactoside in 40 mM citric acid/sodium phosphate, pH 6.0, 5 mM potassium ferrocyanide, 5 mM potassium ferricyanide, 150 mM NaCl, 2 mM $MgCl_2$). The blue stain indicates senescence-associated β-galactosidase activity. Photographs were taken with a 10× or a 20× objective under brightfield illumination using an INFINITY2 digital CCD camera (Lumenera, Canada) mounted on a Nikon Eclipse TS100 inverted microscope. See FIGS. 29-31.

Figure 32:
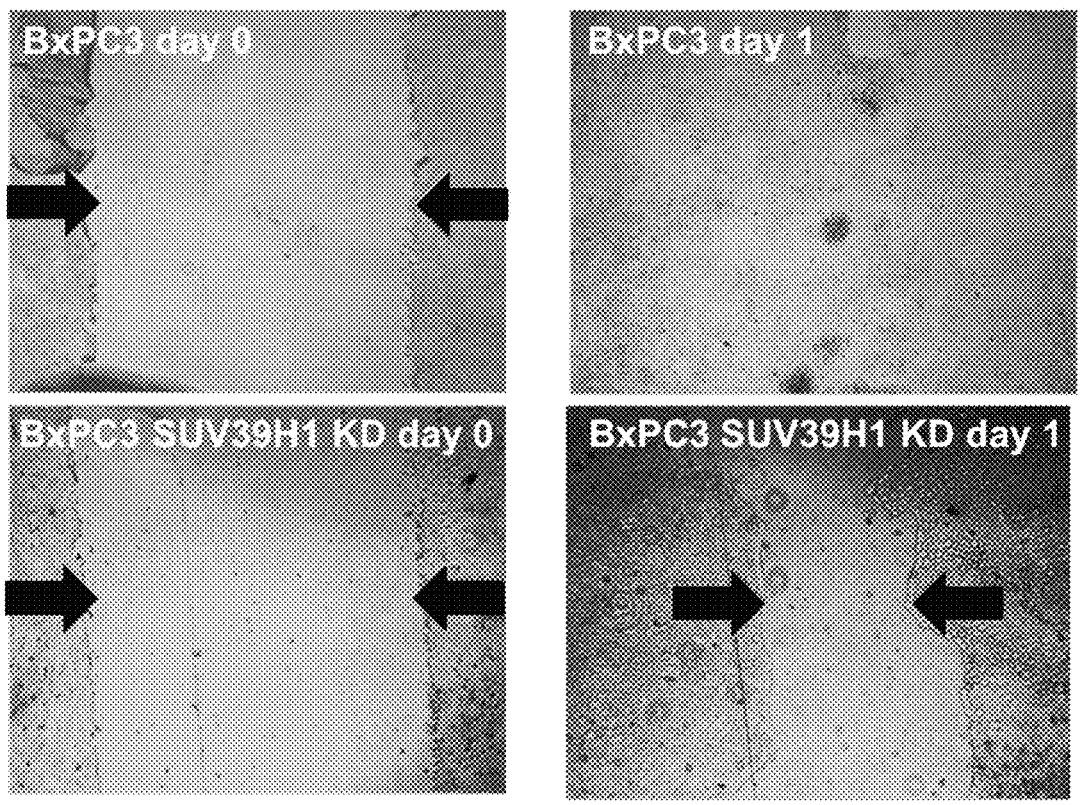
FIG. 32: SUV31H1 knockdown assay decreases cell mobility in wound healing assay. BxPC3 cells expressing (shRNA-mediated) low levels of SUV39H1 migrate into denuded areas (between the arrows) in cell monolayers at a lower rate than unmodified BxPC3 cells, failing to close the "wound" within 24 h.
Figure 33:
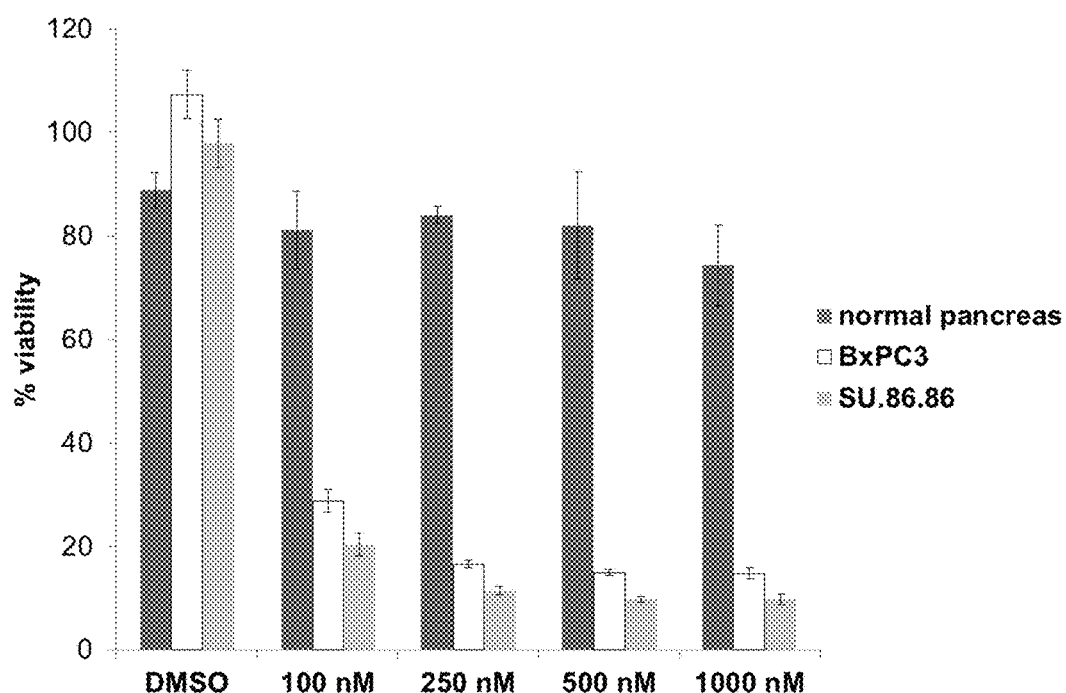
FIG. 33: Viability of normal pancreatic epithelial cells after treatment with ETP69: treatment of normal pancreatic epithelial cells with ETP69 at doses from 100 nM to 1000 nM shows little destruction of normal pancreatic cells but significant killing of cells from BxPC3 and SU86.86 pancreatic cancer cell lines.
Figure 34:
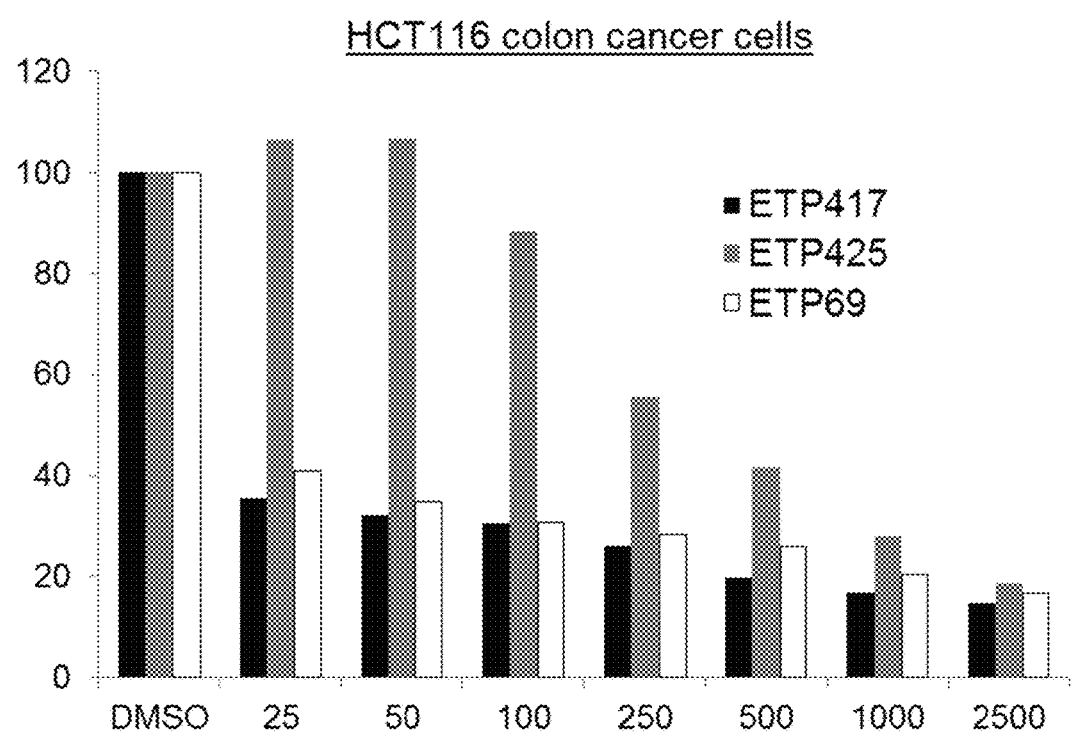
FIG. 34: Effect of racemic and enantiomers on colon cancer cells: ETP417 displays greater viability inhibition on HCT116 colon cancer cells than ETP422 and the ETP69.
Figure 35:
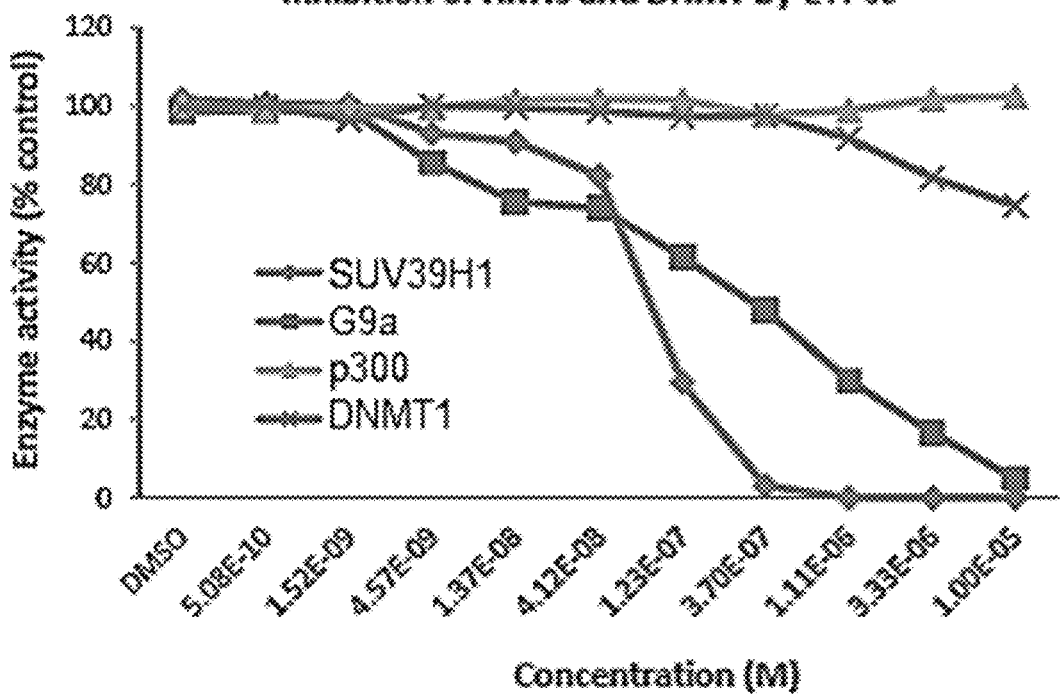
FIG. 35 Inhibition of various HMTs, histone acetyltransferases (HAT) and DNMTs: ETP69 shows specific inhibition of HMT SUV31H1 and G9a, but not HAT p300 and DNMT1.

Migration ("wound healing") assay:

Panel, BxPC3 and SU.86.86 pancreatic cancer cells expressing SUV39H1 shRNA or a non-targeting (NT) control shRNA were grown in 6-well plates. Upon reaching confluence the cell monolayers were scratched with a pipette tip to create uniform "wounds". Cells were then allowed to migrate into the denuded area. Photographs were taken with a 10× objective under brightfield illumination at 0 h and 24 h using an INFINITY2 digital CCD camera (Lumenera, Canada) mounted on a Nikon Eclipse TS100 inverted microscope. See FIG. 32.

Example 8

FLT3 Inhibition Studies

The kinase assays in vitro were performed with recombinant FLT3 protein using the HotSpot protocol (Reaction Biology Corp, Malvern, Pa.). Briefly, proteins, freshly prepared substrates and $^{33}$P-ATP (specific activity 0.01 µCi/µl final) were mixed in reaction buffer (20 mM HEPES pH 7.5, 10 mM $MgCl_2$, 1 mM EGTA, 0.02% Brij35, 0.02 mg/ml BSA, 0.1 mM $Na_3VO_4$, 2 mM DTT) in the presence of DMSO as control or S enantiomer of ETP69. The mixtures were reacted for 120 min at room temperature. Samples were transferred onto P81 ion exchange paper and filters were extensively washed with 0.75% phosphoric acid. The radioactivities were monitored.

Western blot analyses were performed with specific antibodies. Briefly, human A2058 melanoma, DU145 prostate, A549 non-small lung and SKOV3 ovarian cancer cells were treated with ETP69. Whole-cell lysates (40 □g) or histone extracts (10 □g) were resolved by SDS-PAGE. Primary specific antibodies to histone H3 and histone H3 (trimethyl K9) were incubated in PBS (pH 7.5) with 0.1% (v/v) Tween-20 and 5% (w/v) BSA with gentle agitation overnight at 4° C. Other specific antibodies were diluted in PBS (pH 7.5) with 5% (w/v) nonfat milk and 0.1% (v/v) Tween-20 over night at 4° C. Horseradish peroxidase-conjugated secondary antibodies were incubated in PBS (pH 7.5) with 5% (w/v) nonfat milk and 0.1% (v/v) Tween-20 for 1 h at room temperature. Positive immuno-reactive proteins were detected using the ECL system (Pierce, Rockford, Ill.).

For histone methyltranferase (HMT), DNA methyltransferase (DNMT) and Histone acetyltransferase (HAT) assays in vitro, human recombinant HMT, DNMT and HAT proteins were mixed with substrates in the reaction buffer (50 mM Tris-HCl (pH 8.5), 5 mM MgCl2, 50 mM NaCl, 1 mM DTT, 1 mM PMSF, 1% DMSO), including histone $H_3$, histone $H_4$, nucleosomes, or core histone. Racemic ETP69, S enantiomer or DMSO as a vehicle control was preincubated in the mixture. Next, for HMTs and DNMT assays, 1 mM of $^3$H-SAM was added to the mixture for the reaction initiation and conversion of $^3$H-SAM+histone L-lysine to SAH+histone $N^6$-[methyl-$^3$H]-L-lysine was monitored with miniatured radioligand-filter binding platform. For p300 HAT assays, the conversion of acetyl-$^3$H-acetyl coenzyme A to coenzyme A was monitored. The reactions were carried out at 30° C. $IC_{50}$ values were determined using Excel and GraphPad Prism software.

In Vivo Xenograft Procedures for Lung Cancer, Melanoma, and Ovarian Cancer (See FIGS. 15A, 15B, 16A, 16B, 17A, 17B, 18A and 18B):

Human A2058 melanoma cells ($3\times10^6$) were resuspended in serum-free RPMI1640 medium and subcutaneously injected into the flank of 5-6 weeks old Athymic female nude mouse (NCI). When palpable tumor sizes reached at approximately 100 $mm^3$, mice were divided into two groups (vehicle=5, treatment=5). Then, ETP69 was administered with intraperitoneal (IP) injection at 20 mg/kg with vehicle (10% DMSO+0.5% Teen 20+89.5% saline), once daily for 13 days. Tumor volumes were calculated by the formula $1/2a\times b^2$, where a is the long diameter, and b is the short diameter. Tumor volumes correlate with tumor weights. The statistical significance of group differences was analyzed using a Student's t-test with the two-tailed distribution. P values less than 0.05 were considered statistically significant.

Human A549 non-small lung cancer cells ($5\times10^6$) were resuspended in serum-free DMEM medium and Matrigel (ration of 1:1) and subcutaneously injected into the flank of 5-6 weeks old female NOD/SCID/IL-2rg(ko)(NSG). When palpable tumor sizes reached at approximately 50 $mm^3$, mice were divided into two groups (vehicle=10, treatment=10). Then, ETP69 was orally administered at 10 mg/kg with vehicle (10% DMSO+30% Solutol+60% saline), once daily for 31 days. Tumor volumes were calculated by the formula $1/2a\times b^2$, where a is the long diameter, and b is the short diameter. Tumor volumes correlate with tumor weights. The statistical significance of group differences was analyzed using a Student's t-test with the two-tailed distribution. P values less than 0.05 were considered statistically significant.

Human MV4-11 acute myeloid leukemia (AML) cancer cells ($5\times10^6$) that have FLT-ITD mutations were resuspended in serum-free RPMI1640 medium and Matrigel (ration of 1:1) and subcutaneously injected into the flank of 5-6 weeks old female NOD/SCID/IL-2rg(ko)(NSG). When palpable tumor sizes reached at approximately 50 $mm^3$, mice were divided into three groups (vehicle=9, 5 mg/kg dose group=8, 10 dose mg/kg group=8). Then, S enantiomer was orally administered at 5 mg/kg or 10 mg/kg with vehicle (10% DMSO+30% Solutol+60% saline), once daily for 20 days. Tumor volumes were calculated by the formula $1/2a\times b^2$, where a is the long diameter, and b is the short diameter. Tumor volumes correlate with tumor weights. The statistical significance of group differences was analyzed using a Student's t-test with the two-tailed distribution. P values less than 0.05 were considered statistically significant.

Human SKOV3 cancer cells ($4\times10^6$) were resuspended in serum-free McCoy's medium and Matrigel (ration of 1:1) and subcutaneously injected into the flank of 5-6 weeks old female NOD/SCID/IL-2rg(ko)(NSG). When palpable tumor sizes reached at approximately 50 $mm^3$, mice were divided into two groups (vehicle=9, treatment=9). Then, ETP69 was administered with IP injection at 2.5 mg/kg with vehicle (5% DMSO+15% Solutol+80% $H_2O$), once daily for 18 days. Tumor volumes were calculated by the formula $1/2a\times b^2$, where a is the long diameter, and b is the short diameter. Tumor volumes correlate with tumor weights. The statistical significance of group differences was analyzed using a Student's t-test with the two-tailed distribution. P values less than 0.05 were considered statistically significant.

Cell Testing Assays with ETP Derivatives in Combination with DNMT Inhibitors and Multi-Kinase Inhibitors (See FIGS. 12A-12D, 13A-13C and 14A-14C):

MTS assays were performed for cell viability for combination study with ETP69 plus DNMT inhibitors or mutikinase inhibitor. Human SKOV3 ovarian and A549 non-small cancer cells were seeded in 96-well plates (5000/well), incubated overnight at 37° C. in 5% $CO_2$, and exposed to ETP69 plus azacitidine, decitabine or sorafenib for 48. Dimethyl sulfoxide (DMSO) was used as the vehicle control. Viable cell numbers were determined by tetrazolium conversion to its formazan dye and absorbance was measured at 490 nm using an automated ELISA plate reader. Each experiment was performed in quadruplicate.

Figure 8:
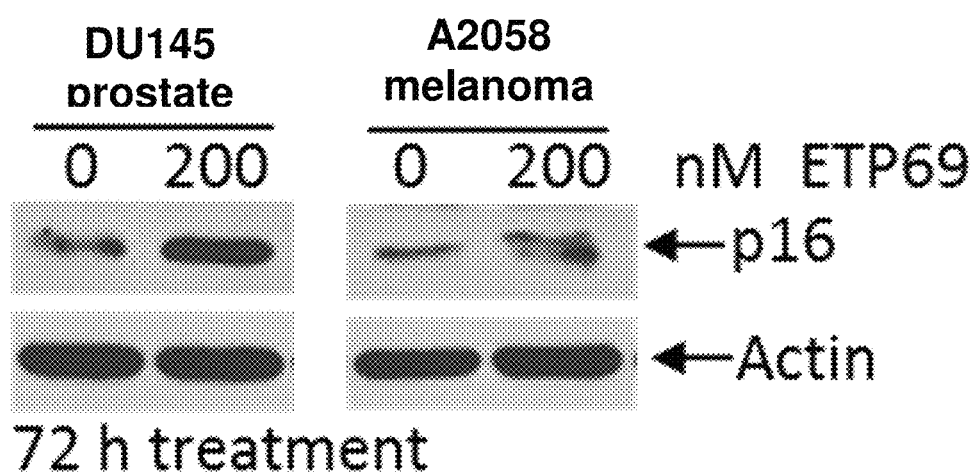
FIG. 8: ETP derivatives induce p16 tumor suppressor. ETP69 induces p16 tumor suppressor in DU145 prostate cancer cells and A2058 melanoma cells. *SKOV3 ovarian cancer cells and A549 non-small cell lung cancer cells are p16-null.
Figure 9:
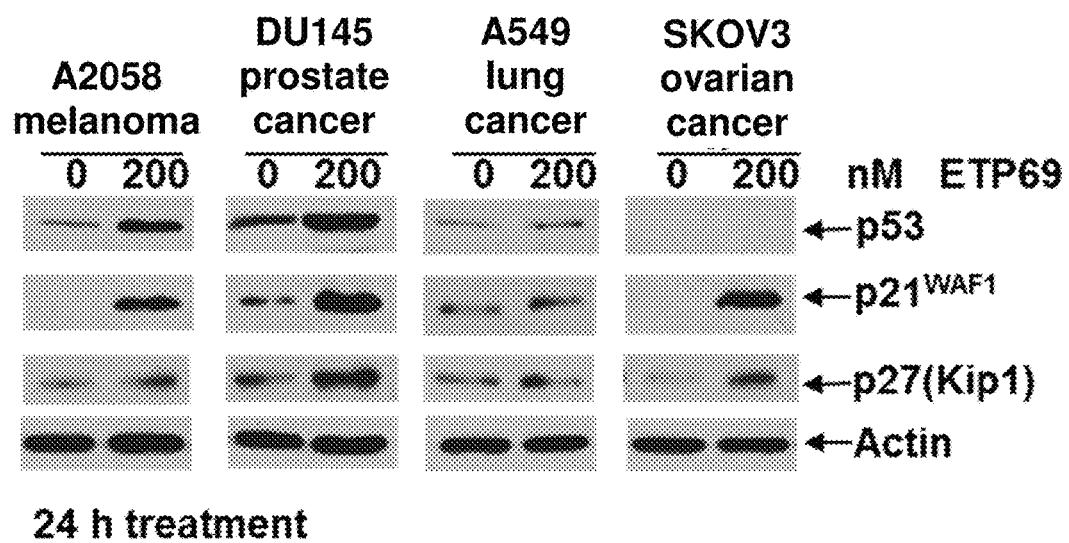
FIG. 9: ETP derivatives induce p53 tumor suppressor, p21WAF1 cyclin-dependent kinase inhibitor 1 and Cyclin-dependent kinase inhibitor 1B p27(Kip1): ETP69 induces p53, p21WAF1 and p27(Kip1) in A2058 melanoma cells, DU145 prostate cancer cells, A549 lung cancer cells, and SKOV3 ovarian cancer cells. *SKOV3 cells do not express p53 protein.
Figures 10, 11:
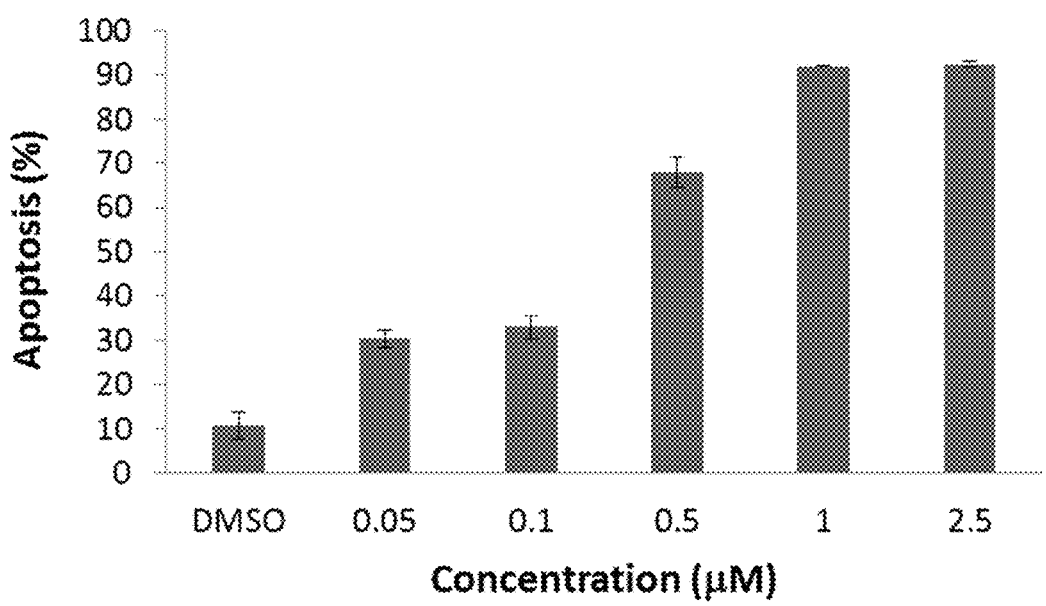
FIG. 10: FLT3 assays with ETP derivative ETP69: Fms-like tyrosine kinase 3 (FLT3) expressed in AMLs is not directly inhibited by ETP69 (S) enantiomer showing antitumor activities from ETP derivatives is not a result of FLT3 inhibition. MV4-11 and MOLM-13 AML cells have internal tandem duplications of FLT3 (FLT-ITD)—these mutations result in a low outcome with a higher relapse rate.
FIG. 11: Effect of ETP69 on SKOV3 ovarian cancer cells: ETP69 induces apoptosis of SKOV3 ovarian cancer cells.
Figure 12A:
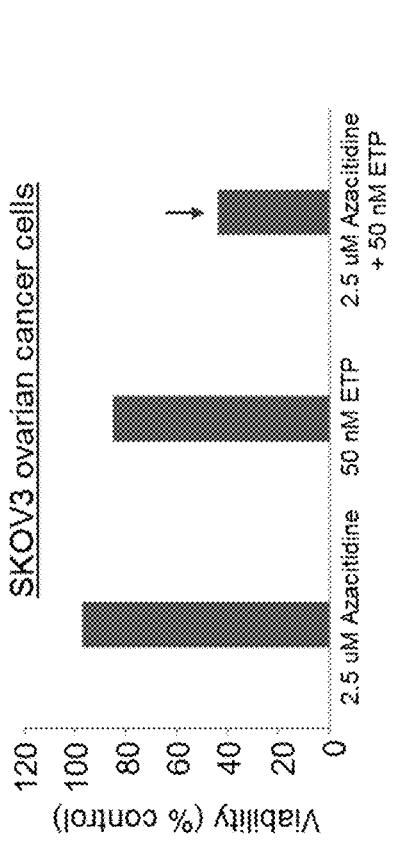
FIGS. 12A-12D: Synergystic effect of ETP and epigenetic inhibitors. ETP69 and azacitidine exhibit a greater effect on reducing viabilities of SKOV3 ovarian cells than when administered alone.
Figure 12B:
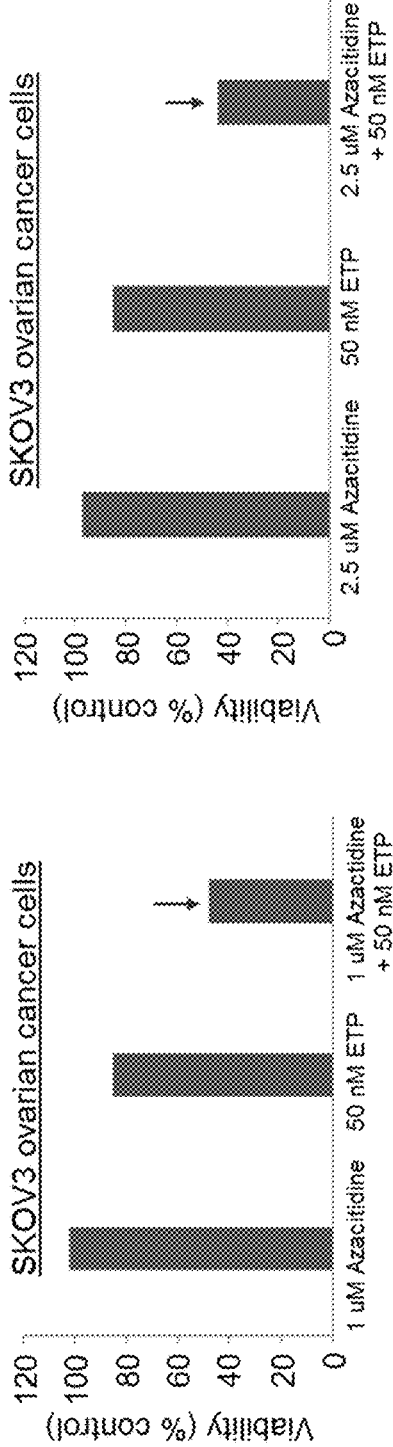
Figure 12C:
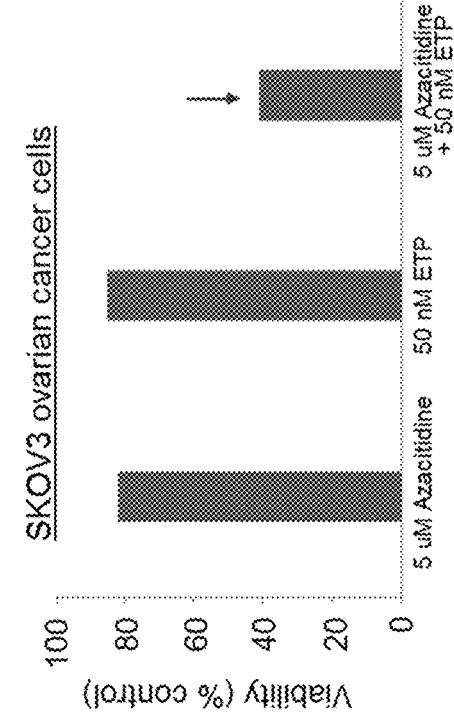
Figure 12D:
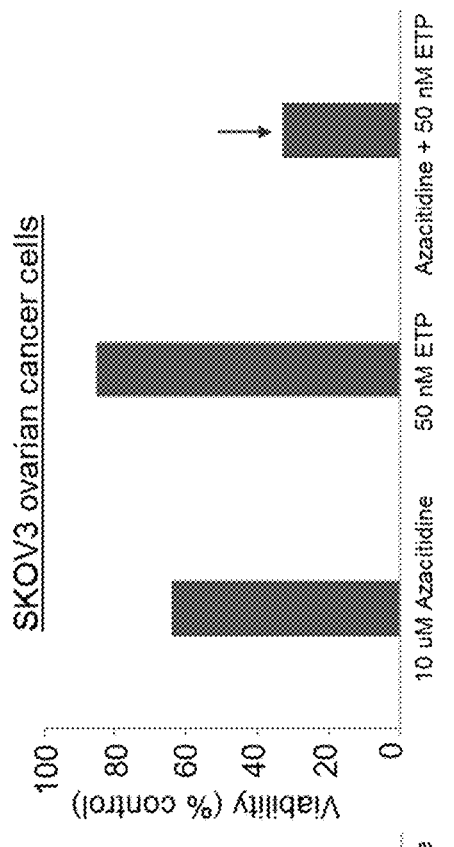
Figure 13A:
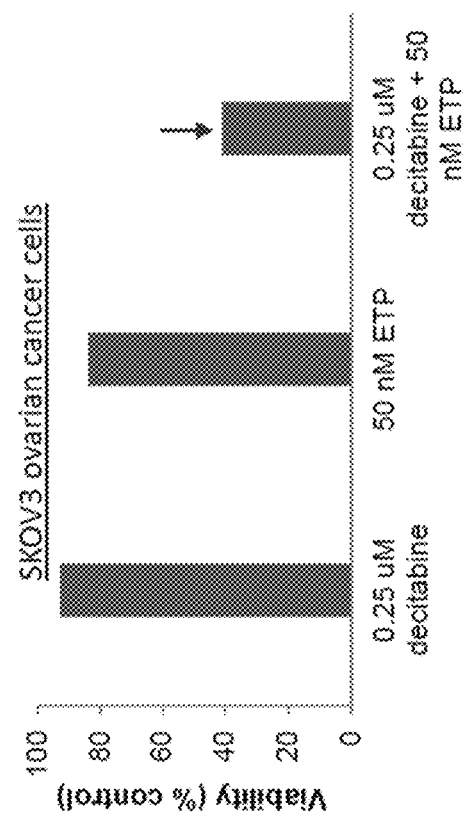
FIGS. 13A-13C: Synergystic effect of ETP and epigenetic inhibitors. ETP69 and decitabine exhibit a greater effect on reducing viabilities of SKOV3 ovarian cells than when administered alone.
Figure 13B:
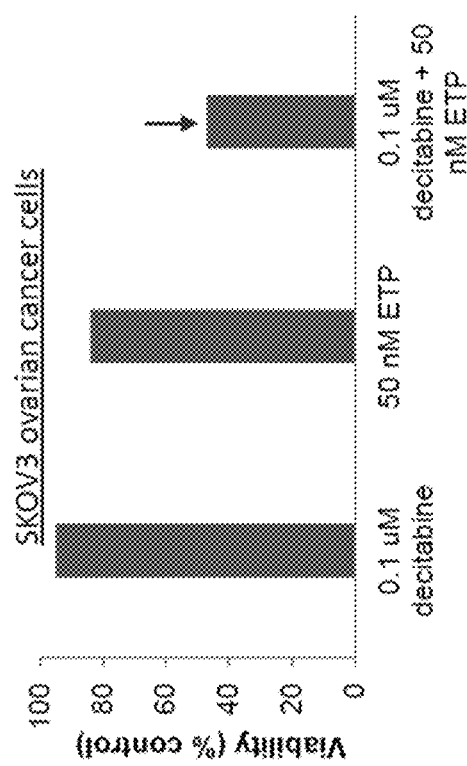
Figure 13C:
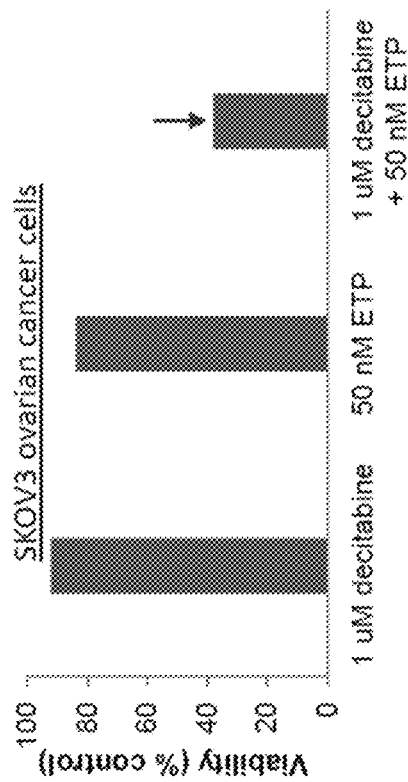
Figure 15A:
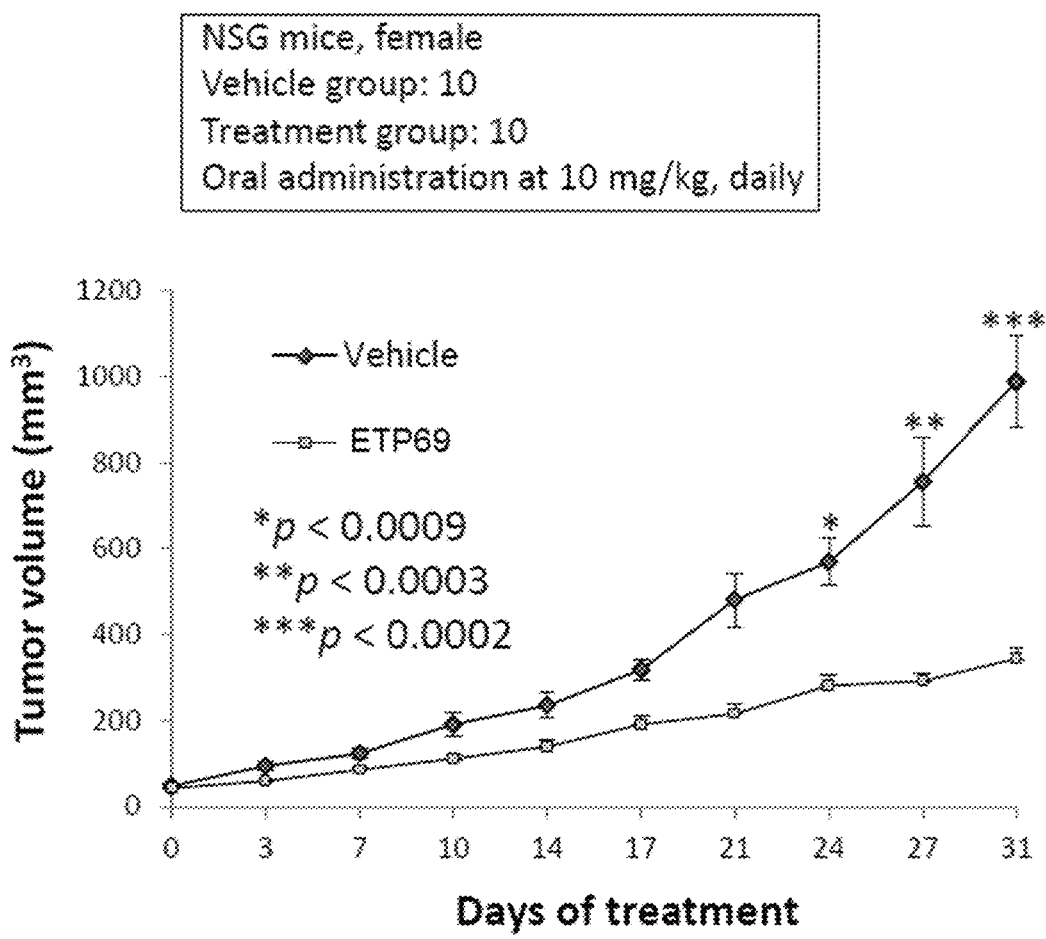
FIGS. 15A-15B: Efficacy of ETP69 on A549 lung cancer SQ xenografts.
Figure 15B:
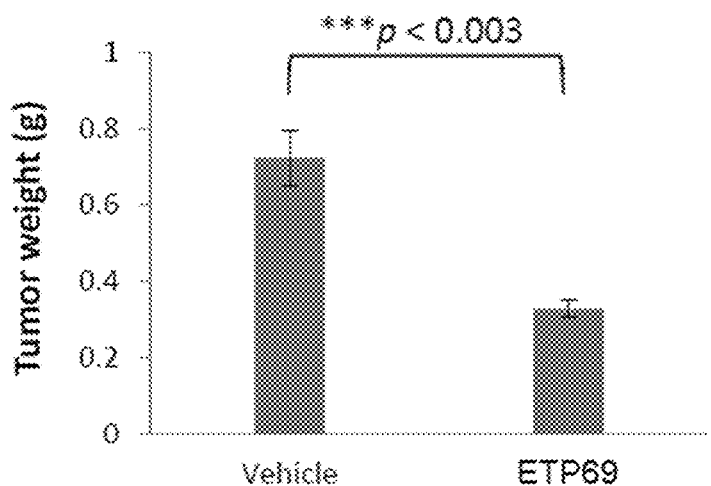
Figure 16A:
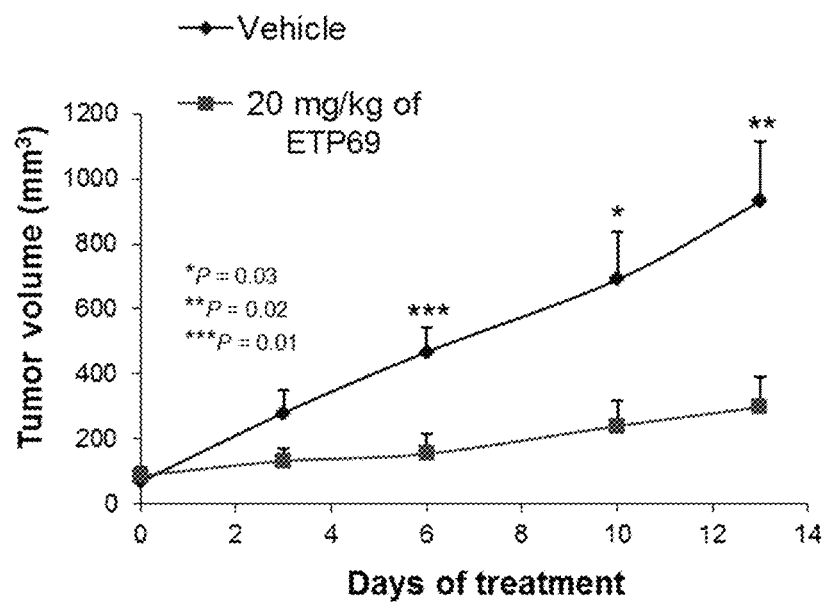
FIGS. 16A-16B: Efficacy of ETP69 on A2058 melanoma SQ xenografts.
Figure 16B:
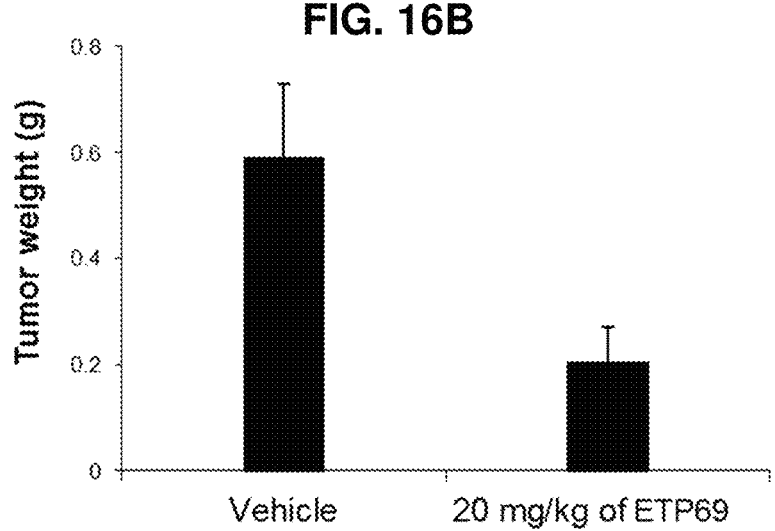
Figure 17A:
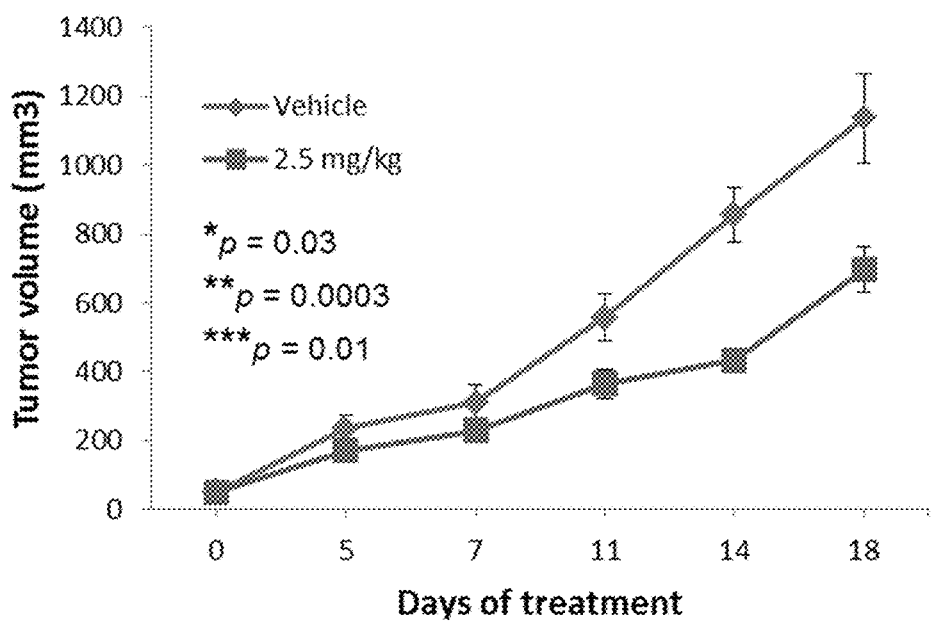
FIGS. 17A-17B: Efficacy of ETP69 on SKOV3 xenografts. Treatment with ETP69 results in decreased tumor volume and tumor weight of mice (FIG. 17A) with no observable toxicity symptoms (FIG. 17B).
Figure 17B:
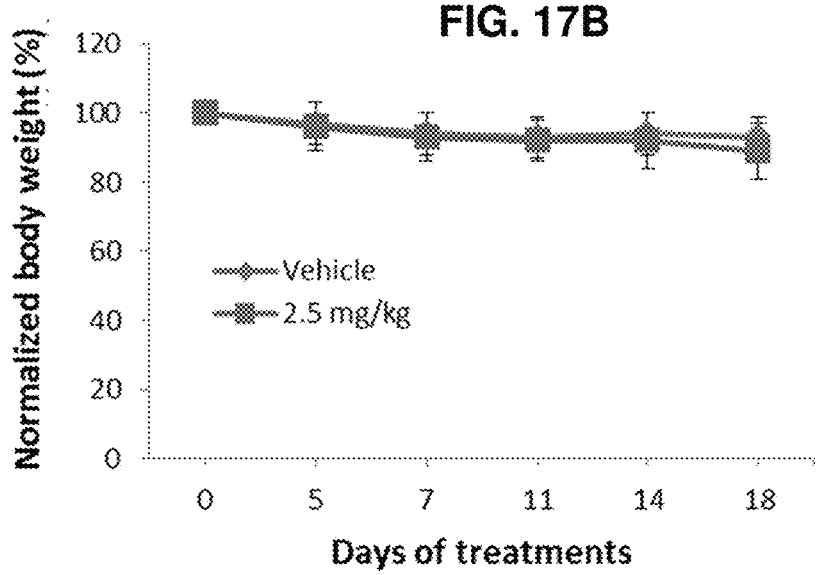
Figure 18A:
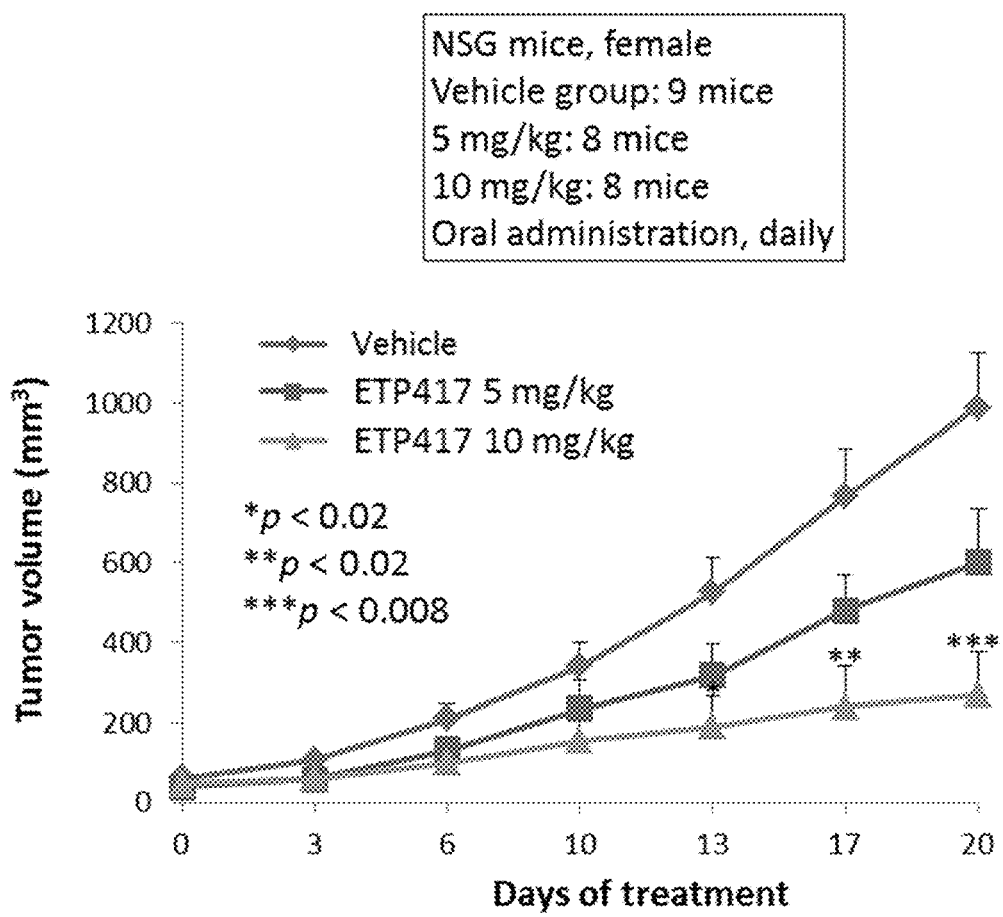
FIGS. 18A-18B: Efficacy of ETP417 on MV4-11 AML SQ xenografts: Treatment with ETP417 results in decreased tumor volume and tumor weight of mice (FIG. 18A) with no observable toxicity symptoms (FIG. 18B).
Figure 18B:
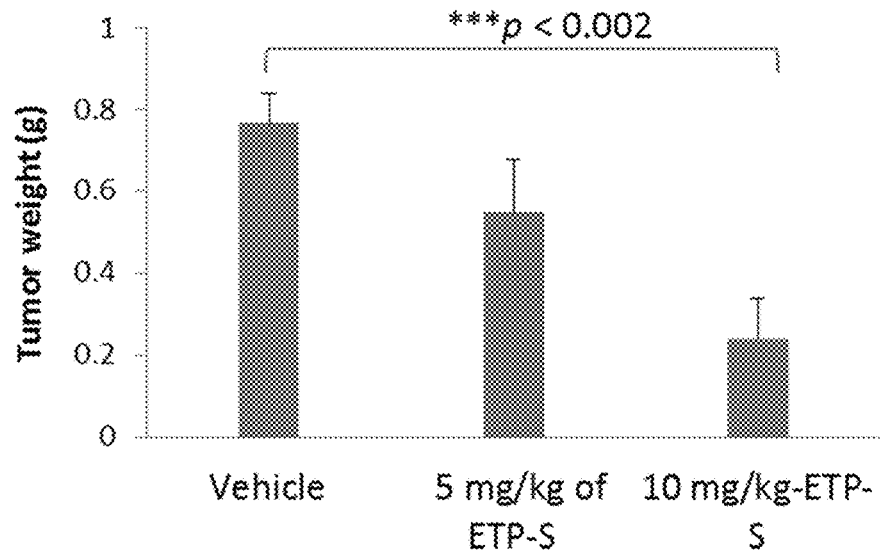
Figure 21:
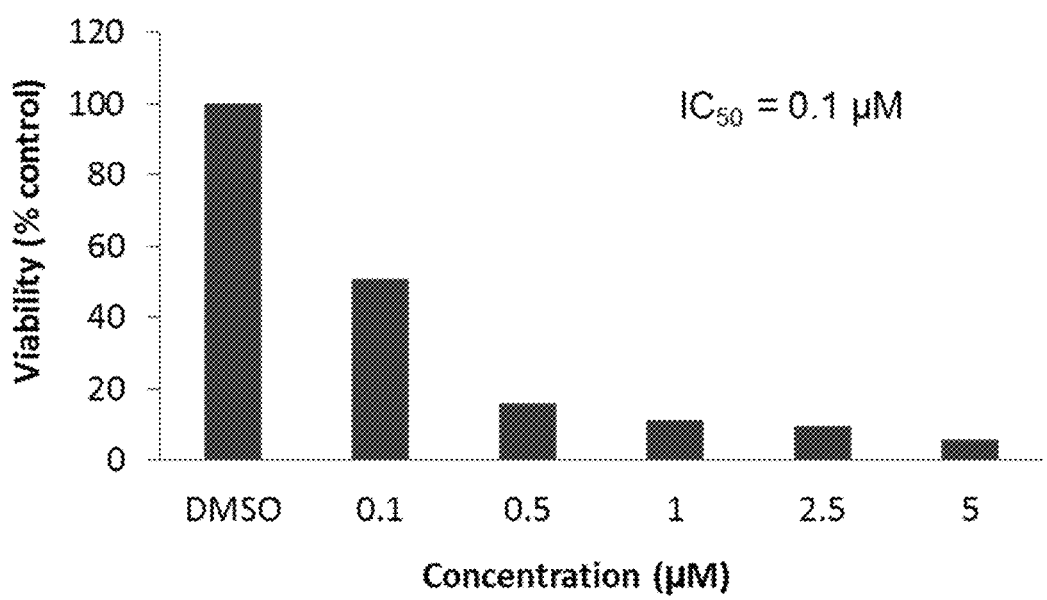
FIG. 21: Effect of ETP69 on A549 lung cancer cells: ETP69 displays antitumor activities with IC50 of 0.1 uM against A549 non-small cell lung cancer cells.
Figure 22A:
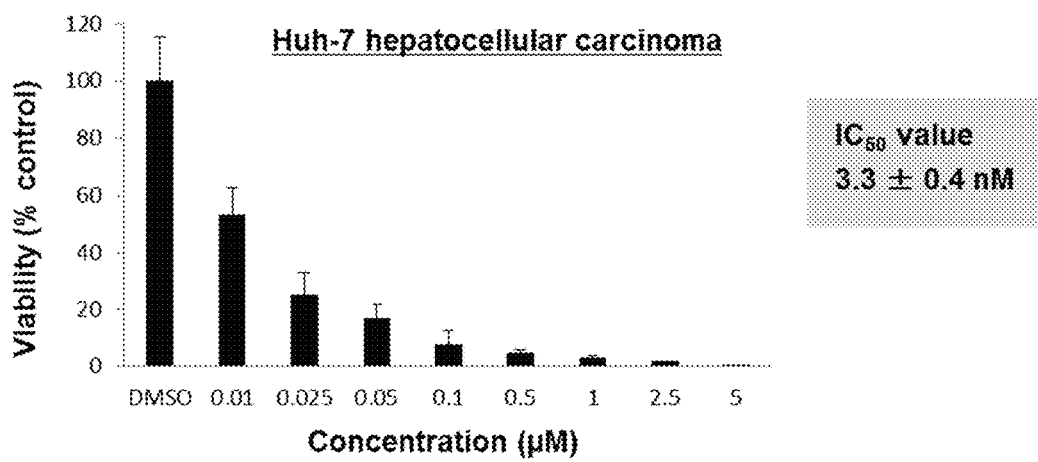
FIGS. 22A-22B: Effect of ETP69 on liver cancer cells: ETP69 displays $IC_{50}$ values of 3.3 nM and 13.8 nM against Huh-7 (FIG. 22A) and HepG2 (FIG. 22B) heapatocullular carcinoma cells respectively.
Figure 22B:
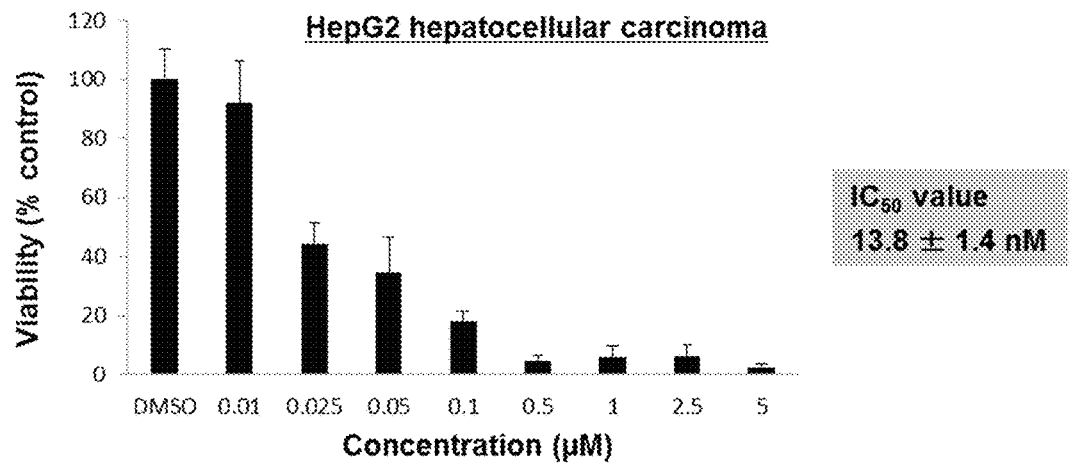
Figure 23:
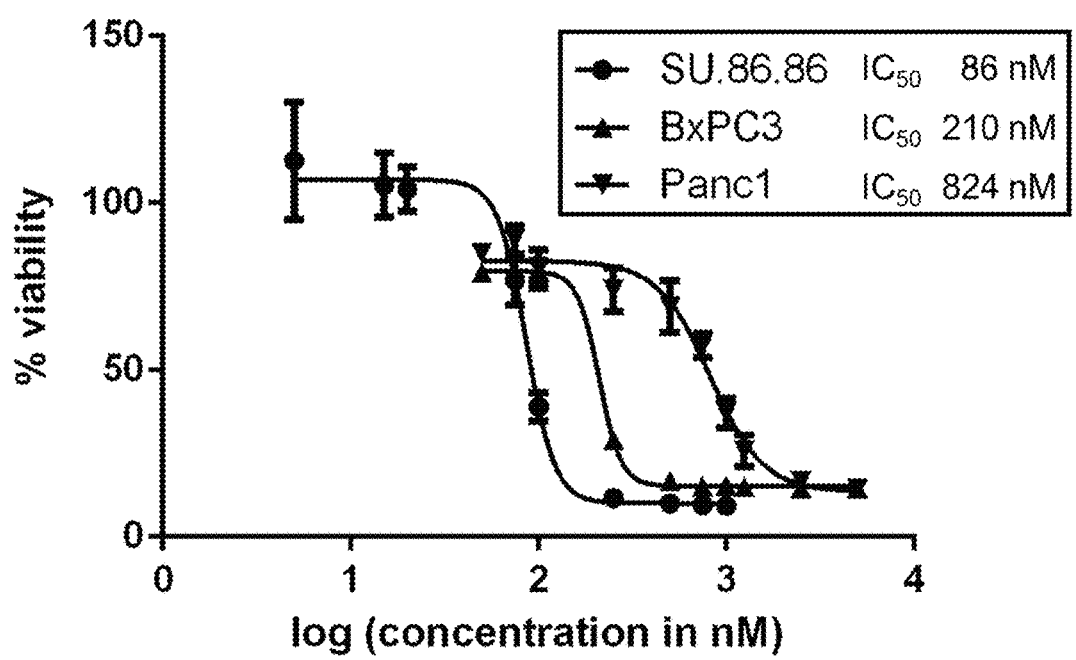
FIG. 23: Effect of ETP69 on pancreatic cancer cells: ETP69 displays $IC_{50}$ values of 86 nM, 210 nM and 824 nM against Su.86.86, BxPC3, and Panc1 pancreatic cancer cell lines respectively.
Figure 24A:
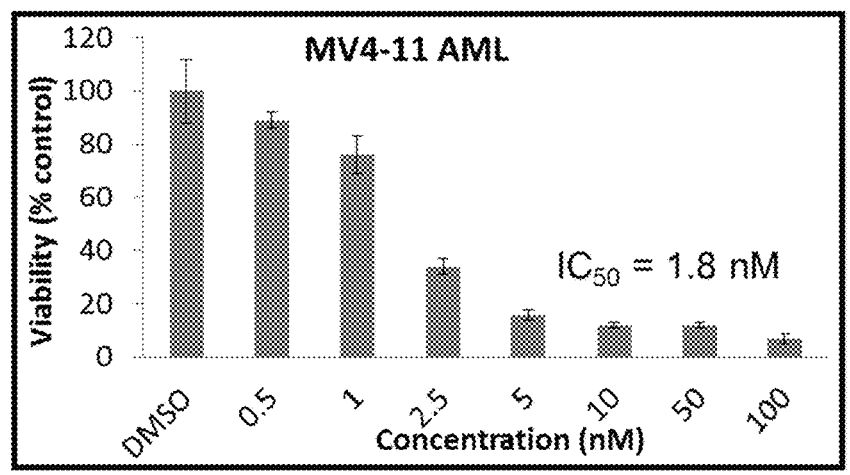
FIGS. 24A-24C: Effect of ETP69 on MV4-11 AML (FIG. 24A), KCL-22 CML (FIG. 24B) and T315I mutant KCL-22 CML cells (FIG. 24C): ETP69 displays $IC_{50}$ values of 1.8 nM, 180 nM, and 170 nM against MV4-11 AML, KCL-22 CML and T315I mutant KCL-22 CML cells respectively.
Figure 24B:
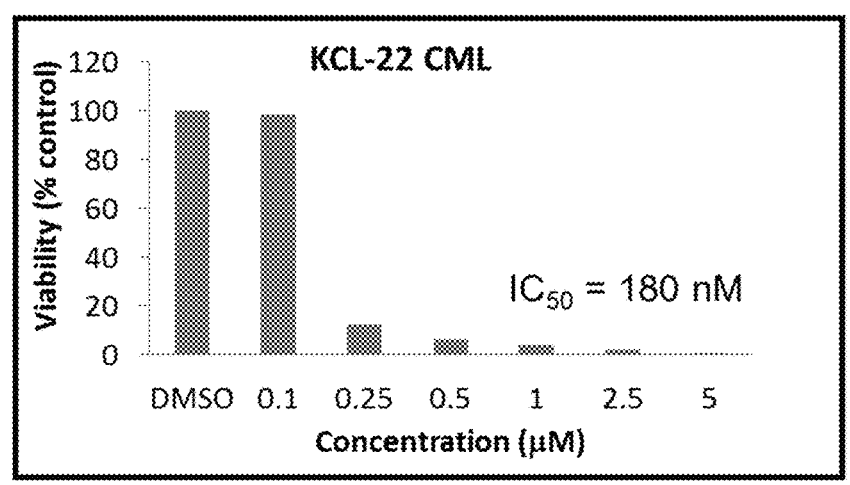
Figure 24C:
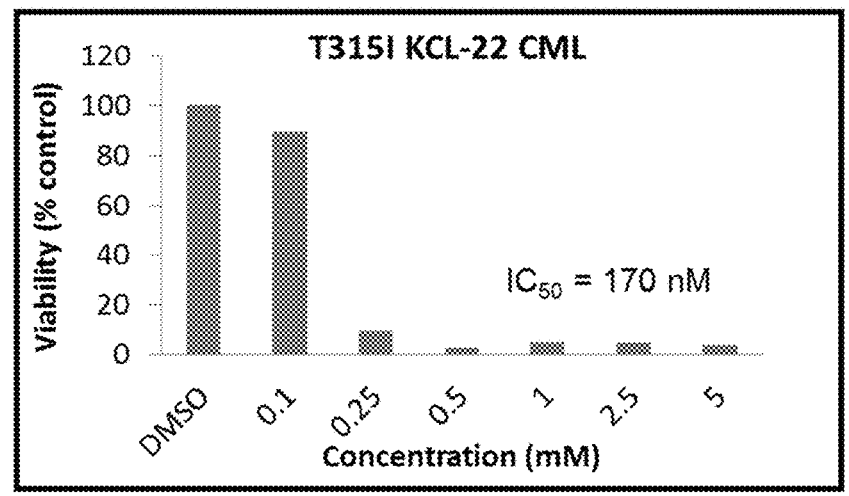
Figure 25A:
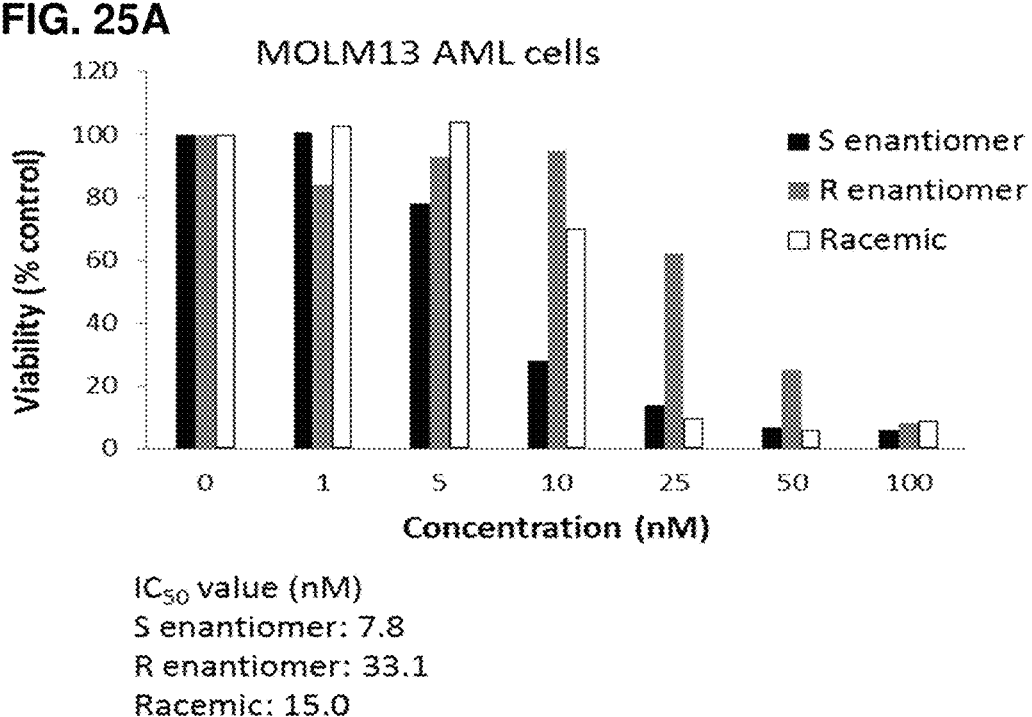
FIGS. 25A-25B: Effect of ETP enantiomers on activity against AML cells: ETP417 (e.g. S enantiomer) has significantly greater activity than its corresponding R enantiomer (ETP422).
Figure 25B:
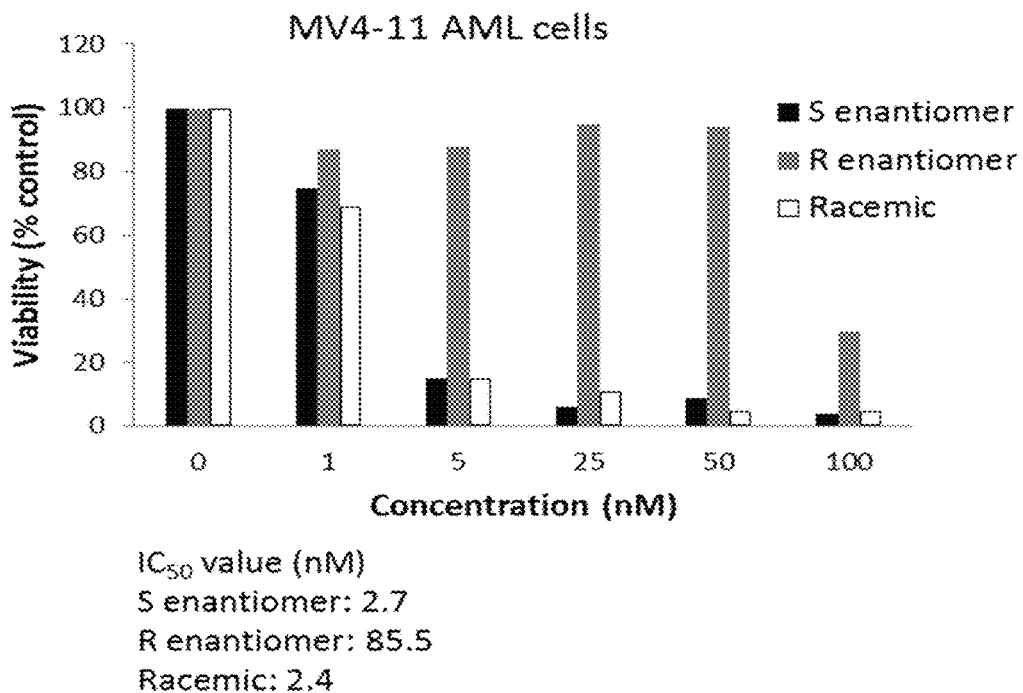

Induction of p16, p53, p21waf1 and p27 (FIGS. 8 and 9):

Western blot analyses were performed with specific antibodies. Briefly, human A2058 melanoma, DU145 prostate, A549 non-small lung and SKOV3 ovarian cancer cells were treated with ETP69. Whole-cell lysates (40 □g) were resolved by SDS-PAGE. Primary specific antibodies to p53, p21$^{WAF1}$, p27(Kip1), p16 and Actin were diluted in PBS (pH 7.5) with 5% (w/v) nonfat milk and 0.1% (v/v) Tween-20 over night at 4° C. Horseradish peroxidase-conjugated secondary antibodies were incubated in PBS (pH 7.5) with 5% (w/v) nonfat milk and 0.1% (v/v) Tween-20 for 1 h at room temperature. Positive immuno-reactive proteins were detected using the ECL system (Pierce, Rockford, Ill.).

Apoptosis Determinations (FIG. 11):

Apoptosis assays of human SKOV3 ovarian cancer cells based on loss of membrane integrity were carried out using Annexin V-FITC. Briefly, cells were seeded in 6-well plates, incubated overnight at 37° C. in 5% (v/v) $CO_2$ and exposed to ETP69 in a dose-dependent manner for 48 h. DMSO was used as the vehicle control. Cells were analyzed using a FACScan flow cytometer to quantify fluorescence. Apoptotic cells were defined as Annexin V-FITC positive. Each experiment was performed in quadruplicate.

IC50 Determinations for Ovarian, Liver, Pancreatic, CML, AML Cancer Cell Lines (See e.g. FIGS. 4, 6A-6C, 21, 22A, 22B, 23, 24A-24C, 25A, 25B and 34):

MTS assays were performed for cell viability. SKOV3 ovarian cancer, Huh-7 hepatocellular carcinoma, MIA-PaCa2 pancreatic cancer, KCL-22 CML, T315I mutant KCL-22 CML, MOLM-13 AML and MV4-11 AML cells were seeded in 96-well plates (5000 cells/well for solid tumors, 10000 cells/well for blood tumors), incubated overnight at 37° C. in 5% $CO_2$, and exposed to racemic ETP69 or S enantiomer in a dose-dependent manner for 48 h. Dimethyl sulfoxide (DMSO) was used as the vehicle control. Viable cell numbers were determined by tetrazolium conversion to its formazan dye and absorbance was measured at 490 nm using an automated ELISA plate reader. Each experiment was performed in quadruplicate.

Example 9

ETP Analogue Acidity

It was found that the prepared ETPs show different $IC_{50}$ values ranging from 0.1 to >5 μM. In general, the aromatic rings incorporated at an early stage seem to have little effect on the observed activities; however, the presence of a nitrile group rather than different esters enhances the potency of such compounds significantly. As such ETP69 was identified as a promising lead structure with an $IC_{50}$ falling in between the monomeric and dimeric ETP natural products (~0.6 and 0.07 μM).

ETP69 was screened against a number of transferases and demonstrate about ten times more potency against several transferases than chaetocin itself. In addition, the data obtained suggests that ETP69 is selective against histone methyltransferases (SUV39H1; G9a) over histone acetylases (p300) and DNA methyl transferases (DNMT1).

ETP69 shows no significant toxicity up to concentrations of 20 mg/kg with intraperitoneal injection (IP) or oral administration.

VI. References

Iwasa, E.; Hamashima, Y.; Sodeoka, M. *J. Isr. Chem.* 2011, 51, 420-433

Isham, C. R.; Tibodeau, J. D.; Jin, W.; Xu, R.; Timm, M. M.; Bible, K. C. *Blood* 2007, 109, 2579-2588.

Scharf, D. H.; Remme, N.; Heinekamp, T.; Hortschansky, P.; Brakhage, A. A.; Hertweck, C. *J. Am. Chem. Soc.* 2010, 132, 10136-10141.

Cook, K. M.; Hilton, S. T.; Mecinovic, J.; Motherwell, W. B.; Figg, W. D.; Schofield, C. J. *J. Biomol. Chem.* 2008, 284, 26831-26838.

Kishi, Y.; Nakatsuka, S.; Fukuyama, T.; Havel, M. *J. Am. Chem. Soc.* 1973, 95, 6493-6495.

Kishi, Y.; Nakatsuka, S.; Fukuyama, T. *J. Am. Chem. Soc.* 1973, 95, 6492-6493.

Kim, J.; Ashenhurst, J. A.; Movassaghi, M. *Science* 2009, 10, 238-241.

Iwasa, E.; Hamashima, Y.; Fujishiro, S.; Higuchi, E.; Ito, A.; Yoshida, M.; Sodeoka, M. *J. Am. Chem. Soc.* 2010, 132, 4078-4079.

Kim, J.; Movassaghi, M. *J. Am. Chem. Soc.* 2010, 132, 14376-14378.

DeLorbe, J. E.; Jabri, S. Y.; Mennen, S. M.; Overman, L. E.; Zhang, F.-L. *J. Am. Chem. Soc.* 2011, 133, 6549-6552.

Block, K. M.; Wang, H.; Szabo, L. Z.; Polaske, N. W.; Henchey, L. K.; Dubey, R.; Kushal, S.; Laszlo, C. F.; Makhoul, J.; Song, Z.; Meuillet, E. J.; Olenyuk, B. Z. *J. Am. Chem. Soc.* 2009, 131, 18078-18088.

Tsuge, O.; Kanemasa, S.; Yoshioka, M. *J. Org. Chem.* 1988, 53, 1384-1391.

Adrio, J.; Carretero, J. C. *Chem. Commun.* 2011, 47, 6784-6794.

Nobuyuki, K.; Ryuzou, A.; Junichi, U. *Tetrahedron Lett.* 2009, 50, 6580-6583.

Firouzabadi, H.; Vessal, B, Naderi, M. *Tetrahedron Lett.* 1982, 23, 1847-1850.

Friedrich, A.; Jainta, M.; Nieger, M.; Braese, S. *Synlett* 2007, 13, 2127-2729.

Nicolaou, K. C.; Totokotsopoulos, S.; Giguerre, D.; Sun, Y.-P.; Sarlah, D. *J. Am. Chem. Soc.* 2011, 133, 8150-8153.

Nicolaou, K. C.; Totokotsopoulos, S.; Giguerre, D.; Sun, Y.-P. *Angew. Chem. Int. Ed.* 2012, 124, 752-756.

Seephonkai, P.; Kongsaeree, P.; Prabpai, S.; Isaka, M.; Thebtaranonth, Y. *Org. Lett.* 2006, 14, 3073-3075.

Codelli, J. A.; Puchlopek, A. L. A.; Reisman, S. E. *J. Am. Chem. Soc.* 2012, 134, 1930-1933.

Öhler, E.; Tataruch, F.; Schmidt, U. *Chem. Ber.* 1973, 106, 396-398.

VII. Embodiments

Embodiment 1

A compound having the formula

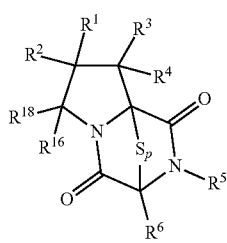

(I)

wherein, p is 2, 3 or 4; $R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34b}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, $-N_3$, $-CF_3$, $-CCl_3$, $-CBr_3$, $-CI_3$, $-CN$, $-CHO$, $-OR^{33}c$, $-NR^{34C}R^{35C}$, $-COOR^{33}c$, $-CONR^{34C}R^{35C}$, $-NO_2$, $-SR^{36C}$, $-SO_{n3}R^{34C}$, $-SO_{n3}OR^{34C}$, $-SO_{n3}NR^{34C}R^{35C}$, $-NHNR^{34C}R^{35C}$, $-ONR^{34C}R^{35C}$, $-NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, $-N_3$, $-CF_3$, $-CCl_3$, $-CBr_3$, $-CI_3$, $-CN$, $-CHO$, $-OR^{33D}$, $-NR^{34D}R^{35D}$, $-COOR^{33D}$, $-CONR^{34D}R^{35D}$, $-NO_2$, $-SR^{36D}$, $-SO_{n4}R^{34D}$, $-SO_{n4}OR^{34D}$, $SO_{n4}NR^{34D}R^{35D}$, $-NHNR^{34D}R^{35D}$, $-ONR^{34D}R^{35D}$, $-NHC(O)NHNR^{34D}R^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, $-N_3$, $-CF_3$, $-CCl_3$, $-CBr_3$, $-CI_3$, $-CN$, $-CHO$, $-OR^{33E}$, $-NR^{34E}R^{35E}$, $-COOR^{33E}$, $-CONR^{34E}R^{35E}$, $-NO_2$, $-SR^{36E}$, $-SO_{n5}R^{34E}$, $-SO_{n5}OR^{34E}$, $-SO_{n5}NR^{34E}R^{35E}$, $-NHNR^{34E}R^{35E}$, $-ONR^{34E}R^{35E}$, $-NHC(O)NHNR^{34E}R^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, halogen, $-N_3$, $-CF_3$, $-CCl_3$, $-CBr_3$, $-CI_3$, $-CN$, $-CHO$, $-OR^{33F}$, $-NR^{34F}R^{35F}$, $-COOR^{33F}$, $-CONR^{34F}R^{35F}$, $-NO_2$, $-SR^{36F}$, $-SO_{n6}R^{34F}$, $-SO_{n6}OR^{34F}$, $-SO_{n6}NR^{34F}R^{35F}$, $-NHNR^{34F}R^{35F}$, $-ONR^{34F}R^{35F}$, $-NHC(O)NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-N_3$, $-CF_3$, $-CCl_3$, $-CBr_3$, $-CI_3$, $-CN$, $-CHO$, $-OR^{33G}$, $-NR^{34G}R^{35G}$, $-COOR^{33G}$, $-CONR^{34G}R^{35G}$, $-NO_2$, $-SR^{36G}$, $-SO_{n7}R^{34G}$, $-SO_{n7}OR^{34G}$, $-SO_{n7}NR^{34G}R^{35G}$, $-NHNR^{34G}R^{35G}$, $-ONR^{34G}R^{35G}$, $-NHC(O)NHNR^{34G}R^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-N_3$, $-CF_3$, $-CCl_3$, $-CBr_3$, $-CI_3$, $-CN$, $-CHO$, $-OR^{33H}$, $-NR^{34H}R^{35H}$, $-COOR^{33H}$, $-CONR^{34H}R^{35H}$, $-NO_2$, $-SR^{36H}$, $-SO_{n8}R^{34H}$, $-SO_{n8}OR^{34H}$, $-SO_{n8}NR^{34H}R^{35H}$, $-NHNR^{34H}R^{35H}$, $-ONR^{34H}R^{35H}$, $-NHC(O)NHNR^{34H}R^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33A}$, $R^{34A}$, $R^{35A}$, $R^{36A}$, $R^{33B}$, $R^{34B}$, $R^{35B}$, $R^{36B}$, $R^{33C}$, $R^{34C}$, $R^{35C}$, $R^{36C}$, $R^{33D}$, $R^{34D}$, $R^{35D}$, $R^{36D}$, $R^{33E}$, $R^{34E}$, $R^{35E}$, $R^{36E}$, $R^{33F}$, $R^{34F}$, $R^{35F}$, $R^{36F}$, $R^{33G}$, $R^{34G}$, $R^{35G}$, $R^{36G}$, $R^{33H}$, $R^{34H}$, $R^{35H}$, and $R^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n6, n7, and n8 are independently 1 or 2.

Embodiment 2

The compound of embodiment 1, wherein $R^{18}$ is substituted or unsubstituted heterocycloalkyl, substituted or unsubstituted aryl, or substituted or unsubstituted heteroaryl.

Embodiment 3

The compound of embodiments 1 or 2, wherein $R^{18}$ is $R^{18a}$-substituted or unsubstituted 5 membered heterocycloalkyl, $R^{18a}$-substituted or unsubstituted 6 membered aryl, $R^{18a}$-substituted or unsubstituted 6 membered heteroaryl, $R^{18a}$-substituted or unsubstituted 6,6 fused ring aryl-heterocycloalkyl, $R^{18a}$-substituted or unsubstituted 6,5 fused ring aryl-heterocycloalkyl, $R^{18a}$-substituted or unsubstituted 5,6 fused ring aryl-heterocycloalkyl; $R^{18a}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2Ph$, $-SO_2NH_2$, $-NHNH_2$, $-ONH_2$, $-NHC(O)NHNH_2$, $R^{18b}$-substituted or unsubstituted $C_1$-$C_8$ alkyl, $R^{18b}$-substituted or unsubstituted 2 to 8 membered heteroalkyl, $R^{18b}$-substituted or unsubstituted 3 to 8 membered cycloalkyl, $R^{18b}$-substituted or unsubstituted 3 to 6 membered heterocycloalkyl, $R^{18b}$-substituted or unsubstituted 5 to 6 membered aryl, or $R^{18b}$-substituted or unsubstituted 5 to 6 membered heteroaryl; and $R^{18b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted $C_1$-$C_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

Embodiment 4

The compound of embodiments 1-3, wherein $R^{18a}$ is halogen, —$SO_2Ph$, $R^{18b}$-substituted or unsubstituted $C_1$-$C_5$ alkyl, or $R^{18b}$-substituted or unsubstituted 2 to 5 membered heteroalkyl, unsubstituted 5 to 6 membered heterocycloalkyl, or unsubstituted phenyl; and $R^{18b}$ is halogen, unsubstituted $C_1$-$C_8$ alkyl, or unsubstituted 2 to 8 membered heteroalkyl.

Embodiment 5

The compound of embodiments 1-4, wherein said $R^{18a}$-substituted 5 membered heterocycloalkyl is an $R^{18a}$-substituted thiophenyl, $R^{18a}$-substituted thiazolyl, $R^{18a}$-substituted oxazolyl, or $R^{18a}$-substituted imidazolyl; and $R^{18a}$ is halogen, unsubstituted $C_1$-$C_5$ alkyl, or unsubstituted 2 to 5 membered heteroalkyl.

Embodiment 6

The compound of embodiment 1-3, wherein $R^{18}$ is unsubstituted heterocycloalkyl, unsubstituted aryl, or unsubstituted heteroaryl.

Embodiment 7

The compound of any one of embodiments 1 to 6, wherein $R^{16}$ is hydrogen.

Embodiment 8

The compound of any one of embodiments 1 to 6, wherein $R^3$ and $R^4$ are hydrogen.

Embodiment 9

The compound of any one of embodiments 1 to 6, wherein $R^1$ is —CN or unsubstituted 2 to 5 membered heteroalkyl.

Embodiment 10

The compound of embodiments 1-9, wherein $R^1$ is —CN

Embodiment 11

The compound of embodiments 1-9, wherein $R^1$ is —$COOR^{33A}$, wherein $R^{33A}$ is $C_1$-$C_3$ unsubstituted alkyl.

Embodiment 12

The compound of any one of embodiments 1 to 6 or 10-11, wherein $R^2$ is —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2a}$-substituted or unsubstituted $C_1$-$C_3$ alkyl, or 2 to 3 membered $R^{2a}$-substituted or unsubstituted heteroalkyl; $R^{2a}$ is —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2b}$-substituted or unsubstituted $C_1$-$C_5$ alkyl, $R^{2b}$-substituted or unsubstituted 2 to 5 membered heteroalkyl, $R^{2b}$-substituted or unsubstituted 3 to 6 membered heterocycloalkyl, $R^{2b}$-substituted or unsubstituted 5 or 6 membered aryl, or $R^{2b}$-substituted or unsubstituted 5 or 6 membered heteroaryl; and $R^{2b}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, unsubstituted $C_1$-$C_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

Embodiment 13

The compound of any one of embodiments 1 to 6 or 10-11, wherein $R^2$ is methyl or methoxy.

Embodiment 14

The compound of any one of embodiments 1 to 6 or 10-11, wherein $R^2$ is $R^{2a}$-substituted or unsubstituted $C_1$-$C_5$ alkyl, or $R^{2a}$-substituted or unsubstituted 2 to 5 membered heteroalkyl, and $R^{2a}$ is unsubstituted 3 to 6 membered heterocycloalkyl, unsubstituted 5 or 6 membered aryl, or unsubstituted 5 or 6 membered heteroaryl.

Embodiment 15

The compound of any one of embodiments 1 to 6 or 10-11, wherein $R^{2a}$ is unsubstituted pyridinyl.

Embodiment 16

The compound of any one of embodiments 1 to 6 or 10 to 11, wherein $R^2$ is $C_1$-$C_5$ substituted or unsubstituted heteroalkyl.

Embodiment 17

The compound of any one of embodiments 1 to 6 or 10-11, wherein $R^2$ is a polar substituent.

Embodiment 18

The compound of embodiments 1-17, wherein $R^5$ and $R^6$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, unsubstituted alkyl, or unsubstituted cycloalkyl.

Embodiment 19

The compound of embodiments 1-18, wherein $R^5$ and $R^6$ are independently hydrogen, unsubstituted $C_1$-$C_3$ alkyl or membered 3 to 5 cycloalkyl.

Embodiment 20

The compound of embodiments 1-18, wherein $R^5$ and $R^6$ are independently hydrogen, methyl, ethyl, allyl, or cyclopropyl.

Embodiment 21

The compound of any one of embodiments 1 to 6, 10 to 11, or 18, wherein p is 2.

Embodiment 22

The compound of embodiments 1-21 having the formula

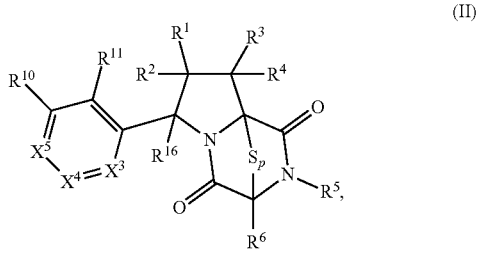

(II)

wherein, $X^3$ is N or $CR^7$; $X^4$ is N or $CR^8$; $X^5$ is N or $CR^9$; $R^7$ is hydrogen, halogen, $-N_3$, $-CF_3$, $-CCl_3$, $-CBr_3$, $-CI_3$, $-CN$, $-CHO$, $-OR^{33I}$, $-NR^{34I}R^{35I}$, $-COOR^{33I}$, $-CONR^{34I}R^{35I}$, $-NO_2$, $-SR^{36I}$, $-SO_{n9}R^{34I}$, $-SO_{n9}OR^{34I}$, $-SO_{n9}NR^{34I}R^{35I}$, $-NHNR^{34I}R^{35I}$, $-ONR^{34I}R^{35I}$, $-NHC(O)NHNR^{34I}R^{35I}$-substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-N_3$, $-CF_3$, $-CCl_3$, $-CBr_3$, $-CI_3$, $-CN$, $-CHO$, $-OR^{33J}$, $-NR^{34J}R^{35J}$, $-COOR^{33J}$, $-CONR^{34J}R^{35J}$, $-NO_2$, $-SR^{36J}$, $-SO_{n10}R^{34J}$, $-SO_{n10}OR^{34J}$, $-SO_{n10}NR^{34J}R^{35J}$, $-NHNR^{34J}R^{35J}$, $-ONR^{34J}R^{35J}$, $-NHC(O)NHNR^{34J}R^{35J}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-N_3$, $-CF_3$, $-CCl_3$, $-CBr_3$, $-CI_3$, $-CN$, $-CHO$, $-OR^{33K}$, $-NR^{34K}R^{35K}$, $-COOR^{33K}$, $-CONR^{34K}R^{35K}$, $-NO_2$, $-SR^{36K}$, $-SO_{n11}R^{34K}$, $-SO_{n11}OR^{34K}$, $-SO_{n11}NR^{34K}R^{35K}$, $-NHNR^{34K}R^{35K}$, $-ONR^{34K}R^{35K}$, $-NHC(O)NHNR^{34K}R^{35K}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ and $R^{11}$ are independently hydrogen, halogen, $-N_3$, $-CF_3$, $-CCl_3$, $-CBr_3$, $-CI_3$, $-CN$, $-CHO$, $-OR^{33L}$, $-NR^{34L}R^{35L}$, $-COOR^{33L}$, $-CONR^{34L}R^{35L}$, $-NO_2$, $-SR^{36L}$, $-SO_{n12}R^{34L}$, $-SO_{n12}OR^{34L}$, $-SO_{n12}NR^{34L}R^{35L}$, $-NHNR^{34L}R^{35L}$, $-ONR^{34L}R^{35L}$, $-NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; $R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n10, n11, and n12 are independently 1 or 2.

Embodiment 23

The compound of embodiments 1-22 having the formula

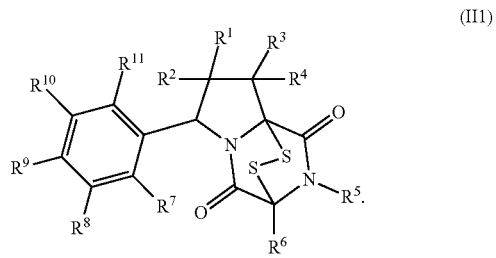

(II1)

Embodiment 24

The compound of embodiments 1-22 having the formula

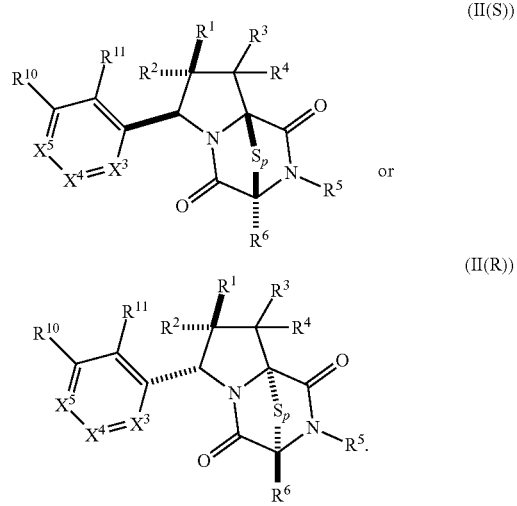

(II(S))

or (II(R))

Embodiment 25

The compound of embodiments 1-22, wherein $R^1$ is $-CN$ or unsubstituted 2 to 5 membered heteroalkyl.

Embodiment 26

The compound of any one of embodiments 1-25, wherein $R^3$ and $R^4$ are hydrogen.

Embodiment 27

The compound of embodiments 1-22 having formula

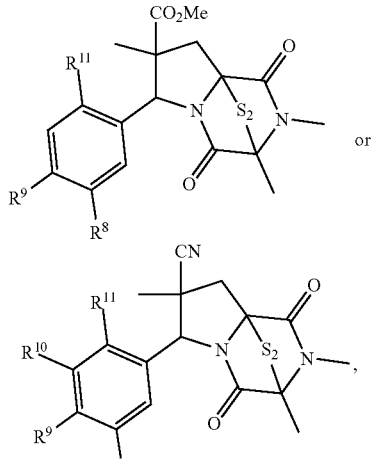

wherein, $R^8$ is hydrogen or $-OR^{33}$; $R^9$, $R^{10}$, and $R^{11}$ are independently hydrogen or halogen; and $R^{33}$ is hydrogen, or unsubstituted alkyl.

Embodiment 28

The compound of embodiments 1 or 22 having formula

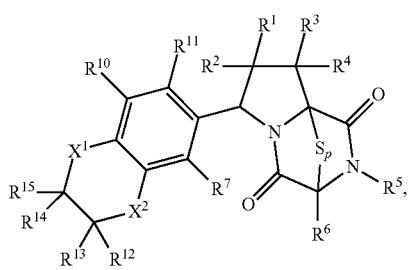

(IV)

wherein, $X^1$ is $CR^{21}R^{21A}$, O, $NR^{21A}$, or S; $X^2$ is $CR^{22}R^{22A}$, O, $NR^{22A}$, or S; $R^{12}$, $R^{13}$, $R^{14}$, $R^{15}$ $R^{21}$, $R^{21A}$, $R^{22}$, and $R^{22A}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

Embodiment 29

The compound of embodiment 28 having formula

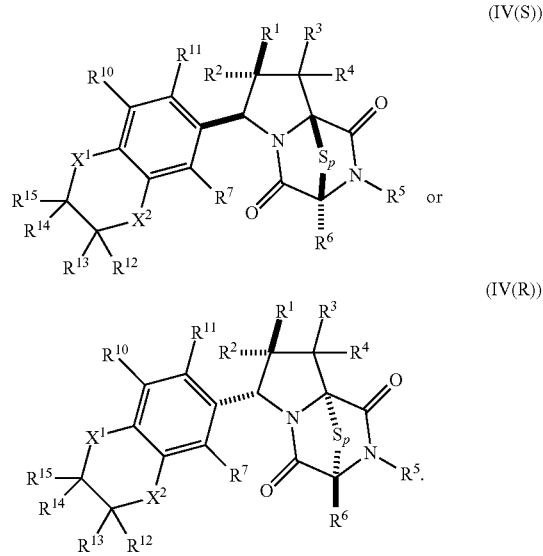

Embodiment 30

The compound of embodiments 28-29, wherein $R^1$ is $-CN$ or unsubstituted 2 to 5 membered heterocycloalkyl.

Embodiment 31

The compound of any one of embodiments 28-30, wherein $R^3$ and $R^4$ are hydrogen.

Embodiment 32

The compound of any one of embodiments 28-30, wherein $R^{10}$ and $R^{11}$ are hydrogen.

Embodiment 33

The compound of any one of embodiments 28-30, wherein $R^{12}$, $R^{13}$, $R^{14}$ and $R^{15}$ are hydrogen.

Embodiment 34

The compound of embodiments 28-33 having formula

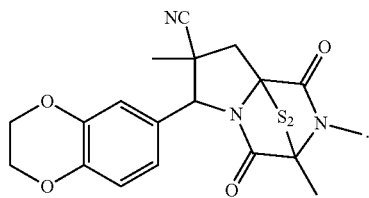

Embodiment 35

The compound of embodiment 1 having formula

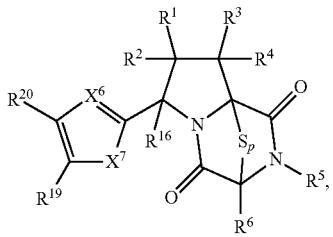

(III)

wherein, $X^6$ is $CR^{21}$ or N; $X^7$ is $CR^{22}R^{23}$, S, O, or $NR^{23}$; $R^{19}$, $R^{20}$, $R^{21}$, $R^{22}$ and $R^{23}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

Embodiment 36

The compound of any one of embodiments 1 or 35 having formula

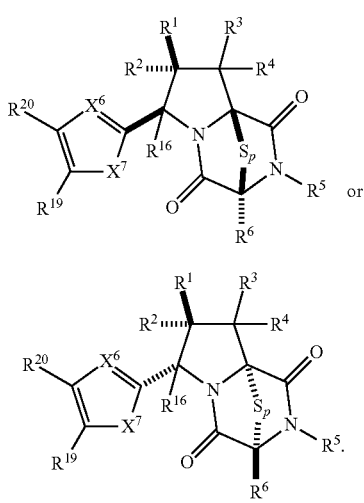

(III(S))

or (III(R))

Embodiment 37

The compound of embodiments 35-36, wherein $R^1$ is $-CN$ or unsubstituted 2 to 5 membered heteroalkyl.

Embodiment 38

The compound of any one of embodiments 35 to 37, wherein $R^3$ and $R^4$ are hydrogen.

Embodiment 39

The compound of any one of embodiments 35 to 37, wherein $R^{19}$ and $R^{20}$ are hydrogen.

Embodiment 40

The compound of embodiment 1 having formula

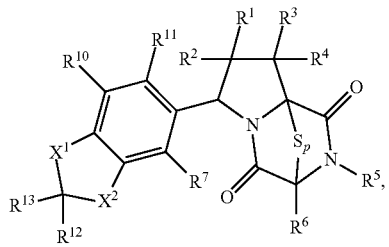

(V)

wherein, $X^1$ is $CR^{21}R^{21A}$, O, $NR^{21A}$, or S; $X^2$ is $CR^{22}R^{22A}$, O, $NR^{22A}$, or S; $R^7$ is hydrogen, halogen, $-N_3$, $-CF_3$, $-CCl_3$, $-CBr_3$, $-CI_3$, $-CN$, $-CHO$, $-OR^{33I}$, $-NR^{34I}R^{35I}$, $-COOR^{33I}$, $-CONR^{34I}R^{35I}$, $-NO_2$, $-SR^{36I}$, $-SO_{n9}R^{34I}$, $-SO_{n9}OR^{34I}$, $-SO_{n9}NR^{34I}R^{35I}$, $-NHNR^{34I}R^{35I}$, $-ONR^{34I}R^{35I}$, $-NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ and $R^{11}$ are independently hydrogen, halogen, $-N_3$, $-CF_3$, $-CCl_3$, $-CBr_3$, $-CI_3$, $-CN$, $-CHO$, $-OR^{33L}$, $-NR^{34L}R^{35L}$, $-COOR^{33L}$, $-CONR^{34L}R^{35L}$, $-NO_2$, $-SR^{36L}$, $-SO_{n12}R^{34L}$, $-SO_{n12}OR^{34L}$, $-SO_{n12}NR^{34L}R^{35L}$, $-NHNR^{34L}R^{35L}$, $-ONR^{34L}R^{35L}$, $-NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; $R^{12}$, $R^{13}$, $R^{21}$, $R^{21A}$, $R^{22}$ and $R^{22A}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n11, and n13 are independently 1 or 2.

Embodiment 41

The compound of embodiment 40 having formula

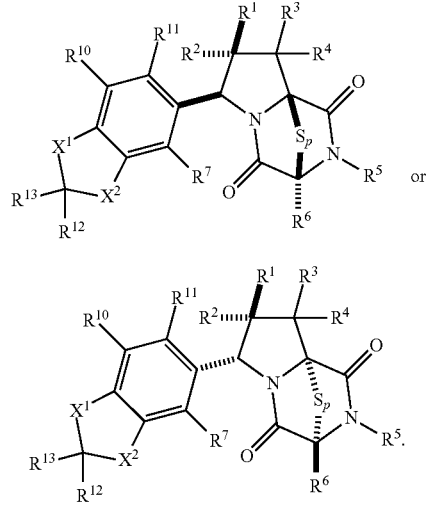

(V(S))

(V(R))

Embodiment 42

The compound of embodiments 40-41 having formula (V2)

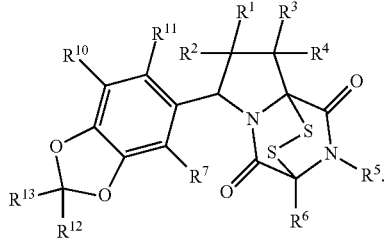

Embodiment 43

The compound of embodiments 40-42 having formula (V2(S))

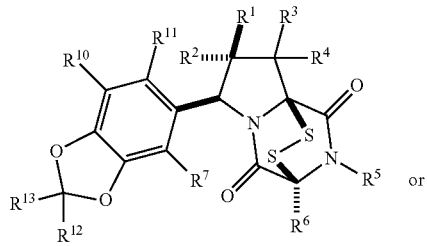

(V2(R))

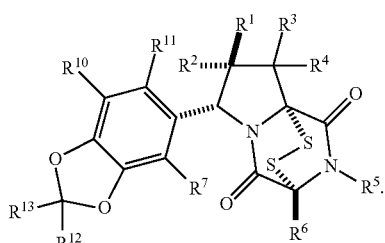

Embodiment 44

The compound of embodiments 40-43, wherein $R^1$ is —CN or unsubstituted 2 to 5 membered heteroalkyl.

Embodiment 45

The compound of any one of embodiments 40 to 44, wherein $R^3$ and $R^4$ are hydrogen.

Embodiment 46

The compound of any one of embodiments 40 to 45, wherein $R^{12}$ and $R^{13}$ are hydrogen.

Embodiment 47

The compound of any one of embodiments 40 to 46, wherein $R^{10}$ and $R^{11}$ are hydrogen.

Embodiment 48

The compound of any one of embodiments 1 or 40-47 having formula

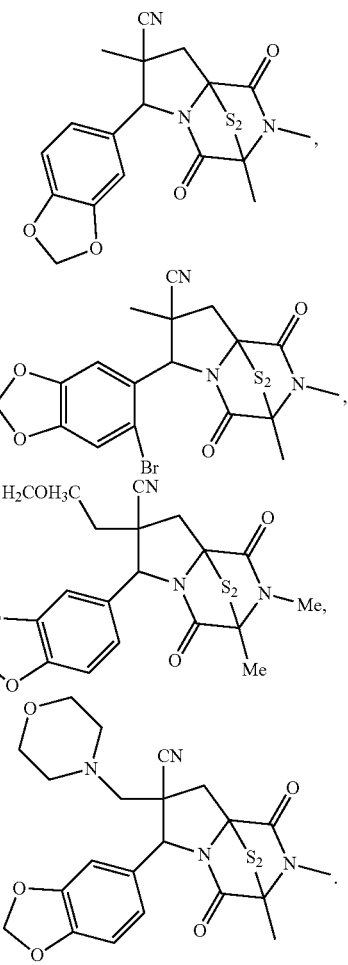

Embodiment 49

The compound of any one of embodiments 1 or 40-47 having formula

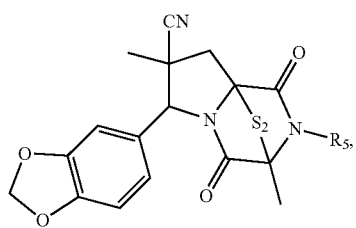
wherein; $R^5$ is unsubstituted 3 to 5 membered cycloalkyl, or $R^{5a}$-substituted or unsubstituted $C_1$-$C_5$ alkyl; $R^{5a}$ is unsubstituted 2 to 5 membered heteroalkyl or 5 to 6 membered heterocycloalkyl, and p is 2 or 3.
Embodiment 50
The compound of any one of embodiments 1 or 40-49 having formula
(ETP69)
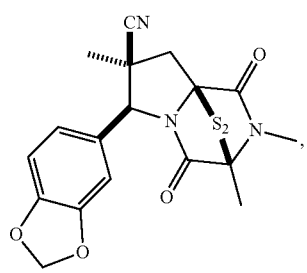
(ETP128)
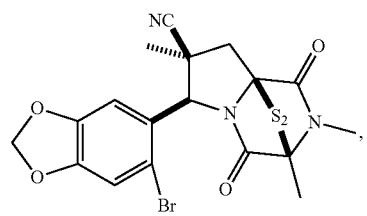
(ETP344)
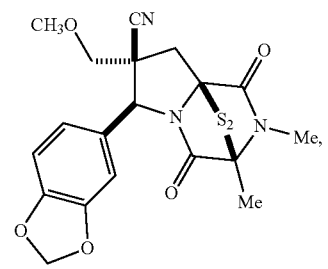
(ETP382)
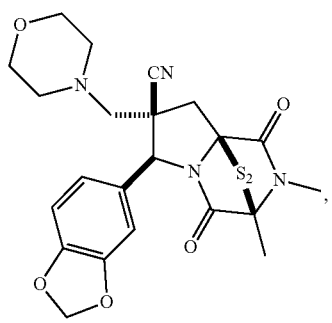
(ETP406)
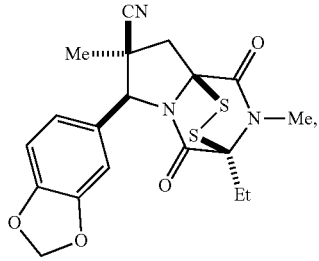
(ETP417)
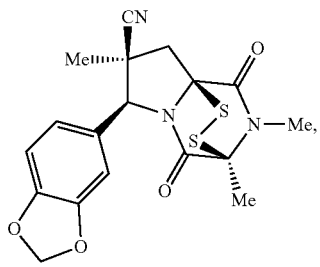
(ETP422)
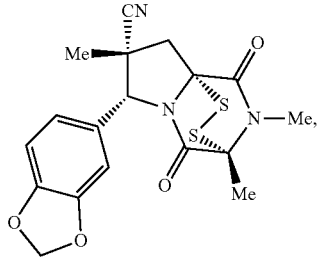
(ETP425)
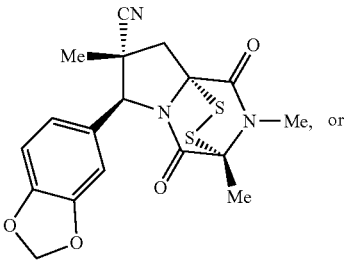
or
(ETP452)
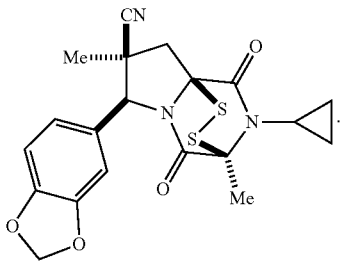

Embodiment 51

The compound of embodiment 1 having formula

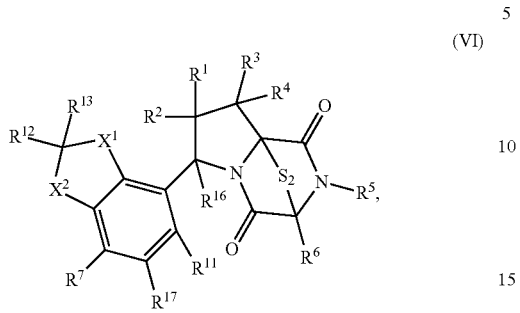

(VI)

wherein, $X^1$ is $CR^{21}R^{21A}$, O, $NR^{21A}$, or S; $X^2$ is $CR^{22}R^{22A}$, O, $NR^{22A}$, or S; $R^7$ is hydrogen, halogen, $-N_3$, $-CF_3$, $-CCl_3$, $-CBr_3$, $-CI_3$, $-CN$, $-CHO$, $-OR^{33I}$, $-NR^{34I}R^{35I}$, $-COOR^{33}$, $-CONR^{34I}R^{35I}$, $-NO_2$, $-SR^{36I}$, $-SO_{n9}R^{34I}$, $-SO_{n9}OR^{34I}$, $-SO_{n9}NR^{34I}R^{35I}$, $-NHNR^{34I}R^{35I}$, $-ONR^{34I}R^{35I}$, $-NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ is hydrogen, halogen, $-N_3$, $-CF_3$, $-CCl_3$, $-CBr_3$, $-CI_3$, $-CN$, $-CHO$, $-OR^{33L}$, $-NR^{34L}R^{35L}$, $-COOR^{33L}$, $-CONR^{34L}R^{35L}$, $-NO_2$, $-SR^{36L}$, $-SO_{n12}R^{34L}$, $-SO_{n12}OR^{34L}$, $-SO_{n12}NR^{34L}R^{35L}$, $-NHNR^{34L}R^{35L}$, $-ONR^{34L}R^{35L}$, $-NHC(O)NHNR^{34L}R^{35L}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; $R^{12}$, $R^{13}$, $R^{21}$, $R^{21A}$, $R^{22}$, and $R^{22A}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, $-N_3$, $-CF_3$, $-CCl_3$, $-CBr_3$, $-CI_3$, $-CN$, $-CHO$, $-OR^{33P}$, $-NR^{34P}R^{35P}$, $-COOR^{33P}$, $-CONR^{34P}R^{35P}$, $-NO_2$, $-SR^{36P}$, $-SO_{n15}R^{34P}$, $-SO_{n15}OR^{34P}$, $-SO_{n15}NR^{34P}R^{35P}$, $-NHNR^{34P}R^{35P}$, $-ONR^{34P}R^{35P}$, $-NHC(O)NHNR^{34P}R^{35P}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl; $R^{33I}$, $R^{34I}$, $R^{35I}$, $R^{36I}$, $R^{33L}$, $R^{34L}$, $R^{35L}$, $R^{36L}$, $R^{33M}$, $R^{34M}$, $R^{35M}$, $R^{36M}$, $R^{33P}$, $R^{34P}$, $R^{35P}$, and $R^{36P}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n12, n13 and n15 are independently 1 or 2.

Embodiment 52

The compound of embodiment 51 having formula

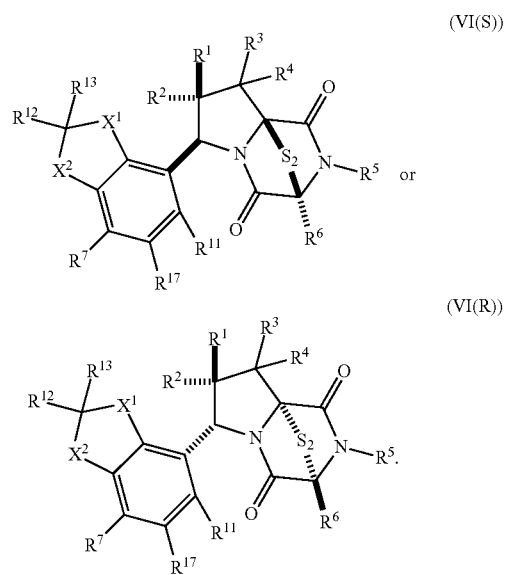

Embodiment 53

The compound of embodiments 51-52, wherein $R^1$ is —CN or unsubstituted 2 to 5 membered heteroalkyl.

Embodiment 54

The compound of any one of embodiments 51 to 53, wherein $R^3$ and $R^4$ are hydrogen.

Embodiment 55

The compound of any one of embodiments 51 to 53, wherein $R^{12}$ and $R^{13}$ are hydrogen.

Embodiment 56

The compound of any one of embodiments 51 to 53, wherein $R^7$, $R^{10}$, and $R^{17}$ are hydrogen.

Embodiment 57

The compound of embodiments 51-56 having formula

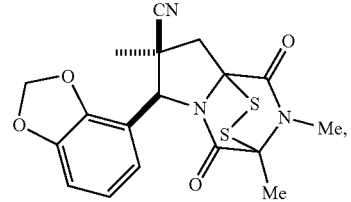

165
-continued

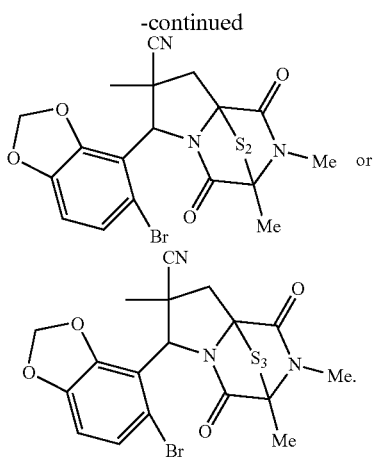

Embodiment 58

The compound of any one of embodiments 1-57, wherein $R^2$ is a polar substituent.

Embodiment 59

The compound of any one of embodiments 1-58, wherein $R^2$ is $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2Ph$, $-SO_2NH_2$, $-NHNH_2$, $-ONH_2$, $R^{2a}$-substituted or unsubstituted $C_1$-$C_3$ alkyl, or 1 to 3 membered $R^{2a}$-substituted or unsubstituted heteroalkyl; $R^{2a}$ is $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2Ph$, $-SO_2NH_2$, $-NHNH_2$, $-ONH_2$, $R^{2b}$-substituted or unsubstituted $C_1$-$C_5$ alkyl, $R^{2b}$-substituted or unsubstituted 2 to 5 membered heteroalkyl, $R^{2b}$-substituted or unsubstituted 3 to 6 membered heterocycloalkyl, $R^{2b}$-substituted or unsubstituted 5 or 6 membered aryl, or $R^{2b}$-substituted or unsubstituted 5 or 6 membered heteroaryl; $R^{2b}$ is halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, unsubstituted $C_1$-$C_8$ alkyl, unsubstituted 2 to 8 membered heteroalkyl, unsubstituted 3 to 8 membered cycloalkyl, unsubstituted 3 to 6 membered heterocycloalkyl, unsubstituted 5 to 6 membered aryl, or unsubstituted 5 to 6 membered heteroaryl.

Embodiment 60

The compound of any one of embodiments 1-59, wherein $R^2$ is $R^{2a}$-substituted or unsubstituted $C_1$-$C_3$ alkyl, or 2 to 3 membered $R^{2a}$-substituted or unsubstituted heteroalkyl, wherein $R^{2a}$ is unsubstituted 3 to 6 membered heterocycloalkyl, unsubstituted 5 or 6 membered aryl, or unsubstituted 5 or 6 membered heteroaryl.

Embodiment 61

The compound of any one of embodiments 1-60, wherein $R^2$ is unsubstituted methyl or unsubstituted methoxy.

Embodiment 62

The compound of any one of embodiments 1-61, wherein $R^{2a}$ is unsubstituted pyridine.

166

Embodiment 63

The compound of any one of embodiments 1-62, wherein $R^5$ and $R^6$ are independently hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, unsubstituted alkyl, or unsubstituted cycloalkyl.

Embodiment 64

The compound of any one of embodiments 1-63, wherein $R^5$ and $R^6$ are independently hydrogen, $C_1$-$C_3$ unsubstituted alkyl or 3 to 5 membered cycloalkyl.

Embodiment 65

The compound of any one of embodiments 1-64, wherein $R^5$ and $R^6$ are independently hydrogen, unsubstituted methyl, unsubstituted ethyl, unsubstituted allyl, or unsubstituted cyclopropyl.

Embodiment 66

A compound having formula

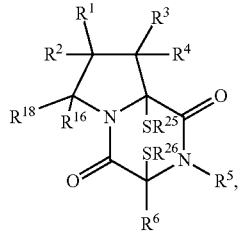

(VII)

wherein $R^1$ is hydrogen, halogen, $-N_3$, $-CF_3$, $-CCl_3$, $-CBr_3$, $-CI_3$, $-CN$, $-CHO$, $-OR^{33A}$, $-NR^{34A}R^{35A}$, $-COOR^{33A}$, $-CONR^{34A}R^{35A}$, $-NO_2$, $-SR^{36A}$, $-SO_{n1}R^{34A}$, $-SO_{n1}OR^{34A}$, $-SO_{n1}NR^{34A}R^{35A}$, $-NHNR^{34A}R^{35A}$, $-ONR^{34A}R^{35A}$, $-NHC(O)NHNR^{34A}R^{35A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $-N_3$, $-CF_3$, $-CCl_3$, $-CBr_3$, $-CI_3$, $-CN$, $-CHO$, $-OR^{33B}$, $-NR^{34B}R^{35B}$, $-COOR^{33B}$, $-CONR^{34B}R^{35B}$, $-NO_2$, $-SR^{36B}$, $-SO_{n2}R^{34b}$, $-SO_{n2}OR^{34B}$, $-SO_{n2}NR^{34B}R^{35B}$, $-NHNR^{34B}R^{35B}$, $-ONR^{34B}R^{35B}$, $-NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, $-N_3$, $-CF_3$, $-CCl_3$, $-CBr_3$, $-CI_3$, $-CN$, $-CHO$, $-OR^{33c}$, $-NR^{34C}R^{35C}$, $-COOR^{33C}$, $-CONR^{34C}R^{35C}$, $-NO_2$, $-SR^{36c}$, $-SO_{n3}R^{34C}$, $-SO_{n3}OR^{34C}$, $-SO_{n3}NR^{34C}R^{35C}$, $-NHNR^{34C}R^{35C}$, $-ONR^{34C}R^{35C}$, $-NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, $-N_3$, $-CF_3$, $-CCl_3$, $-CBr_3$, $-CI_3$, $-CN$, $-CHO$, $-OR^{33D}$, $-NR^{34D}R^{35D}$, $-COOR^{33D}$, $-CONR^{34D}R^{35D}$, $-NO_2$, $-SR^{36D}$, $-SO_{n4}R^{34D}$, $-SO_{n4}OR^{34D}$, $-SO_{n4}NR^{34D}R^{35D}$, $-NHNR^{34D}R^{35D}$, $-ONR^{34D}R^{35D}$, $-NHC(O)NHNR^{34D}R^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, $-N_3$, $-CF_3$, $-CCl_3$, $-CBr_3$, $-CI_3$, $-CN$, $-CHO$, $-OR^{33E}$, $-NR^{34E}R^{35E}$, $-COOR^{33E}$, $-CONR^{34E}R^{35E}$, $-NO_2$, $-SR^{36E}$, $-SO_{n5}R^{34E}$, $-SO_{n5}OR^{34E}$, $-SO_{n5}NR^{34E}R^{35E}$, $-NHNR^{34E}R^{35E}$, $-ONR^{34E}R^{35E}$, $-NHC(O)NHNR^{34E}R^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, halogen, $-N_3$, $-CF_3$, $-CCl_3$, $-CBr_3$, $-CI_3$, $-CN$, $-CHO$, $-OR^{33F}$, $-NR^{34F}R^{35F}$, $-COOR^{33F}$, $-CONR^{34F}R^{35F}$, $-NO_2$, $-SR^{36F}$, $-SO_{n6}R^{34F}$, $-SO_{n6}OR^{34F}$, $-SO_{n6}NR^{34F}R^{35F}$, $-NHNR^{34F}R^{35F}$, $-ONR^{34F}R^{35F}$, $-NHC(O)NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-N_3$, $-CF_3$, $-CCl_3$, $-CBr_3$, $-CI_3$, $-CN$, $-CHO$, $-OR^{33G}$, $-NR^{34G}R^{35G}$, $-COOR^{33G}$, $-CONR^{34G}R^{35G}$, $-NO_2$, $-SR^{36G}$, $-SO_{n7}R^{34G}$, $-SO_{n7}OR^{34G}$, $-SO_{n7}NR^{34G}R^{35G}$, $-NHNR^{34G}R^{35G}$, $-ONR^{34G}R^{35G}$, $-NHC(O)NHNR^{34G}R^{35G}$-substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-N_3$, $-CF_3$, $-CCl_3$, $-CBr_3$, $-CI_3$, $-CN$, $-CHO$, $-OR^{33H}$, $-NR^{34H}R^{35H}$, $-COOR^{33H}$, $-CONR^{34H}R^{35H}$, $-NO_2$, $-SR^{36H}$, $-SO_{n8}R^{34H}$, $-SO_{n8}OR^{34H}$, $-SO_{n5}NR^{34H}R^{35H}$, $-NHNR^{34H}R^{35H}$, $-ONR^{34H}R^{35H}$, $-NHC(O)NHNR^{34H}R^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33A}$, $R^{34A}$, $R^{35A}$, $R^{36A}$, $R^{33B}$, $R^{34B}$, $R^{35B}$, $R^{36B}$, $R^{33C}$, $R^{34C}$, $R^{35C}$, $R^{36C}$, $R^{33D}$, $R^{34D}$, $R^{35D}$, $R^{36D}$, $R^{33E}$, $R^{34E}$, $R^{35E}$, $R^{36E}$, $R^{33F}$, $R^{34F}$, $R^{35F}$, $R^{36F}$, $R^{33G}$, $R^{34G}$, $R^{35G}$, $R^{36G}$, $R^{33H}$, $R^{34H}$, $R^{35H}$, and $R^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n1, n2, n3, n4, n5, n6, n7, and n8 are independently 1 or 2; and $R^{25}$ and $R^{26}$ are independently hydrogen, substituted or unsubstituted alkyl, substituted or unsubstituted heteroalkyl, substituted or unsubstituted aryl, or substituted or unsubstituted heteroaryl.

Embodiment 67

The compound of embodiment 66 having the formula

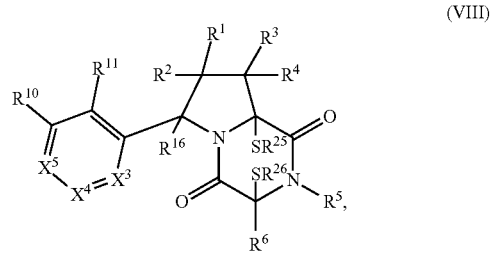

(VIII)

wherein, $X^3$ is N or $CR^7$; $X^4$ is N or $CR^8$; $X^5$ is N or $CR^9$; $R^7$ is hydrogen, halogen, $-N_3$, $-CF_3$, $-CCl_3$, $-CBr_3$, $-CI_3$, $-CN$, $-CHO$, $-OR^{33I}$, $-NR^{34I}R^{35I}$, $-COOR^{33I}$, $-CONR^{34I}R^{35I}$, $-NO_2$, $-SR^{36I}$, $-SO_{n9}R^{34I}$, $-SO_{n9}OR^{34}$, $-SO_{n9}NR^{34I}R^{35I}$, $-NHNR^{34I}R^{35I}$, $-ONR^{34I}R^{35I}$, $-NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-N_3$, $-CF_3$, $-CCl_3$, $-CBr_3$, $-CI_3$, $-CN$, $-CHO$, $-OR^{33J}$, $-NR^{34J}R^{35J}$, $-COOR^{33J}$, $-CONR^{34J}R^{35J}$, $-NO_2$, $-SR^{36J}$, $-SO_{n10}R^{34J}$, $-SO_{n10}OR^{34J}$, $-SO_{n11}NR^{34J}R^{35J}$, $-NHNR^{34J}R^{35J}$, $-ONR^{34J}R^{35J}$, $-NHC(O)NHNR^{34J}R^{35J}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-N_3$, $-CF_3$, $-CCl_3$, $-CBr_3$, $-CI_3$, $-CN$, $-CHO$, $-OR^{33K}$, $-NR^{34K}R^{35K}$, $-COOR^{33K}$, $-CONR^{34K}R^{35K}$, $-NO_2$, $-SR^{36K}$, $-SO_{n11}R^{34K}$, $-SO_{n11}OR^{34K}$, $-SO_{n11}NR^{34K}R^{35K}$, $-NHNR^{34K}R^{35K}$, $-ONR^{34K}R^{35K}$, $-NHC(O)NHNR^{34K}R^{35K}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ and $R^{11}$ are independently hydrogen, halogen, $-N_3$, $-CF_3$, $-CCl_3$, $-CBr_3$, $-CI_3$, $-CN$, $-CHO$, $-OR^{33L}$, $-NR^{34L}R^{35L}$, $-COOR^{33L}$, $-CONR^{34L}R^{35L}$, $-NO_2$, $-SR^{36L}$, $-SO_{n12}R^{34L}$, $-SO_{n12}OR^{34L}$, $-SO_{n12}NR^{34L}R^{35L}$, $-NHNR^{34L}R^{35L}$, $-ONR^{34L}R^{35L}$, $-NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; $R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n10, n11, and n12 are independently 1 or 2.

Embodiment 68

The compound of embodiments 66 or 67 having the formula

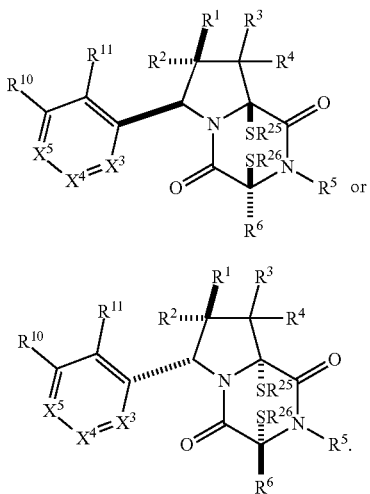

(VIII(S))

(VIII(R))

Embodiment 69

The compound of embodiments 66-68 having the formula

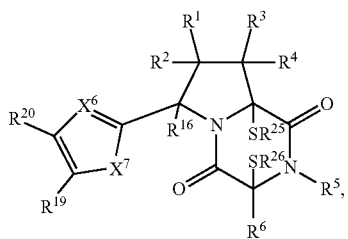

(IX)

$X^6$ is $CR^{21}$ or N; $X^6$ is $CR^{21}$ or N; $X^7$ is $CR^{22}R^{23}$, S, O, or $NR^{23}$; $R^{19}$, $R^{20}$, $R^{21}$, $R^{22}$ and $R^{23}$ are independently hydrogen, halogen, $—N_3$, $—CF_3$, $—CCl_3$, $—CBr_3$, $—CI_3$, $—CN$, $—CHO$, $—OR^{33M}$, $—NR^{34M}R^{35M}$, $—COOR^{33M}$, $—CONR^{34M}R^{35M}$, $—NO_2$, $—SR^{36M}$, $—SO_{n13}R^{34M}$, $—SO_{n13}OR^{34M}$, $—SO_{n13}NR^{34M}R^{35M}$, $—NHNR^{34M}R^{35M}$, $—ONR^{34M}R^{35M}$, $—NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

Embodiment 70

The compound of embodiments 66-69 having the formula

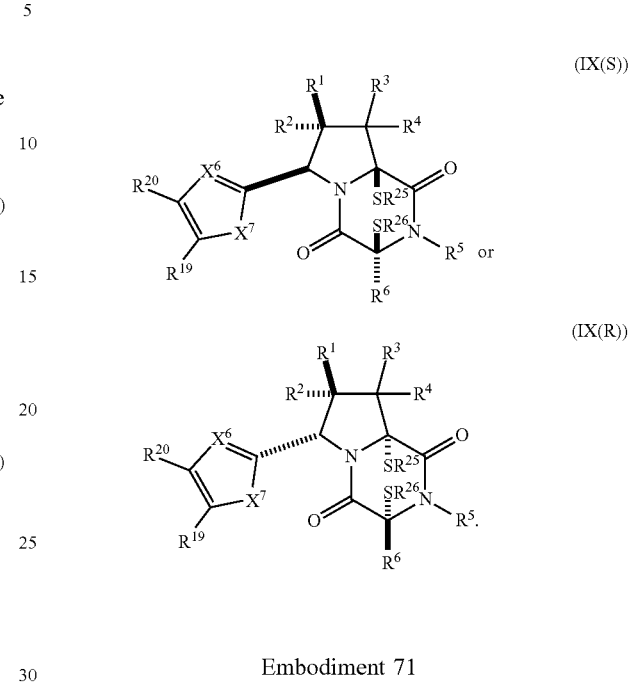

(IX(S))

(IX(R))

Embodiment 71

The compound of embodiments 66-70 having the formula

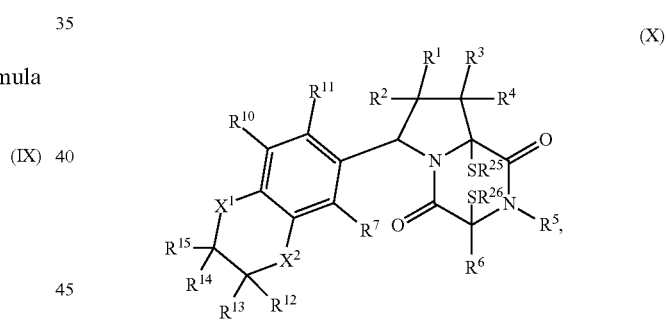

(X)

wherein $X^1$ is $CR^{21}R^{21A}$, O, $NR^{21A}$, or S; $X^2$ is $CR^{22}R^{22A}$, O, $NR^{22A}$, or S; and $R^{12}$, $R^{13}$, $R^{14}$, $R^{15}$ $R^{21}$ $R^{21A}$, $R^{22}$, and $R^{22A}$ are independently hydrogen, halogen, $—N_3$, $—CF_3$, $—CCl_3$, $—CBr_3$, $—CI_3$, $—CN$, $—CHO$, $—OR^{33M}$, $—NR^{34M}R^{35M}$, $—COOR^{33M}$, $—CONR^{34M}R^{35M}$, $—NO_2$, $—SR^{36M}$, $—SO_{n13}R^{34M}$, $—SO_{n13}OR^{34M}$, $—SO_{n13}NR^{34M}R^{35M}$, $—NHNR^{34M}R^{35M}$, $—ONR^{34M}R^{35M}$, $—NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

Embodiment 72

The compound of embodiments 66-71 having the formula

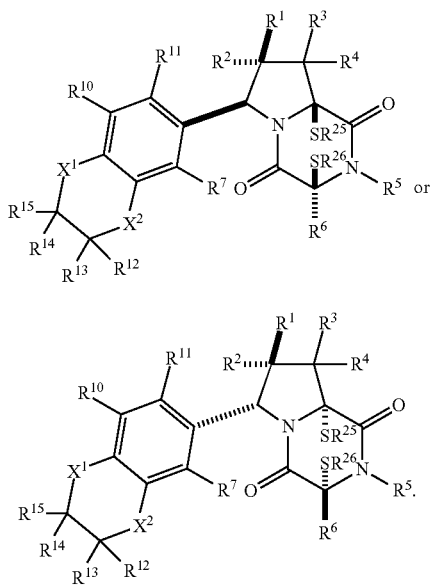

(X(S))

(X(R))

Embodiment 73

The compound of embodiments 6-72 having the formula

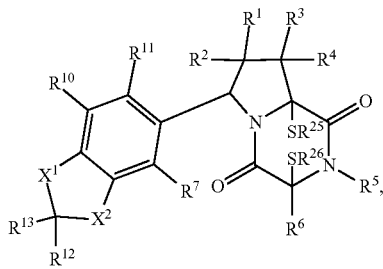

(XI)

wherein, $X^1$ is $CR^{21}R^{21A}$, O, $NR^{21A}$, or S; $X^2$ is $CR^{22}R^{22A}$, O, $NR^{22A}$, or S; $R^7$ is hydrogen, halogen, $-N_3$, $-CF_3$, $-CCl_3$, $-CBr_3$, $-CI_3$, $-CN$, $-CHO$, $-OR^{33I}$, $-NR^{34I}R^{35I}$, $-COOR^{33I}$, $-CONR^{34I}R^{35I}$, $-NO_2$, $-SR^{36I}$, $-SO_{n9}R^{34I}$, $-SO_{n9}OR^{34I}$, $-SO_{n9}NR^{34I}R^{35I}$, $-NHNR^{34I}R^{35I}$, $-ONR^{34I}R^{35I}$, $-NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ and $R^{11}$ are independently hydrogen, halogen, $-N_3$, $-CF_3$, $-CCl_3$, $-CBr_3$, $-CI_3$, $-CN$, $-CHO$, $-OR^{33L}$, $-NR^{34L}R^{35L}$, $-COOR^{33L}$, $-CONR^{34L}R^{35L}$, $-NO_2$, $-SR^{36L}$, $-SO_{n12}R^{34L}$, $-SO_{n12}OR^{34L}$, $-SO_{n12}NR^{34L}R^{35L}$, $-NHNR^{34L}R^{35L}$, $-ONR^{34L}R^{35L}$, $-NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; $R^{12}$, $R^{13}$, $R^{21}$, $R^{21A}$, $R^{22}$ and $R^{22A}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n11, and n13 are independently 1 or 2.

Embodiment 74

The compound of embodiments 66-73 having the formula

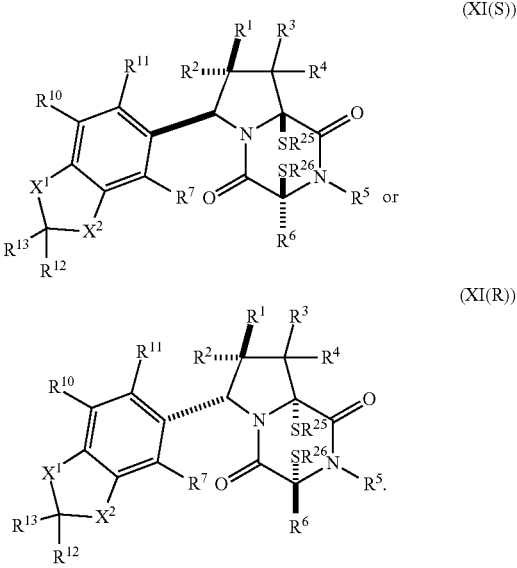

(XI(S))

(XI(R))

Embodiment 75

The compound of embodiments 66-74 having the formula

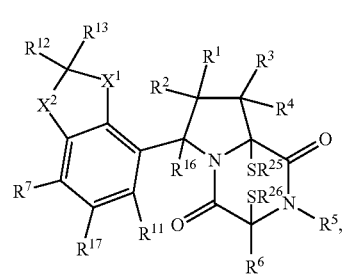

(XII)

wherein, $X^1$ is $CR^{21}R^{21A}$, O, $NR^{21A}$, or S; $X^2$ is $CR^2R^{22A}$, O, $NR^{22A}$, or S; and $R^7$ is hydrogen, halogen, $-N_3$, $-CF_3$, $-CCl_3$, $-CBr_3$, $-CI_3$, $-CN$, $-CHO$, $-OR^{33I}$, —NR³⁴ᴵR³⁵ᴵ, —COOR³³, —CONR³⁴ᴵR³⁵ᴵ, —NO₂, —SR³⁶ᴵ, —SO$_{n9}$R³⁴ᴵ, —SO$_{n9}$OR³⁴ᴵ, —SO$_{n9}$NR³⁴ᴵR³⁵ᴵ, —NHNR³⁴ᴵR³⁵ᴵ, —ONR³⁴ᴵR³⁵ᴵ, —NHC(O)NHNR³⁴ᴵR³⁵ᴵ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹¹ is hydrogen, halogen, —N₃, —CF₃, —CCl₃, —CBr₃, —CI₃, —CN, —CHO, —OR³³ᴸ, —NR³⁴ᴸR³⁵ᴸ, —COOR³³ᴸ, —CONR³⁴ᴸR³⁵ᴸ, —NO₂, —SR³⁶ᴸ, —SO$_{n12}$R³⁴ᴸ, —SO$_{n12}$OR³⁴ᴸ, —SO$_{n12}$NR³⁴ᴸR³⁵ᴸ, —NHNR³⁴ᴸR³⁵ᴸ, —ONR³⁴ᴸR³⁵ᴸ, —NHC(O)NHNR³⁴ᴸR³⁵ᴸ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; R¹², R¹³, R²¹, R²¹ᴬ, R²², and R²²ᴬ are independently hydrogen, halogen, —N₃, —CF₃, —CCl₃, —CBr₃, —CI₃, —CN, —CHO, —OR³³ᴹ, —NR³⁴ᴹR³⁵ᴹ, —COOR³³ᴹ, —CONR³⁴ᴹR³⁵ᴹ, —NO₂, —SR³⁶ᴹ, —SO$_{n13}$R³⁴ᴹ, —SO$_{n13}$OR³⁴ᴹ, —SO$_{n13}$NR³⁴ᴹR³⁵ᴹ, —NHNR³⁴ᴹR³⁵ᴹ, —ONR³⁴ᴹR³⁵ᴹ, —NHC(O)NHNR³⁴ᴹR³⁵ᴹ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹⁷ is hydrogen, halogen, —N₃, —CF₃, —CCl₃, —CBr₃, —CI₃, —CN, —CHO, —OR³³ᴾ, —NR³⁴ᴾR³⁵ᴾ, —COOR³³ᴾ, —CONR³⁴ᴾR³⁵ᴾ, —NO₂, —SR³⁶ᴾ, —SO$_{n15}$R³⁴ᴾ, —SO$_{n15}$OR³⁴ᴾ, —SO$_{n15}$NR³⁴ᴾR³⁵ᴾ, —NHNR³⁴ᴾR³⁵ᴾ, —ONR³⁴ᴾR³⁵ᴾ, —NHC(O)NHNR³⁴ᴾR³⁵ᴾ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl; R³³ᴵ, R³⁴ᴵ, R³⁵ᴵ, R³⁶ᴵ, R³³ᴸ, R³⁴ᴸ, R³⁵ᴸ, R³⁶ᴸ, R³³ᴹ, R³⁴ᴹ, R³⁵ᴹ, R³⁶ᴹ, R³³ᴾ, R³⁴ᴾ, R³⁵ᴾ, and R³⁶ᴾ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n12, n13 and n15 are independently 1 or 2.

Embodiment 76

The compound of embodiments 66-75 having the formula

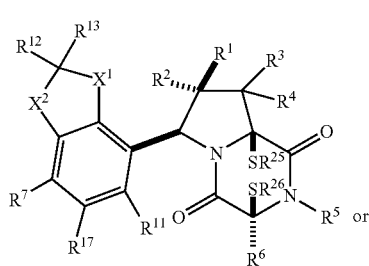

(XII(S))

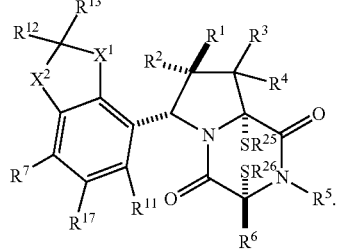

(XII(R))

Embodiment 77

A compound having the formula

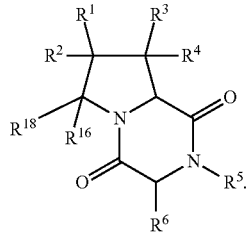

(XIII)

wherein, R¹ is hydrogen, halogen, —N₃, —CF₃, —CCl₃, —CBr₃, —CI₃, —CN, —CHO, —OR³³ᴬ, —NR³⁴ᴬR³⁵ᴬ, —COOR³³ᴬ, —CONR³⁴ᴬR³⁵ᴬ, —NO₂, —SR³⁶ᴬ, —SO$_{n1}$R³⁴ᴬ, —SO$_{n1}$OR³⁴ᴬ, —SO$_{n1}$NR³⁴ᴬR³⁵ᴬ, —NHNR³⁴ᴬR³⁵ᴬ, —ONR³⁴ᴬR³⁵ᴬ, —NHC(O)NHNR³⁴ᴬR³⁵ᴬ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R² is hydrogen, halogen, —N₃, —CF₃, —CCl₃, —CBr₃, —CI₃, —CN, —CHO, —OR³³ᴮ, —NR³⁴ᴮR³⁵ᴮ, —COOR³³ᴮ, —CONR³⁴ᴮR³⁵ᴮ, —NO₂, —SR³⁶ᴮ, —SO$_{n2}$R³⁴ᵇ, —SO$_{n2}$OR³⁴ᴮ, —SO$_{n2}$NR³⁴ᴮR³⁵ᴮ, —NHNR³⁴ᴮR³⁵ᴮ, —ONR³⁴ᴮR³⁵ᴮ, —NHC(O)NHNR³⁴ᴮR³⁵ᴮ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R³ is hydrogen, halogen, —N₃, —CF₃, —CCl₃, —CBr₃, —CI₃, —CN, —CHO, —OR³³c, —NR³⁴ᶜR³⁵ᶜ, —COOR³³ᶜ, —CONR³⁴ᶜR³⁵ᶜ, —NO₂, —SR³⁶c, —SO$_{n3}$R³⁴ᶜ, —SO$_{n3}$OR³⁴ᶜ, —SO$_{n3}$NR³⁴ᶜR³⁵ᶜ, —NHNR³⁴ᶜR³⁵ᶜ, —ONR³⁴ᶜR³⁵ᶜ, —NHC(O)NHNR³⁴ᶜR³⁵ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁴ is hydrogen, halogen, —N₃, —CF₃, —CCl₃, —CBr₃, —CI₃, —CN, —CHO, —OR³³ᴰ, —NR³⁴ᴰR³⁵ᴰ, —COOR³³ᴰ, —CONR³⁴ᴰR³⁵ᴰ, —NO₂, —SR³⁶ᴰ, —SO$_{n4}$R³⁴ᴰ, —SO$_{n40}$R³⁴ᴰ, —SO$_{n4}$NR³⁴ᴰR³⁵ᴰ, —NHNR³⁴ᴰR³⁵ᴰ, —ONR³⁴ᴰR³⁵ᴰ, —NHC(O)NHNR³⁴ᴰR³⁵ᴰ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁵ is hydrogen, halogen, —N₃, —CF₃, —CCl₃, —CBr₃, —CI₃, —CN, —CHO, —OR³³ᴱ, —NR³⁴ᴱR³⁵ᴱ, —COOR³³ᴱ, —CONR³⁴ᴱR³⁵ᴱ, —NO₂, —SR³⁶ᴱ, —SO$_{n5}$R³⁴ᴱ, —SO$_{n5}$OR³⁴ᴱ, —SO$_{n5}$NR³⁴ᴱR³⁵ᴱ, —NHNR³⁴ᴱR³⁵ᴱ, —ONR³⁴ᴱR³⁵ᴱ, —NHC(O)NHNR³⁴ᴱR³⁵ᴱ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is hydrogen, halogen, $-N_3$, $-CF_3$, $-CCl_3$, $-CBr_3$, $-CI_3$, $-CN$, $-CHO$, $-OR^{33F}$, $-NR^{34F}R^{35F}$, $-COOR^{33F}$, $-CONR^{34F}R^{35F}$, $-NO_2$, $-SR^{36F}$, $-SO_{n6}R^{34F}$, $-SO_{n6}OR^{34F}$, $-SO_{n6}NR^{34F}R^{35F}$, $-NHNR^{34F}R^{35F}$, $-ONR^{34F}R^{35F}$, $-NHC(O)NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-N_3$, $-CF_3$, $-CCl_3$, $-CBr_3$, $-CI_3$, $-CN$, $-CHO$, $-OR^{33G}$, $-NR^{34G}R^{35G}$, $-COOR^{33G}$, $-CONR^{34G}R^{35G}$, $-NO_2$, $-SR^{36G}$, $-SO_{n7}R^{34G}$, $-SO_{n7}OR^{34G}$, $-SO_{n7}NR^{34G}R^{35G}$, $-NHNR^{34G}R^{35G}$, $-ONR^{34G}R^{35G}$, $-NHC(O)NHNR^{34G}R^{35G}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-N_3$, $-CF_3$, $-CCl_3$, $-CBr_3$, $-CI_3$, $-CN$, $-CHO$, $-OR^{33H}$, $-NR^{34H}R^{35H}$, $-COOR^{33H}$, $-CONR^{34H}R^{35H}$, $-NO_2$, $-SR^{36H}$, $-SO_{n8}R^{34H}$, $-SO_{n5}OR^{34H}$, $-SO_{n5}NR^{34H}R^{35H}$, $-NHNR^{34H}R^{35H}$, $-ONR^{34H}R^{35H}$, $-NHC(O)NHNR^{34H}R^{35H}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33A}$, $R^{34A}$, $R^{35A}$, $R^{36A}$, $R^{33B}$, $R^{34B}$, $R^{35B}$, $R^{36B}$, $R^{33C}$, $R^{34C}$, $R^{35C}$, $R^{36C}$, $R^{33D}$, $R^{34D}$, $R^{35D}$, $R^{36D}$, $R^{33E}$, $R^{34E}$, $R^{35E}$, $R^{36E}$, $R^{33F}$, $R^{34F}$, $R^{35F}$, $R^{36F}$, $R^{33G}$, $R^{34G}$, $R^{35G}$, $R^{36G}$, $R^{33H}$, $R^{34H}$, $R^{35H}$, and $R^{36H}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n6, n7, and n8 are independently 1 or 2.

Embodiment 78

The compound of embodiment 77 having formula

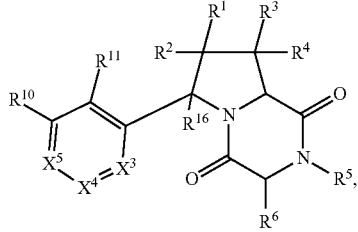

(XIV)

wherein, $X^3$ is N or $CR^7$; $X^4$ is N or $CR^8$; $X^5$ is N or $CR^9$; $R^7$ is hydrogen, halogen, $-N_3$, $-CF_3$, $-CCl_3$, $-CBr_3$, $-CI_3$, $-CN$, $-CHO$, $-OR^{33I}$, $-NR^{34I}R^{35I}$, $-COOR^{33I}$, $-CONR^{34I}R^{35I}$, $-NO_2$, $-SR^{36I}$, $-SO_{n9}R^{34I}$, $-SO_{n9}OR^{34I}$, $-SO_{n9}NR^{34I}R^{35I}$, $-NHNR^{34I}R^{35I}$, $-ONR^{34I}R^{35I}$, $-NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-N_3$, $-CF_3$, $-CCl_3$, $-CBr_3$, $-CI_3$, $-CN$, $-CHO$, $-OR^{33J}$, $-NR^{34J}R^{35J}$, $-COOR^{33J}$, $-CONR^{34J}R^{35J}$, $-NO_2$, $-SR^{36J}$, $-SO_{n10}R^{34J}$, $-SO_{n10}OR^{34J}$, $-SO_{n10}NR^{34J}R^{35J}$, $-NHNR^{34J}R^{35J}$, $-ONR^{34J}R^{35J}$, $-NHC(O)NHNR^{34J}R^{35J}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-N_3$, $-CF_3$, $-CCl_3$, $-CBr_3$, $-CI_3$, $-CN$, $-CHO$, $-OR^{33K}$, $-NR^{34K}R^{35K}$, $-COOR^{33K}$, $-CONR^{34K}R^{35K}$, $-NO_2$, $-SR^{36K}$, $-SO_{n11}R^{34K}$, $-SO_{n11}OR^{34K}$, $-SO_{n11}NR^{34K}R^{35K}$, $-NHNR^{34K}R^{35K}$, $-ONR^{34K}R^{35K}$, $-NHC(O)NHNR^{34K}R^{35K}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ and $R^{11}$ are independently hydrogen, halogen, $-N_3$, $-CF_3$, $-CCl_3$, $-CBr_3$, $-CI_3$, $-CN$, $-CHO$, $-OR^{33L}$, $-NR^{34L}R^{35L}$, $-COOR^{33L}$, $-CONR^{34L}R^{35L}$, $-NO_2$, $-SR^{36L}$, $-SO_{n12}R^{34L}$, $-SO_{n12}OR^{34L}$, $-SO_{n12}NR^{34L}R^{35L}$, $-NHNR^{34L}R^{35L}$, $-ONR^{34L}R^{35L}$, $-NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; $R^{33I}$, $R^{34I}$, $R^{35I}$, $R^{36I}$, $R^{33J}$, $R^{34J}$, $R^{35J}$, $R^{36J}$, $R^{33K}$, $R^{34K}$, $R^{35K}$, $R^{36K}$, $R^{33L}$, $R^{34L}$, $R^{35L}$, and $R^{36L}$, are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n10, n11, and n12 are independently 1 or 2.

Embodiment 79

The compound of embodiments 77-78 having formula

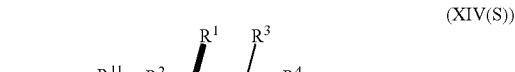

(XIV(S))

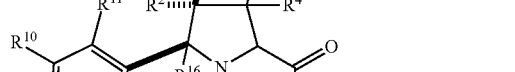

(XIV(R))

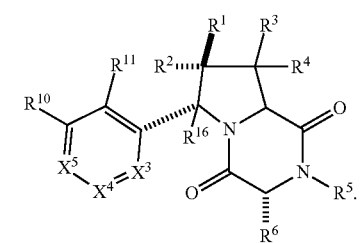

Embodiment 80

The compound of embodiment 77 having formula

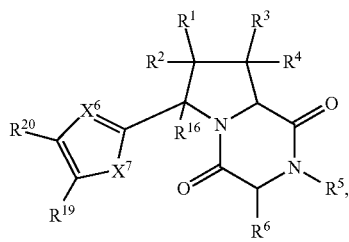
(XV)

wherein, $X^6$ is $CR^{21}$ or N; $X^7$ is $CR^{22}R^{23}$, S, O, or $NR^{23}$; $R^{19}$, $R^{20}$, $R^{21}$, $R^{22}$ and $R^{23}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

Embodiment 81

The compound of embodiments 77 or 80 having formula

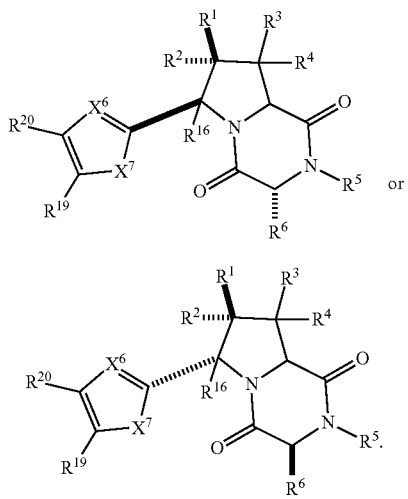

(XV(S))

or (XV(R))

Embodiment 82

The compound of embodiment 77 having formula (XVI)

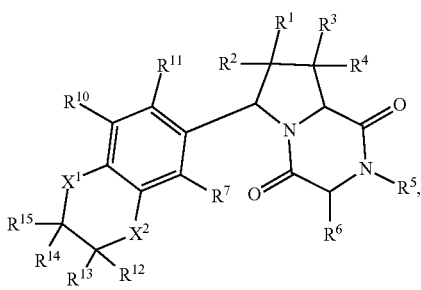

wherein, $X^1$ is $CR^{21}R^{21A}$, O, $NR^{21A}$, or S; $X^2$ is $CR^{22}R^{22A}$, O, $NR^{22A}$, or S; and $R^{12}$, $R^{13}$, $R^{14}$, $R^{15}$ $R^{21}$, $R^{21A}$, $R^{22}$, and $R^{22A}$ are independently hydrogen, halogen, $-N_3$, $-CF_3$, $-CCl_3$, $-CBr_3$, $-CI_3$, $-CN$, $-CHO$, $-OR^{33M}$, $-NR^{34M}R^{35M}$, $-COOR^{33M}$, $-CONR^{34M}R^{35M}$, $-NO_2$, $-SR^{36M}$, $-SO_{n13}R^{34M}$, $-SO_{n13}OR^{34M}$, $-SO_{n13}NR^{34M}R^{35M}$, $-NHNR^{34M}R^{35M}$, $-ONR^{34M}R^{35M}$, $-NHC(O)NHNR^{34M}R^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{33M}$, $R^{34M}$, $R^{35M}$, and $R^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n13 is 1 or 2.

Embodiment 83

The compound of embodiments 77 or 82 having formula

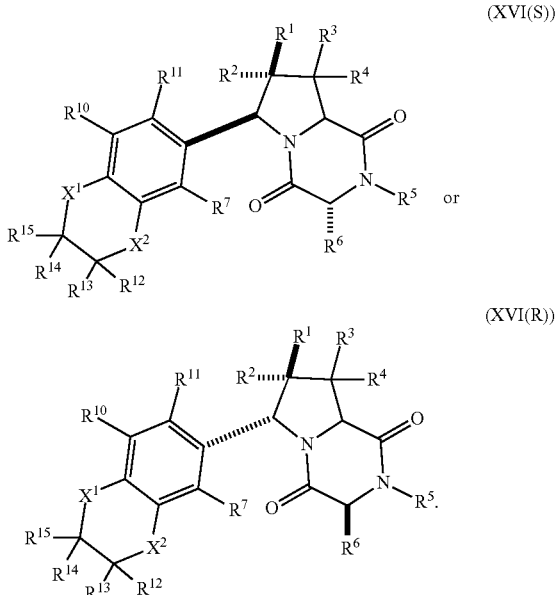

(XVI(S))

or (XVI(R))

Embodiment 84

The compound of embodiment 77 having formula (XVII)

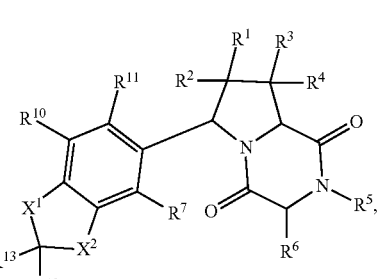

wherein, $X^1$ is $CR^{21}R^{21A}$, O, $NR^{21A}$, or S; $X^2$ is $CR^{22}R^{22A}$, O, $NR^{22A}$, or S; $R^7$ is hydrogen, halogen, $-N_3$, $-CF_3$, —CCl₃, —CBr₃, —Cl₃, —CN, —CHO, —OR³³ᴵ, —NR³⁴ᴵR³⁵ᴵ, —COOR³³ᴵ, —CONR³⁴ᴵR³⁵ᴵ, —NO₂, —SR³⁶ᴵ, —SO$_{n9}$R³⁴ᴵ, —SO$_{n9}$OR³⁴ᴵ, —SO$_{n9}$NR³⁴ᴵR³⁵ᴵ, —NHNR³⁴ᴵR³⁵ᴵ, —ONR³⁴ᴵR³⁵ᴵ, —NHC(O)NHNR³⁴ᴵR³⁵ᴵ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹⁰ and R¹¹ are independently hydrogen, halogen, —N₃, —CF₃, —CCl₃, —CBr₃, —Cl₃, —CN, —CHO, —OR³³ᴸ, —NR³⁴ᴸR³⁵ᴸ, —COOR³³ᴸ, —CONR³⁴ᴸR³⁵ᴸ, —NO₂, —SR³⁶ᴸ, —SO$_{n12}$R³⁴ᴸ, —SO$_{n12}$OR³⁴ᴸ, —SO$_{n12}$NR³⁴ᴸR³⁵ᴸ, —NHNR³⁴ᴸR³⁵ᴸ, —ONR³⁴ᴸR³⁵ᴸ, —NHC(O)NHNR³⁴ᴸR³⁵ᴸ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; R¹², R¹³, R²¹, R²¹ᴬ, R²² and R²²ᴬ are independently hydrogen, halogen, —N₃, —CF₃, —CCl₃, —CBr₃, —Cl₃, —CN, —CHO, —OR³³ᴹ, —NR³⁴ᴹR³⁵ᴹ, —COOR³³ᴹ, —CONR³⁴ᴹR³⁵ᴹ, —NO₂, —SR³⁶ᴹ, —SO$_{n13}$R³⁴ᴹ, —SO$_{n13}$OR³⁴ᴹ, —SO$_{n13}$NR³⁴ᴹR³⁵ᴹ, —NHNR³⁴ᴹR³⁵ᴹ, —ONR³⁴ᴹR³⁵ᴹ, —NHC(O)NHNR³⁴ᴹR³⁵ᴹ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R³³ᴹ, R³⁴ᴹ, R³⁵ᴹ, and R³⁶ᴹ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n11, and n13 are independently 1 or 2.

Embodiment 85

The compound of embodiments 77 or 84 having formula

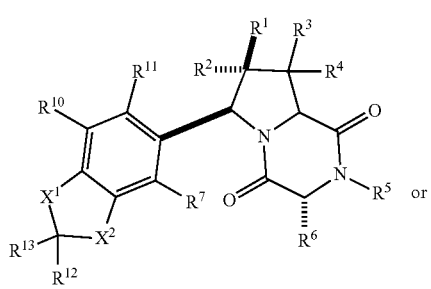

(XVII(S))

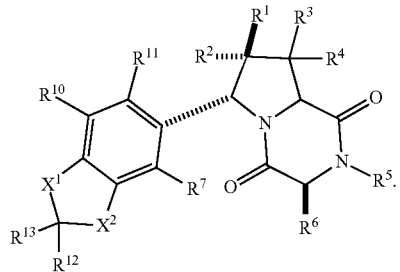

(XVII(R))

Embodiment 86

The compound of embodiment 77 having formula

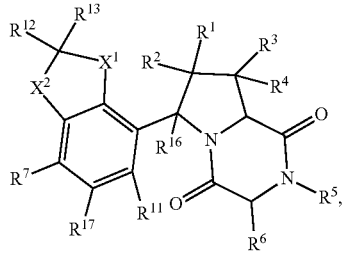

(XVIII)

wherein, X¹ is CR²¹R²¹ᴬ, O, NR²¹ᴬ, or S; X² is CR²²R²²ᴬ, O, NR²²ᴬ, or S; and R⁷ is hydrogen, halogen, —N₃, —CF₃, —CCl₃, —CBr₃, —Cl₃, —CN, —CHO, —OR³³ᴵ, —NR³⁴ᴵR³⁵ᴵ, —COOR³³ᴵ, —CONR³⁴ᴵR³⁵ᴵ, —NO₂, —SR³⁶ᴵ, —SO$_{n9}$R³⁴ᴵ, —SO$_{n9}$OR³⁴ᴵ, —SO$_{n9}$NR³⁴ᴵR³⁵ᴵ, —NHNR³⁴ᴵR³⁵ᴵ, —ONR³⁴ᴵR³⁵ᴵ, —NHC(O)NHNR³⁴ᴵR³⁵ᴵ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹¹ is hydrogen, halogen, —N₃, —CF₃, —CCl₃, —CBr₃, —Cl₃, —CN, —CHO, —OR³³ᴸ, —NR³⁴ᴸR³⁵ᴸ, —COOR³³ᴸ, —CONR³⁴ᴸR³⁵ᴸ, —NO₂, —SR³⁶ᴸ, —SO$_{n12}$R³⁴ᴸ, —SO$_{n12}$OR³⁴ᴸ, —SO$_{n12}$NR³⁴ᴸR³⁵ᴸ, —NHNR³⁴ᴸR³⁵ᴸ, —ONR³⁴ᴸR³⁵ᴸ, —NHC(O)NHNR³⁴ᴸR³⁵ᴸ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl; R¹², R¹³, R²¹' R²¹ᴬ, R²², and R²²ᴬ are independently hydrogen, halogen, —N₃, —CF₃, —CCl₃, —CBr₃, —Cl₃, —CN, —CHO, —OR³³ᴹ, —NR³⁴ᴹR³⁵ᴹ, —COOR³³ᴹ, —CONR³⁴ᴹR³⁵ᴹ, —NO₂, —SR³⁶ᴹ, —SO$_{n13}$R³⁴ᴹ, —SO$_{n13}$OR³⁴ᴹ, —SO$_{n13}$NR³⁴ᴹR³⁵ᴹ, —NHNR³⁴ᴹR³⁵ᴹ, —ONR³⁴ᴹR³⁵ᴹ, —NHC(O)NHNR³⁴ᴹR³⁵ᴹ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹⁷ is hydrogen, halogen, —N₃, —CF₃, —CCl₃, —CBr₃, —Cl₃, —CN, —CHO, —OR³³, —NR³⁴ᴾR³⁵ᴾ, —COOR³³ᴾ, —CONR³⁴ᴾR³⁵ᴾ, —NO₂, —SR³⁶ᴾ, —SO$_{n15}$R³⁴ᴾ, —SO$_{n15}$OR³⁴ᴾ, —SO$_{n15}$NR³⁴ᴾR³⁵ᴾ, —NHNR³⁴ᴾR³⁵ᴾ, —ONR³⁴ᴾR³⁵ᴾ, —NHC(O)NHNR³⁴ᴾR³⁵ᴾ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl; R³³ᴵ, R³⁴ᴵ, R³⁵ᴵ, R³⁶ᴵ, R³³ᴸ, R³⁴ᴸ, R³⁵ᴸ, R³⁶ᴸ, R³³ᴹ, R³⁴ᴹ, R³⁵ᴹ, R³⁶ᴹ, R³³ᴾ, R³⁴ᴾ, R³⁵ᴾ, and R³⁶ᴾ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9, n12, n13 and n15 are independently 1 or 2.

Embodiment 87

The compound of embodiments 77 or 86 having formula

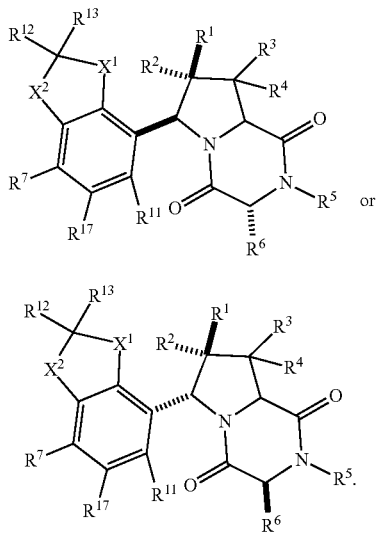

(XVIII(S))

(XVIII(R))

Embodiment 88

The compound of embodiment 1, wherein said compound is an epigenetic inhibitor.

Embodiment 89

The compound of embodiment 88, wherein said compound inhibits the activity of HMT SUV39H1.

Embodiment 90

The compound of embodiments 88-89, wherein said compound specifically inhibits the activity of HMT SUV39H1.

Embodiment 91

The compound of embodiments 88-90, wherein said compound inhibits the activity of HMT G9a.

Embodiment 92

The compound of embodiments 88-91, wherein said compound specifically inhibits the activity of HMT G9a Embodiment 93

The compound of any one of embodiments 88-92, wherein said compound inhibits the activity of HMT SUV39H1 and the activity of HMT G9a.

Embodiment 94

The compound of any one of embodiments 88-93, wherein said compound specifically inhibits the activity of HMT SUV39H1 and the activity of HMT G9a.

Embodiment 95

The compound of embodiment 1, wherein said compound inhibits H3K9 trimethylation or dimethylation.

Embodiment 96

A method of treating cancer, said method comprising administering to a subject in need thereof a therapeutically effective amount of a compound of one of embodiment 1.

Embodiment 97

The method of embodiments 95-96, wherein said cancer is a solid or blood tumor.

Embodiment 98

The method of embodiments 96 or 97, wherein said cancer is ovarian cancer, breast cancer, lung cancer, leukemia, AML, CML, lymphoma, pancreatic cancer, kidney cancer, melanoma, liver cancer, colon cancer, sarcoma, multiple myeloma, brain cancer, or prostate cancer.

Embodiment 99

The method of embodiments 96-98, further comprising administering at least one additional anticancer agent.

Embodiment 100

The method of embodiments 96 to 99, wherein said at least one additional anticancer agent comprises an epigenetic inhibitor or a multi-kinase inhibitor.

Embodiment 101

The method of embodiments 96 to 100, wherein said method comprises administering a first amount of said compound and a second amount of at least one additional anticancer agent, wherein the first amount and second amount are together an effective amount to provide a synergistic therapeutic effect.

Embodiment 102

The method of embodiments 96 to 101, wherein said additional anticancer agent is an epigenetic inhibitor.

Embodiment 103

The method of embodiments 96 or 102, wherein said epigenetic inhibitor is azacitidine or decitadine.

Embodiment 104

The method of embodiments 96 to 103, wherein said compound and said epigenetic inhibitor are co-administered as a pharmaceutical composition.

Embodiment 105

The method embodiments 96-101, wherein said additional anticancer agent is a multi-kinase inhibitor.

Embodiment 106

The method of embodiments 96-105, wherein said multi-kinase inhibitor is sorafenib.

Embodiment 107

The method of embodiment 96-105, wherein said compound and said multi-kinase inhibitor are co-administered as a pharmaceutical composition.

Embodiment 108

The method of embodiments 96 to 107, wherein said cancer is ovarian cancer.

Embodiment 109

A pharmaceutical composition comprising a compound of embodiment 1 and a pharmaceutically acceptable excipient.

Embodiment 110

A pharmaceutical composition comprising a compound of embodiment 1 and at least one additional anticancer agent.

Embodiment 111

The pharmaceutical composition of embodiment 110, wherein said at least one additional anticancer agent comprises a multi-kinase inhibitor or an epigenetic inhibitor.

Embodiment 112

The pharmaceutical composition of embodiments 110 or 111, wherein said combination includes a first amount of said compound and a second amount of a multi-kinase inhibitor, wherein the first amount and second amount are together an effective amount to provide a synergistic therapeutic effect.

Embodiment 113

The pharmaceutical composition of embodiments 110 to 112, wherein said combination includes a first amount of said compound and a second amount of an epigenetic inhibitor, wherein the first amount and second amount are together an effective amount to provide a synergistic therapeutic effect.

Embodiment 114

The pharmaceutical composition of embodiments 110 to 113, wherein said combination includes a first amount of said compound, a second amount of a multi-kinase inhibitor, an a third amount of an epigenetic inhibitor, wherein the first amount, second, and third amounts are together an effective amount to provide a synergistic therapeutic effect.

Embodiment 115

The pharmaceutical composition of any one of embodiments 109 to 113, wherein said multi-kinase inhibitor is sorafenib and said epigenetic inhibitor is azacitidine or decitadine.

Embodiment 116

The pharmaceutical composition of any one of embodiments 109 to 115, for use in cancer.

Embodiment 117

The pharmaceutical composition of any one of embodiments 109 to 116, for use in solid and blood tumors, including ovarian cancer, breast cancer, lung cancer, leukemia, AML, CML, lymphoma, pancreatic cancer, kidney cancer, melanoma, liver cancer, colon cancer, sarcoma, multiple myeloma, brain cancer, or prostate cancer.

Embodiment 118

The pharmaceutical composition of any one of embodiments 109 to 117, for use in non-small cell lung cancer.

Embodiment 119

The pharmaceutical composition of any one of embodiments 109 to 118, wherein said compound and said multi-kinase inhibitor or said epigenetic inhibitor are co-administered as a single dosage form.

Embodiment 120

A compound having the formula

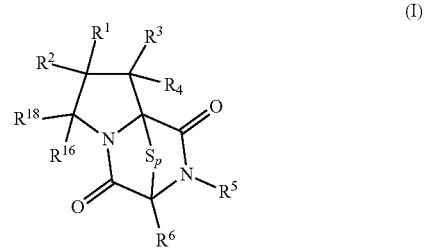

(I)

wherein, p is 2, 3 or 4; and $R^1$, $R^2$, $R^3$, $R^4$, $R^5$, $R^6$, $R^{16}$, and $R^{18}$ are independently hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 121

The compound of embodiment 120, wherein $R^{18}$ is substituted or unsubstituted aryl or substituted or unsubstituted heteroaryl.

Embodiment 122

The compound of embodiment 120-121 having the formula

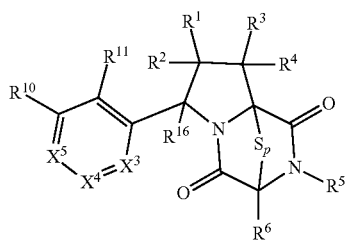

(Ia)

wherein, $X^3$ is N or $CR^7$; $X^4$ is N or $CR^8$; $X^5$ is N or $CR^9$; $R^7$, $R^{10}$ and $R^{11}$ are independently hydrogen, halogen, —N₃, —CF₃, —CCl₃, —CBr₃, —CI₃, —CN, —CHO, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ and $R^9$ are independently hydrogen, halogen, —N₃, —NO₂, —CF₃, —CCl₃, —CBr₃, —CI₃, —CN, —OH, —NH₂, —COOH, —CONH₂, —NO₂, —SH, —SO₂Cl, —SO₃H, —SO₄H, —SO₂NH₂, —NHNH₂, —ONH₂, —OCH₃, —NHCNHNH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^8$ and $R^9$ are optionally joined together to form a substituted or unsubstituted cycloalkyl, a substituted or unsubstituted heterocycloalkyl, a substituted or unsubstituted aryl, or a substituted or unsubstituted heteroaryl; and p is 2, 3, or 4.

Embodiment 123

The compound of embodiment 120-122 having the formula

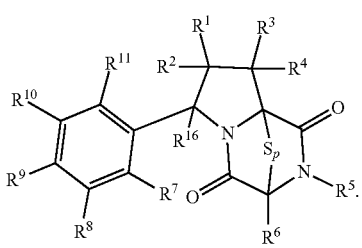

(Ib)

Embodiment 124

The compound of embodiment 120-122 having the formula

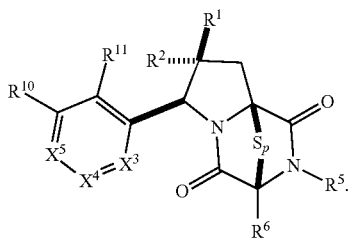

(Ic)

Embodiment 125

The compound of embodiment 120-122 having the formula

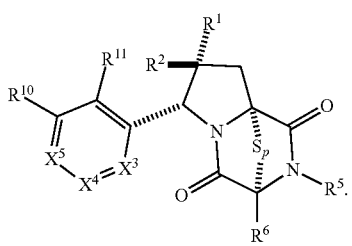

(Id)

Embodiment 126

The compound of any one of embodiments 122-125 having formula

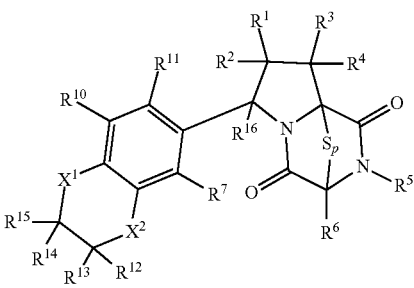

(II)

wherein, $X^1$ and $X^2$ are independently CH₂, O, NH, N, S, or Se; and $R^{12}$, $R^{13}$, $R^{14}$, and $R^{15}$ are independently hydrogen, halogen, —N₃, —NO₂, —CF₃, CCl₃, CBr₃, CI₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂; substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl.

Embodiment 127

The compound of embodiment 126 having formula

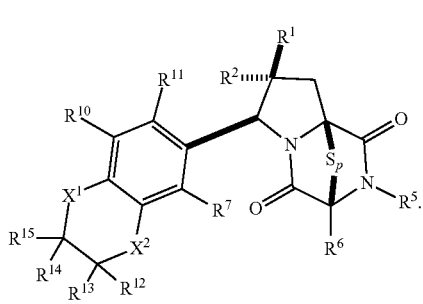

(IIa)

Embodiment 128

The compound of embodiment 127 having formula

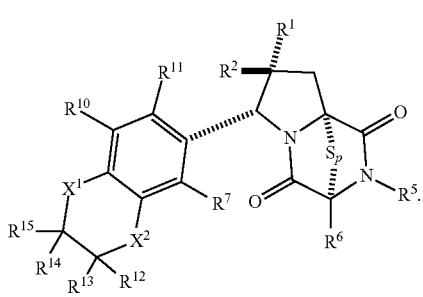

(IIb)

The compound of one of embodiments 120 to 129, wherein p is 2

Embodiment 130

The compound of any one of embodiments 126-129 having formula

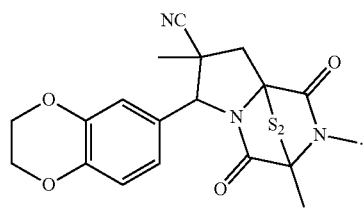

Embodiment 131

The compound of embodiment 120 having formula

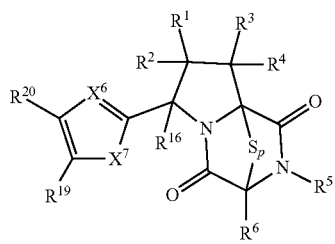

wherein, $X^6$ is CH, $CR^{21}$, S, O, or N; $X^7$ is $CH_2$, $CR^{22}$, S, O, N, or NH; $R^{19}$, $R^{20}$, $R^{21}$, and $R^{22}$ are independently hydrogen, halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$; substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl.

Embodiment 132

The compound of any one of embodiments 120 or 131 having formula

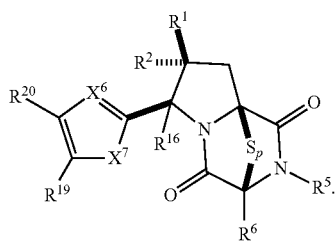

Embodiment 133

The compound of any one of embodiments 120 or 131 having formula

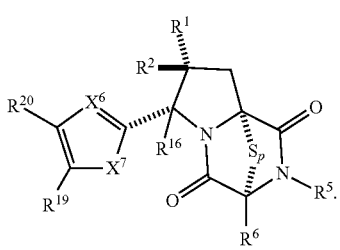

Embodiment 134

The compound of any one of embodiments 120 or 131-133 having formula

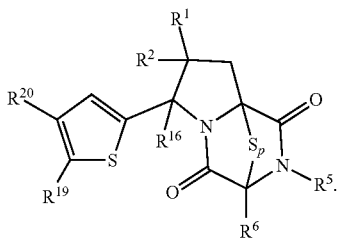

Embodiment 135

The compound of any one of embodiments 120-125 having formula

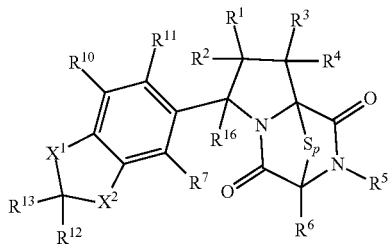

(III)

wherein, $R^{12}$ and $R^{13}$ are independently hydrogen, halogen, —$N_3$, —$CF_3$, $CCl_3$, $CBr_3$, $CI_3$, —CN, —OH, —$NH_2$, —COOH, $CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl.

Embodiment 136

The compound of embodiment 135 having formula

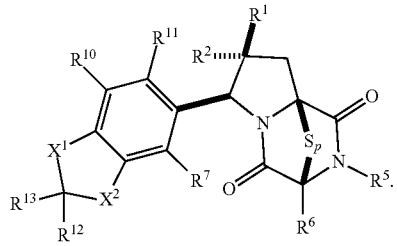

(IIIa)

Embodiment 137

The compound of embodiment 135 having formula

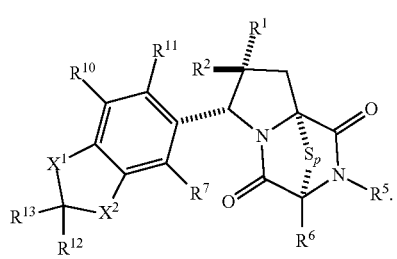

(IIIb)

Embodiment 138

The compound of any one of embodiments 120-125 or 135-137 having formula

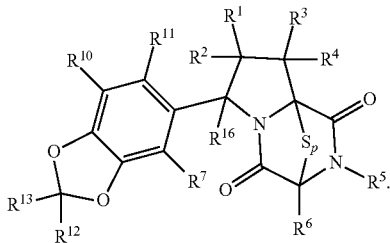

(IV)

Embodiment 139

The compound of embodiment 138 having formula

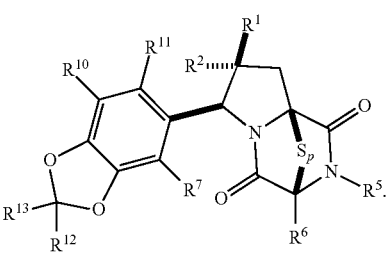

(IVa)

Embodiment 140

The compound of embodiment 138 having formula

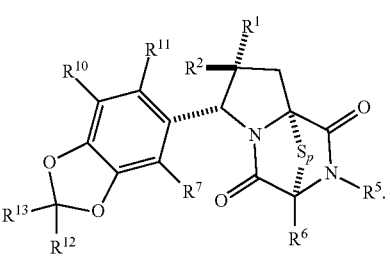

(IVb)

Embodiment 141

The compound of any one of embodiments 135 to 140, wherein p is 2

Embodiment 142

The compound of any one of embodiment 120-128 or 135-141, wherein $R^1$ is halogen, —$N_3$, —$NO_2$, —$CF_3$, $CCl_3$, $CBr_3$, $CI_3$, —CN, —CHO, —$CONH_2$, or substituted or unsubstituted heteroalkyl.

Embodiment 143

The compound of any one of embodiments 120-128 or 135-142, wherein $R^2$ is halogen, —$N_3$, —$NO_2$, —$CF_3$, $CCl_3$, $CBr_3$, $CI_3$, —CN, —CHO, —$CONH_2$, or substituted or unsubstituted heteroalkyl.

Embodiment 144

The compound of any one of embodiments 120-128 or 135-142, wherein $R^1$ is CN.

Embodiment 145

The compound of any one of embodiments 120-128 or 135-144, wherein $R^1$ is $C_1$-$C_5$ substituted or unsubstituted heteroalkyl.

Embodiment 146

The compound of any one of embodiments 120-128 or 135-145, wherein $R^2$ is CN.

Embodiment 147

The compound of any one of embodiments 120-128 or 135-146, wherein $R^2$ is $C_1$-$C_5$ substituted or unsubstituted heteroalkyl.

Embodiment 148

The compound of embodiment 142, wherein said substituted or substituted heteroalkyl provides polarity.

Embodiment 149

The compound of any one of embodiments 120-128 or 135-148, wherein $R^6$ is hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Embodiment 150

The compound of any one of embodiments, 120-122, 126, 135, or 138, wherein $R^{16}$ is hydrogen, halogen, —$N_3$, —$CF_3$, —$CCl_3$, —$CBr_3$, —$Cl_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $C_1$-$C_3$ substituted or unsubstituted alkyl, or $C_1$-$C_3$ substituted or unsubstituted heteroalkyl.

Embodiment 151

The compound of any one of embodiments 120-128 or 135-140, wherein p is 3.

Embodiment 152

The compound of any one of embodiments 135, 136, 138, or 140 having formula

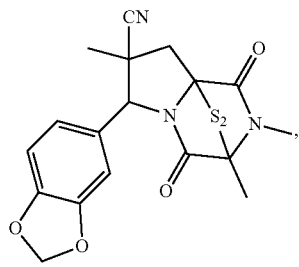

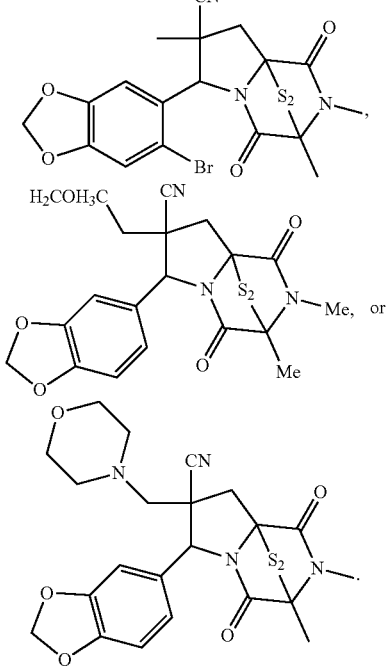

Embodiment 153

The compound of any one of embodiments 120-125 having formula

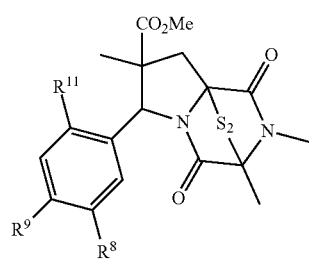

(V)

wherein, $R^8$ is hydrogen or $OCH_3$; and $R^9$ and $R^{11}$ are independently hydrogen or halogen.

Embodiment 154

The compound of any one of embodiments 120-125 having formula

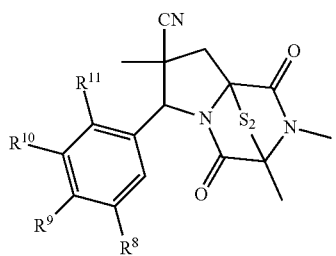

(VI)

wherein, $R^8$ is hydrogen or —$OCH_3$; and $R^9$, $R^{10}$, and $R^{11}$ are independently hydrogen or halogen.

Embodiment 155

The compound of any one of embodiments 135-140 having formula

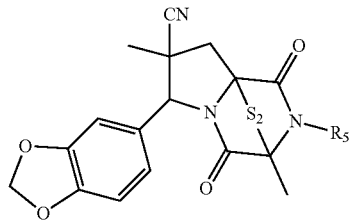

(VIII)

wherein; $R^5$ is unsubstituted alkyl, unsubstituted heteroalkyl, or unsubstituted heterocycloalkyl; and p is 2 or 3.

Embodiment 156

The compound of embodiment 120 having the formula

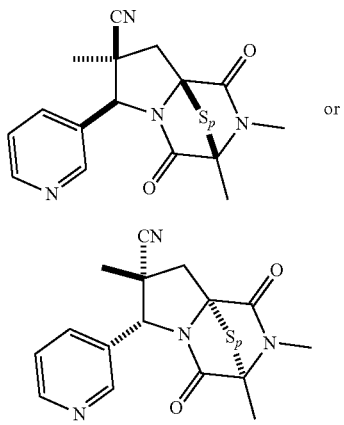

(IXa)

or (IXb)

wherein, p is 2 or 4.

Embodiment 157

The compound of embodiment 155 or 156 wherein p is 2.

Embodiment 158

The compound of embodiment 120 having the formula

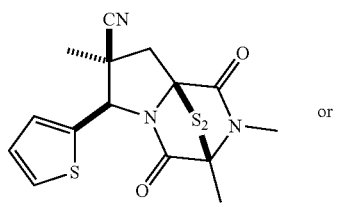

(VIIa)

or

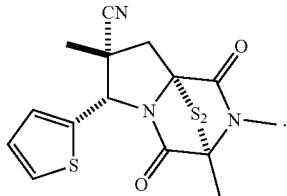

(VIIb)

Embodiment 159

The compound of any one of embodiments 120-128 or 135-140, wherein $R^1$ is CN and $R^2$ is substituted or unsubstituted $C_2$-$C_{20}$ alkyl, substituted or unsubstituted $C_2$-$C_{20}$ heteroalkyl, substituted or unsubstituted cycloalkyl, substituted or unsubstituted heterocycloalkyl, substituted or unsubstituted aryl, or substituted or unsubstituted heteroaryl.

Embodiment 160

A compound having formula

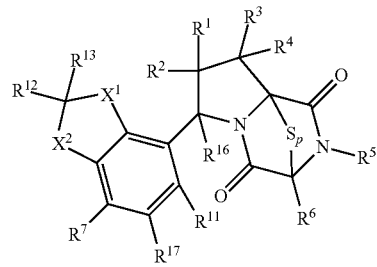

(X)

wherein, $R^{17}$ is hydrogen, halogen, —$N_3$, —$NO_2$, —$CF_3$, $CCl_3$, $CBr_3$, $CI_3$, —CN, —OH, —$NH_2$, —COOH, $CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$; substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl.

Embodiment 161

The compound of embodiment 160 having formula

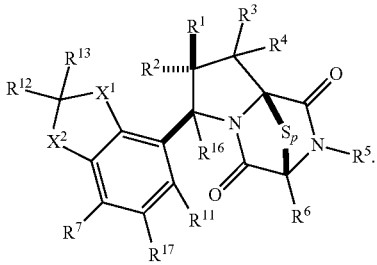

(XI)

Embodiment 162

The compound of embodiment 160 having formula

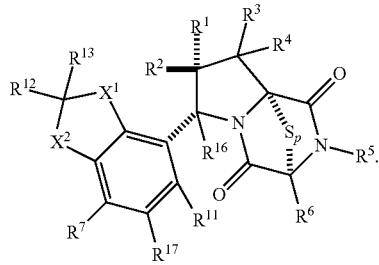
(XII)

Embodiment 163

The compound of embodiment 160 having formula

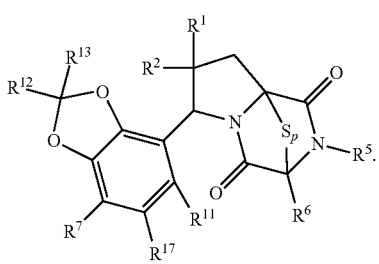
(XIII)

Embodiment 164

The compound of any one of embodiments 160 or 163 having formula

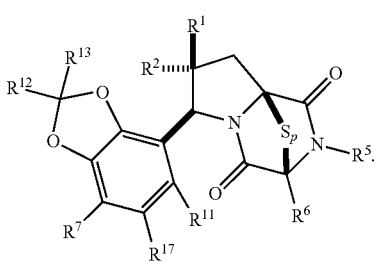
(XIV)

Embodiment 165

The compound of any one of embodiments 152 or 160 having formula

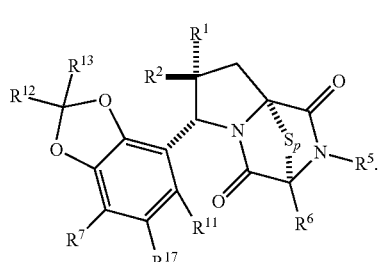
(XV)

Embodiment 166

The compound of any one of embodiments 160-165 wherein p is 2

Embodiment 167

The compound of any one of embodiments 160-165 having formula

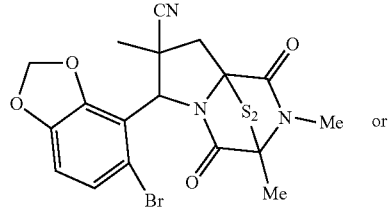 or

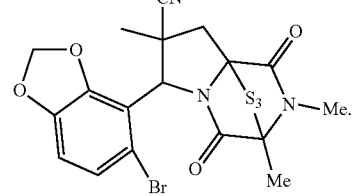

Embodiment 168

A compound having the formula

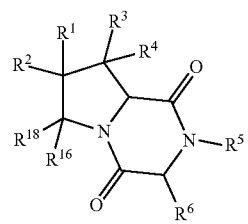
(XVI)

wherein, $R^1$, $R^2$, $R^3$, $R^4$, $R^5$, $R^6$, $R^{16}$, and $R^{18}$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 169

A compound of Formula I

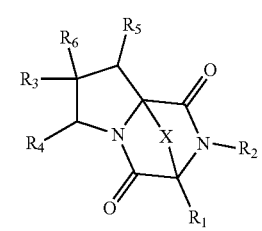
I wherein: X is selected from $S_2$, $S_3$, or $S_4$; $R_1$ is selected from H, alkyl, —C(=O)O-alkyl, alkoxy, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_2$ is selected from H, alkyl, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_3$ is selected from H, alkyl, aryl, heteroaryl, nitrile, F, Cl, OAc, —O-alkyl, or —O-aryl; $R_4$ is selected from alkyl, haloalkyl, biphenyl, thiophenyl, piperidyl, morpholinyl, imidazolyl, piperonyl, benzyl, cycloalkyl, benzodioxinyl, dioxinyl, benzodioxanyl, dioxanyl, benzoxazinyl, piperadinyl-1-methyl, heterocycle, indolyl, pyridinyl, piperazinyl, furyl, thienyl, heteroarylalkyl, or phenyl, or optionally substituted variants thereof; $R_5$ is selected from H, aryl, alkyl, haloalkyl, heteroaryl, phenyl, biphenyl, thiophenyl, piperidyl, morpholinyl, imidazolyl, piperonyl, benzyl, cycloalkyl, benzodioxinyl, dioxinyl, heterocycle, indolyl, or pyridinyl, or optionally substituted variants thereof; $R_6$ is selected from CN, $NO_2$, —$S(O)_2$ alkyl, —$S(O)_2$ aryl, —$S(O)_2R^7$, —$S(O)_2CH_2CN$, —(C=O)$NH_2$, —(N=H)OMe, —(C=O)(CH$_2$)$_{1-4}$CN, —(C=O)(CH$_2$)$_{1-4}$SO$_2$R$_7$, —(C=O)(CH$_2$)$_{1-4}$CO$_2$R$_7$, —(C=O)(CH$_2$)$_{1-4}$CO$_2$H, —(C=O)(CH$_2$)$_{1-4}$CH$_2$NH$_2$, —(C=O)(CH$_2$)$_{1-4}$CH$_2$NHCOR$_5$, —(C=O)(CH$_2$)$_{1-4}$CH$_2$NR$_1$R$_2$, (CH$_2$)$_{1-4}$OH, —(C=O)OH, —(C=O)O-alkyl, CH$_2$NHR$_9$, or CHR$_{10}$NHR$_{11}$; $R_7$ is alkyl; $R_8$ is selected from alkyl, heteroaryl, halo, alkoxy, thioalkyl, haloalkyl, $NO_2$, CN, —C(=O)O-alkyl, sulfonyl, or sulfonamide; $R_9$ is selected from H, alkyl, aryl, heteroaryl, acyl, or —O-carboxy; $R_{10}$ is selected from alkyl, aryl or heteroaryl; and $R_{11}$ is selected from H, alkyl, aryl, heteroaryl, acyl, or —O-carboxy.

Embodiment 170

The compound of embodiment 169, wherein X is $S_2$

Embodiment 171

The compound of embodiments 169-170, wherein $R_1$ is methyl

Embodiment 172

The compound of any one of the embodiments 169-171, wherein $R_2$ is methyl.

Embodiment 173

The compound of any one of embodiments 169-172, wherein $R_3$ is methyl.

Embodiment 174

The compound of any one of embodiments 169-173, wherein $R_4$ is selected from benzodioxinyl, phenyl optionally substituted with one or more substituents selected from the group consisting of halo and alkoxy, or piperonyl.

Embodiment 175

The compound of embodiment 174, wherein $R_4$ is piperonyl

Embodiment 176

The compound of any one of embodiments 169-175, wherein $R_5$ is H

Embodiment 177

The compound of any one of embodiments 169-175, wherein $R_5$ is an aryl optionally substituted with one or more groups selected from —OH, —CN, $NO_2$, —C(=O), halo, haloalkyl, haloaryl, and heteroarylalkyl.

Embodiment 178

The compound of any one of embodiments 169-177, wherein $R_6$ is selected from the group consisting of CN, —(C=O)O-tBu and —(C=O)OMe.

Embodiment 179

The compound of any one of embodiments 169-178, wherein $R_7$ is alkyl.

Embodiment 180

A compound of Formula II

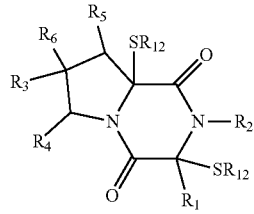

wherein: $R_1$ is selected from H, alkyl, —C(=O)O-alkyl, —C(=O)OR$_7$ aryl, alkoxy, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_2$ is selected from H, alkyl, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_3$ is selected from H, alkyl, aryl, heteroaryl, nitrile, F, Cl, OAc, O-alkyl, and O-aryl; $R_4$ is selected from alkyl, haloalkyl, biphenyl, thiophenyl, piperidyl, morpholinyl, imidazolyl, piperonyl, benzyl, cycloalkyl, benzodioxinyl, dioxinyl, benzodioxanyl, dioxanyl, benzoxazinyl, piperadinyl-1-methyl, heterocycle, indolyl, pyridinyl, piperazinyl, furyl, thienyl, heteroarylalkyl, or phenyl, or optionally substituted variants thereof; $R_5$ is selected from H, aryl, alkyl, haloalkyl, heteroaryl, phenyl, biphenyl, thiophenyl, piperidyl, morpholinyl, imidazolyl, piperonyl, benzyl, cycloalkyl, benzodioxinyl, dioxinyl, heterocycle, indolyl, or pyridinyl, or optionally substituted variants thereof; $R_6$ is selected from CN, $NO_2$, —$S(O)_2$alkyl, —$S(O)_2$ aryl, —$S(O)_2R^7$, —$S(O)_2CH_2CN$, —(C=O)$NH_2$, —(N=H)OMe, —(C=O)(CH$_2$)$_{1-4}$CN; —(C=O)(CH$_2$)$_{1-4}$SO$_2$R$_7$; —(C=O)(CH$_2$)$_{1-4}$CO$_2$R$_7$; —(C=O)(CH$_2$)$_{1-4}$CO$_2$H; —(C=O)(CH$_2$)$_{1-4}$CH$_2$NH$_2$; —(C=O)(CH$_2$)$_{1-4}$CH$_2$NHCOR$_5$; —(C=O)(CH$_2$)$_{1-4}$CH$_2$NR$_1$R$_2$; (CH$_2$)$_{1-4}$OH, —(C=O)OH, —(C=O)O-alkyl; CH$_2$NHR$_9$, or CHR$_{10}$NHR$_{11}$; $R_7$ is alkyl; $R_8$ is selected from alkyl, heteroaryl, halo, alkoxy, thioalkyl, haloalkyl, $NO_2$, CN, —C(=O)O-alkyl, sulfonyl, or sulfonamide; $R_9$ is selected from H, alkyl, aryl, heteroaryl, acyl, or —O-carboxy; $R_{10}$ is selected from alkyl, aryl or heteroaryl; $R_{11}$ is selected from H, alkyl, aryl, heteroaryl, acyl, or —O-carboxy; and $R_{12}$ is selected from methyl or a thiol-protecting group.

Embodiment 181

The compound of embodiment 180, wherein $R_4$ is selected from benzodioxinyl, phenyl optionally substituted with one or more substituents selected from the group consisting of halo and alkoxy, or piperonyl.

Embodiment 182

The compound of embodiment 180, wherein $R_5$ is an aryl optionally substituted with one or more groups selected from —OH, —CN, $NO_2$, —C(=O), halo, haloalkyl, haloaryl, and heteroarylalkyl.

Embodiment 183

A compound of Formula III

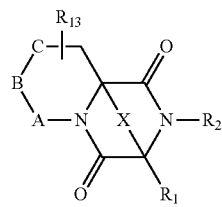

III wherein: X is selected from $S_2$, $S_3$, or $S_4$; $R_1$ is selected from H, alkyl, —C(=O)O, alkyl, alkoxy, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_2$ is selected from H, alkyl, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_7$ is alkyl; $R_8$ is selected from selected from alkyl, heteroaryl, halo, alkoxy, thioalkyl, haloalkyl, $NO_2$, CN, —C(=O)O-alkyl, sulfonyl, or sulfonamide; $R_{13}$ is selected from H, alkyl, aryl, heteroaryl, halo, alkoxy, thioalkyl, haloalkyl, $NO_2$, CN, —C(=O)O-alkyl, sulfonyl, sulfonamide or optionally substituted variants thereof; A is selected from the group consisting of $CH_2$, C=O, NH, $NR_{14}$, O, S, and $SO_2$; B is selected from the group consisting of $CH_2$, C=O, NH, $NR_{14}$, O, S, and $SO_2$; C is selected from the group consisting of $CH_2$, C=O, NH, $NR_{14}$, O, S, and $SO_2$; and $R_{14}$ is selected from the group consisting of alkyl, aryl, acyl, and —O-carboxy.

Embodiment 184

The compound of embodiment 183, wherein $R_1$ is methyl

Embodiment 185

The compound of any one of embodiments 183-184, wherein $R_2$ is methyl.

Embodiment 186

The compound of any one of embodiments 183-185, wherein A is selected from C=O, NH, $NR_{14}$, O, S, and $SO_2$, and both B and C are $CH_2$.

Embodiment 187

The compound of any one of embodiments 183-185, wherein B is selected from C=O, NH, $NR_{14}$, O, S, and $SO_2$, and both A and C are $CH_2$.

Embodiment 188

The compound of any one of embodiments 183-185, wherein C is selected from C=O, NH, $NR_{14}$, O, S, and $SO_2$, and both A and B are $CH_2$.

Embodiment 189

The compound of any one of embodiments 183-185, wherein each of A, B and C is $CH_2$.

Embodiment 190

A compound from the genus of Formula IV

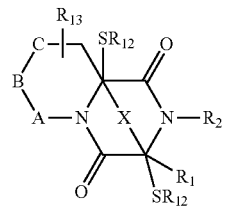

IV wherein: X is selected from $S_2$, $S_3$, or $S_4$; $R_1$ is selected from H, alkyl, —C(=O)O, alkyl, alkoxy, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_2$ is selected from H, alkyl, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_7$ is alkyl; $R_8$ is selected from alkyl, heteroaryl, halo, alkoxy, thioalkyl, haloalkyl, $NO_2$, CN, —C(=O)O-alkyl, sulfonyl, or sulfonamide; $R^{12}$ is selected from methyl or a thiol-protecting group; $R_{13}$ is selected from H, alkyl, aryl, heteroaryl, halo, alkoxy, thioalkyl, haloalkyl, $NO_2$, CN, —C(=O)O-alkyl, sulfonyl, or sulfonamide or optionally substituted variants thereof; A is selected from the group consisting of $CH_2$, C=O, NH, $NR_{14}$, O, S, and $SO_2$; B is selected from the group consisting of $CH_2$, C=O, NH, $NR_{14}$, O, S, and $SO_2$; C is selected from the group consisting of $CH_2$, —C=O, NH, $NR_{14}$, O, S, and $SO_2$; and $R_{14}$ is selected from the group consisting of alkyl, aryl, acyl, and —O-carboxy.

Embodiment 191

The compound of embodiment 190, wherein $R_1$ is selected from methyl or hydrogen.

Embodiment 192

The compound of embodiments 190-191, wherein $R_2$ is selected from methyl or hydrogen.

Embodiment 193

The compound of any one of embodiments 190-192, wherein $R_{13}$ is piperonyl.

Embodiment 194

The compound of any one of embodiments 190-192, wherein $R_{13}$ is a phenyl substituted with one or more substituents selected from halo and alkoxy.

Embodiment 195

The compound of any one of embodiments 190-192, wherein $R_{13}$ is hydrogen.

Embodiment 196

The compound of any one of embodiments 190-192, wherein $R_{13}$ is CN.

Embodiment 197

The compound of any one of embodiments 190-192, wherein $R_{13}$ is —C(=O)O-alkyl.

Embodiment 198

The compound of any one of embodiments 190-197, wherein A is selected from C=O, NH, $NR_{14}$, O, S, and $SO_2$, and both B and C are $CH_2$.

Embodiment 199

The compound of any one of embodiments 190-197, wherein B is selected from C=O, NH, $NR_{14}$, O, S, and $SO_2$, and both A and C are $CH_2$.

Embodiment 200

The compound of any one of embodiments 190-197, wherein C is selected from C=O, NH, $NR_{14}$, O, S, and $SO_2$, and both A and B are $CH_2$.

Embodiment 201

The compound of any one of embodiments 189-196, wherein each of A, B and C is $CH_2$.

Embodiment 202

A compound of Formula V for treating a diseased state

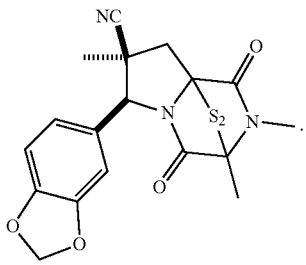

V

Embodiment 203

A compound of Formula VI for treating a diseased state

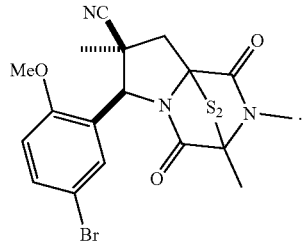

VI

Embodiment 204

A compound of Formula VII for treating a diseased state

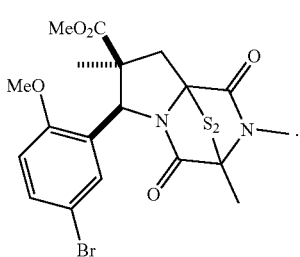

VII

Embodiment 205

A pharmaceutically acceptable salt, prodrug, hydrate, solvate, or acid salt hydrate of the compound of any one of embodiments 170-204.

Embodiment 206

A pharmaceutical composition comprising an effective amount of a compound of any one of embodiments 170-204 or a pharmaceutically acceptable salt, prodrug, hydrate, solvate, or acid salt hydrate of the compound of embodiment 205.

Embodiment 207

The pharmaceutical composition of embodiment 206, wherein the composition contains a stereoisomer, prodrug, pharmaceutically acceptable salt, hydrate, solvate, acid salt hydrate, N-oxide, prodrug ester, or isomorphic crystalline form of the compound.

Embodiment 208

The pharmaceutical composition of any one of embodiments 206-207, wherein the compound is mixed with a pharmaceutically acceptable carrier, diluent, excipient or combination thereof.

Embodiment 209

A method of dysregulating a histone methyltransferase comprising administering an effective amount of a compound of any one of embodiments 170-204, a pharmaceutically-acceptable salt, prodrug, hydrate, solvate, or acid salt hydrate of embodiment 205, or a pharmaceutical composition of any one of embodiments 206-208 to a subject in need thereof.

Embodiment 210

The method of embodiment 209, wherein the subject is a human

Embodiment 211

The method of any one of embodiments 209-210, wherein the compound is selected from group consisting of

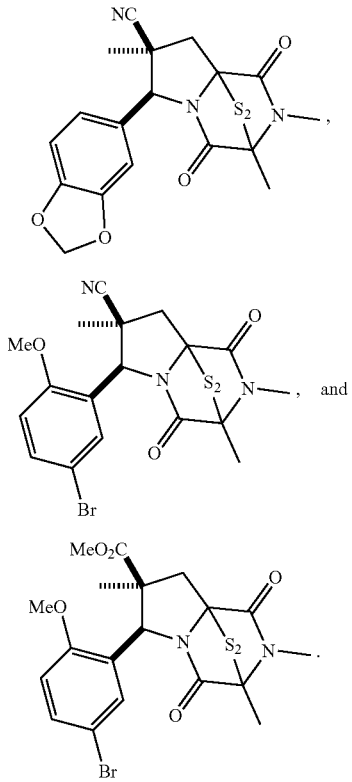

Embodiment 212

A method for treating or preventing a disease condition comprising administering an effective amount of the compound of any one of embodiments 170-204, a pharmaceutically-acceptable salt, prodrug, hydrate, solvate, or acid salt hydrate of embodiment 205, or a pharmaceutical composition of any one of embodiments 206-208 to a subject in need of.

Embodiment 213

The method of embodiment 212, wherein the disease condition is selected from cancer, diabetes, an infectious disease, an autoimmune disease, or pain.

Embodiment 214

The method of embodiment 213, wherein the cancer is selected from prostate cancer, ovarian cancer, pancreatic cancer, chronic myelogenous (or myeloid) leukemia, or melanoma.

Embodiment 215

A compound of Formula VIII

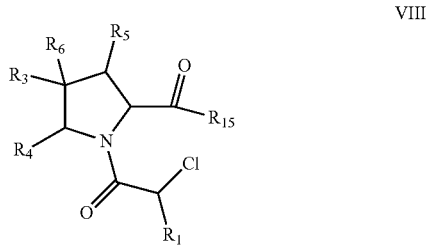

wherein: X is selected from $S_2$, $S_3$, or $S_4$; $R_1$ is selected from H, or alkyl, —C(=O)O-alkyl, alkoxy, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_3$ is selected from H, alkyl, aryl or heteroaryl; $R_4$ is selected from alkyl, haloalkyl, biphenyl, thiophenyl, piperidyl, morpholinyl, imidazolyl, piperonyl, benzyl, cycloalkyl, benzodioxinyl, dioxinyl, benzodioxanyl, dioxanyl, benzoxazinyl, piperadinyl-1-methyl, heterocycle, indolyl, pyridinyl, piperazinyl, furyl, thienyl, heteroarylalkyl, or phenyl, or optionally substituted variants thereof; $R_5$ is selected from H, aryl, alkyl, haloalkyl, heteroaryl, phenyl, biphenyl, thiophenyl, piperidyl, morpholinyl, imidazolyl, piperonyl, benzyl, cycloalkyl, benzodioxinyl, dioxinyl, heterocycle, indolyl, or pyridinyl, or optionally substituted variants thereof; $R_6$ is selected from CN, $NO_2$, —S(O)$_2$alkyl, —S(O)$_2$ aryl, —S(O)$_2R^7$, —S(O)$_2CH_2CN$, —(C=O)NH$_2$, —(N=H)OMe, —(C=O)(CH$_2$)$_{1-4}$CN; —(C=O)(CH$_2$)$_{1-4}$SO$_2R_7$; —(C=O)(CH$_2$)$_{1-4}$CO$_2R_7$; —(C=O)(CH$_2$)$_{1-4}$CO$_2$H; —(C=O)(CH$_2$)$_{1-4}$CH$_2$NH$_2$; —(C=O)(CH$_2$)$_{1-4}$CH$_2$NHCOR$_5$; —(C=O)(CH$_2$)$_{1-4}$CH$_2NR_1R_2$; (CH$_2$)$_{1-4}$OH, —(C=O)OH, —(C=O)O-alkyl; CH$_2$NHR$_9$ or CHR$_{10}$NHR$_{11}$; $R_7$ is selected from H or alkyl; $R^8$ is selected from alkyl, heteroaryl, halo, alkoxy, thioalkyl, haloalkyl, $NO_2$, CN, —C(=O)O-alkyl, sulfonyl, or sulfonamide; $R_9$ is selected from H, alkyl, aryl, heteroaryl, acyl, or —O-carboxy; $R_{10}$ is selected from alkyl, aryl or heteroaryl; and $R_{11}$ is selected from H, alkyl, aryl, heteroaryl, acyl, or —O-carboxy; and $R_{15}$ is selected from —OH, —Oaryl, —Oalkyl, Cl, F, —O-carboxy, or $N_3$.

Embodiment 216

The compound of embodiment 215, wherein $R_1$ is methyl

Embodiment 217

The compound of embodiments 215-216, wherein $R_3$ is methyl

Embodiment 218

The compound of any one of embodiments 215-216, wherein $R_4$ is selected from benzodioxinyl, phenyl optionally substituted with one or more substituents selected from the group consisting of halo and alkoxy, or piperonyl.

Embodiment 219

The compound of embodiment 218, wherein $R_4$ is piperonyl

Embodiment 220

The compound of any one of embodiments 215-219, wherein $R_5$ is H

Embodiment 221

The compound of any one of embodiments 215-219, wherein $R_5$ is an aryl optionally substituted with one or more groups selected from —OH, —CN, $NO_2$, —C(=O), halo, haloalkyl, haloaryl, and heteroarylalkyl.

Embodiment 222

The compound of any one of embodiments 215-219, wherein $R_6$ is selected from the group consisting of CN, —C(=O)O-tBu and —C(=O)OMe.

Embodiment 223

A compound of Formula IX

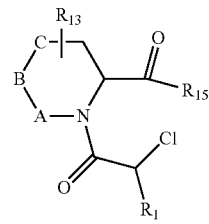

wherein: X is selected from $S_2$, $S_3$, or $S_4$; $R_1$ is selected from H, alkyl, —C(=O)O, alkyl, alkoxy, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_2$ is selected from H, alkyl, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_7$ is selected from H or alkyl; $R_8$ is selected from alkyl, heteroaryl, halo, alkoxy, thioalkyl, haloalkyl, $NO_2$, CN, —C(=O)O-alkyl, sulfonyl, or sulfonamide; $R_{13}$ is selected from H, alkyl, aryl, heteroaryl, halo, alkoxy, thioalkyl, haloalkyl, $NO_2$, CN, —C(=O)O-alkyl, sulfonyl, or sulfonamide; or optionally substituted variants thereof; A is selected from the group consisting of $CH_2$, C=O, NH, $NR_{14}$, O, S, and $SO_2$; B is selected from the group consisting of $CH_2$, C=O, NH, $NR_{14}$, O, S, and $SO_2$; C is selected from the group consisting of $CH_2$, C=O, NH, $NR_{14}$, O, S, and $SO_2$; and $R_{15}$ is selected from the group consisting of alkyl, aryl, acyl, and —O-carboxy.

Embodiment 224

A method for synthesizing a compound of embodiment 170, comprising reacting a compound of Formula VIII with $R_2NH_2$ to form a diketopiperazine ring; introducing the sulfur ring to form a compound of Formula I:

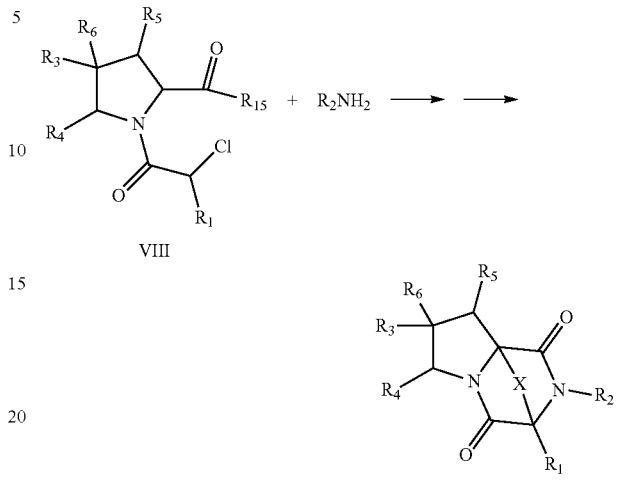

wherein X is selected from $S_2$, $S_3$, or $S_4$; $R_1$ is selected from H, alkyl, —C(=O)O-alkyl, alkoxy, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_2$ is selected from H, alkyl, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_3$ is selected from H, alkyl, aryl or heteroaryl; $R_4$ is selected from alkyl, haloalkyl, biphenyl, thiophenyl, piperidyl, morpholinyl, imidazolyl, piperonyl, benzyl, cycloalkyl, benzodioxinyl, dioxinyl, benzodioxanyl, dioxanyl, benzoxazinyl, piperadinyl-1-methyl, heterocycle, indolyl, pyridinyl, piperazinyl, furyl, thienyl, heteroarylalkyl, or phenyl, or optionally substituted variants thereof; $R_5$ is selected from H, aryl, alkyl, haloalkyl, heteroaryl, phenyl, biphenyl, thiophenyl, piperidyl, morpholinyl, imidazolyl, piperonyl, benzyl, cycloalkyl, benzodioxinyl, dioxinyl, heterocycle, indolyl, or pyridinyl, or optionally substituted variants thereof; $R_6$ is selected from CN, $NO_2$, —S(O)$_2$alkyl, —S(O)$_2$ aryl, —S(O)$_2R^7$, —S(O)$_2$ $CH_2CN$, —C(=O)$NH_2$, —(N=H)OMe, —C(=O) $(CH_2)_{1-4}CN$; —C(=O)$(CH_2)_{1-4}SO_2R_7$; —C(=O) $(CH_2)_{1-4}CO_2R_7$; —C(=O)$(CH_2)_{1-4}CO_2H$; —C(=O) $(CH_2)_{1-4}CH_2NH_2$; —C(=O)$(CH_2)_{1-4}CH_2NHCOR_5$; —C(=O)$(CH_2)_{1-4}CH_2NR_1R_2$; $(CH_2)_{1-4}OH$, —C(=O)OH, —C(=O)O-alkyl; $CH_2NHR_9$ or $CHR_{10}NHR_{11}$; $R_7$ is selected from H or alkyl; $R_8$ is selected from alkyl, heteroaryl, halo, alkoxy, thioalkyl, haloalkyl, $NO_2$, CN, —C(=O)O-alkyl, sulfonyl, or sulfonamide; $R_9$ is selected from H, alkyl, aryl, heteroaryl, acyl, or —O-carboxy; $R_{10}$ is selected from alkyl, aryl or heteroaryl; $R_{11}$ is selected from H, alkyl, aryl, heteroaryl, acyl, or —O-carboxy; and $R_{15}$ is selected from —OH, —Oaryl, —Oalkyl, Cl, F, —O-carboxy, or $N_3$.

Embodiment 225

A method of synthesizing a compound of embodiment 180 comprising reacting a compound of Formula VIII with $R_2NH_2$ to form a diketopiperazine ring; introducing two thioether substituents to form a compound of Formula II:

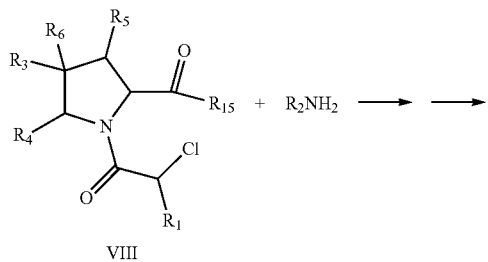

VIII

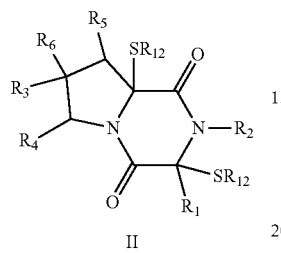

II wherein: R$_1$ is selected from H, alkyl, —C(=O)O-alkyl, —C(=O)OR$_7$ aryl, alkoxy, R$_7$NHR$_8$, R$_7$ cycloalkyl, R$_7$ aryl, R$_7$ morpholinyl, heteroarylalkyl, or R$_7$ piperazinyl, R$_7$ piperazinyl with an alkyl group substituted off the 4-N position of the piperazine ring; R$_2$ is selected from H, alkyl, R$_7$NHR$_7$, R$_7$NHR$_8$, R$_7$ cycloalkyl, R$_7$ aryl, R$_7$ morpholinyl, heteroarylalkyl, R$_7$ piperazinyl, or R$_7$ piperazinyl with an alkyl group substituted off the 4-N position of the piperazine ring; R$_3$ is selected from H, alkyl, aryl, heteroaryl, nitrile, F, Cl, OAc, O-alkyl, or O-aryl; R$_4$ is selected from alkyl, haloalkyl, biphenyl, thiophenyl, piperidyl, morpholinyl, imidazolyl, piperonyl, benzyl, cycloalkyl, benzodioxinyl, dioxinyl, benzodioxanyl, dioxanyl, benzoxazinyl, piperadinyl-1-methyl, heterocycle, indolyl, pyridinyl, piperazinyl, furyl, thienyl, heteroarylalkyl, or phenyl, or optionally substituted variants thereof; R$_5$ is selected from H, aryl, alkyl, haloalkyl, heteroaryl, phenyl, biphenyl, thiophenyl, piperidyl, morpholinyl, imidazolyl, piperonyl, benzyl, cycloalkyl, benzodioxinyl, dioxinyl, heterocycle, indolyl, or pyridinyl, or optionally substituted variants thereof; R$_6$ is selected from CN, NO$_2$, —S(O)$_2$alkyl, —S(O)$_2$ aryl, —S(O)$_2$R$^7$, —S(O)$_2$CH$_2$CN, —(C=O)NH$_2$, —(N=H)OMe, —(C=O)(CH$_2$)$_{1-4}$CN; —(C=O)(CH$_2$)$_{1-4}$SO$_2$R$_7$; —(C=O)(CH$_2$)$_{1-4}$CO$_2$R$_7$; —(C=O)(CH$_2$)$_{1-4}$CO$_2$H; —(C=O)(CH$_2$)$_{1-4}$CH$_2$NH$_2$; —(C=O)(CH$_2$)$_{1-4}$CH$_2$NHCOR$_5$; —(C=O)(CH$_2$)$_{1-4}$CH$_2$NR$_1$R$_2$; (CH$_2$)$_{1-4}$OH, —(C=O)OH, —(C=O)O-alkyl; CH$_2$NHR$_9$, CHR$_{10}$NHR$_{11}$; R$_7$ is alkyl; R$_8$ is selected from alkyl, heteroaryl, halo, alkoxy, thioalkyl, haloalkyl, NO$_2$, CN, —C(=O)O-alkyl, sulfonyl, or sulfonamide; R$_9$ is selected from H, alkyl, aryl, heteroaryl, acyl, or —O-carboxy; R$_{10}$ is selected from alkyl, aryl or heteroaryl; R$_{11}$ is selected from H, alkyl, aryl, heteroaryl, acyl, or —O-carboxy; R$_{12}$ is selected from methyl or a thiol-protecting group; and R$_{15}$ is selected from —OH, —Oaryl, —Oalkyl, Cl, F, —O-carboxy, or N$_3$.

Embodiment 226

A method for synthesizing a compound of embodiment 183 comprising: reacting a compound of Formula VIII with R$_2$NH$_2$ to form a diketopiperazine ring; introducing the sulfur ring to form a compound of Formula III:

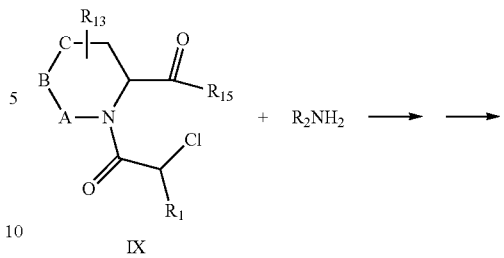

IX

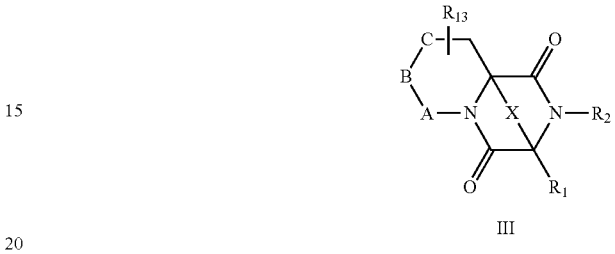

III wherein: X is selected from S$_2$, S$_3$, or S$_4$; R$_1$ is selected from H, alkyl, —C(=O)O, alkyl, alkoxy, R$_7$NHR$_7$, R$_7$NHR$_8$, R$_7$ cycloalkyl, R$_7$ aryl, R$_7$ morpholinyl, heteroarylalkyl, R$_7$ piperazinyl, or R$_7$ piperazinyl with an alkyl group substituted off the 4-N position of the piperazine ring; R$_2$ is selected from H, alkyl, R$_7$NHR$_7$, R$_7$NHR$_8$, R$_7$ cycloalkyl, R$_7$ aryl, R$_7$ morpholinyl, heteroarylalkyl, R$_7$ piperazinyl, or R$_7$ piperazinyl with an alkyl group substituted off the 4-N position of the piperazine ring; R$_7$ is alkyl; R$_8$ is selected from alkyl, heteroaryl, halo, alkoxy, thioalkyl, haloalkyl, NO$_2$, CN, —C(=O)O-alkyl, sulfonyl, or sulfonamide; R$_{13}$ is selected from H, alkyl, aryl, heteroaryl, halo, alkoxy, thioalkyl, haloalkyl, NO$_2$, CN, —C(=O)O-alkyl, sulfonyl, or sulfonamide; or optionally substituted variants thereof; A is selected from the group consisting of CH$_2$, C=O, NH, NR$_{14}$, O, S, and SO$_2$; B is selected from the group consisting of CH$_2$, C=O, NH, NR$_{14}$, O, S, and SO$_2$; C is selected from the group consisting of CH$_2$, C=O, NH, NR$_{14}$, O, S, and SO$_2$; and R$_{15}$ is —OH, —Oaryl, —Oalkyl, Cl, F, —O-carboxy, or N$_3$.

Embodiment 227

A method for synthesizing a compound of embodiment 190 comprising: reacting a compound of Formula VIII with R$_2$NH$_2$ to form a diketopiperazine ring; introducing two thioether substituents to form a compound of Formula IV:

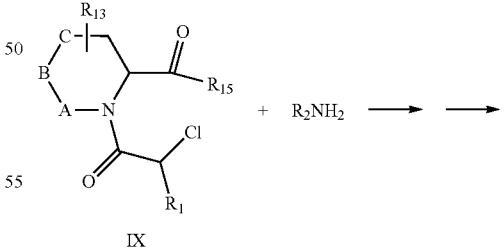

IX

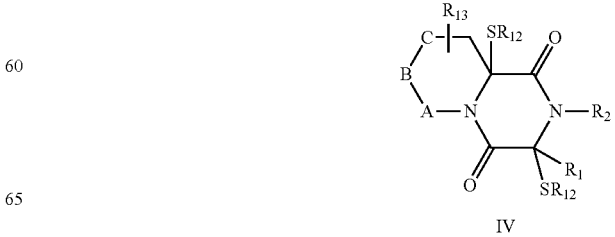

IV wherein: X is selected from $S_2$, $S_3$, or $S_4$; $R_1$ is selected from H, alkyl, —C(=O)O, alkyl, alkoxy, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_2$ is selected from H, alkyl, $R_7NHR_7$, $R_7NHR_8$, $R_7$ cycloalkyl, $R_7$ aryl, $R_7$ morpholinyl, heteroarylalkyl, $R_7$ piperazinyl, or $R_7$ piperazinyl with an alkyl group substituted off the 4-N position of the piperazine ring; $R_7$ is alkyl; $R_8$ is selected from alkyl, heteroaryl, halo, alkoxy, thioalkyl, haloalkyl, $NO_2$, CN, —C(=O)O-alkyl, sulfonyl, or sulfonamide; $R_{12}$ is selected from methyl or a thiol-protecting group; $R_{13}$ is selected from H, alkyl, aryl, heteroaryl, halo, alkoxy, thioalkyl, haloalkyl, $NO_2$, CN, —C(=O)O-alkyl, sulfonyl, or sulfonamide; or optionally substituted variants thereof; A is selected from the group consisting of $CH_2$, C=O, NH, $NR_{14}$, O, S, and $SO_2$; B is selected from the group consisting of $CH_2$, C=O, NH, $NR_{14}$, O, S, and $SO_2$; C is selected from the group consisting of $CH_2$, C=O, NH, $NR_{14}$, O, S, and $SO_2$; $R_{14}$ is selected from the group consisting of alkyl, aryl, acyl, and —O-carboxy; and $R_{15}$ is selected from —OH, —Oaryl, —Oalkyl, Cl, F, —O-carboxy, or $N_3$.

What is claimed is:

1. A compound having formula:

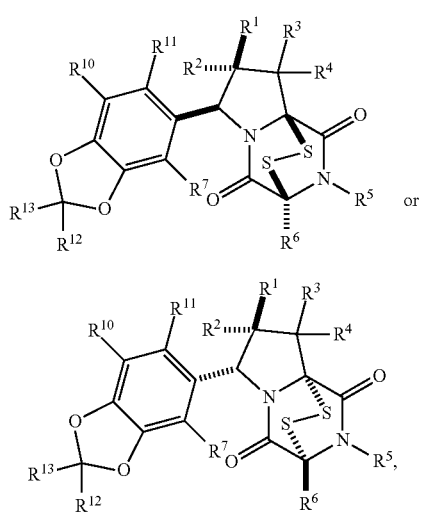

(V2(S))

(V2(R))

wherein:

$R^1$ is hydrogen, halogen, —$CF_3$, —CN, —CHO, or substituted or unsubstituted alkyl;

$R^2$ is hydrogen, halogen, —$N_3$, —$CF_3$, —$CCl_3$, —$CBr_3$, —$CI_3$, —CN, —CHO, —$OR^{33B}$, —$NR^{34B}R^{35B}$, —$COOR^{33B}$, —$CONR^{34B}R^{35B}$, —$NO_2$, —$SR^{36B}$, —$SO_{n2}R^{34B}$, —$SO_{n2}OR^{34B}$, —$SO_{n2}NR^{34B}R^{35B}$, —$NHNR^{34B}R^{35B}$, —$ONR^{34B}R^{35B}$, —NHC(O)NHNR^{34B}R^{35B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, —$OR^{33C}$, —$NR^{34C}R^{35C}$, —$COOR^{33C}$, —$CONR^{34C}R^{35C}$, —$NO_2$, —$SR^{36C}$, —$SO_{n3}R^{34C}$, —$SO_{n3}OR^{34C}$, —$SO_{n3}NR^{34C}R^{35C}$, —$NHNR^{34C}R^{35C}$, —$ONR^{34C}R^{35C}$, —NHC(O)NHNR^{34C}R^{35C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$N_3$, —$CF_3$, —$CCl_3$, —$CBr_3$, —$CI_3$, —CN, —CHO, —$OR^{33D}$, —$NR^{34D}R^{35D}$, —$COOR^{33D}$, —$CONR^{34D}R^{35D}$, —$NO_2$, —$SR^{36D}$, —$SO_{n4}R^{34D}$, —$SO_{n4}OR^{34D}$, —$SO_{n4}NR^{34D}R^{35D}$, —$NHNR^{34D}R^{35D}$, —$ONR^{34D}R^{35D}$, —NHC(O)NHNR^{34D}R^{35D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$N_3$, —$CF_3$, —$CCl_3$, —$CBr_3$, —$CI_3$, —CN, —CHO, —$OR^{33E}$, —$NR^{34E}R^{35E}$, —$COOR^{33E}$, —$CONR^{34E}R^{35E}$, —$NO_2$, —$SR^{36E}$, —$SO_{n5}R^{34E}$, —$SO_{n5}OR^{34E}$, —$SO_{n5}NR^{34E}R^{35E}$, —$NHNR^{34E}R^{35E}$, —$ONR^{34E}R^{35E}$, —NHC(O)NHNR^{34E}R^{35E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$N_3$, —$CF_3$, —$CCl_3$, —$CBr_3$, —$CI_3$, —CN, —CHO, —$OR^{33F}$, —$NR^{34F}R^{35F}$, —$COOR^{33F}$, —$CONR^{34F}R^{35F}$, —$NO_2$, —$SR^{36F}$, —$SO_{n6}R^{34F}$, —$SO_{n6}OR^{34F}$, —$SO_{n6}NR^{34F}R^{35F}$, —$NHNR^{34F}R^{35F}$, —$ONR^{34F}R^{35F}$, —NHC(O)NHNR^{34F}R^{35F}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$N_3$, —$CF_3$, —$CCl_3$, —$CBr_3$, —$CI_3$, —CN, —CHO, —$OR^{33I}$, —$NR^{34I}R^{35I}$, —$COOR^{33I}$, —$CONR^{34I}R^{35I}$, —$NO_2$, —$SR^{36I}$, —$SO_{n9}R^{34I}$, —$SO_{n9}OR^{34I}$, —$SO_{n9}NR^{34I}R^{35I}$, —$NHNR^{34I}R^{35I}$, —$ONR^{34I}R^{35I}$, —NHC(O)NHNR^{34I}R^{35I}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ and $R^{11}$ are independently hydrogen, halogen, —$N_3$, —$CF_3$, —$CCl_3$, —$CBr_3$, —$CI_3$, —CN, —CHO, —$OR^{33L}$, —$NR^{34L}R^{35L}$, —$COOR^{33L}$, —$CONR^{34L}R^{35L}$, —$NO_2$, —$SR^{36L}$, —$SO_{n12}R^{34L}$, —$SO_{n12}OR^{34L}$, —$SO_{n12}NR^{34L}R^{35L}$, —$NHNR^{34L}R^{35L}$, —$ONR^{34L}R^{35L}$, —NHC(O)NHNR^{34L}R^{35L}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally joined together to form a substituted or unsubstituted cycloalkyl, a substituted or unsubstituted heterocycloalkyl, a substituted or unsubstituted aryl, or a substituted or unsubstituted heteroaryl;

$R^{12}$ and $R^{13}$ are independently hydrogen, halogen, —$N_3$, —$CF_3$, —$CCl_3$, —$CBr_3$, —$CI_3$, —CN, —CHO, —$OR^{33M}$, —$NR^{34M}R^{35M}$, —$COOR^{33M}$, —$CONR^{34M}R^{35M}$, —$NO_2$, —$SR^{36M}$, —$SO_{n13}R^{34M}$, —$SO_{n13}OR^{34M}$, —$SO_{n13}NR^{34M}R^{35M}$, —NHNR$^{34M}$R$^{35M}$, —ONR$^{34M}$R$^{35M}$, —NHC(O)NHNR$^{34M}$R$^{35M}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^{33A}$, R$^{34A}$, R$^{35A}$, R$^{36A}$, R$^{33B}$, R$^{34B}$, R$^{35B}$, R$^{36B}$, R$^{33C}$, R$^{34C}$, R$^{35C}$, R$^{36C}$, R$^{33D}$, R$^{34D}$, R$^{35D}$, R$^{36D}$, R$^{33E}$, R$^{34E}$, R$^{35E}$, R$^{36E}$, R$^{33F}$, R$^{34F}$, R$^{35F}$, R$^{36F}$, R$^{33I}$, R$^{34I}$, R$^{35I}$, R$^{36I}$, R$^{33L}$, R$^{34L}$, R$^{35L}$, R$^{36L}$, R$^{33M}$, R$^{34M}$, R$^{35M}$, and R$^{36M}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n6, n9, n12, and n13 are independently 1 or 2.

2. The compound of claim 1, wherein R$^1$ is hydrogen, —CN, or unsubstituted alkyl.

3. The compound of claim 1, wherein R$^2$ is hydrogen, halogen, —CF$_3$, —CN, —OR$^{33B}$, or substituted or unsubstituted alkyl.

4. The compound of claim 3, wherein R$^2$ is hydrogen, —CN, —OR$^{33B}$, or unsubstituted alkyl, wherein R$^{33B}$ is hydrogen, or substituted or unsubstituted alkyl.

5. The compound of claim 1, wherein R$^3$ is hydrogen, halogen, —CF$_3$, —CN, or —CHO; and R$^4$ is hydrogen, halogen, —CF$_3$, —CN, or —CHO.

6. The compound of claim 5, wherein R$^3$ is hydrogen or halogen; and R$^4$ is hydrogen or halogen.

7. The compound of claim 1, wherein R$^5$ is hydrogen, halogen, —CF$_3$, —CN, —CHO, or substituted or unsubstituted alkyl.

8. The compound of claim 7, wherein R$^5$ is hydrogen, —F, —Cl, —Br, —I, —CF$_3$, or unsubstituted alkyl.

9. The compound of claim 1, wherein R$^6$ is hydrogen, halogen, —CF$_3$, —CN, —CHO, or substituted or unsubstituted alkyl.

10. The compound of claim 9, wherein R$^6$ is hydrogen, —F, —Cl, —Br, —I, —CF$_3$, or substituted or unsubstituted alkyl.

11. The compound of claim 1, wherein R$^7$ is hydrogen or halogen; R$^{10}$ is hydrogen or halogen; and R$^{11}$ is hydrogen or halogen.

12. The compound of claim 1, wherein R$^{12}$ is hydrogen or halogen; and R$^{13}$ is hydrogen or halogen.

13. The compound of claim 1, wherein the compound has the formula:

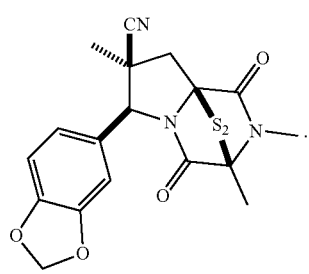
(ETP69)

14. The compound of claim 1, wherein the compound has the formula:

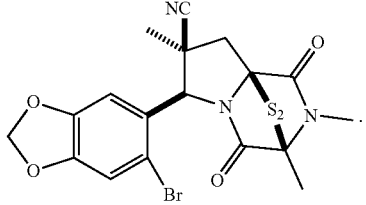
(ETP128)

15. The compound of claim 1, wherein the compound has the formula

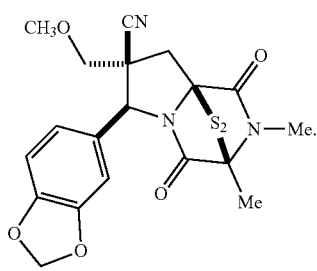
(ETP344)

16. The compound of claim 1, wherein the compound has the formula

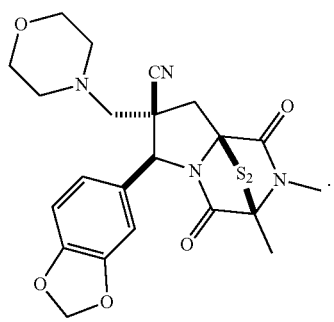
(ETP382)

17. The compound of claim 1, wherein the compound has the formula

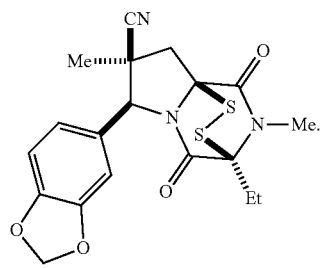
(ETP406)

18. A method of treating cancer, comprising administering to a subject in need thereof a therapeutically effective amount of a compound of claim 1, wherein the cancer is ovarian cancer, breast cancer, lung cancer, leukemia, lymphoma, pancreatic cancer, kidney cancer, melanoma, liver cancer, colon cancer, sarcoma, multiple myeloma, brain cancer, or prostate cancer.

19. The method of claim 18, wherein the cancer is ovarian cancer, breast cancer, lung cancer, or leukemia.

20. The method of claim 18, wherein the leukemia is acute myeloid leukemia or chronic myeloid leukemia.

21. The method of claim 18, wherein the cancer is lymphoma, pancreatic cancer, kidney cancer, melanoma, liver cancer, colon cancer, sarcoma, multiple myeloma, brain cancer, or prostate cancer.

* * * * *